(12) United States Patent
West et al.

(10) Patent No.: US 11,566,018 B2
(45) Date of Patent: Jan. 31, 2023

(54) TREATMENT OF INFECTIOUS DISEASE

(71) Applicant: The Governors of the University of Alberta, Edmonton (CA)

(72) Inventors: Frederick Glenn West, Edmonton (CA); David J. Marchant, Edmonton (CA); Bren Jordan P. Atienza, Edmonton (CA); Lionel D. Jensen, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 16/971,269

(22) PCT Filed: Mar. 27, 2019

(86) PCT No.: PCT/CA2019/050380
§ 371 (c)(1),
(2) Date: Aug. 19, 2020

(87) PCT Pub. No.: WO2019/183729
PCT Pub. Date: Oct. 3, 2019

(65) Prior Publication Data
US 2021/0009563 A1 Jan. 14, 2021

Related U.S. Application Data

(60) Provisional application No. 62/649,220, filed on Mar. 28, 2018.

(51) Int. Cl.
*C07D 403/04* (2006.01)
(52) U.S. Cl.
CPC .................. *C07D 403/04* (2013.01)
(58) Field of Classification Search
CPC .................................... C07D 403/04
See application file for complete search history.

(56) References Cited

U.S. PATENT DOCUMENTS

2011/0028564 A1  2/2011  Johansen et al.
2014/0179637 A1  6/2014  Leis et al.

FOREIGN PATENT DOCUMENTS

WO  WO 2015/154169  10/2015
WO  WO 2017/055396   4/2017

OTHER PUBLICATIONS

Chien et al. Chem. Pharm. Bull. 33(5) 1843-1848 (1985).*
Registry No. 53904-10-2, File Registry on STN, Nov. 16, 1984.*
McClay et al. AMB Expr (2015) 5:38, pp. 1-8.*
Astolfi, et al.; "Radical intermediates in the peroxidation of indoles"; J. Chem. Soc., Perkin Trans.; vol. 2, pp. 1634-1640 (2001).
Atienza, et al.; Dual Catalytic Synthesis of Antiviral Compounds Based on Metallocarbene-Azide Cascade Chemistry; J. Org. Chem.; vol. 83, pp. 6829-6842 (2018).
Banerji, et al.; "Metal Reagents in Organic Reactions. Part-VI[1,2], Oxidation of Indoles with Thallium(III) Acetate"; J. Indian Chem. Soc.; vol. 75, pp. 698-704 (1998).
Bayindir, et al.; "A facile one-pot method to synthesise 2-alkylated indole and 2,2'-bis(indolyl)methane derivatives using ketones as electrophiles and their anion sensing ability"; RSC Adv.; vol. 6, pp. 72959-72967 (2016).
Berti, et al.; "Electrochemical, Chemical, and E.s.r. Study of the Reduction Mechanism of Substituted Indoxyls in Media with Controlled Proton Availability"; J. Chem. Research; pp. 340-341 (1981).
Bott, et al.; "Azide trapping of metallocarbenes: generation of reactive C-acylimines and domino trapping with nucleophiles"; RSC Adv.; vol. 4, pp. 31955-31959 (2014).
Colonna, et al.; "Reaction of 2-Phenyl-3H-Indol-3-One With Indoles"; Gazzetta Chimiza Italiana; vol. 105, pp. 985-992 (1975).
Ding, et al.; "Photocatalytic aerobic oxidation/semipinacol rearrangement sequence: a concise route to the core of pseudoindoxyl alkaloids"; Tetrahedron Letters; vol. 55, pp. 4648-4652 (2014).
Greci, et al.; "Radical cations: reactions of 2-phenylindole with aromatic amines under anodic oxidation. B-Scission of an amino alkoxy radical"; J. Chem. Soc., Perkin Trans. 2; pp. 1749-1755 (2000).
Guchhait, et al.; "Oxidative Dearomatization of Indoles via Pd-Catalyzed C—H Oxygenation: An Entry to C2-Quaternary Indolin-3-ones"; Org. Lett.; vol. 18, pp. 1534-1537 (2016).
Higuchi, et al.; "Preparation of 2,2-disubstituted 1,2-dihydro-3H-indol-3-ones via oxidation of 2-substituted indoles and Mannich-type reaction"; Tetrahedron; vol. 66, pp. 1236-1243 (2010).
Jessing, et al.; "Oxidative Coupling of Indoles with 3-Oxindoles"; Heterocycles; vol. 82, No. 2, pp. 1739-1745 (2011).
Li, et al.; "Gold/Copper-Co-catalyzed Tandem Reactions of 2-Alkynylanilines: A Synthetic Strategy for the C2-Quaternary Indolin-3-ones"; Org. Lett.; vol. 19, pp. 1160-1163 (2017).
Ling, et al.; Sensitized Photooxidative Coupling of 2-Arylindoles; Youji Huaxue; vol. 6, No. 6, pp. 518-523 (Jan. 1, 1996).
Ling, et al.; "Singlet oxygenation of [2,3'-bi-1H-indol]-3(2H)-ones"; Youji Huaxue; vol. 16, No. 2, pp. 152-156 (Jan. 1, 1996).
Ling, et al.; "Synthesis of Bulky 2,2-Diaryl-1,2-dihydro-3H-indol-3-ones via Singlet Oxygenation of 2-Arylindoles"; Synthetic Communications; vol. 26, No. 1, pp. 149-152 (1996).
Preciado, et al.; "Exploration of Forbidden Povarov Processes as a Source of Unexpected Reactivity: A multicomponent Mannich-Ritter Transformation"; Angew. Chem. Int. Ed.; vol. 51, pp. 6874-6877 (2012).
Saito, et al.; "Photoinduced Reactions. LXV. Photosensitized Oxygenation of 2-Methylindoles"; Chemistry Letters; pp. 1173-1176(1972).

(Continued)

*Primary Examiner* — Rebecca L Anderson
(74) *Attorney, Agent, or Firm* — Bozicevic Field & Francis, LLP; Paula A. Borden; Mandar A. Joshi

(57) ABSTRACT

The present disclosure relates to 2-(3-indoyl)indolin-3-one derivatives of the natural product isatisine A, synthesized from dual catalytic synthesis on metallocarbene-azide cascade chemistry, useful for treating a subject having or suspected of having an infectious disease, wherein the infection disease is caused by a virus, wherein the virus is from the family flaviviridae or paramyxoviridae.

4 Claims, 58 Drawing Sheets

Specification includes a Sequence Listing.

(56) References Cited

OTHER PUBLICATIONS

Yarlagadda, et al.; "Oxidative Asymmetric Aza-Friedel-Crafts Alkylation of Indoles with 3-Indolinone-2-carboxylates Catalyzed by a BINOL Phosphoric Acid and Promoted by DDQ"; Chem. Asian J.; vol. 13, pp. 1327-1334 (2018).

Yin, et al.; "Chiral phosphoric acid-catalysed Friedel-Crafts alkylation reaction of indoles with racemic spiro indolin-3-ones"; Chem. Sci.; vol. 2, pp. 1344-1348 (2011).

Kong, et al.; "Copper-catalyzed oxidative trimerization of indoles by using TEMPO to construct quaternary carbon centers: the synthesis of 2-(1H-indol-3-yl)-2,3'-biindolin-3-ones"; Canadian Journal of Chemistry; vol. 92, No. 4, pp. 269-273 (Dec. 5, 2013).

Lin, et al.; "Silver-catalyzed TEMPO oxidative homocoupling of indoles for the synthesis of 3,3'-biindolin-2-ones"; RSC Advances, vol. 5, No. 46, pp. 37018-37022 (Apr. 13, 2015).

Mutule, et al.; "Catalytic Direct Acetoxylation of Indoles"; The Journal of Organic Chemistry; vol. 74, No. 18, pp. 7195-7198 (Aug. 18, 2009).

Patterson, et al.; "319. Isatogens. Part II. 2-2'-Pyridylisatogen", Journal of the Chemical Society; pp. 1706-1711 (Jan. 1, 1965).

Shimizu, et al.; "Synthesis of Indolin-3-ones and Tetrahydro-4-quinolones from [alpha]-Imino Esters"; Asian Journal of Organic Chemistry, vol. 2, No. 2, pp. 130-134 (Jan. 17, 2013).

Zhang, et al.; "Palladium-Catalyzed One-Pot Synthesis of C2-Quaternary Indolin-3-ones via 1H-indole-3-sulfonates Generated in Situ from 2-Alkynyl Arylazides and Sulfonic Acids"; Advanced Synthesis and Catalysis; vol. 359, No. 23, pp. 4147-4152 (Oct. 4, 2017).

Zhou, et al.; "Ruthenium-Catalyzed Oxidative Dearomatization of Indoles for the Construction of C2-Quaternary Indolin-3-ones"; SYNLETT; vol. 29, No. 06, pp. 835-839 (Jan. 15, 2018).

* cited by examiner

```
   1 mdpiingnsa nvyltdsyik gvisfsecna lgsyifngpy lkndytnlis rqnpliehis
  61 lkkisitqsi iskyhkgeik ieeptyfqsl lmtyksmtss egittnlik kiirraieis
 121 dvkvyailnk iglkekdkik snnggdedns vittiikddi ilavkdngsh lkadknhstk
 181 qkdtikttli kklmcsmqhp pswlihwinl ytkinsiltq yrssevknhg fiilidnhtln
 241 gfqfilnqyg civyhkeikr itvttynqfl twkdislsri nvclitwisn clntinkslg
 301 lrcgfnnvii tqlflygdci lklfhneefy iikevegfim sliliniteed qfrkrfynsm
 361 lnnitdaank aqknllsrvc htlidktvsd niingrwiii iskflkliki agdnninnls
 421 elyflfrifg hpmvderqam davkvncnet kfyilsslsm irgafiyrii kgfvnynyrw
 481 ptirnaivlp lrwltyykin typsilelte rdiivlsgir fyrefripkk vdlemiindk
 541 aisppkniiw tsfprnymps hiqnyiehek lkfsesdksr rvleyyirdn kfnecdlync
 601 vvnqsylnnp nhvvsltgke relsvgrmfa mqpqmfrqvq ilaekmiaen ilqffpeslt
 661 rygdielqki ielkagisnk snrynanynn yiskcsiitd iskfnqafry etscicsdvl
 721 deihgvqslf swhlitiphv tiiictyrhap pyirdhlvdi dnqsidiskp ryhmggiegw
 781 cqkiwtieai slidlisikg kfsitaling dnqsidiskp vrlmeqqtha qadyilains
 841 lkiiykeyag ighklkgtet yisrdmqfms ktiqhngvyy pasikkvirv gpwintildd
 901 fkvsiesigs itqeleyrge slicsiiifrn vwlynqiaiq iknhalcnnk lyidilkvlk
 961 hiktffnldn idtaltlymn lpmlfgggdp nilyrsfyrr tpdflteaiv hsvfiilsyyt
1021 nhdikdklgd isddrlnkfi tciitfdknp naefvtlmrd pqalgserqa kitseinrla
1081 vtevistapn kifsksaghy ttteidindi mqnieptyph qlrvvyesip fykaekivnl
1141 isgtksitni lektsaidit didratenmr knitlliiril pldcnrdkre ilsmenlsit
1201 elskyvrers wslsnivgvt spsimytmdi kyttstiasg iliekynvns ltrgergptk
1261 pwvgsstqek ktmpvynrqv ltkkqrdqid liakldwvya sidnkdefme elsigtlglt
1321 yekakkllfpq yisvnylhri tvssrpcefp asipayrttn yhfdtspinr iltekygded
1381 idivfqncis fglsmsvve qftnvcpnri iliipklneih lmkppiftgd vdihkikqvi
1441 qkqhmflpdk isltqyveif lsnktlksgs nvnsnlilah kisdyfhnty ilstniaghw
1501 iliiqlmkds kgifekdwge gyitdhmfin lkvffnaykt yllcfhkgyg raklecdmnt
1561 sdlicvleli dssywksmsk vfleqkviky ilsqdasihr vkgchsfklw flkrlnvaef
1621 tvcpwvvnid yhpthmkaii tyidlvzmgi inidriyikn khkfndefyt snifyinynf
1681 sdnthlltkh irianseles nynklyhptp etieniltnp vksndkktls dscigknvds
1741 imipilsnkk liksstmirt nysrqdlynl fptvvidkii dhsgntaksn qlytttshqi
```

FIG. 57B

```
1801 slvhnstsly cmlpwhhinr fnfvfsstgc kisieyilkd lkikdpncia figegagnll
1861 lrtvvelhpd iryiyrslkd cndhslpief lrlynghini dygenltipa tdatnnihws
1921 ylhikfaepi slfvcdaelp vtvnwskiii ewskhvrkck ycssvnkctl ivkyhaqddi
1981 dfkldnitil ktyvclgskl kgsevylvlt igpanvfpvf nvvqnaklil srtknfimpk
2041 kadkesidan ikslipflcy pitkkginta lsklksvvsg dilsysiagr nevfsnklin
2101 hkhmnilkwf nhvlnfrste lnynhlymve styphlsell nslttnelkk likitgslly
2161 nfrne
```

TREATMENT OF INFECTIOUS DISEASE

CROSS-REFERENCE

This application is a national phase filing under 35 U.S.C. § 371 of PCT/CA2019/050380, filed Mar. 27, 2019, which application claims the benefit of U.S. Provisional Patent Application No. 62/649,220, filed Mar. 28, 2018, which applications are incorporated herein by reference in their entirety.

FIELD

The present disclosure relates generally to the treatment of infectious disease.

BACKGROUND

Annually, Respiratory Syncytial Virus (RSV) causes an estimated 3.4 million severe lower respiratory infections requiring hospitalization in children under 5 years of agwe. Recent vaccine development efforts have not been fruitful, and no licensed efficacious therapeutics are available to treat infection. A viral RNA-dependent RNA polymerase complex (RdRp), required for expression and replication of the viral genome, provides an attractive target for inhibition of the viral replication cycle. The absence of an X-ray crystal structure of this complex rules out in silico approaches for inhibitor development.

ZIKV infection, in contrast to RSV, has only recently been identified as an unmet therapeutic need. The most recent severe ZIKV outbreak to date occurred in Brazil, with an estimated incidence of 30,000 infections since first detection in May 2015. While primary symptoms are usually mild, the association of ZIKV infection with congenital microcephaly and its mosquito-based transmission underscore the importance of developing therapeutics against it, especially from a prophylactic vantage point. Currently no vaccine or specific antiviral treatments are available for ZIKV.

SUMMARY

In an aspect of the present application there is provided a compound of formula (I)

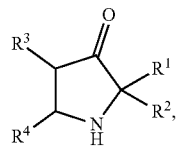

(I)

or
   a stereoisomer, a racemate, a tautomer, a pharmaceutically acceptable salt, a solvate, or a functional derivative thereof,
   wherein:
   $R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;
   $R^2$ is independently aryl, benzyl, or heterocycle, each of which is optionally substituted; and
   $R^3$ and $R^4$ are each independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or $R^3$ and $R^4$, together with the atoms to which they are attached, are connected to form a cycle or heterocycle, each of which is optionally substituted.

In another aspect, there is provided a compound having the formula (II)

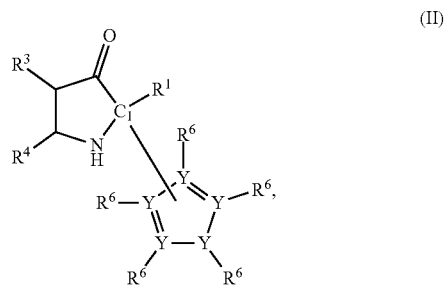

(II)

or
   a stereoisomer, a racemate, a tautomer, a pharmaceutically acceptable salt, a solvate, or a functional derivative thereof,
wherein:
Y is independently C or a heteroatom;
$R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;
$R^3$ and $R^4$ are each independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or $R^3$ and $R^4$, together with the atoms to which they are attached, are connected to form a cycle or heterocycle, each of which is optionally substituted; and
$R^6$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^6$, together with the atoms to which they are attached, are connected to form a cycle or heterocycle, each of which is optionally substituted; and wherein one Y is bonded to $C_1$ and the corresponding $R^6$ is absent.

In another aspect, there is provided a compound having the formula (III)

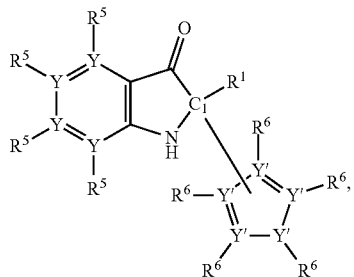

(III)

or
  a stereoisomer, a racemate, a tautomer, a pharmaceutically acceptable salt, a solvate, or a functional derivative thereof,
  wherein:
  Y and Y' are each independently C or a heteroatom;
  $R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;
  $R^5$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted; and
  $R^6$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^6$, together with the atoms to which they are attached, are connected to form a cycle or heterocycle, each of which is optionally substituted; and wherein one Y' is bonded to $C_1$ and the corresponding $R^6$ is absent.

In another aspect, there is provided a compound having the formula (IV)

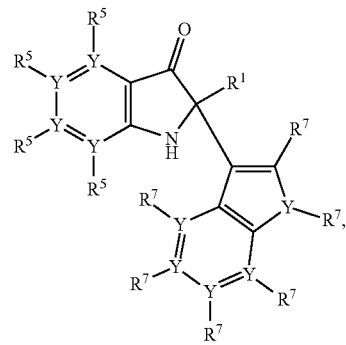

(IV)

or
  a stereoisomer, a racemate, a tautomer, a pharmaceutically acceptable salt, a solvate, or a functional derivative thereof,
  wherein:
  Y is independently C or a heteroatom;
  $R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;
  $R^5$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted; and
  $R^7$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^7$, together with the atoms to which they are attached, are connected to form a cycle or heterocycle, each of which is optionally substituted.

In another aspect, there is provided a compound having the formula (V)

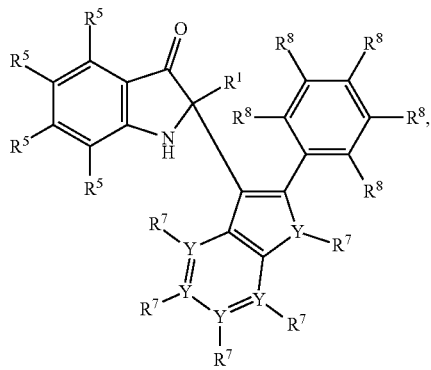

(V)

or
  a stereoisomer, a racemate, a tautomer, a pharmaceutically acceptable salt, a solvate, or a functional derivative thereof,
  wherein:
  Y is independently C or a heteroatom;
  $R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;
  $R^5$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted;

R$^7$ is independently absent, H, C$_1$-C$_{10}$ alkyl, C$_{10}$-C$_{20}$ alkyl, C$_2$-C$_{10}$ alkenyl, C$_{10}$-C$_{20}$ alkenyl, C$_2$-C$_{10}$ alkynyl, C$_{10}$-C$_{20}$ alkynyl, C$_3$-C$_{20}$ carbocycle, aryl, benzyl, heterocycle, C$_1$-C$_{10}$ alkoxy, C$_{10}$-C$_{20}$ alkoxy, alcohol, ether, ketone, carboxylic acid, ester, thiol, thioether, amine, amide, carbamate, nitro, cyano, or halo, each of which is optionally substituted; or two of R$^7$, together with the atoms to which they are attached, are connected to form a cycle or heterocycle, each of which is optionally substituted; and, R$^8$ is independently H, C$_1$-C$_{10}$ alkyl, C$_{10}$-C$_{20}$ alkyl, C$_2$-C$_{10}$ alkenyl, C$_{10}$-C$_{20}$ alkenyl, C$_2$-C$_{10}$ alkynyl, C$_{10}$-C$_{20}$ alkynyl, C$_3$-C$_{20}$ carbocycle, aryl, benzyl, heterocycle, C$_1$-C$_{10}$ alkoxy, C$_{10}$-C$_{20}$ alkoxy, alcohol, ether, ketone, carboxylic acid, ester, thiol, thioether, amine, amide, carbamate, nitro, cyano, or halo, each of which is optionally substituted; or two of R$^8$, together with the atoms to which they are attached, are connected to form a cycle or heterocycle, each of which is optionally substituted.

In another aspect, there is provided a compound having the formula (VI)

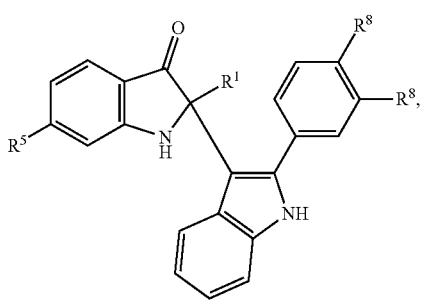

(VI)

or a stereoisomer, a racemate, a tautomer, a pharmaceutically acceptable salt, a solvate, or a functional derivative thereof, wherein:

R$^1$ is an ester;

R$^5$ is a halo; and,

R$^8$ is independently H, C$_1$-C$_{10}$ alkoxy, or halo, each of which is optionally substituted.

In an embodiment of the present application, there is provided a compound having the structure

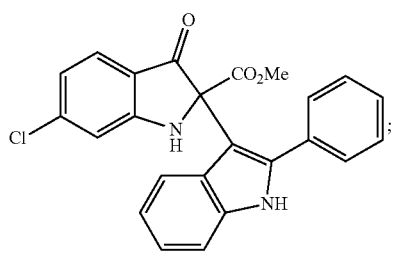

-continued

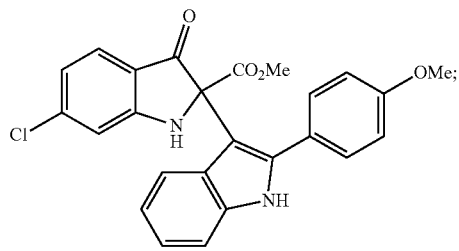

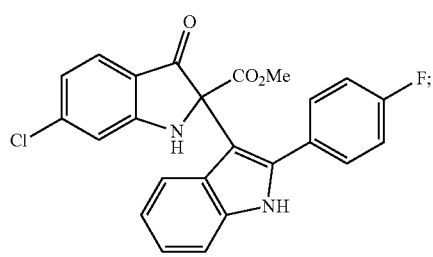

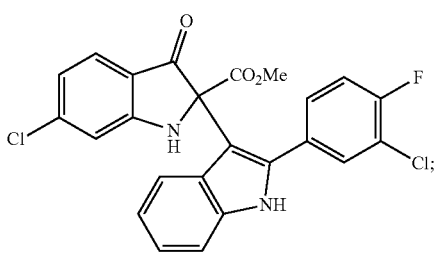

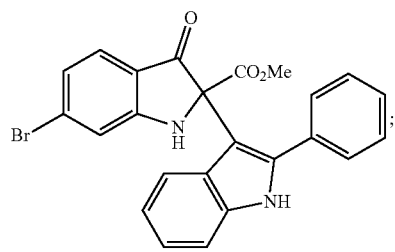

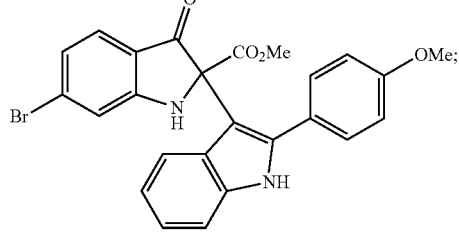

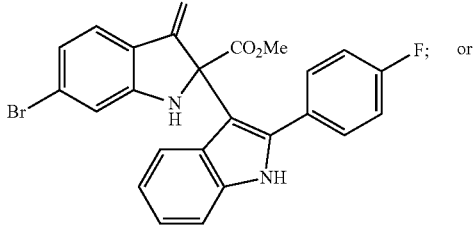

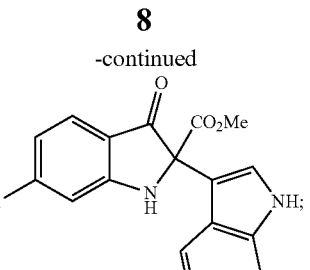
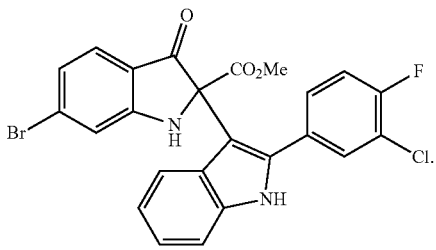
In another embodiment, there is provided a compound having the structure
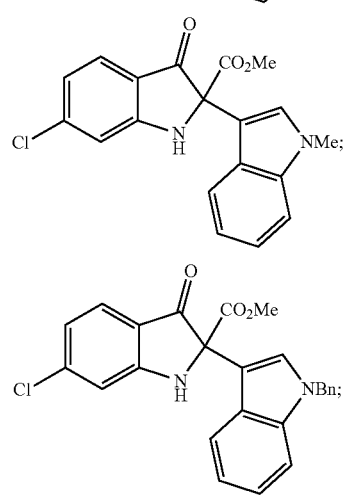
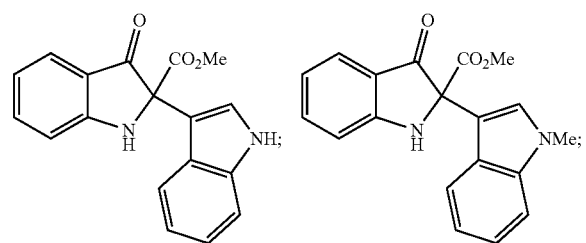
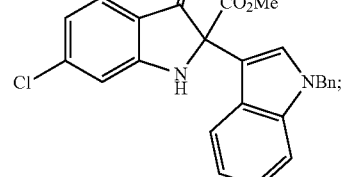
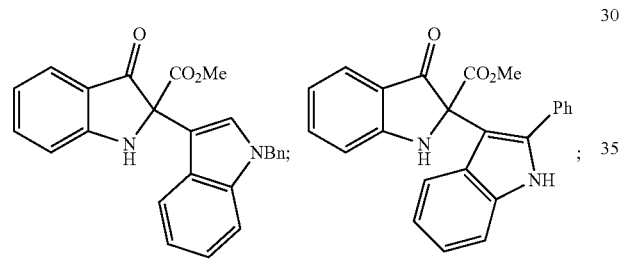
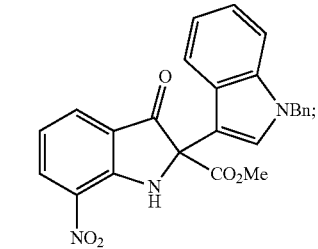
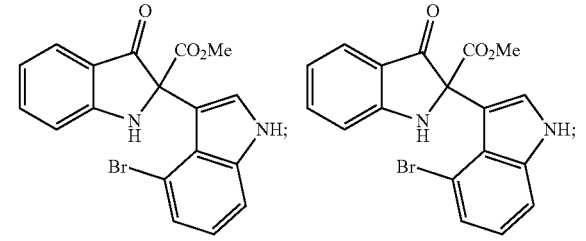
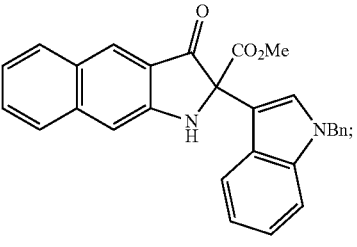
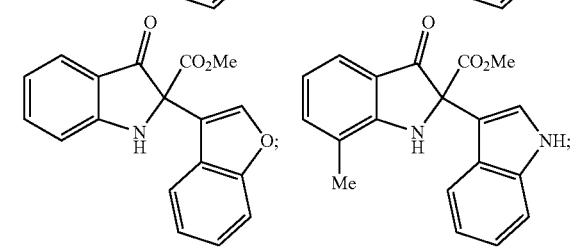
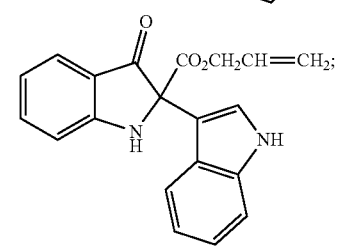
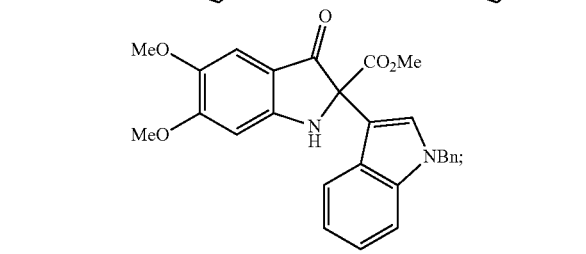
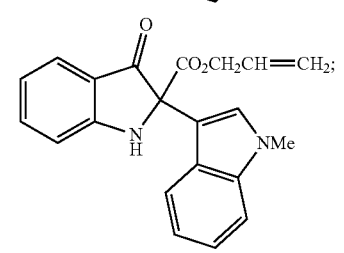

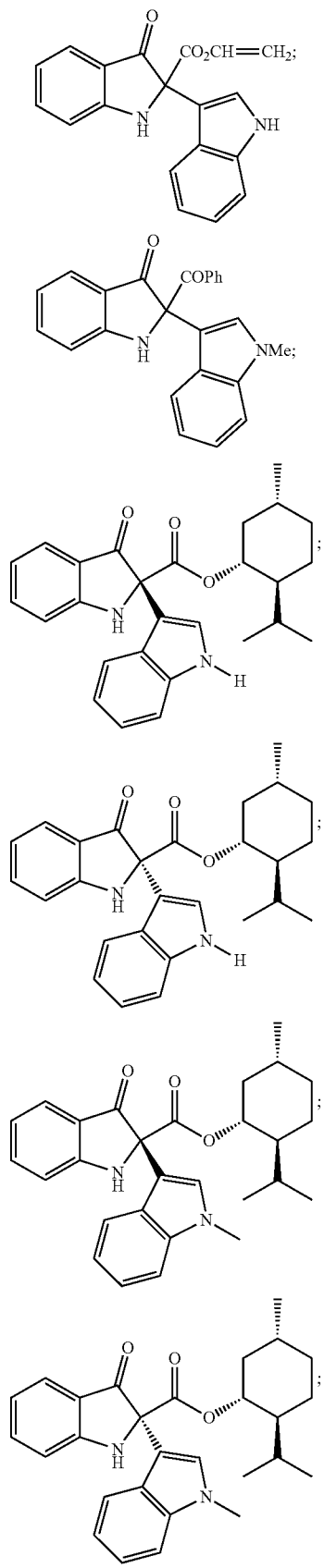

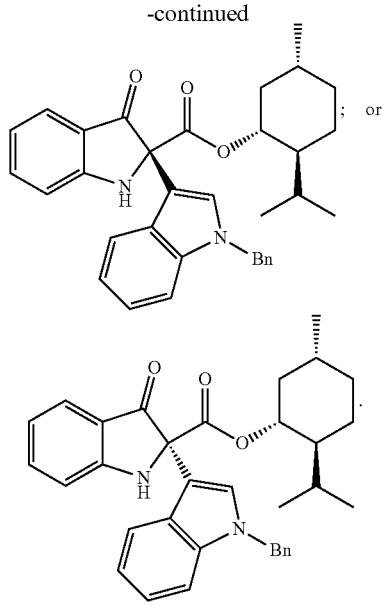

In another aspect of the present application, there is provided a method of synthesizing a compound as described herein, comprising:
a) reacting an organoazide-dizaoketone compound with a transition metal catalyst;
b) forming a metallocarbene from the reaction of the organoazide-dizaoketone compound with a transition metal catalyst;
c) generating an electrophilic C-acylimine from the metallocarbene; and,
d) reacting the electrophilic C-acylimine with a nucleophilic compound.

In an embodiment of the present application, there is provided a method wherein step d) further comprises reacting the electrophilic C-acylimine with a nucleophilic compound in the presence of a Bronsted acid catalyst.

In another embodiment, there is provided a method wherein the transition metal catalyst is a Cu catalyst. In another embodiment, the transition metal catalyst is Cu(hfacac)$_2$, Cu(OTf)$_2$, or CuOTf.Ph(CH$_3$).

In another embodiment, there is provided a method wherein the nucleophilic compound is a heteroatom-containing compound. In another embodiment, the heteroatom-containing compound is a heterocycle or a cycle substituted with a heteroatom-containing moiety. In another embodiment, the heterocycle is pyrrole, furan, thiophene, pyridine, indole, benzofuran, benzothiphene, imidazole, or derivatives thereof, each of which is optionally substituted.

In another aspect of the present application, there is provided a pharmaceutical composition comprising a compound as described herein, or a compound syntheized by the method as described herein, and a pharmaceutically acceptable carrier, diluent, or vehicle.

In another aspect of the present application, there is provided a method of treating a subject having or suspected of having an infectious disease, comprising: administering a therapeutically effective amount of a compound as described herein, or a compound syntheized by the method as described herein, or a pharmaceutical composition as described herein.

In another aspect of the present application, there is provided a method of treating a subject having or suspected of having an infectious disease, comprising: administering a therapeutically effective amount of a compound as described herein, or a compound syntheized by the method as described herein, or a pharmaceutical composition as described herein, wherein said infectious disease is caused by a virus.

In another embodiment of the present application, there is provided a method wherein said virus is a virus from the family Flaviviridae. In another embodiment, the virus is from the genera *Hepacivirus, Flavivirus, Pegivirus,* or *Pestivirus*. In another embodiment, *Flavivirus* is yellow fever virus (YFV), Japanese encephalitis virus (JEV), Tick-borne encephalitis virus (TBEV), Dengue virus (DENV), West Nile virus (WNV), Zika virus (ZIKAV), or any combination thereof.

In another embodiment, there is provided a method wherein said virus is from the family Paramyxoviridae. In another embodiment, said virus is from the genera *Paramyxovirus, Pneumovirus,* or *Morbillivirus*. In another embodiment, *Paramyxovirus* is parainfluenza virus or mumpus virus. In another embodiment, *Pneumovirus* is respiratory syncytial virus (RSV). In another embodiment, said *Morbillivirus* is measles virus.

In another embodiment, there is provided a method wherein said subject is a human, a domesticated animal, livestock, a laboratory animal, a non-human mammal, a non-human primate, a rodent, a bird, a reptile, an amphibian, or a fish. In some cases, the individual to be treated with a method of the present disclosure is a human. In some cases, the individual to be treated with a method of the present disclosure is an ungulate (e.g., a bovine; an ovine; a caprine; an equine; etc.).

In another aspect of the present application, there is provided a use of a compound of as described herein, or a compound syntheized by the method as described herein, or a pharmaceutical composition as described herein for treating a subject having or suspected of having an infectious disease.

In another aspect of the present application, there is provided a use of a compound as described herein, or a compound syntheized by the method as described herein, or a pharmaceutical composition as described herein in the manufacture of a medicament for treating a subject having or suspected of having an infectious disease.

In another aspect of the present application, there is provided a use of a compound as described herein, or a compound syntheized by the method as described herein, or a pharmaceutical composition as described herein for treating a subject having or suspected of having an infectious disease, wherein said infectious disease is caused by a virus.

In another aspect of the present application, there is provided a use of a compound as described herein, or a compound syntheized by the method as described herein, or a pharmaceutical composition as described herein in the manufacture of a medicament for treating a subject having or suspect of having an infectious disease, wherein said infectious disease is caused by a virus.

In another embodiment of the present application, there is provided a use wherein said virus is a virus from the family Flaviviridae. In another embodiment, the virus is from the genera *Hepacivirus, Flavivirus, Pegivirus,* or *Pestivirus*. In another embodiment, *Flavivirus* is yellow fever virus (YFV), Japanese encephalitis virus (JEV), Tick-borne encephalitis virus (TBEV), Dengue virus (DENV), West Nile virus (WNV), Zika virus (ZIKAV), or any combination thereof.

In another embodiment of the present application, there is provided a use wherein said virus is a virus from the family Paramyxoviridae. In another embodiment, said virus is from the genera *Paramyxovirus, Pneumovirus,* or *Morbillivirus*. In another embodiment, *Paramyxovirus* is parainfluenza virus or mumpus virus. In another embodiment, *Pneumovirus* is respiratory syncytial virus (RSV). In another embodiment, said *Morbillivirus* is measles virus.

In another embodiment of the present application, there is provided a usewherein said subject is a human, a domesticated animal, livestock, a laboratory animal, a non-human mammal, a non-human primate, a rodent, a bird, a reptile, an amphibian, or a fish.

BRIEF DESCRIPTION OF THE FIGURES

Embodiments of the present disclosure will now be described, by way of example only, with reference to the attached Figures.

FIG. 7 depicts differential scanning calorimetry (DSC) data for compound 1a;

FIG. 8 depicts thermogravimetric analysis (TGA) data for compound 1a;

FIG. 9 depicts an in-situ IR spectroscopic analysis of decomposition of compound 1a;

FIG. 12 depicts electrospray mass spectra of crude reaction mixture to make compound 2a;

FIG. 13 depicts an ORTEP structure for compound 1a;
FIG. 14 depicts an ORTEP structure for compound 2a;
FIG. 23 depicts an NMR spectrum of compound 2a.

FIG. 47 depicts an NMR spectrum of compound 5a;
FIG. 57A-57B provide an amino acid sequence of human RSV-L protein (SEQ ID NO:1).

DETAILED DESCRIPTION

Figure 1:
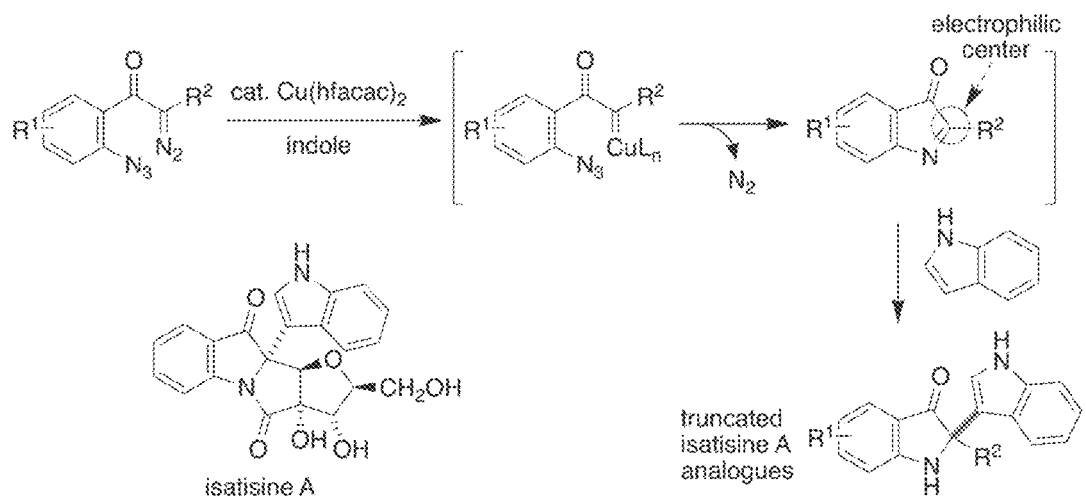
FIG. 1 depicts a one-step synthesis of Isatisine A analogs.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term 'optionally substituted' refers to being substituted or unsubstituted.

As used herein, the term "unsubstituted" refers to any open valence of an atom being occupied by hydrogen. Also, if an occupant of an open valence position on an atom is not specified then it is hydrogen.

As used herein, the term "substituted" refers to having one or more substituents or substituent moieties whose presence either facilitates or improves a desired reaction/property, or does not impede a desired reaction/property. A "substituent" is an atom or group of bonded atoms that can be considered to have replaced one or more hydrogen atoms attached to a parent molecular entity; and, whose presence either facilitates or improves desired reactions, properties, and/or functions of an invention, or does not impede desired reactions, properties, and/or functions of an invention. Examples of substituents include alkyl, alkenyl, alkynyl, aryl, polycyclic aryl, benzyl, polycyclic benzyl, fused aromatic rings, aryl-halide, heteroaryl, polycyclic heteroaryl, fused heteroaromatic rings, cycloalkyl (non-aromatic ring), halo, alkoxyl, perfluoronated alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, Si(alkyl)$_3$, Si(alkoxy)$_3$, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents provided above, such as alkyl, alkenyl, alkynyl, aryl, aryl-halide, heteroaryl, cycloalkyl (non-aromatic ring).

As used herein, "alkyl" refers to a linear or branched saturated hydrocarbon moiety that consists solely of single-bonded carbon and hydrogen atoms, which can be unsubstituted or substituted with one or more substituents. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl, and 1-octyl.

As used herein, "alkenyl" refers to a linear or branched hydrocarbon moiety that comprises at least one carbon to carbon double bond, which can be unsubstituted or substituted with one or more substituents. "Alkynyl" refers to a linear or branched hydrocarbon moiety that comprises at least one carbon to carbon triple bond, which can be unsubstituted or substituted with one or more substituents.

The term "carbocycle" as used herein refers to a non-aromatic, saturated or partially saturated monocyclic or polycyclic hydrocarbon ring moiety containing at least 3 carbon atoms. Examples of $C_3$-$C_n$ carbocycles include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "aryl" and/or "aromatic ring" refers to an aromatic (unsaturated cyclic) hydrocarbon moiety having 6 to 100 atoms, or 6 to 50 atoms, or 6 to 25 atoms, or 6 to 15 atoms, which can be unsubstituted or substituted with one or more substituents. The aromatic hydrocarbon moiety may be derived from benzene or a benzene derivative; may be monocyclic or polycyclic, where polycyclic may include a fused ring system. Examples include, but are not limited to, phenyl, naphthyl, xylene, phenyl ethane, substituted phenyl, substituted naphthyl, substituted xylene, substituted 4-ethylphenyl, benzyl, etc.

As used herein, "cycle" refers to an aromatic or nonaromatic monocyclic, polycyclic, or fused ring hydrocarbon moiety, which can be substituted or unsubstituted. Included within the term "cycle" are carbocycles and aryls, as defined above.

As used herein, "heteroaryl" or "heteroaromatic" refers to an aryl (including fused aryl rings) that includes heteroatoms selected from oxygen, nitrogen, sulfur, and phosphorus. A "heteroatom" refers to an atom that is not carbon or hydrogen, such as nitrogen, oxygen, sulfur, or phosphorus. Heteroaryl or heteroaromatic groups include, for example, furanyl, thiophenyl, pyrrolyl, imidazoyl, benzamidazoyl, 1,2- or 1,3-oxazolyl, 1,2- or 1,3-diazolyl, 1,2,3- or 1,2,4-triazolyl, and the like.

As used herein, a "heterocycle" is an aromatic or non-aromatic monocyclic, polycyclic, or fused ring moiety of carbon atoms and at least one heteroatom, or 1 to 4 heteroatoms, or 1 to 10 heteroatoms. A "heteroatom" refers to an atom that is not carbon or hydrogen, such as nitrogen, oxygen, sulfur, or phosphorus. Included within the term "heterocycle" is "heteroaryl", which refers to an aromatic (unsaturated cyclic) moiety of carbon atoms and at least one heteroatom, or 1 to 4 heteroatoms, or 1 to 10 heteroatoms, having a total of 6 to 100 atoms, or 6 to 50 atoms, or 6 to 25 atoms, or 6 to 15 atoms, which can be unsubstituted or substituted with one or more substituents. Also included within this term are monocyclic and bicyclic rings that include one or more double and/or triple bonds within the ring. Examples of 3- to 9-membered heterocycles include, but are not limited to, furanyl, thiophenyl, pyrrolyl, imidazoyl, benzamidazoyl, 1,2- or 1,3-oxazolyl, 1,2- or 1,3-diazolyl, 1,2,3- or 1,2,4-triazolyl, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, "halo" refers to F, Cl, Br, I.

The term "subject", as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

The term "treatment", "treat", or "treating" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment.

The term "amelioration" or "ameliorates" as used herein refers to a decrease, reduction or elimination of a condition, disease, disorder, or phenotype, including an abnormality or symptom.

The term "functional derivative" as used herein refers to a molecule that retains a biological activity (either function or structural) that is substantially similar to that of the original compound. A functional derivative or equivalent may be a natural derivative or is prepared synthetically.

Also encompassed is prodrug or "physiologically functional derivative". The term "physiologically functional derivative" as used herein refers to compounds which are not pharmaceutically active themselves but which are transformed into their pharmaceutically active form in vivo, i.e. in the subject to which the compound is administered. The term "prodrug" as used herein, refers to a derivative of a substance that, following administration, is metabolized in vivo, e.g. by hydrolysis or by processing through an enzyme, into an active metabolite.

In some cases, a compound of the present disclosure inhibits enzymatic activity of an RNA polymerase (e.g., an RNA-dependent RNA polymerase) encoded by an RNA virus. For example, in some cases, a compound of the present disclosure inhibits enzymatic activity of an RNA polymerase by at least 10%, at least 20%, at least 30%, at least 40%, at least 50%, at least 60%, at least 70%, at least 80%, at least 90%, at least 95%, at least 98%, at least 99%, or 100%, compared to the enzymatic activity of the RNA polymerase in the absence of the compound.

An RNA polymerase (e.g., an RNA-dependent RNA polymerase) that can be inhibited by a compound of the present disclosure can be an RNA polymerase encoded by any of the following RNA viruses: a Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, a Deltavirus, Coronavirus, SARS coronavirus, MERS coronavirus, Poliovirus, Rhinovirus, Hepatitis A virus, Hepatitis B virus, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza virus (e.g., swine influenza virus; avian influenza virus; H1N1, H3N2, H7N9, H5N1, etc.), porcine respiratory and reproductive disease syndrome virus (PRRSV), Seneca valley virus, porcine epidemic diarrhea virus (PEDV), porcine delta coronavirus (PDCV), porcine circoviral associated diseases (PCVAD), and Hepatitis D virus. In some cases, the RNA polymerase that is inhibited by a compound of the present disclosure is encoded by Zika virus. In some cases, the RNA polymerase that is inhibited by a compound of the present disclosure is encoded by Ebola virus. In some cases, the RNA polymerase that is inhibited by a compound of the present disclosure is encoded by human respiratory syncytial virus (RSV). In some cases, the RNA polymerase that is inhibited by a compound of the present disclosure is encoded by bovine RSV.

RNA-dependent RNA polymerases (RdRP) are known in the art. In some cases, an RNA polymerase (e.g., an RNA-dependent RNA polymerase) that is inhibited by a compound of the present disclosure comprises an amino acid sequence having at least 20%, at least 30%, at least 40%, at least 50%, at least 60%, at least 70%, at least 80%, at least 90%, at least 95%, at least 98%, at least 99%, or 100%, with the amino acid sequence depicted in FIG. 57A-57B. In some cases, the RNA-dependent RNA polymerase comprises an Asp at a position corresponding to 686 of the amino acid sequence depicted in FIG. 57A-57B.

The present disclosure provides methods of treating a viral infection, the methods comprising administering to an individual having the viral infection a therapeutically effective amount of a compound of the present disclosure, or a composition comprising a compound of the present disclosure.

As used herein, the term "therapeutically effective amount" refers to an amount that is effective for preventing, ameliorating, or treating a disease or disorder (e.g., an infection disease, such as a viral disease).

In some cases, a therapeutically effective amount of a compound of the present disclosure is an amount that is effective to reduce the amount of virus in a tissue, organ, or fluid in an individual being treated. For example, in some cases, a therapeutically effective amount of a compound of the present disclosure is an amount that is effective to reduce the amount of virus in a tissue, organ, or fluid in an individual being treated by at least 10%, at least 20%, at least 30%, at least 40%, at least 50%, at least 60%, at least 70%, at least 80%, or more than 80%, compared to the amount of virus present in the tissue, organ, or fluid in the individual before treatment with the compound.

In an aspect, there is described a compound, compositions, methods, and uses, for the treatment of a subject having, or suspected of having, an infectious disease.

In an example the infectious disease is caused by a virus.

Viral infections that can be treated with a method of the present disclosure include infections caused by any of the following: a Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, a Deltavirus, Coronavirus, SARS, Poliovirus, Rhinovirus, Hepatitis A virus, Hepatitis B virus, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, bovine respiratory syncytial virus, Rabies virus, Lassa virus, Hantavirus, Crimean-Congo hemorrhagic fever virus, Influenza virus (e.g., swine influenza virus; avian influenza virus; etc.), porcine respiratory and reproductive disease syndrome virus (PRRSV), Seneca valley virus, porcine epidemic diarrhea virus (PEDV), porcine delta coronavirus (PDCV), porcine circoviral associated diseases (PCVAD), and Hepatitis D virus. In some cases, the viral infection is caused by a positive-strand RNA virus. In some cases, the viral infection is caused by a negative-strand RNA virus.

In an example, the virus is from the family Flaviviridae. In another example, the virus I from the genera *Hepacivirus, Flavivirus, Pegivirus,* or *Pestivirus*

Non-limiting examples of *flavivirus* include yellow fever virus (YFV), Japanese encephalitis virus (JEV), Tick-borne encephalitis virus (TBEV), Dengue virus (DENV), West Nile virus (WNV), Zika virus (ZIKAV), or any combination thereof.

In a specific example, the viral infection is Zika virus.

In an example, the virus is from the family of Paramyxoviridae. In another example, the virus is from the genera *Paramyxovirus, Pneumovirus,* or *Morbillivirus*

Non-limiting example of paramyxovirus include parainfluenza virus and mumpus virus.

Non-limiting examples of *Pneumovirus* include respiratory syncytial virus (RSV).

Non-limiting examples of *Morbillivirus* include measles virus.

In a specific example, the viral infection is respiratory syncytial virus (RSV). As one example, in some cases, the viral infection is human RSV. As another example, in some cases, the viral infection is bovine RSV.

In another aspect, there is described a compound of formula (I)

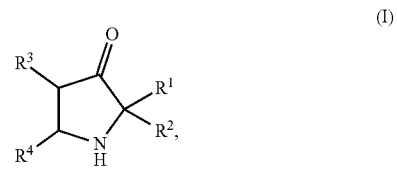

or
a stereoisomer, a racemate, a tautomer, a pharmaceutically acceptable salt, a solvate, or a functional derivative thereof, wherein:

$R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;

$R^2$ is independently aryl, benzyl, or heterocycle, each of which is optionally substituted; and $R^3$ and $R^4$ are each independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or $R^3$ and $R^4$, together with the atoms to which they are attached, are connected to form a cycle or heterocycle, each of which is optionally substituted.

In an example, there is described a compound having the formula (II)

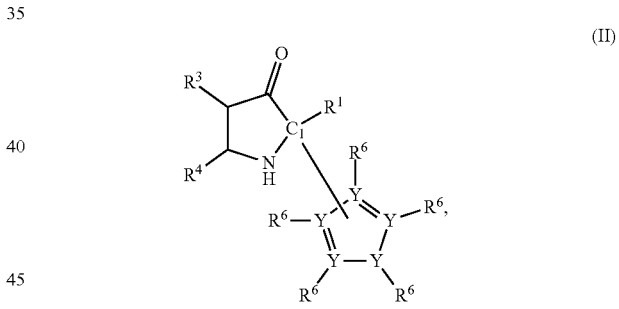

or
a stereoisomer, a racemate, a tautomer, a pharmaceutically acceptable salt, a solvate, or a functional derivative thereof, wherein:

Y is independently C or a heteroatom;

$R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;

$R^3$ and $R^4$ are each independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or $R^3$ and $R^4$, together with the atoms to which they are attached, are connected to form a cycle or heterocycle, each of which is optionally substituted; and $R^6$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^6$, together with the atoms to which they are attached, are connected to form a cycle or heterocycle, each of which is optionally substituted; and wherein one Y is bonded to C1 and the corresponding $R^6$ is absent.

In another example, there is described a compound having the formula (III)

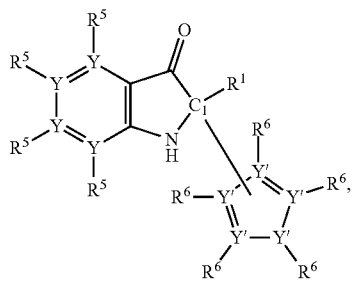

(III)

or a stereoisomer, a racemate, a tautomer, a pharmaceutically acceptable salt, a solvate, or a functional derivative thereof, wherein:

Y and Y' are each independently C or a heteroatom;

$R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;

$R^5$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted; and $R^6$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^6$, together with the atoms to which they are attached, are connected to form a cycle or heterocycle, each of which is optionally substituted; and wherein one Y' is bonded to $C_1$ and the corresponding $R^6$ is absent.

In another example, there is described a compound having the formula (IV)

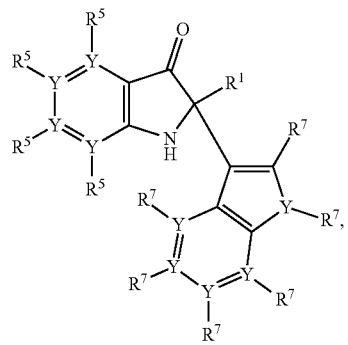

(IV)

or a stereoisomer, a racemate, a tautomer, a pharmaceutically acceptable salt, a solvate, or a functional derivative thereof, wherein:

Y is independently C or a heteroatom;

$R^1$ is independently H, $C_1$-$C_{10}$ alkyl, $C_{10}$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted;

$R^5$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted; and $R^7$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^7$, together with the atoms to which they are attached, are connected to form a cycle or heterocycle, each of which is optionally substituted.

In another example, there is described a compound having the formula (V)

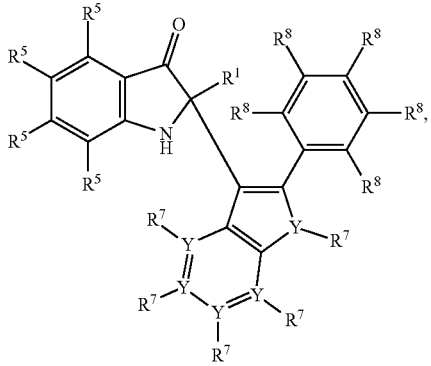

(V)

or
a stereoisomer, a racemate, a tautomer, a pharmaceutically acceptable salt, a solvate, or a functional derivative thereof, wherein:

Y is independently C or a heteroatom;

$R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted;

$R^5$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted;

$R^7$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted; or two of $R^7$, together with the atoms to which they are attached, are connected to form a cycle or heterocycle, each of which is optionally substituted; and, $R^8$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^8$, together with the atoms to which they are attached, are connected to form a cycle or heterocycle, each of which is optionally substituted.

In another example, there is described a compound having the formula (VI)

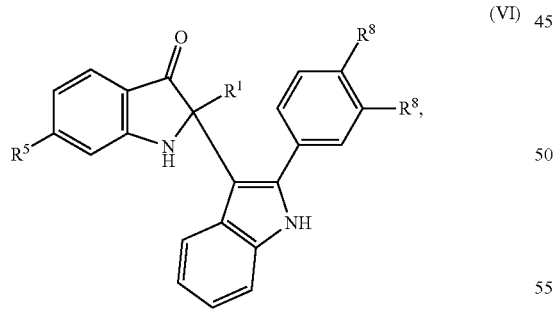

(VI)

or
a stereoisomer, a racemate, a tautomer, a pharmaceutically acceptable salt, a solvate, or a functional derivative thereof, wherein:

$R^1$ is an ester;

$R^5$ is a halo; and, $R^8$ is independently H, $C_1$-$C_{10}$ alkoxy, or halo, each of which is optionally substituted.

In some examples, the compounds as described herein have the structure

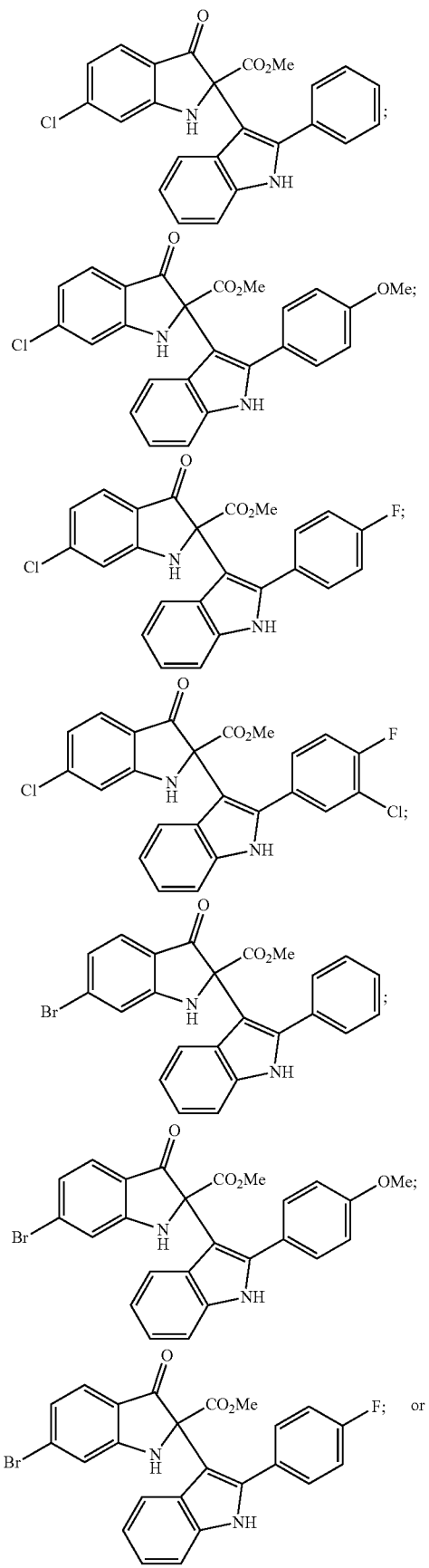

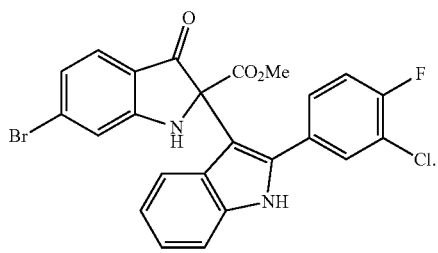
In some examples, the compounds as described herein have the structure
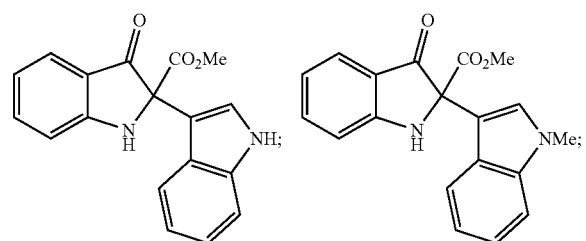
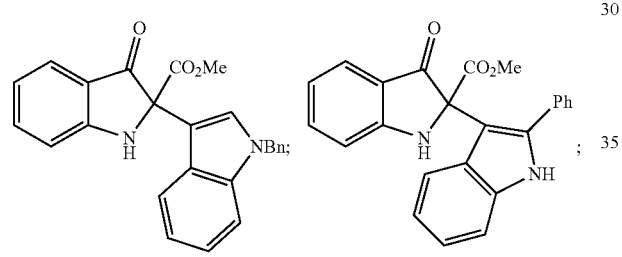
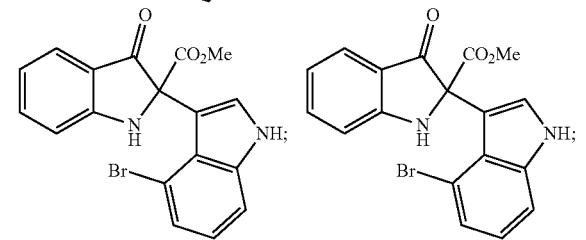
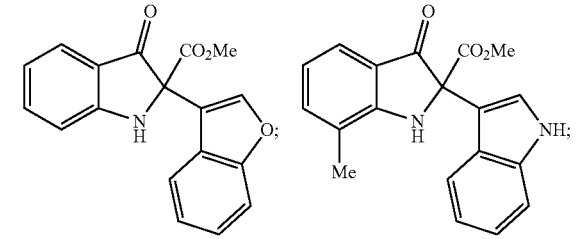
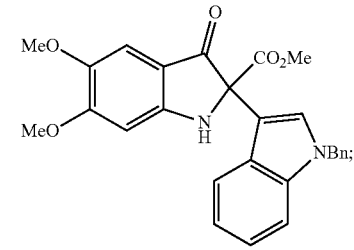
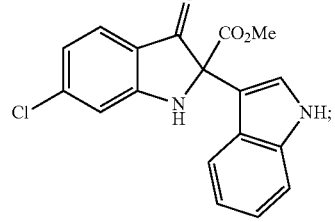
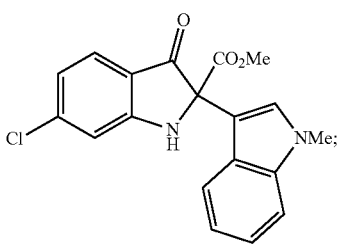
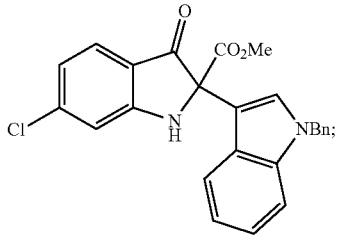
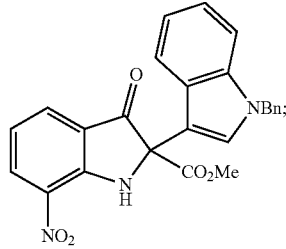
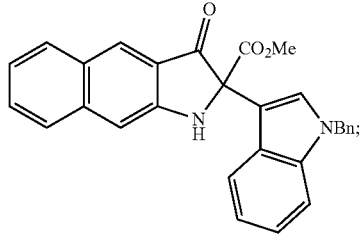
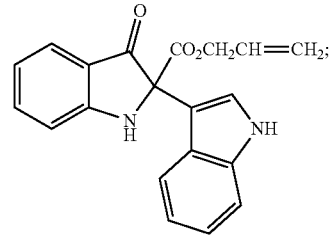
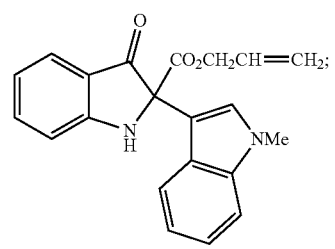

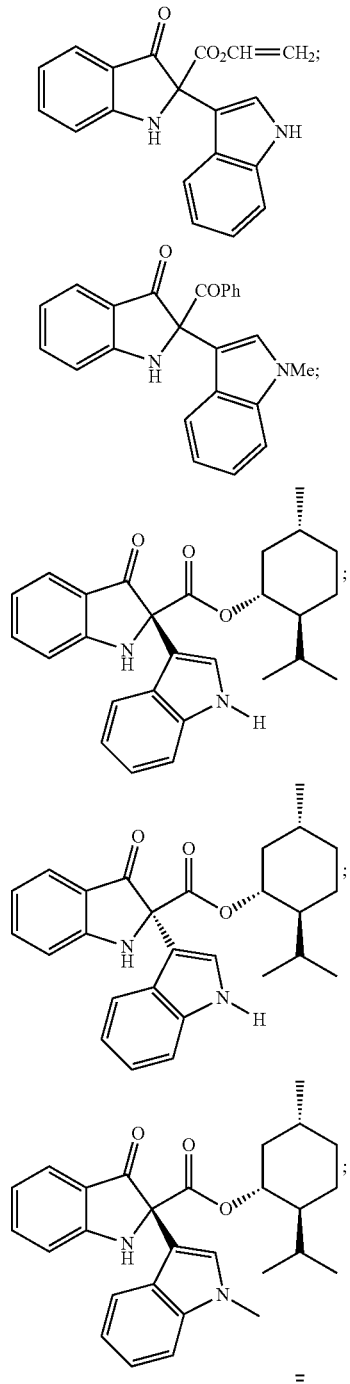
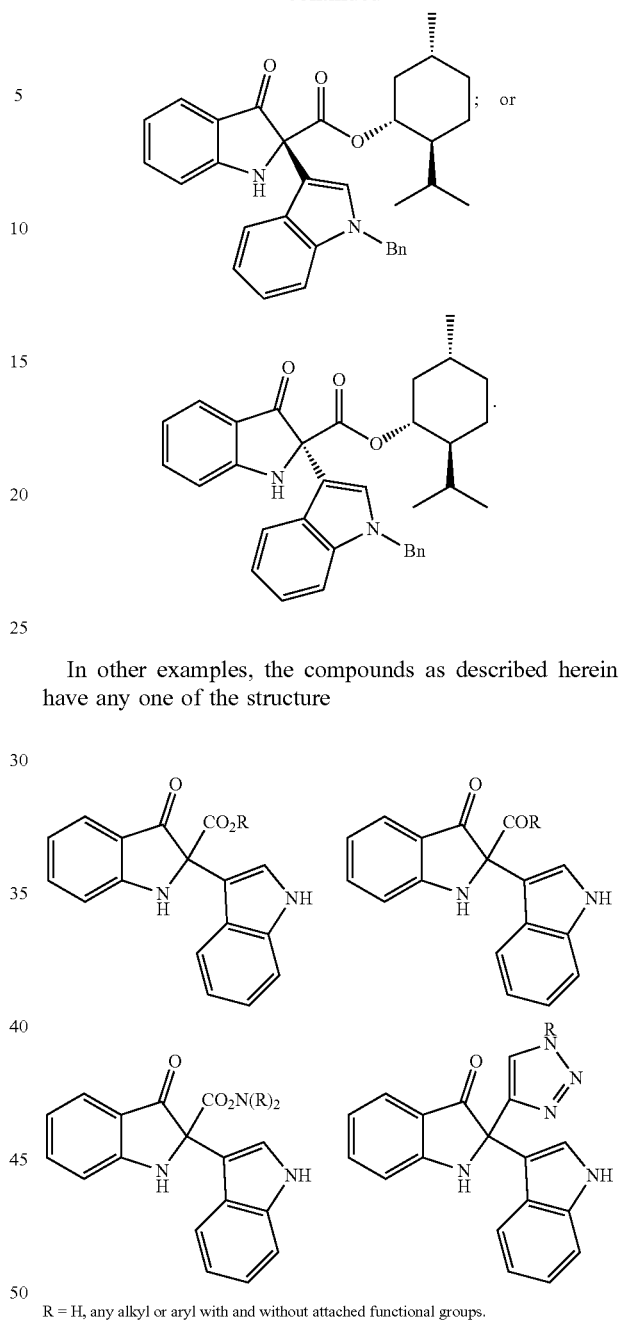
In other examples, the compounds as described herein have any one of the structure
R = H, any alkyl or aryl with and without attached functional groups.
In other examples, the compounds as described herein have any one of the structure
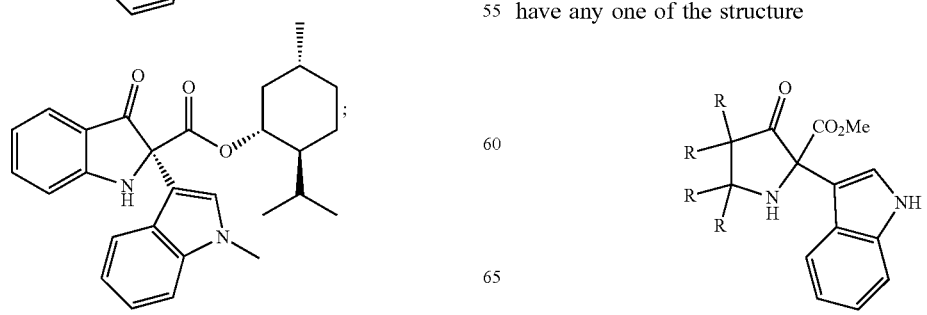

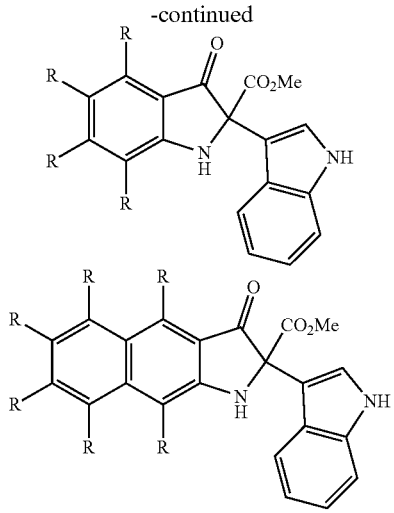

R = H, F, Cl, Br, I, any alkyl group, any aryl groups, any heteroaryl group, alcohol, thiol, amine alkoxy, trifluoromethoxy, ester, amide, carboxylic acid, nitro, cyano, alkene, alkyne.

In other examples, the compounds as described herein have any one of the structure

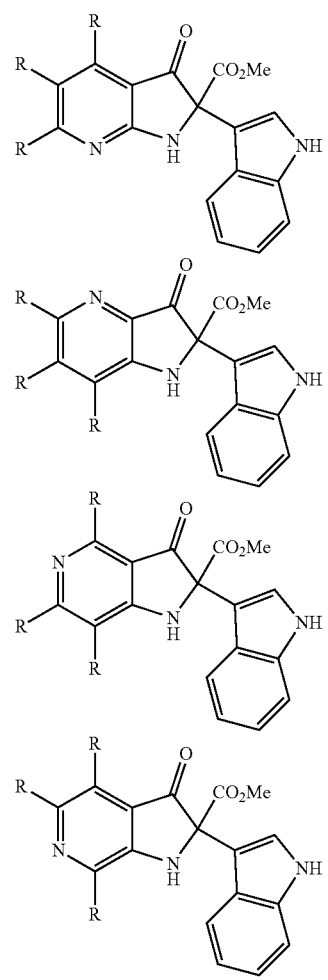

R = H, F, Cl, Br, I, any alkyl group, any aryl groups, any heteroaryl group, alcohol, thiol, amine alkoxy, trifluoromethoxy, ester, amide, carboxylic acid, nitro, cyano, alkene, alkyne.

In other examples, the compounds as described herein have any one of the structure

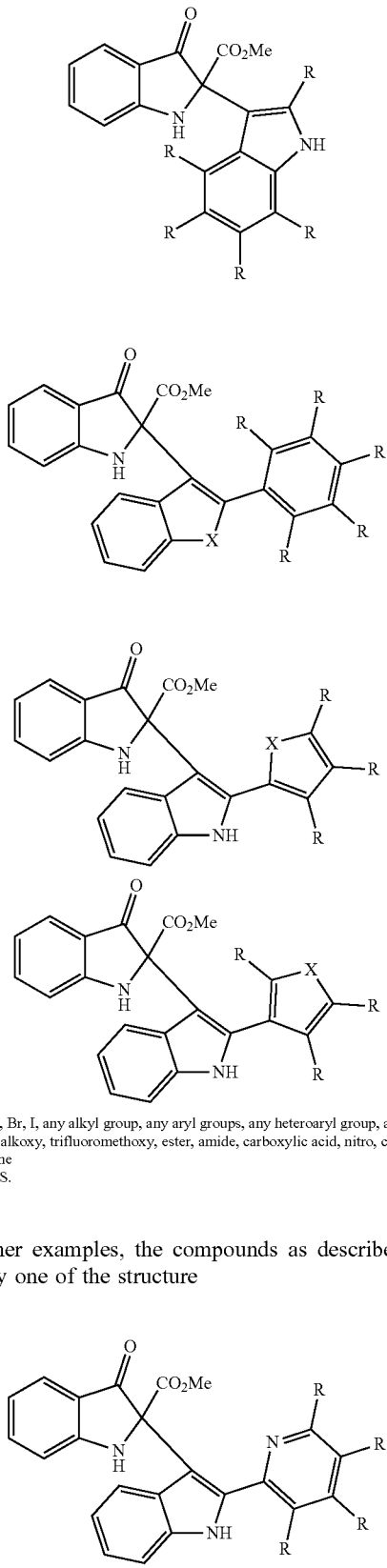

R = H, F, Cl, Br, I, any alkyl group, any aryl groups, any heteroaryl group, alcohol, thiol, amine alkoxy, trifluoromethoxy, ester, amide, carboxylic acid, nitro, cyano, alkene, alkyne
X = NH, O, S.

In other examples, the compounds as described herein have any one of the structure

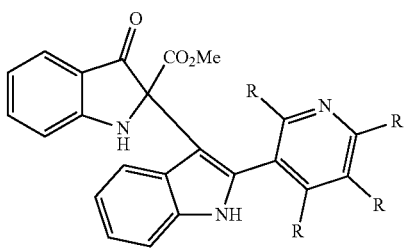

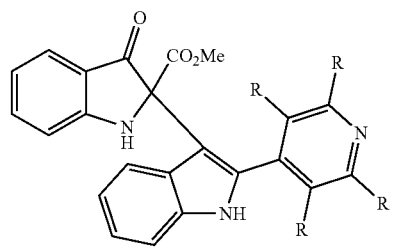

R = H, F, Cl, Br, I, any alkyl group, any aryl groups, any heteroaryl group, alcohol, thiol, amine alkoxy, trifluoromethoxy, ester, amide, carboxylic acid, nitro, alkene, alkyne.

In other examples, the compounds as described herein have any one of the structure

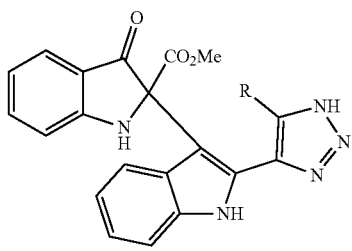

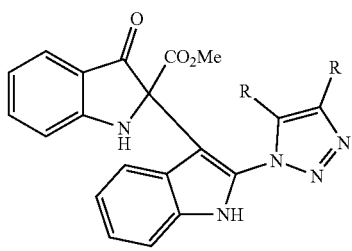

R = H, F, Cl, Br, I, any alkyl group, any aryl groups, any heteroaryl group, alcohol, thiol, amine alkoxy, trifluoromethoxy, ester, amide, carboxylic acid, nitro, alkene, alkyne.

In other examples, the compounds as described herein have any one of the structure

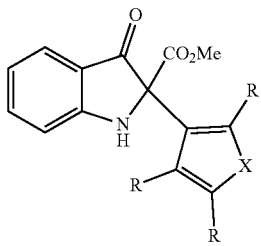

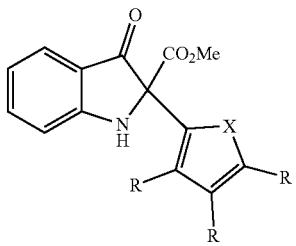

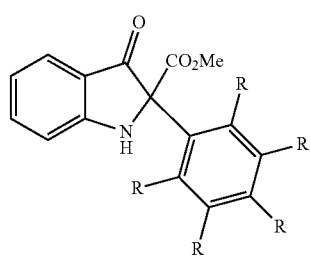

R = H, F, Cl, Br, I, any alkyl group, any aryl groups, any heteroaryl group, alcohol, thiol, amine alkoxy, trifluoromethoxy, ester, amide, carboxylic acid, nitro, cyano, alkene, alkyne
X = NH, O, S.

In other examples, the compounds as described herein have any one of the structure

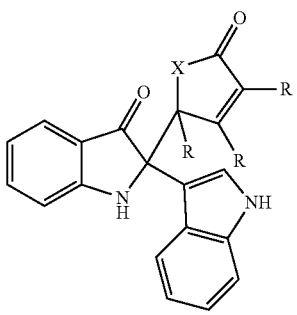

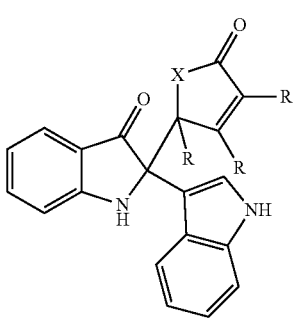

R = H, F, Cl, Br, I, any alkyl group, any aryl groups, any heteroaryl group, alcohol, thiol, amine alkoxy, trifluoromethoxy, ester, amide, carboxylic acid, nitro, cyano, alkene
X = NH, O, S.

In other examples, the compounds as described herein have any one of the structure

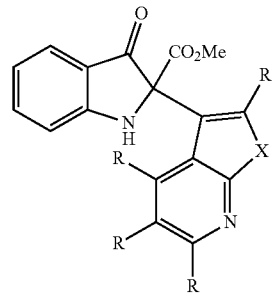 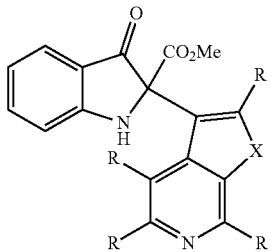

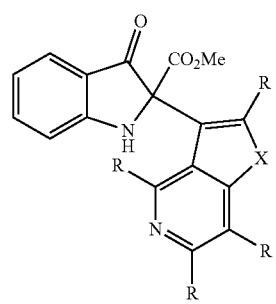 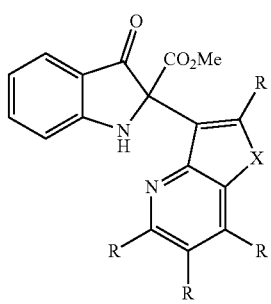

R = H, F, Cl, Br, I, any alkyl group, any aryl groups, any heteroaryl group, alcohol, thiol, amine alkoxy, trifluoromethoxy, ester, amide, carboxylic acid, nitro, cyano, alkene, alkyne
X = NH, O, S.

In other examples, the compounds as described herein have any one of the structure

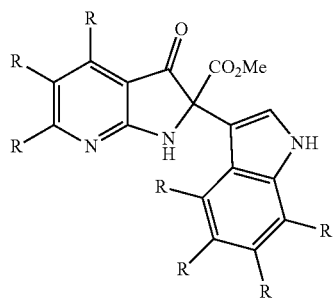

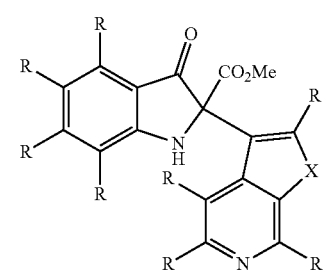

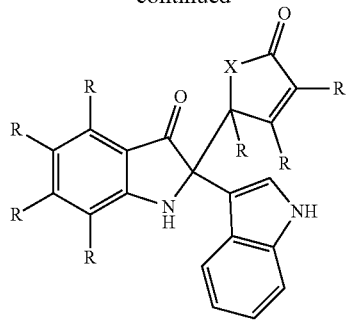

R = H, F, Cl, Br, I, any alkyl group, any aryl groups, any heteroaryl group, alcohol, thiol, amine alkoxy, trifluoromethoxy, ester, amide, carboxylic acid, nitro, cyano, alkene, alkyne
X = NH, O, S.

In another example, the absolute stereochemistry of the quaternary stereocentre (chiral carbon) of the compounds as described herein may be R, S, or a mixture of R and S.

In another example, when the compounds as described herein comprise two or more stereocentres (chiral carbons), the absolute stereochemistry may be any permutation of R and S, or a mixture of any permutation.

In another aspect, there is described a method of synthesizing the compounds as described herein, the method comprising:
a) reacting an organoazide-dizaoketone compound with a transition metal catalyst;
b) forming a metallocarbene from the reaction of the organoazide-dizaoketone compound with a transition metal catalyst;
c) generating an electrophilic C-acylimine from the metallocarbene; and,
d) reacting the electrophilic C-acylimine with a nucleophilic compound.

In an example, of the method as described herein step d) further comprises reacting the electrophilic C-acylimine with a nucleophilic compound in the presence of a Bronsted acid catalyst.

In another example of the method as described herein, the transition metal catalyst is a Cu catalyst. In another example, the transition metal catalyst is Cu(hfacac)$_2$, Cu(OTf)$_2$, or CuOTf.Ph(CH$_3$).

In another example of the method as described herein, the nucleophilic compound is a heteroatom-containing compound. In another example the heteroatom-containing compound is a heterocycle or a cycle substituted with a heteroatom-containing moiety. In another example, the heterocycle is pyrrole, furan, thiophene, pyridine, indole, benzofuran, benzothiphene, imidazole, or derivatives thereof, each of which is optionally substituted.

In some examples, the compounds as described herein are an enantiomer, a racemate, a tautomer, or a pharmaceutically acceptable salt, or a solvate, or a functional derivative thereof.

In some examples, there is described a composition comprising a compound as described herein, and a pharmaceutically acceptable carrier, diluent, or vehicle.

A compound or composition may be administered alone or in combination with other treatments, either simultaneously or sequentially, dependent upon the condition to be treated.

In treating a subject, a therapeutically effective amount may be administered to the subject.

Formulations may conveniently be presented in unit dosage form and may be prepared by any methods known in the art. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Compounds and/or compositions comprising compounds disclosed herein may be used in the methods described herein in combination with standard treatment regimes, as would be known to the skilled worker.

Methods of the invention are conveniently practiced by providing the compounds and/or compositions used in such method in the form of a kit. Such kit preferably contains the composition. Such a kit preferably contains instructions for the use thereof.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-41 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A compound of formula (I)

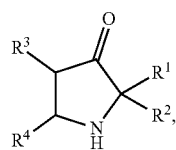

(I)

or
a stereoisomer, a racemate, a tautomer, a pharmaceutically acceptable salt, a solvate, or a functional derivative thereof,
wherein:
$R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, $C_1$-$C_{10}$ alkoxy, $C_{10}$-$C_{20}$ alkoxy, alcohol, ether, ketone, carboxylic acid, ester, thiol, thioether, amine, amide, carbamate, nitro, cyano, or halo, each of which is optionally substituted;

$R^2$ is independently aryl, benzyl, or heterocycle, each of which is optionally substituted; and $R^3$ and $R^4$ are each independently H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or $R^3$ and $R^4$, together with the atoms to which they are attached, are connected to form a cycle or heterocycle, each of which is optionally substituted.

Aspect 2. The compound of aspect 1, having the formula (II)

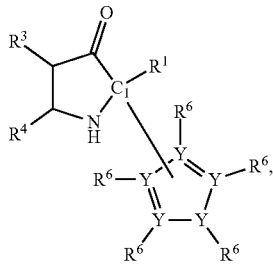

(II)

or
a stereoisomer, a racemate, a tautomer, a pharmaceutically acceptable salt, a solvate, or a functional derivative thereof,
wherein:
Y is independently C or a heteroatom;

$R^1$ is independently H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted;

$R^3$ and $R^4$ are each independently H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or $R^3$ and $R^4$, together with the atoms to which they are attached, are connected to form a cycle or heterocycle, each of which is optionally substituted; and $R^6$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^6$, together with the atoms to which they are attached, are connected to form a cycle or heterocycle, each of which is optionally substituted; and wherein one Y is bonded to $C_1$ and the corresponding $R^6$ is absent.

Aspect 3. The compound of aspect 1 or 2, having the formula (III)

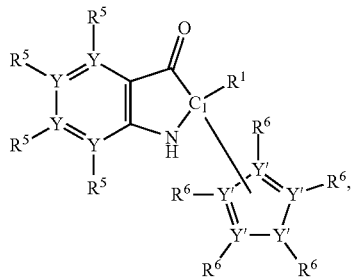

(III)

or
a stereoisomer, a racemate, a tautomer, a pharmaceutically acceptable salt, a solvate, or a functional derivative thereof, wherein:

Y and Y' are each independently C or a heteroatom;

$R^1$ is independently H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted;

$R^5$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted; and $R^6$ is independently H, $C_1$-$C_{10}$ alkyl, $C_{10}$-$C_{20}$ alkyl, $C_2$-$C_{10}$ alkenyl, $C_2$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^6$, together with the atoms to which they are attached, are connected to form a cycle or heterocycle, each of which is optionally substituted; and wherein one Y' is bonded to C1 and the corresponding $R^6$ is absent.

Aspect 4. The compound of any one of aspects 1 to 3, having the formula (IV)

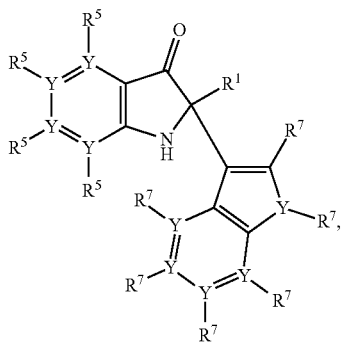

(IV)

or
a stereoisomer, a racemate, a tautomer, a pharmaceutically acceptable salt, a solvate, or a functional derivative thereof, wherein:

Y is independently C or a heteroatom;

$R^1$ is independently H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted;

$R^5$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted; and $R^7$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^7$, together with the atoms to which they are attached, are connected to form a cycle or heterocycle, each of which is optionally substituted.

Aspect 5. The compound of any one of aspects 1 to 4, having the formula (V)

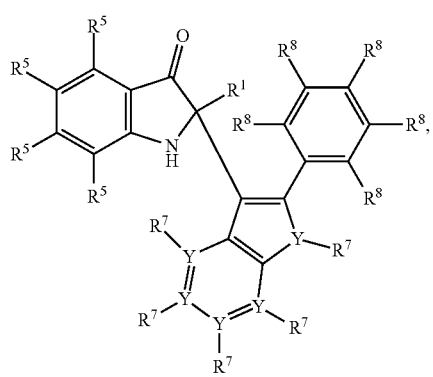

(V)

or
a stereoisomer, a racemate, a tautomer, a pharmaceutically acceptable salt, a solvate, or a functional derivative thereof, wherein:

Y is independently C or a heteroatom;

$R^1$ is independently H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted;

$R^5$ is independently absent, H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^5$, together with the atoms to which they are attached, are connected to form a cycle or heterocycle, each of which is optionally substituted;

$R^7$ is independently absent, H, $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_2$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^7$, together with the atoms to which they are attached, are connected to form a cycle or heterocycle, each of which is optionally substituted; and, $R^8$ is independently H, $C_1$-$C_{10}$ alkyl, $C_2$-$C_{20}$ alkyl, $C_2$-$C_{10}$ alkenyl, $C_2$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_2$-$C_{20}$ alkoxy, alcohol, ether, ketone, carboxylic acid, ester, thiol, thioether, amine, amide, carbamate, nitro, cyano, or halo, each of which is optionally substituted; or two of $R^8$, together with the atoms to which they are attached, are connected to form a cycle or heterocycle, each of which is optionally substituted.

Aspect 6. The compound of any one of aspects 1 to 5, having the formula (VI)

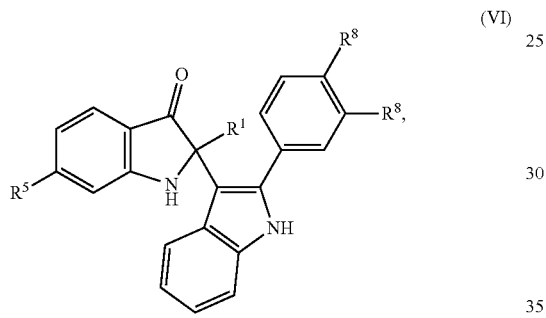

(VI)

or a stereoisomer, a racemate, a tautomer, a pharmaceutically acceptable salt, a solvate, or a functional derivative thereof, wherein:

$R^1$ is an ester;

$R^5$ is a halo; and, $R^8$ is independently H, $C_1$-$C_{10}$ alkoxy, or halo, each of which is optionally substituted.

Aspect 7. The compound of any one of aspects 1 to 6, having the structure

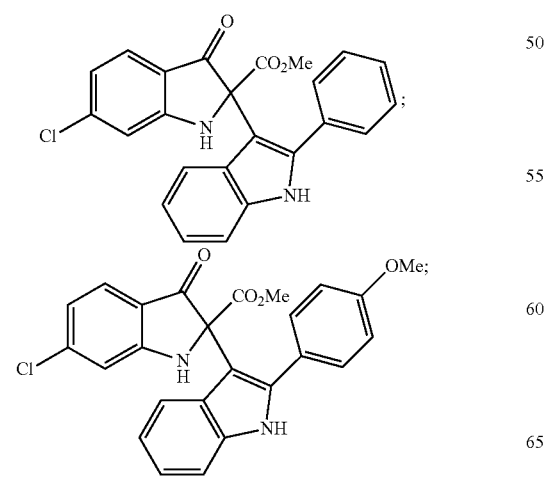

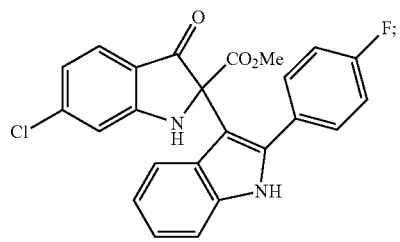

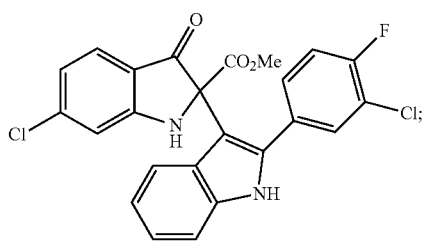

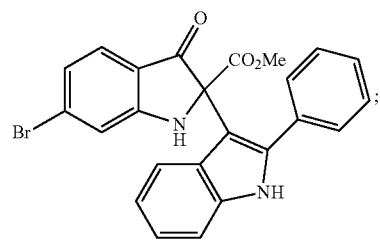

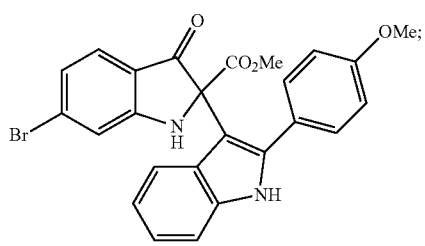

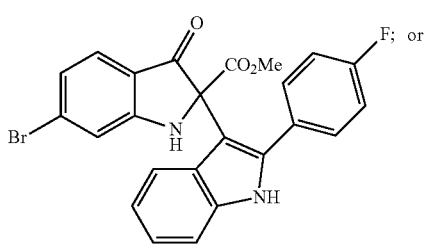

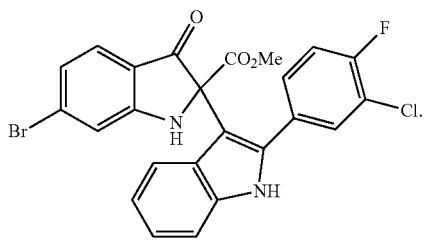
Aspect 8. The compound of any one of aspects 1 to 4, having the structure
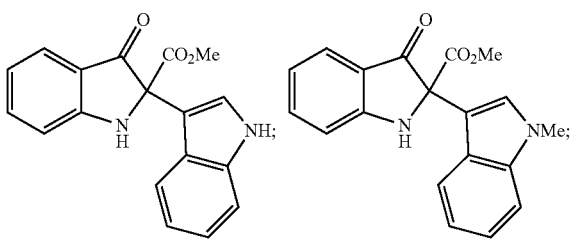
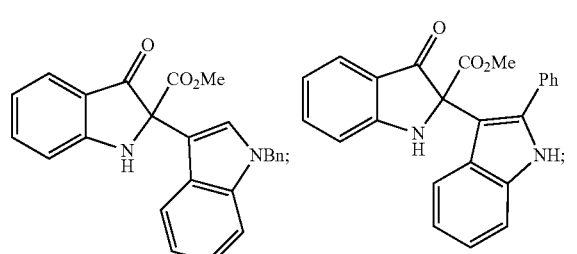
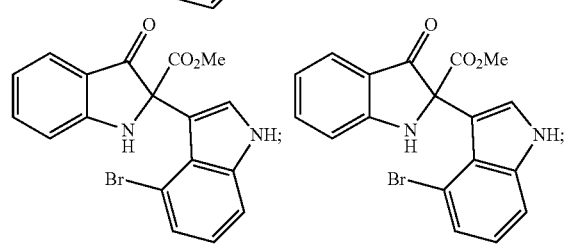
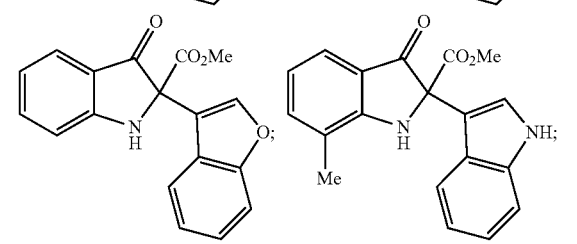
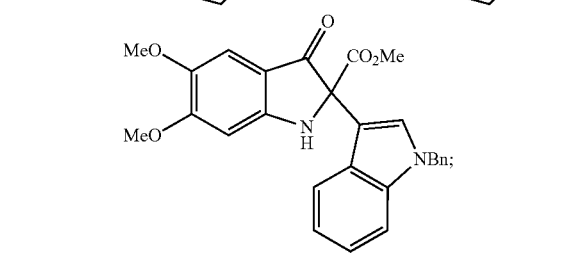
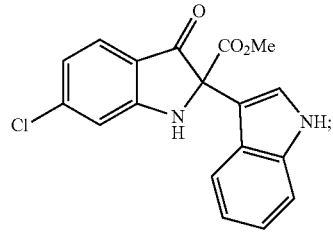
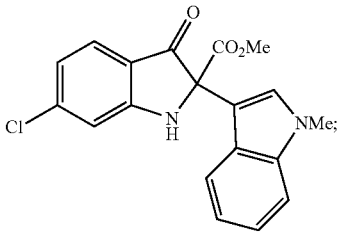
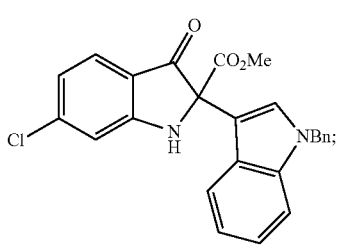
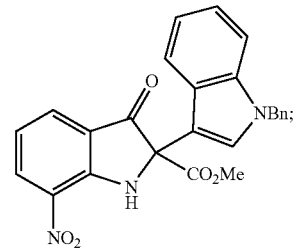
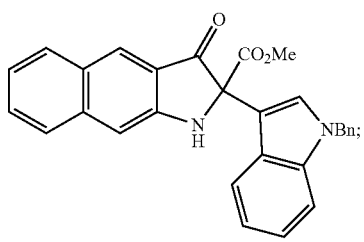
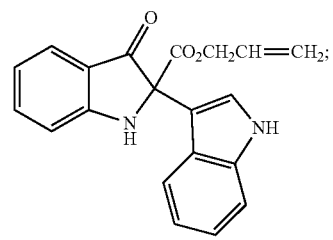
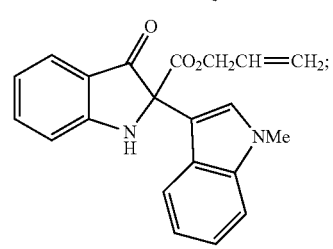

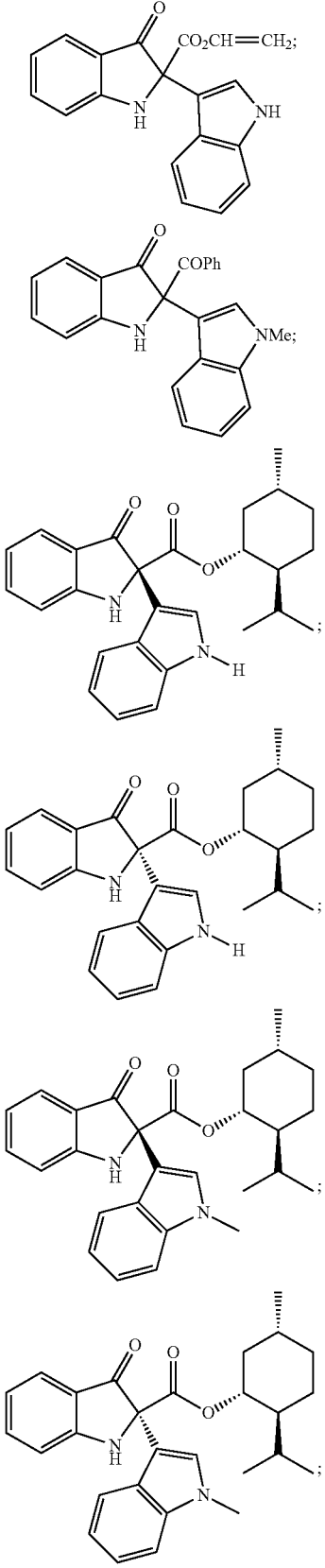

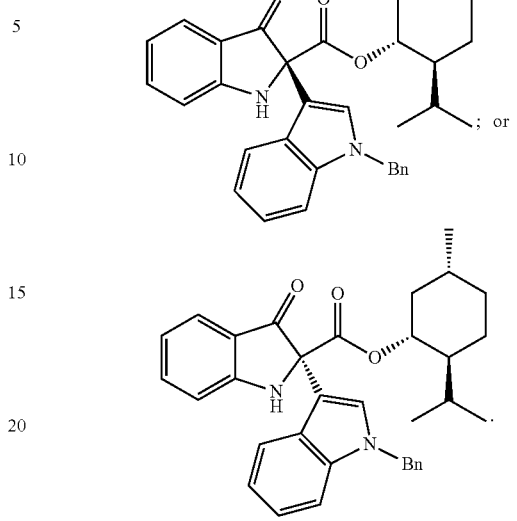

Aspect 9. A method of synthesizing a compound of any one of aspects 1 to 8, comprising:
 a) reacting an organoazide-dizaoketone compound with a transition metal catalyst
 b) forming a metallocarbene from the reaction of the organoazide-dizaoketone compound with a transition metal catalyst;
 c) generating an electrophilic C-acylimine from the metallocarbene; and
 d) reacting the electrophilic C-acylimine with a nucleophilic compound.

Aspect 10. The method of aspect 9, wherein step d) further comprises reacting the electrophilic C-acylimine with a nucleophilic compound in the presence of a Bronsted acid catalyst.

Aspect 11. The method of aspect 9 or 10, wherein the transition metal catalyst is a Cu catalyst.

Aspect 12. The method of aspect 11, wherein the transition metal catalyst is Cu(hfacac)$_2$, Cu(OTf)$_2$, or CuOTf.Ph(CH$_3$).

Aspect 13. The method of any one of aspects 9 to 12, wherein the nucleophilic compound is a heteroatom-containing compound.

Aspect 14. The method of aspect 13, wherein the heteroatom-containing compound is a heterocycle or a cycle substituted with a heteroatom-containing moiety.

Aspect 15. The method of aspect 14, wherein the heterocycle is pyrrole, furan, thiophene, pyridine, indole, benzofuran, benzothiphene, imidazole, or derivatives thereof, each of which is optionally substituted.

Aspect 16. A pharmaceutical composition comprising a compound of any one of aspects 1 to 8, or a compound syntheized by the method of any one of aspects 8 to 15, and a pharmaceutically acceptable carrier, diluent, or vehicle.

Aspect 17. A method of treating a subject having or suspected of having an infectious disease, comprising: administering a therapeutically effective amount of a compound of any one of aspects 1 to 8, or a compound syntheized by the method of any one of aspects 8 to 15, or a pharmaceutical composition of aspect 16.

Aspect 18. A method of treating a subject having or suspected of having an infectious disease, comprising:

administering a therapeutically effective amount of a compound of any one of aspects 1 to 8, or a compound syntheized by the method of any one of aspects 8 to 15, or a pharmaceutical composition of aspect 16, wherein said infectious disease is caused by a virus.

Aspect 19. The method of aspects 18, wherein said virus is a virus from the family Flaviviridae.

Aspect 20. The method of aspect 19, wherein the virus is from the genera *Hepacivirus, Flavivirus, Pegivirus*, or *Pestivirus*.

Aspect 21. The method of aspect 20, wherein said flavivirus is yellow fever virus (YFV), Japanese encephalitis virus (JEV), Tick-borne encephalitis virus (TBEV), Dengue virus (DENV), West Nile virus (WNV), Zika virus (ZIKAV), or any combination thereof.

Aspect 22. The method of aspect 18, wherein said virus is from the family Paramyxoviridae.

Aspect 23. The method of aspect 22, wherein said virus is from the genera *Paramyxovirus, Pneumovirus*, or *Morbillivirus*.

Aspect 24. The method of aspect 23, wherein *Paramyxovirus* is parainfluenza virus or mumpus virus.

Aspect 25. The method of aspect 23, wherein said *Pneumovirus* is respiratory syncytial virus (RSV).

Aspect 26. The method of aspect 23, wherein said *Morbillivirus* is measles virus.

Aspect 27. The method of any one of aspects 17 to 26, wherein said subject is a human, a domesticated animal, livestock, a laboratory animal, a non-human mammal, a non-human primate, a rodent, a bird, a reptile, an amphibian, or a fish.

Aspect 28. Use of a compound of any one of aspects 1 to 8, or a compound syntheized by the method of any one of aspects 8 to 15, or a pharmaceutical composition of aspect 16 for treating a subject having or suspected of having an infectious disease.

Aspect 29. Use of a compound of any one of aspects 1 to 8, or a compound syntheized by the method of any one of aspects 8 to 15, or a pharmaceutical composition of aspect 16 in the manufacture of a medicament for treating a subject having or suspected of having an infectious disease.

Aspect 30. Use of a compound of any one of aspects 1 to 8, or a compound syntheized by the method of any one of aspects 8 to 15, or a pharmaceutical composition of aspect 16 for treating a subject having or suspected of having an infectious disease, wherein said infectious disease is caused by a virus.

Aspect 31. Use of a compound of any one of aspects 1 to 8, or a compound syntheized by the method of any one of aspects 8 to 15, or a pharmaceutical composition of aspect 16 in the manufacture of a medicament for treating a subject having or suspect of having an infectious disease, wherein said infectious disease is caused by a virus.

Aspect 32. The use of aspect 30 or 31, wherein said virus is a virus from the family Flaviviridae.

Aspect 33. The use of aspect 32, wherein the virus is from the genera *Hepacivirus, Flavivirus, Pegivirus*, or *Pestivirus*.

Aspect 34. The use of aspect 33, wherein said flavivirus is yellow fever virus (YFV), Japanese encephalitis virus (JEV), Tick-borne encephalitis virus (TBEV), Dengue virus (DENV), West Nile virus (WNV), Zika virus (ZIKAV), or any combination thereof.

Aspect 35. The use of aspect 30 or 31, wherein said virus is a virus from the family Paramyxoviridae.

Aspect 36. The use of aspect 35, wherein said virus is from the genera *Paramyxovirus, Pneumovirus*, or *Morbillivirus*.

Aspect 37. The use of aspect 36, wherein *Paramyxovirus* is parainfluenza virus or mumpus virus.

Aspect 38. The use of aspect 36, wherein said Pneumovirus is respiratory syncytial virus (RSV).

Aspect 39. The use of aspect 36, wherein said Morbillivirus is measles virus.

Aspect 40. The use of any one of aspects 28 to 39, wherein said subject is a human, a domesticated animal, livestock, a laboratory animal, a non-human mammal, a non-human primate, a rodent, a bird, a reptile, an amphibian, or a fish.

Aspect 41. A method of inhibiting an RNA-dependent RNA polymerase (RdRP) of an RNA virus, the method comprising contacting the RdRP with a compound according to any one of aspects 1-8.

EXAMPLES

To gain a better understanding of the invention described herein, the following examples are set forth. It should be understood that these examples are for illustrative purposes only. Therefore, they should not limit the scope of this invention in anyway.

Example 1

Dual Catalytic Synthesis of Antiviral Compounds Based on Metal-Locarbene-Azide Cascade Chemistry Aryl azides trapped ortho metallocarbene intermediates to generate indolenones possessing a reactive C-acylimine moiety, which reacted with added indole nucleophiles to afford a 2-(3-indolyl)indolin-3-one scaffold found in antiviral natural product isatisine A. This overall process occurred through a dual catalytic sequence at room temperature. Redox activation of a $Cu(OTf)_2$ precatalyst by indole resulted in catalytically competent Cu(I) required for azide-metallocarbene coupling. A Bronsted acid that formed from $Cu(OTf)_2$ reduction was responsible for catalysis of the C—C bond-forming indole addition step. This modular method allowed for rapid assembly of bis(indole) libraries, several of which demonstrated anti-infective activity against respiratory syncytial virus and Zika virus.

Reaction sequences proceeding through high-energy reactive intermediates, generated catalytically, can offer an approach for rapid construction of structurally complex products. Metallocarbenes generated from diazoketone precursors can be intercepted by a variety of nucleophilic heteroatom-containing functionalities to afford ylide intermediates that then undergo rearrangement processes. Use of an organoazide functionality to trap metallocarbene intermediates presents an alternative approach for strategic assembly of substituted heterocyclics. This process is catalyzed by inexpensive copper catalysts, with two equivalents of nitrogen gas being the only by-products generated, and C-acylimines formed from this coupling are subject to further reaction via in situ intermolecular nucleophilic trapping to give highly substituted indolin-3-one products through a one-pot cascade process. This process delivers a nucleophilic addend adjacent to one or more carbonyl moieties in umpollung fashion. Indoles were found to be an especially effective class of traps, and it was noted that there are structural similarities between these bis(indole) adducts to isatisine A, a naturally occurring compound with antiviral properties.

Given the modular nature of the diazoketone→metallocarbene→C-acylimine→indole adduct cascade sequence, construction of a library of unnatural Isatisine A-inspired bis(indole) compounds lacking a ribose-derived 'eastern' fragment was undertaken (see FIG. 1). Such compounds were screened for their potential activity against viral diseases for which there are no effective chemotherapeutic treatments, such as Respiratory Syncytial Virus (RSV; a well-studied and widely disseminated pathogen) and Zika Virus (ZIKV; an emerging pathogen of great concern).

Experimental Details

Reactions were carried out in oven (130° C.) or flame-dried glassware under a positive argon atmosphere unless otherwise stated. Transfer of anhydrous reagents was accomplished with oven-dried syringes or cannulae. Solvents were distilled before use: acetonitrile ($CH_3CN$), dichloromethane (DCM) and dichloroethane (DCE) from calcium hydride, toluene (PhMe) from sodium metal, diethyl ether ($Et_2O$) and tetrahydrofuran (THF) from sodium metal/benzophenone ketyl. Thin layer chromatography was performed on glass plates pre-coated with 0.25 mm silica gel with fluorescent indicator $UV_{254}$ (Rose Scientific). Flash chromatography columns were packed with 230-400 mesh silica gel (Silacycle). Proton nuclear magnetic resonance spectra ($^1H$ NMR) were recorded at 400 MHz, or 500 MHz and coupling constants (J) are reported in Hertz (Hz). Carbon nuclear magnetic resonance spectra ($^{13}C$ NMR) were recorded at 125 MHz, as proton decoupled or as attached proton test (APT). Chemical shifts are reported on a δ scale (ppm) and referenced to residual solvent peaks: $CDCl_3$ (7.26 ppm, $^1H$; 77.06 ppm, $^{13}C$), $d_6$-DMSO (2.49 ppm, $^1H$; 39.5 ppm, $^{13}C$), and $d_2$-DCM (5.32 ppm, $^1H$; 53.5 ppm, $^{13}C$).

All reagents were purchased from commercial suppliers: Sigma Aldrich, AK Scientific, and Acros, at purity greater than (95%). Nuclear Magnetic Resonance (NMR) measurements (chemical shift, integration, coupling constants, relative peak intensity) were performed using Agilent 400 MHz, Varian 400 MHz, or Varian 500 MHz NMR instruments. Mass measurements were acquired using Agilent Technologies 1100 MSD (Single Quadruple), Waters (Micromass) Q-TOF Premier (Quadruple TOF), Kratos Analytical MS-50G, Agilent Technologies 6220 oaTOF, or AB Sciex QTRAP 2000 instruments. UV-VIS spectra were acquired using Cary UV-Vis, or Hewlett Packard 8453 UV-VIS Spectrometers. Elemental Analysis was performed using Thermo Flash 2000 Elemental Analyzer. Infrared spectra were acquired using Mattson Galaxy Series FT-IR 3000, Nicolet Magna 750 FTIR Spectrometer equipped a Nic-Plan FTIR Microscope, or Thermo Nicolet 8700 FTIR Spectrometer equipped with a Continuum FTIR Microscope. Differential Scanning calorimetry and Thermogravimetric analysis were performed using Perkin Elmer Pyris 1, or Mettler Toledo TGA/DSC instruments.

For virology procedures: MEM media (HyClone, GE Healthcare Life Sciences); Opti-MEM media (Gibco, Thermofisher); fetal bovine serum (FBS) (Gibco, Thermofisher); DMEM (HyClone, GE Healthcare Life Sciences); Methanol (HPLC Grade, Fisher Chemical); Acetone (ACS Certified, Fisher Chemical); Goat anti-RSV polyclonal antibody (Meridian Life Science B65860G); Alexafluor 647 (LifeTech A-21469); MTT ((3-(4,5-dimethylthiazol-2-yl)-2,5-diphenyl tetrazolium bromide)); Phosphate buffered saline (PBS) (Gibco, Thermofisher); Dimethyl sulfoxide (DMSO) (ACS Certified, Fisher Chemical); [a 32-P] UTP was purchased from PerkinElmer. All remaining reagents (actinomycin D, lysolecithin, Tris-acetate, Magnesium acetate, Potassium acetate, DTT, spermidine, creatine phosphatase, aprotinin, creatine phosphokinase, ATP, GTP, CTP, UTP, and RNaseH) were purchased from Sigma Aldrich at purity greater than (95%).

Substrate Preparation

Preparation of compounds 1a, 1b, 1d, and 1g have been reported previously by Bott, T. M.; Atienza, B. J.; West, F. G. RSC Adv. 2014, 4, 31955-31959.

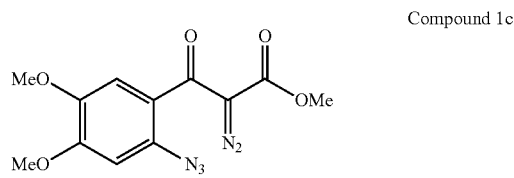

Compound 1c

Dichloromethane (DCM, 35 mL) was added to a conical flask containing 4,5-dimethoxy-2-azido benzoic acid (1.0 g, 4.5 mmol) and the suspension was cooled to 0° C. before addition of methyl acetate (1.0 equiv) and trichloroacetyl chloride (1.2 equiv). This solution was slowly transferred via cannula to a suspension of NaH (1.2 equiv) in DCM (10-20 mL) at 0° C. After stirring at 0° C. for 15 min, the solution was cooled to −45° C. before addition of 1-methylimidazole (1.2 equiv). The solution was then stirred for an additional 10 min at −45° C. before slowly adding $TiCl_4$ (3.4 equiv) followed by $NEt_3$ (4.0 equiv). The dark red-brown solution was kept at −78° C. for 30 min before being warmed to 0° C. and kept for 1 h and subsequently quenched with water (30 mL). The organic layer was separated and aqueous layer was washed 3x with equal portions of DCM. The combined organic layers were washed with an equivalent volume of water and brine, dried over $MgSO_4$, filtered, and concentrated under reduced pressure. Crude product was partially purified by flash chromatography to afford an orange oil whose $R_f$ was about 0.3 (7:3 hexanes:EtOAc). The orange oil was concentrated and added to a stirred solution of triethylamine (1.2 equiv) in $CH_3CN$ (20 mL). Tosyl azide (1.0 equiv) in $CH_3CN$ (10 mL) was transferred via cannula into the flask and the reaction was left to stir overnight. Concentration under reduced pressure followed by purification via flash chromatography (silica gel, 8:2 hexanes:EtOAc→7:3 hexanes:EtOAc slowly added in gradient) furnished 1c as a yellow oil in 50% yield (from starting 4,5-dimethoxy-2-azidobenzoic acid).

$R_f$=0.25 (7:3 hexanes:EtOAc); IR (cast film) 2978, 2134, 1711, 1695, 1565, 1292 $cm^{-1}$; $^1H$ NMR (500 MHz, $CDCl_3$) δ 6.87 (s, 1H), 6.62 (s, 1H), 3.94 (s, 3H), 3.86 (s, 3H), 3.78 (s, 3H); $^{13}C$ NMR (125 MHz, $CDCl_3$) δ 184.5, 161.2, 152.4, 146.4, 131.4, 121.9, 111.6, 101.5, 56.3, 56.2, 52.3; HRMS calc'd for $C_{12}H_{11}N_5O_5Na$ $[M+Na]^+$ 328.0652, found 328.0651. (NB.: $^{13}C$ signal for the diazo carbon was not detected due to quadrupolar broadening.).

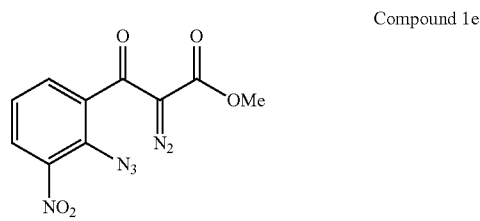

Compound 1e

Prepared analogously to 1c using 3-nitro-2-azido benzoic acid in place of 2-azido-4,5-dimethoxybenzoic acid. Isolated as a brown oil in 23% yield: $R_f$=0.19 (7:3 hexanes:EtOAc); IR (cast film) 3022, 2141, 1732, 1694, 1637, 1567, 1293 cm$^{-1}$; $^1$H NMR (500 MHz, CDCl$_3$) δ 8.14 (dd, J=8.2, 1.6 Hz, 1H), 7.51 (dd, J=7.6, 1.6 Hz, 1H), 7.38 (dd, J=8.2, 7.6 Hz, 1H), 3.76 (s, 3H); $^{13}$C NMR (125 MHz, CDCl$_3$) δ 184.2, 160.5, 135.8, 132.7, 132.5, 132.4, 127.8, 125.8, 52.6; LC-MS calc'd for $C_{10}H_7N_6O_5$ [M+H]$^+$291.1, found 291.1. (NB.: (a) preparation for this starting material was limited to 70-100 mg; (b) $^{13}$C signal for the diazo carbon was not detected due to quadrupolar broadennin).

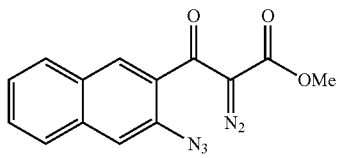

Compound 1f

Prepared analogously to 1c using 3-azido-2-napthoic acid in place of 2-azido-4,5-dimethoxybenzoic acid.

Isolated as a brown oil in 51% yield: $R_f$=0.68 (7:3 hexanes:EtOAc); IR (cast film) 2971, 2136, 1724, 1693, 1633, 1567, 1290 cm$^{-1}$; $^1$H NMR (500 MHz, CDCl$_3$) δ 7.83-7.76 (m, 3H), 7.53 (br s, 1H), 7.54 (ddd, J=8.2, 6.9, 1.2 Hz, 1H), 7.24 (ddd, J=8.2, 7.0, 1.2 Hz, 1H), 3.74 (s, 3H); $^{13}$C NMR (125 MHz, CDCl$_3$) δ 185.6, 160.9, 135.2, 134.7, 130.3, 129.5, 128.9, 128.7, 128.4, 126.7, 126.2, 115.6, 52.3; HRMS calc'd for $C_{14}H_9N_5O_3Na$ [M+Na]$^+$318.0597, found 318.0594. (NB.: $^3$C signal for the diazo carbon was not detected due to quadrupolar broadening.).

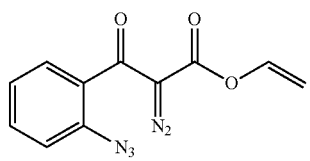

Compound 1h

Prepared analogously to 1c using vinyl acetate in place of methyl acetate, and using 2-azido benzoic acid in place of 2-azido-4,5-dimethoxy benzoic acid.

Isolated as a yellow oil in 46% yield: $R_f$=0.51 (7:3 hexanes:EtOAc); IR (cast film) 2924, 2931, 2136, 1724, 1684 cm$^{-1}$; $^1$H NMR (400 MHz, CDCl$_3$) 6 7.47 (ddd, J=8.1, 7.5, 1.6 Hz, 1H), 7.28-7.25 (m, 1H), 7.17-7.12 (m, 3H), 4.70 (dd, J=13.9, 2.0 Hz, 1H), 4.54 (dd, J=6.2, 2.0 Hz, 1H); $^{13}$C NMR (125 MHz, CDCl$_3$) δ 185.3, 157.7, 140.1, 137.9, 132.2, 130.2, 128.6, 124.8, 118.3, 98.5; HRMS calc'd for $C_{11}H_7N_5O_3Na$ [M+Na]$^+$280.0441, found 280.0439. (NB.: $^{13}$C signal for the diazo carbon was not detected due to quadrupolar broadening.).

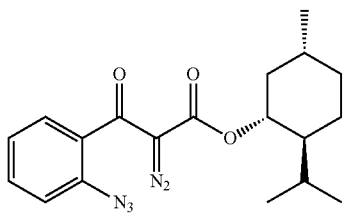

Compound 1j

Prepared analogously to 1c using (+)-menthyl acetate in place of methyl acetate, and using 2-azido-benzoic acid in place of 2-azido-4,5-dimethoxy benzoic acid.

Isolated as a yellow oil in 48% yield: $R_f$=0.64 (7:3 hexanes:EtOAc); $[α]_D^{20}$:−67.76 (c=0.52, DCM) IR (cast film) 2956, 2928, 2870, 2130, 1719, 1691, 1302, 958 cm$^{-1}$; $^1$HNMR (500 MHz, CDCl$_3$) δ 7.45 (ddd, J=8.1, 7.4, 1.7 Hz, 1H), 7.30-7.28 (m, 1H), 7.19-7.14 (m, 2H), 4.70 (ddd, J=10.9, 10.9, 4.4, 1H), 2.00-1.96 (m, 1H), 1.71-1.58 (m, 3H), 1.44-1.36 (m, 1H), 1.15-0.93 (m, 2H), 0.87 (d, J=6.5 Hz, 3H), 0.83 (d, J=7.0 Hz, 3H), 0.87-0.83 (m, 2H), 0.72 (d, J=7.0 Hz, 3H); $^{13}$C NMR (125 MHz, CDCl$_3$) δ 185.9, 160.3, 137.6, 131.7, 130.8, 128.3, 124.7, 118.1, 75.9, 46.9, 40.9, 34.0, 31.3, 26.4, 23.4, 21.9, 20.7, 16.3; HRMS calc'd for $C_{19}H_{23}N_5O_3Na$ [M+Na]$^+$392.1693, found 392.1692. (NB.: $^{13}$C signal for the diazo carbon was not detected due to quadrupolar broadening.).

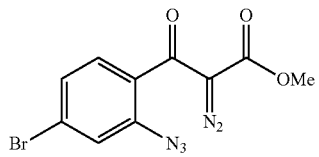

Compound 1k

Prepared analogously to 1c using 2-azido-3-bromo benzoic acid in place of 2-azido-4,5-dimethoxybenzoic acid. Product was obtained in 43% yield (unoptimized due to procedure being run only once, on a sufficient scale to permit its use in multiple coupling experiments).

Isolated as a yellow oil: $R_f$=0.64 (3:7, EtOAc:hexanes); IR (cast film) 3026, 2955, 2111, 1729, 1634, 1585, 1565 cm$^{-1}$; $^1$H NMR (500 MHz, CDCl$_3$): δ 7.35-7.33 (m, 2H), 7.18 (d, J=8.5 Hz, 1H), 3.78 (s, 3H); $^{13}$C NMR (125 MHz, CDCl$_3$): δ 184.7, 160.7, 139.2, 129.7, 129.2, 128.0, 125.7, 121.5, 52.4; HRMS calc'd for $C_{10}H_6BrN_5NaO_3$ [M+Na]$^+$ 345.9546, found 345.9549. (NB.: $^{13}$C signal for the diazo carbon was not detected due to quadrupolar broadening.).

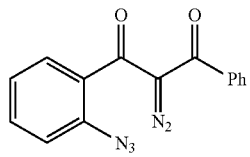

Compound 1l

A solution of LiHMDS (6.2 mL of 1M THF solution; 6.2 mmol) was added to a solution of 2-azido-acetophenone (1.0 g, 6.2 mmol) in 10 mL THF at −78° C. The mixture was allowed to stir for 30 min. Then, a solution of benzoyl cyanide (822 mg, 6.20 mmol, dissolved in 10 mL THF) was added dropwise. The mixture was allowed to stir for 1 h then quenched with saturated NH$_4$Cl (15 mL). The mixture was diluted with diethyl ether (10 mL). The organic layer was separated and washed with water (20 mL, 3×). The organic layer was washed with brine and dried with MgSO$_4$. The solution was concentrated under pressure to afford yellow oil. The yellow oil was purified using flash column chromatography eluting 10% % EtOAc in hexanes to furnish 1.13 g (69%) of intermediate β-diketone (isolated as an enol) as a yellow oil:

R$_f$=0.63 (7:3 hexanes:EtOAc); IR (cast film) 3064, 2420, 2125, 1599, 1281, 1604, 778, 1126, 750 cm$^{-1}$; $^1$H NMR (500 MHz, CDCl$_3$) δ 8.01-7.87 (m, 3H), 7.59-7.48 (m, 4H), 7.28-6.99 (m, 2H), 7.00 (s, 1H); $^{13}$C NMR (125 MHz, CDCl$_3$,) δ 185.5, 184.4, 138.3, 135.4, 132.6, 132.5, 130.4, 128.7, 128.3, 127.3, 125.0, 119.3, 98.3; HRMS calc'd for C$_{11}$H$_{11}$N$_3$O$_2$ [M]$^+$265.0851, found: 294.0849. (NB.: enol H was not detected.)

Triethylamine (715 µL, 5.1 mmol) was added to a stirred solution of the intermediate diketone (500 mg, 1.89 mmol) in CH$_3$CN (8 mL). Tosyl azide (400 mg, 2.00 mmol) in CH$_3$CN (5 mL) was transferred via cannula into the flask and the reaction was left to stir overnight. Concentration under reduced pressure followed by purification via flash chromatography (silica gel, 7:3 hexanes:EtOAc) resulted in a quantitative yield of 11(551 mg) as a pale yellow oil. To prevent decomposition, product was stored under Ar in a freezer in a foil wrapped flask. Under these conditions the compound was stable over several months.

R$_f$=0.71 (7:3 hexanes:EtOAc); IR (cast film) 3053, 2451, 2132, 1641, 1283, 1607, 779, 1136, 754 cm$^{-1}$; $^1$H NMR (500 MHz, CDCl$_3$) δ 7.55-7.53 (m, 2H), 7.43-7.28 (m, 5H), 7.13 (ddd, J=7.6, 7.6, 0.8 Hz, 1H), 6.92 (d, J=8.0 Hz, 1H); $^{13}$C NMR (125 MHz, CDCl$_3$) δ 185.9, 184.9, 137.5, 136.7, 132.5, 132.5, 130.0, 129.5, 128.2, 128.0, 125.0, 118.2, 98.3; LC-MS calc'd for C$_{15}$H$_9$N$_5$O$_2$ [M+H]$^+$291.2, found: 291.2.

Dual-Catalytic Formation of Bis(Indole) Products 2 and 5

Representative Procedure for Small-Scale Synthesis of 2a (Method A):

A solution of diazoazide 1a (0.250 g, 1.02 mmol) in DCM (25 mL) was added to a solution of indole (0.239 g, 2.04 mmol) and Cu(OTf)$_2$ (37 mg, 0.102 mmol) in DCM (25 mL) at room temperature via syringe pump over 1 h. The reaction mixture turned light green over 1-2 h and slowly turned dark brown over 24 h. Once addition was complete, the reaction was monitored by TLC for consumption of 1a, (for some diazoazide starting materials, the reaction mixture was heated further at reflux for 10-15 minutes to ensure completion). Upon consumption of 1a, the reaction mixture was concentrated under reduced pressure, purified by flash chromatography (silica gel, 7:3 hexanes:EtOAc), and recrystallization (MeOH) (See Example 2 for more details). Total isolated yield of 2a was 0.287 g (92%), as a combined yellow amorphous powder and crystals. Suitable single crystals of 2a for X-ray diffraction were grown from 1:1 MeOH-EtOAc via slow evaporation of solvent.

Representative Procedure for Gram-Scale Synthesis of 2a (Method B):

A solution of diazoazide 1a (5.00 g, 20.4 mmol) in DCM (150-250 mL) was added to a solution of indole (4.78 g, 40.8 mmol) and Cu(OTf)$_2$ (740 mg, 2.04 mmol) in DCM (150-250 mL) at room temperature via syringe pump. The reaction mixture turned light green over 2 h and slowly turned dark brown with suspended green solid over 24 h. The reaction was monitored by TLC for consumption of 1a. Upon consumption of 1a, the suspended solid was filtered from the reaction mixture to afford green needles of 2a. The green needles were directly recrystallized with minimum amount of ethyl acetate (hot), followed by slow addition of pentane or hexane to furnish adduct 2a as a fine dark yellow solid in 74% (69-78%) yield. The mother liquor contained ca. 10% of the product and could still be purified by flash chromatography (silica gel, 7:3 Hexanes:EtOAc) to afford yellow oil, which precipitated when left standing at −4° C. overnight.

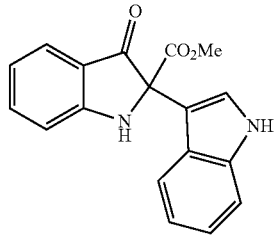

Compound 2a

Following Method A, 0.231 g (74%) of dark yellow crystalline 2a was isolated after recrystallization. Concentration of mother liquor afforded another 0.056 g (18%) of yellow/brown amorphous powder. Combined total of 2a was 0.287 g (92%), m.p. ~110° C. (typical for the yellow/brown powder), m.p.=225-226° C. (crystals); IR (cast film) 3392, 3059, 2953, 1726, 1697, 1491, 1434, 1214, 748 cm$^{-1}$; $^1$H NMR (500 MHz, CDCl$_3$) δ 8.22 (br s, 1H), 7.70 (d, J=7.7 Hz, 1H), 7.59 (d, J=8.3 Hz, 1H), 7.53 (app td, J=8.3, 1.3 Hz, 1H), 7.40 (d, J=2.4 Hz, 1H), 7.37 (d, J=8.1 Hz, 1H), 7.20 (app t, J=7.2 Hz, 1H), 7.11 (app t, J=7.9 Hz, 1H), 7.01 (d, J=8.3 Hz, 1H), 6.93 (app t, J=7.7 Hz, 1H), 5.73 (br s, 1H), 3.80 (s, 3H); $^{13}$C NMR (125 MHz, CDCl$_3$) 193.3, 168.5, 159.5, 140.4, 136.5, 127.8, 125.3, 123.5, 122.8, 121.4, 120.5, 119.4, 115.1, 112.6, 111.7, 111.2, 73.0, 53.9; HRMS calc'd for C$_{18}$H$_{15}$N$_2$O$_3$ [M+H]$^+$307.1077, found 307.1078; Elemental analysis calc'd for C$_{18}$H$_{14}$N$_2$O$_3$: 70.58% C, 4.61% H, 9.15% N, 15.67% O, found, 70.48% C, 4.62% H, 9.13% N. $^1$H-NMR spectral data were in good agreement with those reported in the literature [Jessing, M.; Barran, P. S. *Heterocycles* 2011, 82, 1739-1745]. $^{13}$C-NMR spectral varied by up to 0.6 ppm for some $^{13}$C NMR resonances. There were also additional three carbon resonances reported here not included in the earlier data. Similar to $^1$H-NMR spectral characterizations, IR wavenumbers were likewise in good agreement.

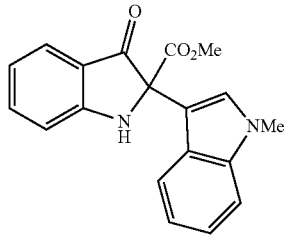

Compound 2b (Method A) Isolated as yellow cubic crystals in 89% yield (using methanol as crystallizing solvent): m.p.=215-216° C. (reported for powder 82° C. [Jessing, M.; Barran, P.S. *Heterocycles* 2011, 82, 1739-1745] and [Bolt, T. M.; Atienza, B. J.; West, F. G. *RSC Adv.* 2014, 4, 31955-31959]); R$_f$=0.31 (yellow spot, 7:3 hexanes:EtOAc); IR (cast film) 3366, 3051, 1744, 1702, 1616, 1485, 1293, 742 cm$^{-1}$; $^1$H NMR (500 MHz, CDCl$_3$): δ 7.73 (d, J=7.0 Hz, 1H), 7.62 (d, J=7.5 Hz, 1H), 7.54 (app t, J=6.5 Hz, 1H), 7.34 (d, J=8.0 Hz, 1H), 7.30 (d, J=5.5 Hz, 1H), 7.27 (app t, J=7.0 Hz, 1H), 7.14 (app t, J=7.0 Hz, 1H), 7.00 (d, J=8.0 Hz, 1H), 6.96 (app t, J=6.8 Hz, 1H), 5.34 (br s, 1H), 3.84 (s, 3H), 3.77 (s, 3H); $^{13}$C NMR (125 MHz, CDCl$_3$): δ 195.2, 169.1, 161.0, 137.9, 137.4, 128.0 126.0, 125.4, 122.3, 120.4, 120.0, 119.9, 119.5, 113.6, 109.8, 109.8, 72.4, 53.8, 32.9; HRMS calc'd for C$_{19}$H$_{17}$N$_2$O$_3$ [M+H]$^+$ 321.1234, found 321.1233.

Compound 2c

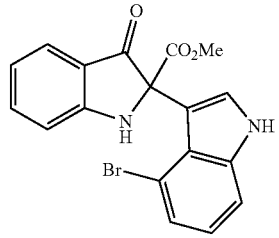

(Method A) Isolated as a yellow crystalline solid in 93% combined yield (Method B: 77-83% yield if direct recrystallization from crude reaction mixture using methanol as the solvent): m.p.=181-183° C.; R$_f$=0.40 (yellow spot, 7:3 hexanes:EtOAc); IR (cast film) 3370, 3051, 2920, 1742, 1704, 1616, 1486, 743 cm$^{-1}$; $^1$H NMR (500 MHz, CDCl$_3$): δ 7.72 (d, J=7.7 Hz, 1H), 7.64 (d, J=7.9 Hz, 1H), 7.55 (ddd, J=8.3, 7.2, 1.3 Hz, 1H), 7.42 (s, 1H), 7.32-7.25 (m, 4H), 7.20 (app td, J=8.3, 1.0 Hz, 1H), 7.15-7.11 (m, 3H), 7.02 (d, J=8.3 Hz, 1H), 6.95 (app t, J=7.9 Hz, 1H), 5.79 (br s, 1H), 5.30 (s, 2H), 3.83 (s, 3H); $^{13}$C NMR (125 MHz, CDCl$_3$): δ 194.7, 169.0, 161.0, 137.9, 137.0, 136.9, 128.8, 127.7, 127.6, 126.9, 126.3, 125.4, 122.4, 120.4, 120.2, 119.9, 119.8, 113.6, 110.5, 110.3, 72.4, 53.8, 50.4; HRMS calc'd for C$_{25}$H$_{20}$N$_2$O$_3$Na [M+Na]$^+$ 419.1366, found: 419.1363; Fluorescent properties in methanol solution: excitation wavelengths at 290 nm and 395 nm, emission wavelength at 500 nm (both excitation wavelength).

Compound 2d (Method A) Isolated as a bright yellow microcrystals in 88% yield; m.p.=127° C. (decomp.); R$_f$=0.28 (yellow spot, 7:3 hexanes:EtOAc); IR (cast film) 3360, 3062, 2950, 1710, 1617, 1487, 1239, 748 cm$^{-1}$; $^1$H NMR (500 MHz, CDCl$_3$): δ 8.29 (br s, 1H), 7.66 (br d, J=8.1 Hz, 1H), 7.57 (ddd, J=8.4, 7.2, 1.5 Hz, 1H), 7.48-7.46 (m, 2H), 7.42-7.37 (m, 3H), 7.35 (d, J=8.1 Hz, 1H), 7.23 (d, J=8.3 Hz, 1H), 7.20 (ddd, J=8.3, 7.2, 1.1 Hz, 1H), 7.05 (ddd, J=8.3, 7.2, 1.1 Hz, 1H), 7.00 (d, J=8.3 Hz, 1H), 6.97 (app t, J=7.9 Hz, 1H), 5.62 (br s, 1H), 3.24 (s, 3H); $^{13}$C NMR (125 MHz, CDCl$_3$): δ 195.1, 168.8, 160.8, 138.0, 137.9, 135.5, 132.5, 129.6, 128.8, 128.4, 126.8, 125.2, 122.7, 120.6, 120.4, 120.2, 119.7, 113.4, 111.2, 108.2, 73.3, 53.2; HRMS calc'd for C$_{24}$H$_{19}$N$_2$O$_3$ [M+H]$^+$ 383.1390, found 383.1385.

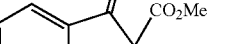

Compound 2e

Compound 2f (Method A) Isolated as a light green crystalline solid in 71% yield; m.p.=242-243° C.; R$_f$=0.23 (yellow spot, 7:3 hexanes:EtOAc); IR (microscope) 3365, 3006, 2953, 1726, 1706, 1610, 1488, 1219, 792 cm$^{-1}$; $^1$H NMR (500 MHz, d$^6$-DMSO): δ 7.60 (br s, 1H), 7.55 (d, J=7.9 Hz, 1H), 7.51 (app t, J=8.3 Hz, 1H), 7.45 (d, J=7.9 Hz, 1H), 7.27 (d, J=7.5 Hz, 1H), 7.10 (d, J=2.8 Hz, 1H), 7.06 (app t, J=7.9 Hz, 1H), 7.04 (d, J=8.3 Hz, 1H), 6.81 (app t, J=7.5 Hz, 1H), 3.61 (s, 3H) (Note: one NH proton was not detected); $^{13}$C NMR (125 MHz, d$^6$-DMSO): δ 195.9, 169.9, 162.2, 138.6 (2×), 126.4, 125.1, 125.0, 124.0, 123.3, 118.9, 118.0, 114.0, 113.0, 112.1, 111.4, 72.4, 53.5; HRMS calc'd for C$_{18}$H$_{14}$$^{79}$BrN$_2$O$_3$ [M+H]$^+$ 385.0182, found 385.0182; Elemental analysis calc'd for C$_{18}$H$_{13}$BrN$_2$O$_3$: 56.12% C, 3.40% H, 7.27% N; found, 55.98% C, 3.41% H, 7.24% N.

(Method A) Isolated as bright yellow crystals in 78% yield; m.p.=186-188° C.; R$_f$=0.11 (yellow spot, 7:3 hexanes: EtOAc); IR (cast film) 3301, 3060, 2947, 1742, 1685, 1487, 1232, 1218, 756 cm$^{-1}$; $^1$H NMR (500 MHz, CDCl$_3$): δ 8.19 (br s, 1H), 7.74 (dd, J=7.9, 0.6 Hz, 1H), 7.56 (app td, J=8.3, 1.3 Hz, 1H), 7.38 (d, J=2.6 Hz, 1H), 7.30-7.26 (m, 2H), 7.06-7.04 (m, 2H), 6.98 (app t, J=7.2 Hz, 1H), 6.89 (dd, J=8.8, 2.4 Hz, 1H), 5.71 (br s, 1H), 3.81 (s, 3H), 3.77 (s, 3H); $^{13}$C NMR (125 MHz, CDCl$_3$): δ 194.9, 169.0, 161.0, 154.4, 137.9, 131.7, 125.8, 125.4, 124.3, 120.4, 120.0, 113.5, 112.7, 112.3, 111.2, 101.5, 72.4, 55.8, 53.7; HRMS calc'd for C$_{19}$H$_{17}$N$_2$O$_4$ [M+H]$^+$ 337.1183, found 337.1185.

Compound 2h

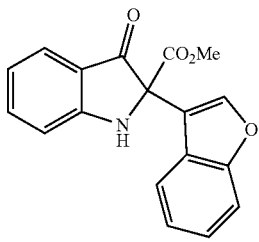

(Method A, with following modification: after addition of diazo-azide 1a by syringe pump, reaction mixture was heated to reflux and stirred at that temperature until consumption of 1a was observed) Isolated as a yellow oil in 46% yield; $R_f$=0.40 (yellow spot, 7:3 hexanes:EtOAc); IR (cast film) 3363, 3065, 2954, 1748, 1711, 1617, 1488, 1242, 751 cm$^{-1}$; $^1$H NMR (500 MHz, CDCl$_3$): δ 7.69 (d, J=7.9 Hz, 1H), 7.55 (dd, J=7.7, 0.6 Hz, 1H), 7.54 (ddd, J=8.3, 7.2, 1.3 Hz, 1H), 7.45 (dd, J=8.1, 0.6 Hz, 1H), 7.28 (app td, J=7.2, 1.3 Hz, 1H), 7.21 (app td, J=7.9, 1.1 Hz, 1H), 7.03 (d, J=8.3 Hz, 1H), 6.95 (overlapped app td, J=7.7, 0.6 Hz, 1H), 6.94 (overlapped s, 1H), 5.74 (br s, 1H), 3.85 (s, 3H); $^{13}$C NMR (125 MHz, CDCl$_3$): δ 191.3, 166.6, 161.2, 155.0, 150.9, 138.2, 127.7, 125.7, 124.9, 123.1, 121.6, 120.8, 119.3, 113.7, 111.3, 105.6, 71.9, 54.2; HRMS calc'd for C$_{18}$H$_{13}$NO$_4$Na [M+Na]$^+$330.0737, found 330.0739.

Compound 2i

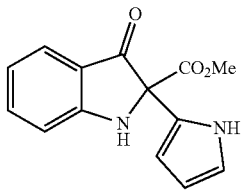

(Method A) Isolated as a yellow oil in 68% yield: $R_f$=0.34 (yellow spot, 7:3 hexanes:EtOAc); IR (cast film) 3426, 3390, 3056, 2954, 1726, 1697, 1488, 1233, 751 cm$^{-1}$; $^1$H NMR (500 MHz, CDCl$_3$): δ 9.43 (br s, 1H), 7.63 (d, J=7.9 Hz, 1H), 7.56 (apparent (app) td, J=7.5, 1.5 Hz, 1H), 7.09 (d, J=7.5 Hz, 1H), 6.94 (app td, J=7.2, 0.7 Hz, 1H), 6.87 (app td, J=2.6, 1.7 Hz, 1H), 6.33 (ddd, J=3.5, 2.7, 1.7 Hz, 1H), 6.19-6.14 (m, 1H), 5.68 (br s, 1H), 3.84 (s, 3H); $^{13}$C NMR (125 MHz, CDCl$_3$): δ 193.2, 167.6, 161.6, 138.0, 125.8, 124.8, 120.7, 119.2, 118.8, 113.6, 108.2, 106.3, 71.8, 53.9; HRMS calc'd for C$_{14}$H$_{13}$N$_2$O$_3$[M+H]$^+$257.0921, found 257.0915.

Compound 2j

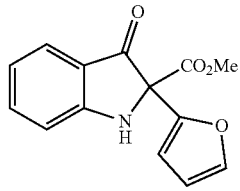

(Method A, with following modification: after addition of diazoazide 1a by syringe pump, the reaction mixture was heated to reflux and stirred at that temperature until consumption of 1a was observed) Isolated as a yellow oil in 48% yield; $R_f$=0.37 (yellow spot, 7:3 hexanes:EtOAc); IR (cast film) 3362, 3125, 2954, 1748, 1710, 1617, 1488, 1233, 751 cm$^{-1}$; $^1$H NMR (500 MHz, CDCl$_3$): δ 7.69 (d, J=7.2 Hz, 1H), 7.55 (app td, J=7.2, 0.9 Hz, 1H), 7.44 (dd, J=1.8, 0.9 Hz, 1H), 7.03 (d, J=8.3 Hz, 1H), 6.96 (app t, J=7.7 Hz, 1H), 6.56 (d, J=3.3 Hz, 1H), 6.42 (dd, J=3.3, 1.9 Hz, 1H), 5.66 (br s, 1H), 3.86 (s, 3H); $^{13}$C NMR (125 MHz, CDCl$_3$): δ 191.8, 166.9, 161.1, 148.4, 143.3, 138.1, 125.7, 120.7, 119.3, 113.6, 110.7, 108.8, 71.7, 54.1; HRMS calc'd for C$_{14}$H$_{12}$NO$_4$[M+H]$^+$258.0761, found 258.0764.

Compound 2k

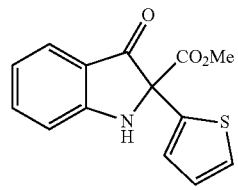

(Method A, with following modification: after addition of diazoazide 1a by syringe pump, reaction mixture was heated to reflux and stirred at that temperature until consumption of 1a was observed) Isolated as a yellow oil in 41% yield; $R_f$=0.42 (7:3 hexanes:EtOAc); IR (cast film) 3360, 3071, 2952, 1747, 1709, 1616, 1486, 1231, 754 cm$^{-1}$; $^1$H NMR (500 MHz, CDCl$_3$): δ 7.62 (ddd, J=7.2, 1.4, 0.7 Hz, 1H), 7.54 (ddd, J=8.4, 7.2, 1.4 Hz, 1H), 7.49 (dd, J=3.7, 1.3 Hz, 1H), 7.24 (dd, J=5.1, 1.3 Hz, 1H), 7.07 (d, J=8.3 Hz, 1H), 7.03 (dd, J=5.1, 3.7 Hz, 1H), 6.95 (app td, J=7.9, 0.7 Hz, 1H), 5.79 (br s, 1H), 3.85 (s, 3H); $^{13}$C NMR (125 MHz, CDCl$_3$): δ 192.2, 167.4, 160.9, 138.8, 137.9, 127.6, 125.9, 125.7, 125.5, 121.1, 119.0, 113.7, 73.4, 54.1; HRMS calc'd for C$_{14}$H$_{12}$NSO$_3$[M+H]$^+$274.0532, found 274.0536.

Compound 2l

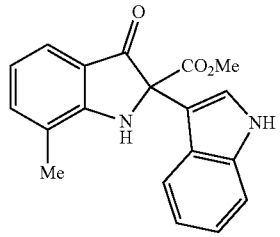

(Method A) Isolated as yellow crystals in 86% yield; m.p.=192-193° C.; $R_f$=0.16 (yellow spot, 7:3 hexanes:EtOAc); IR(cast film) 3371, 3057, 2952, 1739, 1702, 1608, 1459, 1238, 745 cm$^{-1}$; $^1$H NMR (500 MHz, CDCl$_3$): δ 8.40 (br s, 1H), 7.58-7.55 (m, 2H), 7.37-7.31 (m, 3H), 7.18 (ddd, J=7.9, 7.0, 1.2 Hz, 1H), 7.10 (ddd, J=8.1, 7.1, 1.0 Hz, 1H), 6.89 (app t, J=7.5 Hz, 1H), 5.53 (br s, 1H), 3.79 (s, 3H), 2.30 (s, 3H); $^{13}$C NMR (125 MHz, CDCl$_3$) δ 195.2, 169.2, 160.3, 138.0, 136.6, 125.5, 123.7, 122.8 (2×), 122.7, 120.6, 120.4, 119.5 (2×), 111.8, 111.7, 72.6, 53.8, 15.8; HRMS calc'd for C$_{19}$H$_{17}$N$_2$O$_3$ [M+H]$^+$321.1234, found: 321.1233.

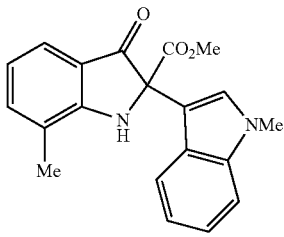

Compound 2m (Method A) Isolated as yellow crystals in 84% yield (using MeOH as the recrystallization solvent); m.p.=170-171° C.; $R_f$=0.35 (yellow spot, 7:3 hexanes:EtOAc); IR(cast film) 3359, 3055, 2950, 1746, 1705, 1608, 1460, 1241, 743 cm$^{-1}$; $^1$H NMR (500 MHz, CDCl$_3$) δ 7.61 (2 overlapping app t, J=8.2 Hz, 2H), 7.39-7.26 (m, 4H), 7.15 (app t, J=7.9 Hz, 1H), 6.91 (app t, J=7.3 Hz, 1H), 5.58 (br s, 1H), 3.84 (s, 3H), 3.79 (s, 3H), 2.33 (s, 3H); $^{13}$C NMR (125 MHz, CDCl$_3$) δ 195.2, 169.2, 160.2, 137.9, 137.4, 128.1, 126.1, 122.8, 122.7, 122.2, 120.5, 119.9, 119.5, 119.5, 110.0, 109.8, 72.5, 53.8, 32.9, 15.8; HRMS calc'd for $C_{20}H_{19}N_2O_3$ [M+H]$^+$ 335.1390, found: 335.1388.

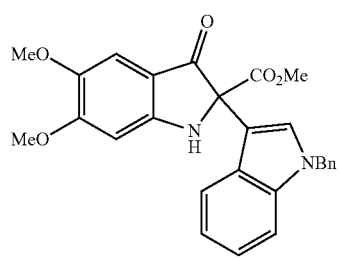

Compound 2n (Method A) Isolated as a yellow powder in 94% yield (using methanol as recrystallization solvent): m.p.=184-186° C.; $R_f$=0.16 (7:3 hexanes:EtOAc); IR (cast film) 3349, 3015, 2942, 1748, 1712, 1623, 1451, 1239, 731 cm$^{-1}$; $^1$H NMR (500 MHz, CDCl$_3$) δ 7.61 (d, J=7.8 Hz, 1H), 7.60 (s, 1H), 7.28-7.09 (m, 10H), 6.48 (br s, 1H), 5.28 (s, 2H), 3.92 (s, 3H), 3.87 (s, 3H), 3.82 (s, 3H); $^{13}$C NMR (125 MHz, CDCl$_3$) δ 192.7, 169.4, 158.9 (2×), 145.2, 136.9 (2×), 128.7, 127.6 (2×), 126.8, 126.4, 122.3, 120.1, 119.5, 111.5, 110.8, 110.3, 104.5, 95.8, 73.0, 56.3, 56.2, 53.7, 50.3; HRMS calc'd for $C_{27}H_{25}N_2O_3$ [M+H]$^+$457.1685, found: 457.1683.

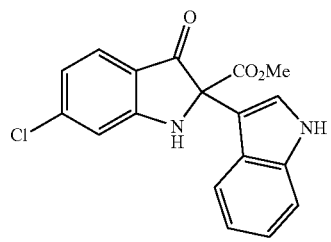

Compound 2o (Method A) Isolated as a yellow powder in 89% yield: m.p.=236-238° C.; $R_f$=0.19 (yellow spot, 7:3 hexanes:EtOAc); IR (cast film) 3364, 3052, 2952, 1746, 1711, 1610, 1242, 741 cm$^{-1}$; $^1$H NMR (500 MHz, CDCl$_3$): δ 8.21 (br s, 1H), 7.61 (d, J=8.3 Hz, 1H), 7.55 (d, J=8.1 Hz, 1H), 7.40-7.37 (m, 2H), 7.22 (app t, J=7.7 Hz, 1H), 7.12 (app t, J=8.1 Hz, 1H), 7.00 (d, J=1.1 Hz, 1H), 6.90 (dd, J=8.3, 1.7 Hz, 1H), 5.77 (br s, 1H), 3.81 (s, 3H); $^{13}$C NMR (125 MHz, CDCl$_3$) δ 193.2, 168.6, 161.2, 144.5, 136.5, 126.5, 125.3, 123.5, 122.9 121.2, 120.6, 119.4, 118.3, 113.4, 111.7, 111.3, 72.8, 53.9; HRMS calc'd for $C_{18}H_{13}ClN_2O_3Na$ [M+Na]$^+$ 363.0507, found: 363.0508; Elemental analysis calc'd for $C_{18}H_{13}ClN_2O_3$: 63.45% C, 3.85% H, 8.22% N; found, 63.35% C, 3.87% H, 8.13% N.

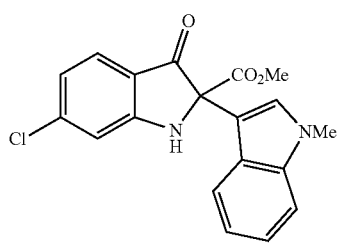

Compound 2p (Method A) Isolated as bright yellow crystals in 76% yield (using methanol as recrystallization solvent): m.p.=194-195° C.; $R_f$=0.35 (7:3 hexanes:EtOAc); IR (cast film) 3364, 3052, 2952, 1746, 1711, 1610, 1242, 741 cm$^{-1}$; $^1$H NMR (500 MHz, CDCl$_3$): δ 7.61 (d, J=8.0 Hz, 1H), 7.52 (ddd, J=8.0, 1.8, 1.0 Hz, 1H), 7.31 (ddd, J=8.3, 1.8, 1.1 Hz, 1H), 7.26-7.22 (m, 2H), 7.10 (ddd, J=8.1, 7.0, 1.1 Hz, 1H), 6.99 (dd, J=1.7, 0.5 Hz, 1H), 6.89 (dd, J=8.3, 1.7 Hz, 1H) 5.80 (br s, 1H), 3.81 (s, 3H), 3.75 (s, 3H); $^{13}$C NMR (125 MHz, CDCl$_3$) δ 193.3, 168.6, 161.1, 144.5, 137.3, 128.0, 126.4, 125.8, 122.3, 121.1, 120.1, 119.3, 118.1, 113.3, 109.8, 109.3, 72.7, 53.9, 32.9; HRMS calc'd for $C_{19}H_{16}{}^{35}ClN_2O_3$ [M+H]$^+$355.0844, found: 355.0846.

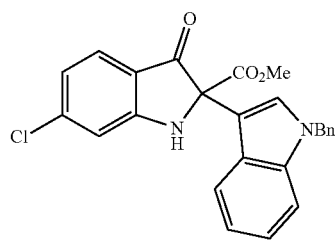

Compound 2q (Method A) Isolated as bright yellow crystals in 90% yield (80% yield from direct recrystallization of crude and using methanol as recrystallization solvent): m.p.=174-175° C.; $R_f$=0.42 (yellow spot, 7:3 hexanes:EtOAc); IR (cast film) 3364, 3052, 2952, 1746, 1711, 1610, 1242, 741 cm$^{-1}$; $^1$H NMR (500 MHz, CDCl$_3$): δ 7.62 (app t, J=8.3 Hz, 2H), 7.40 (s, 1H), 7.31-7.26 (m, 4H), 7.20 (app td, J=7.0, 0.9 Hz, 1H), 7.14-7.11 (m, 3H), 6.97 (d, J=1.7 Hz, 1H), 6.89 (dd, J=8.3, 1.7 Hz, 1H) 5.96 (br s, 1H), 5.26 (s, 2H), 3.81 (s, 3H); $^{13}$C NMR (125 MHz, CDCl$_3$) δ 193.3, 168.6, 161.1, 144.4, 136.9, 136.8 128.8, 127.7, 127.6, 126.8, 126.4, 126.1, 122.5, 120.9, 120.2, 119.7, 118.0, 113.2, 110.4, 110.0, 72.8, 53.8, 50.3; HRMS calc'd for $C25H19{}^{35}ClN_2NaO_3$ [M+Na]$^+$ 453.0976, found: 453.0984.

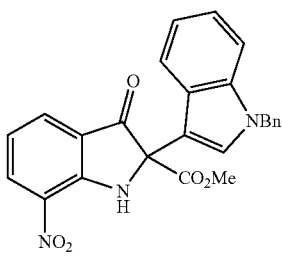

Compound 2r (Method A; Note: due to concerns about potential hazards associated with starting material, this reaction was carried out on 20 mg scale. As a result, only partial characterization was obtained.) Light yellow solid in ca. 14% yield (corrected for impurity from EtOAc and water present): $R_f$=0.24 (yellow spot, 7:3 hexanes:EtOAc); IR (cast film) 3324, 3048, 2956, 1738, 1714, 1610, 1251, 731 cm$^{-1}$; $^1$H NMR (500 MHz, CDCl$_3$): δ 8.38 (dd, J=8.2, 1.2 Hz, 1H), 8.01 (s, 1H), 8.00-7.98 (m, 2H), 7.56 (dd, J=8.1, 1.0 Hz, 1H), 7.38 (br s, 1H), 7.29-7.12 (m, 5H), 6.95 (dd, J=8.2, 7.3 Hz, 1H), 5.26 (s, 2H), 3.83 (s, 3H); LC-MS calc'd for C$_{25}$H$_{19}$N$_3$O$_5$ [M+H]$^+$442.1, found: 442.1. (Due to small scale, no $^{13}$C NMR or HRMS data were obtained.)

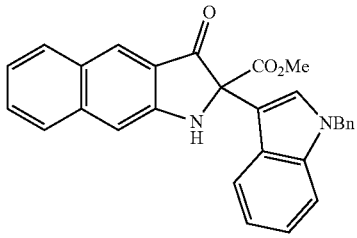

Compound 2s (Method A) Isolated as an orange oil in 96% yield: $R_f$=0.47 (orange spot, 7:3 hexanes:EtOAc); IR(cast film) 3359, 3055, 2950, 1746, 1705, 1608, 1460, 1241, 743 cm$^{-1}$; $^1$H NMR (500 MHz, CDCl$_3$) δ 8.29 (s, 1H), 7.84 (d, J=8.3 Hz, 1H), 7.67 (d, J=8.4 Hz, 1H), 7.64 (d, J=8.1 Hz, 1H), 7.48 (ddd, J=8.1, 6.8, 1.1 Hz, 1H), 7.42 (s, 1H), 7.29-7.23 (m, 6H), 7.17 (app t, J=8.1 Hz, 1H), 7.11 (dd, J=8.0, 1.5 Hz, 2H), 7.08 (app td, J=8.1, 7.2 Hz, 1H), 5.76 (br s, 1H), 5.27 (s, 2H), 3.81 (s, 3H); $^{13}$C NMR (125 MHz, CDCl$_3$) δ 195.7, 169.3, 153.7, 139.9, 137.1, 136.9, 130.8, 129.6, 128.8, 128.6, 127.7, 127.6, 127.2, 126.9, 126.7, 126.2, 123.7, 122.4, 121.8, 120.2, 120.1, 110.8, 110.3, 107.0, 72.7, 53.7, 50.4; HRMS calc'd for C$_{29}$H$_{22}$N$_2$O$_3$Na [M+Na]$^+$469.1523, found: 447.1530.

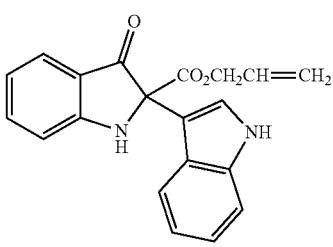

Compound 2t (Method A) Isolated as a yellow powder in 81% yield: m.p.=158-159° C.; $R_f$=0.19 (yellow spot, 7:3 hexanes:EtOAc); IR (cast film) 3368, 3055, 2919, 1732, 1711, 1635, 1491, 1225, 757 cm$^{-1}$; $^1$H NMR (500 MHz, CDCl$_3$): δ 8.36 (br s, 1H), 7.69 (ddd, J=7.8, 1.3, 0.7 Hz, 1H), 7.57 (d, J=8.1 Hz, 1H), 7.52 (ddd, J=8.4, 7.1, 1.4 Hz, 1H), 7.32 (d, J=1.3 Hz, 1H), 7.30 (app t, J=1.0 Hz, 1H) 7.17 (ddd, J=8.3, 7.1, 1.3 Hz, 1H), 7.08 (ddd, J=8.2, 7.1, 1.2 Hz, 1H), 6.98 (dt, J=8.3, 0.7 Hz, 1H), 6.93 (ddd, J=7.9, 7.1, 0.9 Hz, 1H), 5.84 (tdd, J=5.6, 10.5, 17.2 Hz, 1H), 5.83 (br s, 1H), 5.23 (tdd, J=1.5, 1.5, 17.2 Hz, 1H), 5.16 (tdd, J=1.3, 1.3, 10.5 Hz, 1H), 4.71-4.67 (m, 2H); $^{13}$C NMR (125 MHz, CDCl$_3$,): δ 194.8, 168.2, 161.1, 137.9, 136.5, 131.1, 125.4 (2×), 123.8, 122.6, 120.3 (2×), 119.8, 119.6, 119.2, 113.5, 111.7, 111.3, 72.6, 67.2; HRMS calc'd for C$_{20}$H$_{17}$N$_2$O$_3$ [M+H]$^+$333.1234, found: 333.1232.

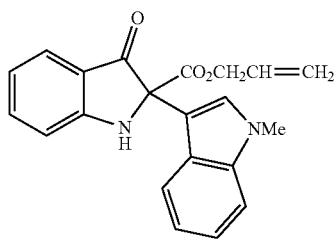

Compound 2u (Method A) Isolated as yellow crystals in 83% yield (using methanol as the recrystallization solvent): m.p.=148-150° C.; $R_f$=0.36 (yellow spot, 7:3 hexanes:EtOAc); IR (cast film) 3371, 3051, 2919, 1742, 1703, 1615, 1485, 1225, 743 cm$^{-1}$; $^1$H NMR (500 MHz, CDCl$_3$): δ 7.72 (d, J=7.8 Hz, 1H), 7.63 (d, J=8.1 Hz, 1H), 7.52 (ddd, J=8.3, 7.1, 1.3 Hz, 1H), 7.32-7.30 (m, 2H), 7.26 (ddd, J=8.2, 7.0, 1.1 Hz, 1H), 7.12 (ddd, J=8.0, 7.0, 1.1 Hz, 1H), 6.99 (d, J=8.2 Hz, 1H), 6.94 (app t, J=7.8 Hz, 1H), 5.88 (ddt, J=17.2, 10.5, 5.6 Hz, 1H), 5.83 (br s, 1H), 5.29 (ddt, J=17.2, 1.5, 1.5 Hz, 1H), 5.22 (ddt, J=10.4, 1.2, 1.2 Hz, 1H), 4.75-4.71 (m, 2H), 3.73 (s, 3H); $^{13}$C NMR (125 MHz, CDCl$_3$,): δ 194.7, 168.3, 161.0, 137.8, 137.4, 131.2, 128.1, 126.0, 125.4, 122.2, 120.2, 119.9(2×), 119.8, 119.1, 113.5, 109.8, 109.7, 72.5, 67.1, 32.9; HRMS calc'd for C$_{21}$H$_{19}$N$_2$O$_3$ [M+H]$^+$347.1390, found: 347.1393.

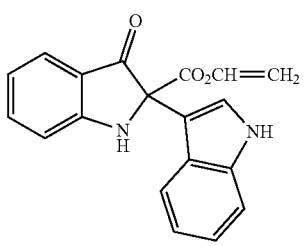

Compound 2v (Method A) Isolated as a yellow powder in 73% yield: m.p.=193-195° C.; $R_f$=0.21 (yellow spot, 7:3 hexanes:EtOAc); IR (cast film) 3351, 3011, 2915, 1738, 1712, 1635, 1465, 1233, 758 cm$^{-1}$; $^1$H NMR (500 MHz, CDCl$_3$): δ 8.25 (br s, 1H), 7.70 (d, J=8.0 Hz, 1H), 7.60 (dd, J=8.1, 0.9 Hz, 1H), 7.54 (ddd, J=8.3, 7.2, 1.4 Hz, 1H), 7.43 (d, J=2.7 Hz, 1H), 7.37 (app dt, J=8.2, 0.8 Hz, 1H), 7.25 (dd, J=13.9, 6.2 Hz, 1H), 7.20 (ddd, J=8.2, 7.2, 1.1 Hz, 1H), 7.10 (ddd, J=8.2, 7.2, 1.0 Hz, 1H), 7.01 (d, J=8.3 Hz, 1H), 6.94 (app t, J=7.8

Hz, 1H), 5.68 (br s, 1H), 4.99 (dd, J=13.9, 2.0 Hz, 1H), 4.66 (dd, J=6.1, 2.0 Hz, 1H); $^{13}$C NMR (125 MHz, CDCl$_3$): δ 194.0, 165.8, 160.9, 141.3, 138.0, 136.5, 125.5, 125.3, 123.7, 122.8, 120.5 (2×), 119.7, 119.6, 113.5, 111.6, 111.0, 100.0, 72.1; HRMS calc'd for C$_{19}$H$_{14}$N$_2$O$_3$Na [M+Na]$^+$ 318.1004, found: 318.1007.

Compound 2w

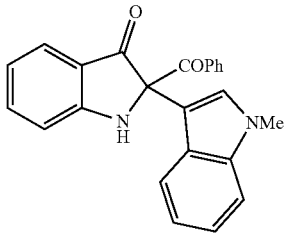

(Method A) Isolated as bright yellow crystals in 71% yield: m.p.=195-196° C.; R$_f$=0.20 (yellow spot, 7:3 hexanes:EtOAc); IR (cast film) 3364, 3052, 2952, 1711, 1610, 1242, 741 cm$^{-1}$; $^1$H NMR (500 MHz, CDCl$_3$): δ 8.16 (m, 2H), 7.66 (d, J=8.5 Hz, 1H), 7.51 (ddd, J=8.4, 7.1, 1.4 Hz, 1H), 7.46-7.38 (m, 2H), 7.31-7.19 (m, 5H), 7.06 (ddd, J=8.1, 7.0, 1.0 Hz, 1H), 7.01 (d, J=8.3 Hz, 1H), 6.92 (app t, J=7.8 Hz, 1H), 6.26 (br s, 1H), 3.77 (s, 3H); $^{13}$C NMR (125 MHz, CDCl$_3$) δ 195.2, 193.6, 161.1, 137.8, 137.4, 134.2, 133.2, 131.3, 127.9, 127.6, 126.1, 125.2, 122.4, 120.5, 120.3, 120.1, 119.3, 114.0, 112.0, 109.8, 79.0, 33.0; LC-MS calc'd for C$_{24}$H$_{19}$N$_2$O$_2$ [M+H]$^+$366.1, found: 366.1.

Compounds 2xa and 2xb

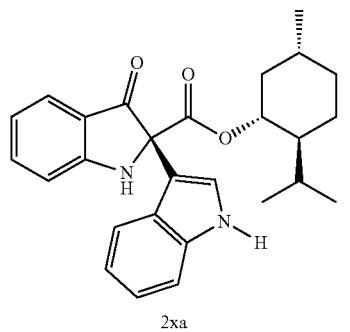

(Method A) Isolated as bright yellow powder in 81% yield, inseparable mixture (HPLC, ca. 1.3:1 ratio of 2xa:2xb, characterized as mixture of diastereomers): R$_f$=0.21 (yellow spot, 7:3 hexanes:EtOAc); IR (cast film) 3362, 3051, 2955, 1705, 1618, 1242, 739 cm$^{-1}$; $^1$H NMR (500 MHz, CDCl$_3$): δ (major isomer 2xa) 8.26 (br s, 1H), 7.69 (dddd, J=7.8, 1.4, 0.7, 0.7 Hz, 1H), 7.59-7.58 (m, 1H), 7.51 (ddd, J=8.3, 7.2, 1.4, 1H), 7.50 (ddd, J=8.3, 7.2, 1.4, 1H), 7.37 (d, J=2.7 Hz, 1H), 7.34 (ddd, J=8.2, 0.9, 0.9 Hz, 1H), 7.09 (ddd, J=8.1, 7.1, 1.1 Hz, 1H), 6.99 (dd, J=0.8, 0.8 Hz, 1H), 6.93 (ddd, J=7.1, 0.9, 0.9 Hz, 1H), 5.65 (br s, 1H) 4.77 (ddd, J=10.9, 10.9, 4.3 Hz, 1H), 0.84 (d, J=6.5 Hz, 3H), 0.82 (d, J=7.0 Hz, 3H), 0.64 (d, J=6.9 Hz, 3H), δ (minor isomer 2xb) 8.24 (br s, 1H), 7.70 (dddd, J=7.8, 1.4, 0.6, 0.6 Hz, 1H), 7.61-7.60 (m, 1H), 7.38 (d, J=2.7 Hz, 1H), 7.33 (ddd, J=8.1, 0.9, 0.9 Hz, 1H), 7.06 (ddd, J=8.1, 7.1, 1.0 Hz, 1H), 7.00 (dd, J=0.7, 0.7 Hz, 1H), 6.92 (ddd, J=7.1, 0.9, 0.9 Hz, 1H), 5.76 (br s, 1H), 4.72 (ddd, J=11.0, 11.0, 4.4 Hz, 1H), 0.86 (d, J=6.5 Hz, 3H), 0.51 (d, J=7.1 Hz, 3H), 0.43 (d, J=6.9 Hz, 3H) (Note: some protons could not be properly assigned due to extensive spectral overlap); $^{13}$C NMR (125 MHz, CDCl$_3$) δ 194.8, 194.6, 168.0 (2×), 161.2, 161.0, 137.7, 137.6, 136.6, 136.5, 125.7, 125.6, 125.4, 125.3, 123.7, 123.4, 122.6 (2×), 120.3, 120.2 (2×), 120.1 (3×), 120.0, 119.6, 113.7, 113.5, 111.9, 111.8, 111.5 (2×), 77.5, 77.4, 72.8, 72.7, 46.8, 46.7, 40.3, 40.2, 34.1 (2×), 31.5, 25.8, 25.5, 23.2, 23.0, 22.0, 20.8, 20.4, 15.9, 15.7 (Note: 2 aliphatic carbon resonances were not detected due to extensive spectral overlap); HRMS calc'd for C$_{27}$H$_{31}$N$_2$O$_3$ [M+H]$^+$431.2329, found: 431.2332.

Compounds 2ya and 2yb

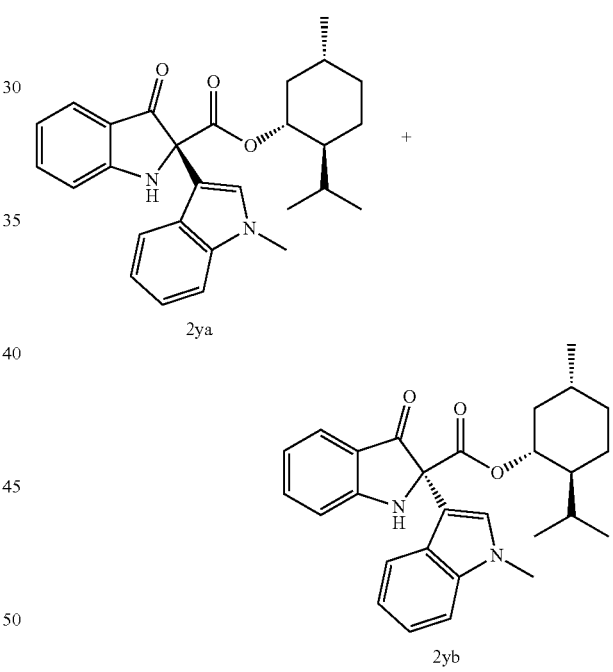

2ya

2yb (Method A) Isolated as bright yellow powder in 79% yield, inseparable mixture (HPLC, ca. 2.3:1 ratio of 2ya:2yb, characterized as mixture of diastereomers): R$_f$=0.33 (yellow spot, 7:3 hexanes:EtOAc); IR (cast film) 3362, 3051, 2955, 1704, 1618, 1242, 740 cm$^{-1}$; $^1$H NMR (500 MHz, CDCl$_3$): δ (major isomer 2ya) 7.58 (ddd, J=8.0, 1.0, 1.0 Hz, 1H), 7.51 (ddd, J=8.3, 7.1, 1.3 Hz, 1H), 7.06 (ddd, J=8.1, 7.1, 1.1 Hz), 5.65 (br s, 1H), 4.77 (ddd, J=10.8, 10.8, 4.3 Hz, 1H), 3.75 (s, 3H), 1.85 (sepd, J=7.1, 2.9 Hz, 1H), 0.87 (d, J=6.6 Hz, 3H), 0.83 (d, J=7.0 Hz, 3H), 0.64 (d, J=7.0 Hz, 3H), δ (minor isomer 2yb) 7.59 (ddd, J=8.0, 0.9, 0.9 Hz, 1H), 7.50 (ddd, J=8.4, 7.2, 1.4, 1H), 7.09 (ddd, J=8.1, 7.1, 1.0 Hz, 1H), 5.76 (br s, 1H), 4.73 (ddd, J=10.9, 10.9, 4.4 Hz, 1H), 3.74 (s, 3H), 1.19 (sepd, J=7.0, 2.9 Hz), 0.86 (d, J=6.6 Hz, 3H), 0.52 (d, J=7.0 Hz, 3H), 0.44 (d, J=6.9 Hz, 3H) (Note: some protons could not be properly assigned due to extensive spectral overlap); $^{13}$C NMR (125 MHz, CDCl$_3$) δ 194.9, 194.7, 168.1, 168.0, 161.2, 160.9, 137.7, 137.6, 137.3 (2×), 128.1, 127.9, 126.2, 126.0, 125.4, 125.3, 122.1 (2×), 120.2 (2×), 120.0 (3×), 119.7 (3×), 113.7, 113.5, 110.1, 110.0, 109.6, 109.5, 77.4, 77.3, 72.8, 72.7, 46.7, 46.6, 40.3, 40.2, 34.1 (2×), 32.9 (2×), 31.4, 25.7, 25.4, 23.1, 23.0, 21.9, 20.8, 20.4, 15.9, 15.7 (Note: two carbon resonances could not be found due to extensive overlap); HRMS calc'd for C$_{28}$H$_{32}$N$_2$O$_3$ [M+H]$^+$445.2486, found: 445.2492.

Compounds 2za and 2zb:

(Method A) Isolated in 92% combined yield (2.7:1 ratio of 2za:2zb).

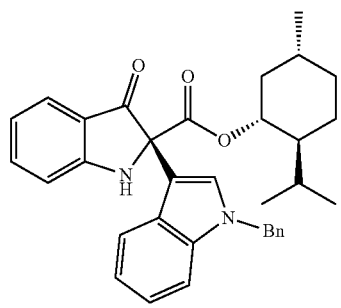 [SMILES: CC(C)[C@@H]1CC[C@@H](C)C[C@H]1OC(=O)[C@]1(c2cn(Cc3ccccc3)c3ccccc23)Nc2ccccc2C1=O]

Major diastereomer 2za (isolated as green needles from partial separation of mixture): R$_f$=0.42 (yellow spot, 7:3 hexanes:EtOAc); [α]$_D$$^{20}$: +23.76 (c=1.01, DCM); IR (cast film) cm$^{-1}$; $^1$H NMR (500 MHz, CDCl$_3$): δ 7.68 (d, J=7.8 Hz, 1H), 7.62 (d, J=8.8 Hz, 1H), 7.52 (ddd, J=8.3, 7.2, 1.3, 1H), 7.39 (s, 1H), 7.30-7.22 (m, 4H), 7.14 (ddd, J=8.2, 7.1, 1.1, 1H), 7.13-7.11 (m, 2H), 7.06 (ddd, J=8.1, 7.1, 1.0, 1H), 7.01 (d, J=8.2 Hz, 1H), 6.92 (app t, J=7.8 Hz, 1H), 5.66 (br s, 1H), 5.28 (app br s, 2H), 4.75 (ddd, J=11.0, 11.0, 4.4 Hz, 1H), 1.91-1.88 (m, 1H), 1.81 (sepd, J=7.0, 2.9 Hz, 1H), 1.66-1.61 (m, 2H), 1.45-1.39 (m, 2H), 1.03-0.96 (m, 1H), 0.88 (app td, J=12.2, 11.0 Hz, 1H) 0.87-0.70 (m, 1H), 0.84 (d, J=6.6 Hz, 3H), 0.81 (d, J=7.0 Hz, 3H), 0.62 (d, J=7.0 Hz, 3H); $^{13}$C NMR (125 MHz, CDCl$_3$) δ 194.8, 167.9, 161.0, 137.6, 137.1, 137.0, 128.8, 127.7, 127.6, 127.0, 126.3, 125.4, 122.3, 120.3, 120.2, 120.1, 120.0, 113.5, 110.7, 110.1, 77.4, 72.8, 50.3, 46.8, 40.2, 34.1, 31.4, 25.8, 23.2, 22.0, 20.7, 15.9; HRMS calc'd for C$_{34}$H$_{37}$N$_2$O$_3$ [M+H]$^+$521.2799, found: 521.2810.

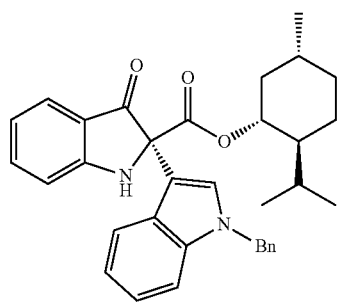 [SMILES: CC(C)[C@@H]1CC[C@@H](C)C[C@H]1OC(=O)[C@@]1(c2cn(Cc3ccccc3)c3ccccc23)Nc2ccccc2C1=O]

Minor diastereomer 2zb (partial assignment based on deduction, using spectra of mixture of diastereomers and spectra of major diastereomer; multiplicity of some peaks could not be properly assigned due to substantial overlap): $^1$H NMR (500 MHz, CDCl$_3$): δ 7.68 (d, J=7.8 Hz, 1H), 7.65 (d, J=7.6 Hz, 1H), 7.51 (ddd, J=8.4, 7.2, 1.3 Hz, 1H), 7.41 (s, 1H), 7.30-7.22 (m, 4H), 7.15 (app t, J=7.2 Hz, 1H), 7.12-7.11 (m, 3H), 7.02 (d, J=8.16 Hz, 1H), 6.92 (app t, J=7.8 Hz, 1H), 5.80 (br s, 1H), 5.28 (app br s, 2H), 4.72 (ddd, J=11.0, 10.9, 4.4 Hz, 1H), 1.95-1.92 (m, 1H), 1.66-1.55 (m, 2H), 1.47-1.33 (m, 2H), 1.15 (sepd, J=6.9, 2.9 Hz, 1H), 0.87 (d, J=6.6 Hz, 3H), 0.48 (d, J=7.0 Hz, 3H), 0.40 (d, J=6.9 Hz, 3H) (NB.: three protons in aliphatic region could not be properly assigned due to extensive spectral overlap); $^{13}$C NMR (125 MHz, CDCl$_3$) δ 194.5, 168.1, 161.2, 137.7, 137.2, 136.9, 128.8, 127.7, 127.4, 126.7, 126.5, 125.4, 122.3, 120.3, 120.2, 120.0, 113.7, 110.9, 110.1, 77.4, 72.7, 50.3, 46.7, 40.3, 34.1, 31.4, 25.5, 23.0, 22.0, 20.4, 15.7 (NB.: one resonance $^{13}$C was missing and could not be properly assigned due to extensive spectral overlap).

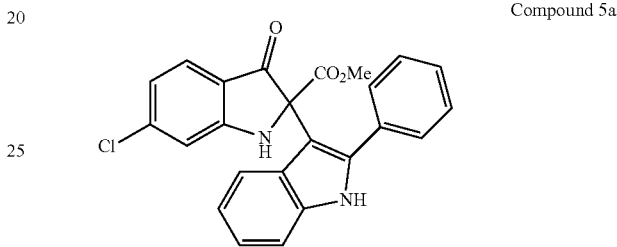

Compound 5a (Method A) Isolated as a bright yellow powder in 84% yield: m.p.=120° C. (dec.); R$_f$=0.32 (3:7, EtOAc:hexanes); IR(cast film) 3345, 3015, 2960, 1744, 1712, 1617, 1465, 1234, 733 cm$^{-1}$ $^1$H NMR (500 MHz, CDCl$_3$): δ 8.41 (s, 1H), 7.50 (d, J=8.3 Hz, 1H), 7.40-7.28 (m, 6H), 7.21-7.16 (m, 2H), 7.05 (app. t, J=7.7 Hz, 1H), 6.91 (d, J=1.5 Hz, 1H), 6.89 (dd, J=8.3, 1.7 Hz, 1H), 5.73 (s, 1H), 3.22 (s, 3H); $^{13}$C NMR (125 MHz, CDCl$_3$): δ 193.7, 168.5, 160.8, 144.3, 138.0, 135.4, 132.4, 129.5, 128.8, 128.3, 126.7, 126.1, 122.6, 121.0, 120.6, 119.4, 118.4, 113.0, 111.3, 107.5, 73.6, 53.2; HRMS calc'd for C$_{24}$H$_{17}$$^{35}$ClN$_2$NaO$_3$[M+Na]$^+$439.0822, found 439.0822.

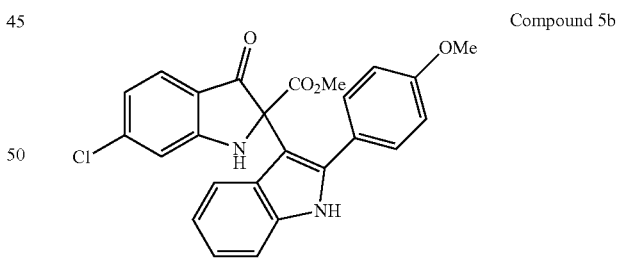

Compound 5b (Method A) Isolated as a bright yellow powder in 88% yield: m.p.=120° C. (dec.); R$_f$=0.17 (3:7, EtOAc:hexanes); IR (cast film) 3338, 3027, 2953, 1741, 1708, 1624, 1461, 1237, 747 cm$^{-1}$$^1$H NMR (500 MHz, CDCl$_3$): δ 8.20 (s, 1H), 7.52 (d, J=8.2 Hz, 1H), 7.33-7.30 (m, 3H), 7.19-7.15 (m, 2H), 7.03 (ddd, J=8.2, 7.2, 1.1 Hz, 1H), 6.94 (dd, J=1.7, 0.6 Hz, 1H), 6.89-6.85 (m, 3H), 5.63 (s, 1H), 3.82 (s, 3H), 3.31 (s, 3H); $^{13}$C NMR (125 MHz, CDCl$_3$): δ 193.7, 168.6, 160.8, 160.1, 144.3, 137.9, 135.3, 130.9, 126.8, 126.2, 124.7, 122.6, 121.0, 120.6, 119.4, 118.6, 113.8, 113.1, 111.2, 107.5, 73.6, 55.4; 53.4; HRMS calc'd for C$_{25}$H$_{20}$$^{35}$ClN$_2$O$_4$[M+H]$^+$ 447.1106, found 447.1105.

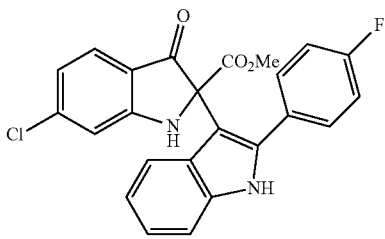

Compound 5c (Method A) Isolated as a bright yellow powder in 67% yield: m.p.=135° C. (dec.), $R_f$=0.21 (3:7, EtOAc:hexanes); IR(cast film) 3336, 3021, 2945, 1739, 1712, 1615, 1471, 1239, 749 cm$^{-1}$ $^1$H NMR (500 MHz, CDCl$_3$): δ 8.15 (s, 1H), 7.51 (dd, J=8.2, 0.6 Hz, 1H), 7.43-7.40 (m, 2H), 7.36 (d, J=8.0 Hz, 1H), 7.22-7.18 (m, 2H), 7.07-7.04 (m, 3H), 6.98 (dd, J=1.7, 0.5 Hz, 1H), 6.90 (dd, J=8.2, 1.7 Hz, 1H), 5.62 (s, 1H), 3.35 (s, 3H); $^{13}$C NMR (125 MHz, CDCl$_3$): δ 193.4, 168.5, 163.1 (d, J=249.5 Hz), 160.7, 144.5, 136.8, 135.4, 131.6 (d, J=8.3 Hz), 128.5, 126.7, 126.2, 123.0, 121.3, 120.9, 119.4, 118.6, 115.5 (d, J=21.7 Hz), 113.1, 111.2, 108.2, 73.4, 53.5; $^{19}$F NMR (469 MHz, CDCl$_3$): δ-111.7 (br s); HRMS calc'd for C$_{24}$H$_{17}$$^{35}$ClFN$_2$O$_3$ [M+H]$^+$435.0904, found 435.0906.

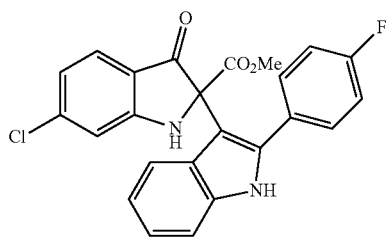

Compound 5d (Method A) Isolated as a bright yellow solid in 51% yield: m.p.=148° C. (dec.), $R_f$=0.30 (3:7, EtOAc:hexanes); IR(cast film) 3344, 3039, 2957, 1729, 1712, 1659, 1464, 1239, 731 cm$^{-1}$; $^1$H NMR (500 MHz, CDCl$_3$): δ 8.17 (br s, 1H), 7.48 (d, J=8.2 Hz, 1H), 7.47 (dd, J=7.0, 2.2 Hz, 1H), 7.37 (d, J=10.3 Hz, 1H), 7.32 (ddd, J=6.8, 4.6, 2.2 Hz, 1H), 7.27-7.21 (m, 2H), 7.13-7.07 (m, 2H), 7.01 (d, J=1.6 Hz, 1H), 6.91 (dd, J=8.3, 1.7 Hz, 1H), 5.66 (s, 1H), 3.48 (s, 3H); $^{13}$C NMR (125 MHz, CDCl$_3$): δ 193.2, 168.6, 163.0 (d, J=249.5 Hz), 160.4, 157.4, 144.6, 135.5, 135.2, 132.0, 129.5 (d, J=19.9 Hz), 129.4, 126.8, 126.1, 123.3, 121.5, 121.0, 119.3, 118.7, 116.6 (d, J=25.1 Hz), 113.2, 111.4, 108.9, 73.2, 53.6; $^{19}$F NMR (469 MHz, CDCl$_3$): δ-114.2 (br s); HRMS calc'd for C$_{24}$H$_{15}$Cl$_2$FN$_2$O$_3$Na [M+Na]$^+$491.0336, found 491.0334.

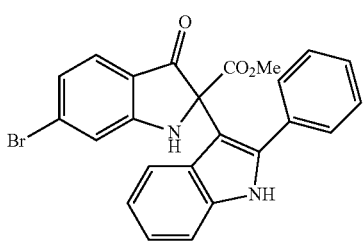

Compound 5e (Method A) Isolated as a bright yellow powder in 74% yield; m.p.=120° C. (dec.); $R_f$=0.32 (3:7, EtOAc:hexanes); IR(cast film) 3342, 3025, 2950, 1741, 1709, 1618, 1460, 1231, 733 cm$^{-1}$; $^1$H NMR (500 MHz, CDCl$_3$): δ 8.32 (s, 1H), 7.42 (d, J=8.3 Hz, 1H), 7.26-7.39 (m, 6H), 7.14-7.19 (m, 2H), 7.10 (d, J=1.5 Hz, 1H), 7.01-7.05 (m, 2H), 5.67 (s, 1H), 3.21 (s, 3H); $^{13}$C NMR (125 MHz, CDCl$_3$): δ 193.9, 168.4, 160.8, 138.0, 135.4, 133.3, 132.4, 129.5, 128.8, 128.4, 126.7, 126.2, 123.8 122.7, 120.6, 119.4, 118.8, 116.1, 111.3, 107.6, 73.5, 53.2. HRMS calc'd for C$_{24}$H$_{18}$BrN$_2$O$_3$ [M+H]$^+$461.0495, found 461.0501.

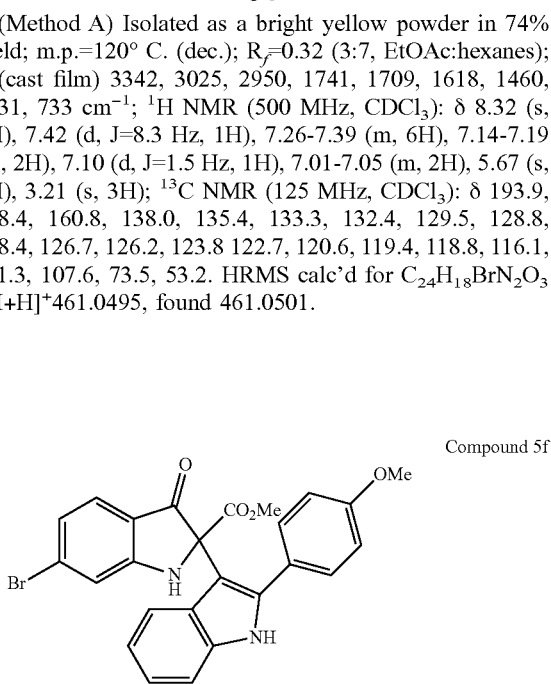

Compound 5f (Method A) Isolated as a bright yellow solid in 76% yield; m.p.=120° C. (dec.); $R_f$=0.32 (3:7, EtOAc:hexanes); IR(cast film) 3347, 3033, 2956, 1731, 1713, 1638, 1465, 1236, 713 cm$^{-1}$; $^1$H NMR (500 MHz, CDCl$_3$): δ 8.12 (br s, 1H), 7.46 (d, J=8.3 Hz, 1H), 7.26-7.12 (m, 3H), 7.19-7.14 (m, 3H), 7.05-7.03 (m, 2H), 7.02-6.88 (m, 2H), 5.59 (s, 1H), 3.83 (s, 3H), 3.32 (s, 3H); $^{13}$C NMR (125 MHz, CDCl$_3$): δ 193.9, 168.6, 160.8, 160.1, 138.0, 135.4, 133.3, 130.9, 126.8, 126.2, 124.7, 123.8, 121.0, 120.6, 119.4, 118.7, 116.1, 113.8, 111.2, 107.6, 73.5, 55.4, 53.4; FIRMS calc'd for C$_{25}$H$_{20}$$^{79}$BrN$_2$O$_4$ [M+H]$^+$491.0601, found 491.0605.

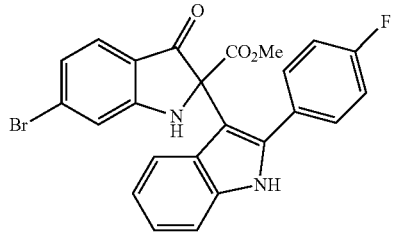

Compound 5g (Method A) Isolated as a bright yellow solid in 52% yield: m.p.=120° C. (dec.); $R_f$=0.32 (3:7, EtOAc:hexanes); IR(cast film) 3339, 3035, 2954, 1728, 1718, 1648, 1464, 1229, 728 cm$^{-1}$; $^1$H NMR (500 MHz, CDCl$_3$): δ 8.17 (br s, 1H), 7.46 (d, J=8.3 Hz, 1H), 7.26-7.12 (m, 3H), 7.19-7.14 (m, 3H), 7.05-7.03 (m, 2H), 7.02-6.88 (m, 2H), 5.59 (s, 1H), 3.32 (s, 3H); $^{13}$C NMR (125 MHz, CDCl$_3$): δ 193.7, 168.4, 163.1 (d, J=249.5 Hz), 160.7, 136.8, 135.4, 133.4, 131.6 (d, J=8.3 Hz), 128.5, 126.7, 126.2, 124.0, 123.0, 120.9, 119.4, 119.0, 116.2, 115.5 (d, J=21.6 Hz), 111.2, 108.1, 73.3, 53.5; $^{19}$F NMR (469 MHz, CDCl$_3$): δ-111.7 (br s); HRMS calc'd for C$_{24}$H$_{17}$$^{79}$BrFN$_2$O$_3$ [M+H]$^+$479.0402, found 479.0404.

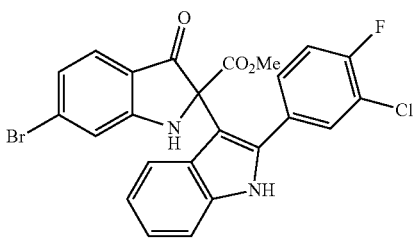

Compound 5h (Method A) Isolated as a bright yellow solid in 38% yield: m.p.=120° C. (dec.); $R_f$=0.30 (3:7, EtOAc:hexanes); IR(cast film) 3341, 3037, 2951, 1724, 1716, 1651, 1465, 1234, 737 cm$^{-1}$; $^1$H NMR (500 MHz, CDCl$_3$): δ 8.21 (br s, 1H), 7.46 (dd, J=7.0, 2.2 Hz, 1H), 7.40 (d, J=8.2 Hz, 1H), 7.35 (d, J=8.2 Hz, 1H), 7.30 (ddd, J=6.8, 4.5, 2.2 Hz, 1H), 7.24-7.20 (m, 2H), 7.19 (dd, J=1.5, 0.4 Hz, 1H), 7.11-7.06 (m, 3H), 5.66 (s, 1H), 3.48 (s, 3H); $^{13}$C NMR (125 MHz, CDCl$_3$): δ 193.2, 168.6, 163.0 (d, J=249.5 Hz), 160.4, 151.1, 142.0, 133.3, 133.2, 132.0, 129.5, 129.4 (d, J=19.9 Hz), 126.8, 126.1, 124.5, 123.2, 121.0, 119.3, 119.0, 116.6 (d, J=25.1 Hz), 116.3, 111.4, 108.9, 73.2, 53.6; $^{19}$F NMR (469 MHz, CDCl$_3$): δ -114.2 (br s); HRMS calc'd for C$_{24}$H$_{16}$$^{79}$Br$^{35}$ClFN$_2$O$_3$[M+H]$^+$ 513.0012, found 513.0015.

Virology Procedures

Cells and virus. Hep-2 cells were grown in Opti-MEM media supplemented with 2% fetal bovine serum (FBS), 1HAEo-cells were grown in MEM media supplemented with 10% FBS, and Hela cells grown in DMEM supplemented with 10% FBS. Infections were conducted using human RSV strain A2 or RSV-A2-GFP strain described previously [Hallak, L. K.; Spillmann, D.; Collins, P. L.; Peeples, M. E. J. Virol. 2000, 74, 10508-10513]. A549 cells and Vero cells were grown in DMEM supplemented with 10% FBS and used for experiments with ZIKV (Cambodia strain).

Structure activity relationship screens of antiviral activity. 1HAEo-cells were seeded at 80% confluency and incubated overnight. In SAR1 cells were preincubated with compounds for one hour at 20 μM prior to infection, followed by dilution to 10 μM and infection with RSV-A2-GFP at an MOI of 1 for 2 hours. In SAR2 1HAEo-cells were infected with RSV-A2-GFP at an MOI of 0.5 for 2 hours without pre-incubation with compounds. At 2 hours post infection, infectious media was removed from wells to prevent carry over of infecting virus into progeny collections. Fresh media containing compounds at 10 μM was added for remainder of 48 hour incubation. HeLa cells, used to titrate progeny virus, were plated at 80% confluency and incubated overnight. Progeny virus collected at 48 hours was immediately transferred to HeLa cells in duplicate technical replicates without dilution. At 2 hours post infection media was replaced with fresh compound-free media. Infection was stopped at 20 hours post infection, preventing cell to cell spread of virus, and infected cells were identified via indirect immunofluorescence assay.

Progeny virus quantification via indirect immunofluorescence. HeLa cells were fixed in 1:1 methanol:acetone, incubated with goat anti-RSV polyclonal antibody (Meridian Life Science B65860G) for 1 hour at room temperature, and then incubated with chicken anti-goat polyclonal antibody conjugated to Alexafluor 647 (LifeTech A-21469). Finally, cell nuclei were stained with DAPI. Total cells (identified by DAPI staining) and infected cells were counted via the Operetta high content imaging system at 20x objective magnification.

MTT cell viability assay. 1HAEo-cells were grown in parallel with infected and compound treated cells in SAR and dose response experiments. 0.3 mg/mL of MTT ((3-(4, 5-dimethylthiazol-2-yl)-2,5-diphenyl tetrazolium bromide)) in PBS was added to wells and incubated for 1 hour. Precipitate was dissolved in DMSO and absorbance was measured at 570 nm.

Cell extract-based in vitro inhibition of viral transcription. The protocol utilized to examine in vitro viral transcription was first developed for virus vesicular stomatitis virus [Canter, D. M.; Jackson, R. L.; Perrault, J. Virology 1993, 194, 518-529], and adapted for RSV as published previously [Noton, S. L.; Nagendra, K.; Dunn, E. F.; Mawhorter, M. E.; Yu, Q.; Fearns, R. J. Virol. 2015, 89, 7786-7798]. Briefly, HEp-2 cells were grown in 6 well plates overnight to approximately 80% confluence and infected with RSV A2 at an MOI of 5 for 1 hour before incubating overnight in fresh media. Immediately before cell lysis, cells were incubated in 2 μg/mL actinomycin D to block cellular transcription. Cells were lysed on ice via 1 minute treatment with lysolecithin, and cell extract was subsequently collected in transcription buffer containing 50 mM Tris-acetate at pH 8, 8 mM Mg acetate, 300 mM K acetate, 2 mM DTT, 1 mM spermidine, 10 mM creatine phosphatase, 1 μg/mL aprotinin, 16 U creatine phosphokinase, 1 mM each of ATP, GTP, and CTP, 50 μM UTP, and 2 μg/mL actinomycin D. Cell debris was removed via refrigerated centrifugation. In vitro transcription reaction was performed by combining soluble cell extract, additional transcription buffer, RNase Inhibitor, compound 28 diluted in DMSO, and 10 μCi [α 32-P] UTP, incubated at 30° C. for 3 hours. RNA extraction was performed with Qiagen RNeasy kit as per manufacturer protocol to purify samples, followed by hybridization with oligo(dT) to facilitate RNaseH digestion of mRNA transcript poly(A) tails. Denaturing electrophoresis of samples was performed using 4% acrylamide containing 7 M urea gels. Gels were dried and autoradiography captured during 4 day exposure. Viral RNA products were quantified by densitometry analysis following phosphorimaging (n=4).

Dose response experiments. 1HAEo-cells were infected as described, progeny virus collected, and tittered on HeLa cells in duplicate as described in SAR 2. During initial infection in 1HAEo-cells infectious media was replaced with media containing compounds at indicated concentrations at 2 hours post infection. Proportion of virus infected cells were quantified via indirect immunofluorescence assay.

Mutant escape assay. 1HAEo-cells were infected with RSV-GFP-A2 at an initial MOI of 0.1 and serial passaged over incubation periods of 48-72 hours. Samples were collected during passaging and stored in liquid nitrogen for tittering via indirect immunofluorescence assay. Ongoing low level viral infection during passaging was confirmed by identification of green fluorescence from GFP produced by the RSV-GFP in infected cells.

Zika Virus antiviral screen. Vero cells were pre-treated with bis(indole) compounds at 10 μM for 4 hours before infection with ZIKV at an MOI of 1. After 48 hour infection progeny ZIKV was collected, serial diluted over 6 logs, and transferred onto fresh Vero cell monolayers and incubated for 4 days. Vero cell monolayers were then fixed with 10% formaldehyde and stained with crystal violet; viral infection was quantified via plaque assay.

Results and Discussion

Conditions originally employed for the cascade process utilized 10 mol % Cu(hfacac)$_2$ and heating (toluene at reflux). Catalytic generation of copper metallocarbenes from diazoketone precursors is generally accepted to require the Cu(I) oxidation state, necessitating in situ reduction of the starting Cu(II) salt by added reductant or a sacrificial quantity of the diazo substrate. Once tthe C-acylimine was formed, it was considered that nucleophilic trapping involved activation of the imine nitrogen atom by either Cu(I) or unreduced Cu(II). Using substrate 1a and indole as the trap, only moderate yields of the desired adduct 2a were observed under standard conditions, complicated by varying amounts of the regioisomer resulting from Friedel-Crafts trapping at C-2 (Table 1, entry 1). Attempts to improve selectivity by reducing reaction temperature were not fruitful, providing only traces of 2a after 24 h, which was attributed to slow production of catalytically competent Cu(I) (entry 2). Cu(OTf).PhCH$_3$ in DCM at rt afforded 2a in only 12% yield, although 1a was consumed quickly (Table 1, entry 3). In contrast, use of 10 mol % Cu(OTf)$_2$ required extended stirring in DCM at rt, but ultimately provided 2a in 92% yield (Table 1, entry 4), and these conditions were scalable (Table 1, entry 5). Induction time was consistent with a pre-activation step to generate CuOTf, but the high yield in this case (in contrast to entry 3) suggested a requirement for another component besides Cu(I) to attain efficient production of indole adduct 2a.

Figure 2:
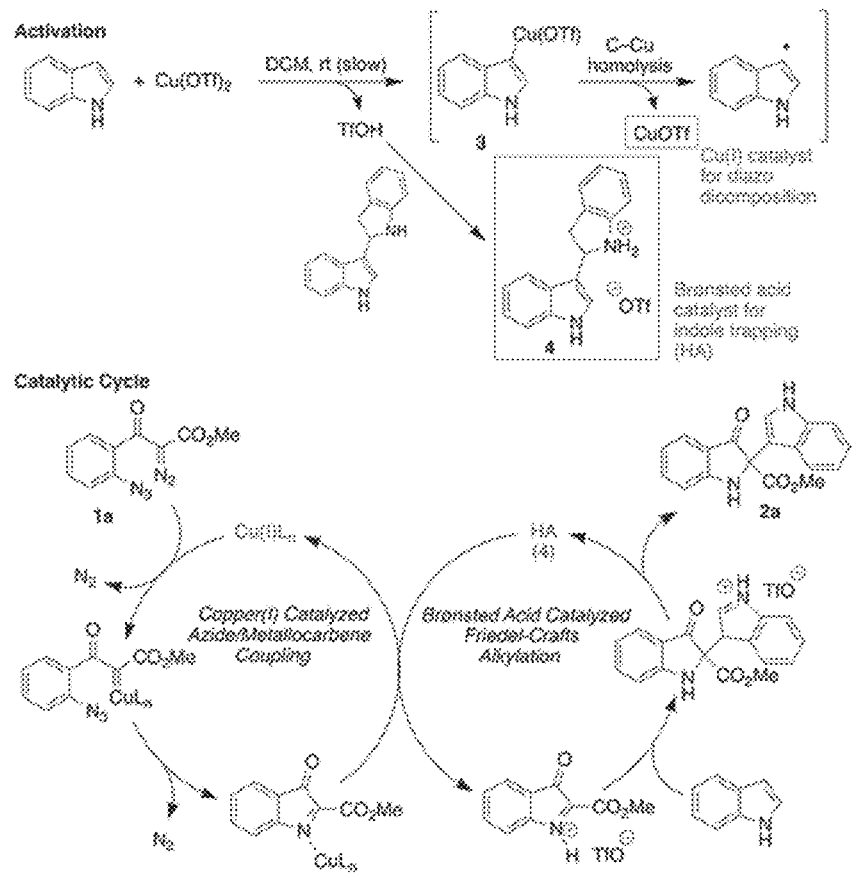
FIG. 2 depicts redox activation of Cu(OTf)$_2$ and dual catalysis.

Species responsible for reduction of Cu(OTf)$_2$ was not clear. As noted above, diazo compounds are known to play this role, but the presence of excess indole suggested an alternative possibility. Gaunt and co-workers have shown that direct C-3 arylation of indoles can be accomplished using catalytic Cu(OTf)$_2$, involving C-3 cupration of the indole by a Cu(III) intermediate, ArCu(OTf)$_2$, which is formed via CuOTf insertion to an aryliodonium salt [Phipps, R. J.; Grimster, N. P.; Gaunt, M. J. *J. Am. Chem. Soc.* 2008, 130, 8172-8174]. In the present context, it was considered that indole C-3 cupration by Cu(OTf)$_2$ could form organocopper(II) complex 3, which could furnish CuOTf through hemolytic cleavage of the weak C—Cu bond (See FIG. 2). Alternatively, it was considered that disproportionation of 3 with another molecule of Cu(OTf)$_2$ would afford the required CuOTf along with a Cu(III) complex. It was noted that 1a was recovered unconsumed after stirring for 72 h at rt in the presence of Cu(OTf)$_2$ in the absence of indole (Table 1, entry 6), whereas 1a was rapidly consumed to give mostly uncharacterizable products when stirred at rt with CuOTf.PhCH$_3$. Thus, it was considered that Cu(I) may be necessary for consumption of the diazo substrate, and that the diazo compound was not sufficient for reduction of Cu(II), at least at rt. Copper(0) was ineffective at catalyzing the process (Table 1, entry 7), and other solvents gave results inferior to those using DCM (Table 1, entries 8-10). Use of a lower reaction temperature (Table 1, entry 11) or addition of a bidentate bis(oxazoline) ligand (Table 1, entry 12) suppressed consumption of 1a.

One equivalent of the strong Bronsted acid TfOH was produced along with each equivalent of CuOTf, and its presence appeared to be required for clean trapping by indole to furnish 2a. Thus, while treatment of 1a with 10 mol % CuOTf.PhMe gave minor amounts of 2a despite complete consumption of starting material (Table 1, entry 3), when 10 mol % Cu(OTf)$_2$ was pretreated with 0.2 equiv indole and stirred for 2 h (green solution) then added to a solution of 1a and 1.8 equiv indole, 2a was obtained in 83% yield. The exact nature of the Bronsted acid catalyst responsible for indole addition was unclear, but the indolylindoline triflate salt 4 was considered a feasible candidate. This dimeric product is readily formed from indole in the presence of Bronsted or Lewis acid and various electrophilic reagents, and evidence for its formation was observed during the indole/copper(II) redox process (see Example 2). Overall, the cascade process was considered to involve a dual catalytic cycle involving Cu(I)-catalyzed conversion of 1a to the cyclized indolen-3-one intermediate, followed by Bronsted acid activation of the imine (and concomitant turnover of Cu(I)) for Friedel-Crafts alkylation of indole to afford 2a (see FIG. 2).

Figure 3:
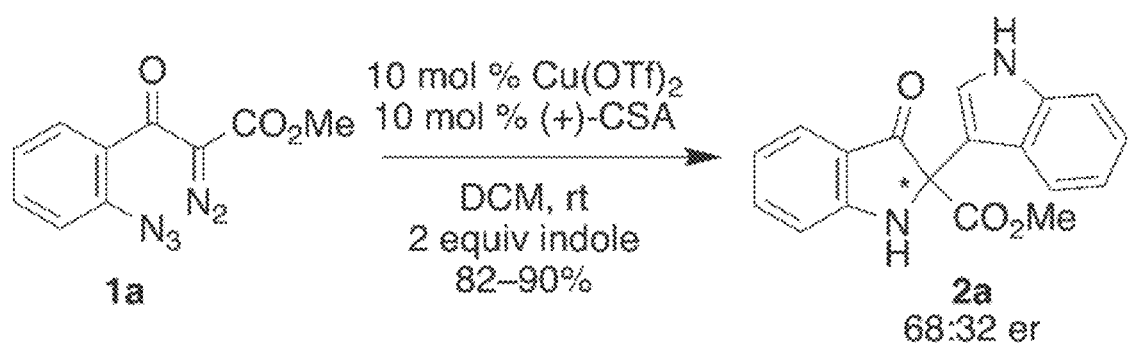
FIG. 3 depicts asymmetric induction by chiral Bronsted acid.

Direct involvement of Bronsted acid in the indole addition step is borne out by the observation of an enantiomeric excess of 36% when the reaction was carried out in the presence of (+)-camphorsulfonic acid (see FIG. 3). In this case, it was assumed that (+)-CSA competes effectively with the indolinium triflate Bronsted acid to catalyze indole trapping with asymmetric induction occurring via the chiral counterion. The modest enantiomeric excess may arise from a competing racemic background process, or from weak asymmetric induction by the camphorsulfonate.

Figure 4:
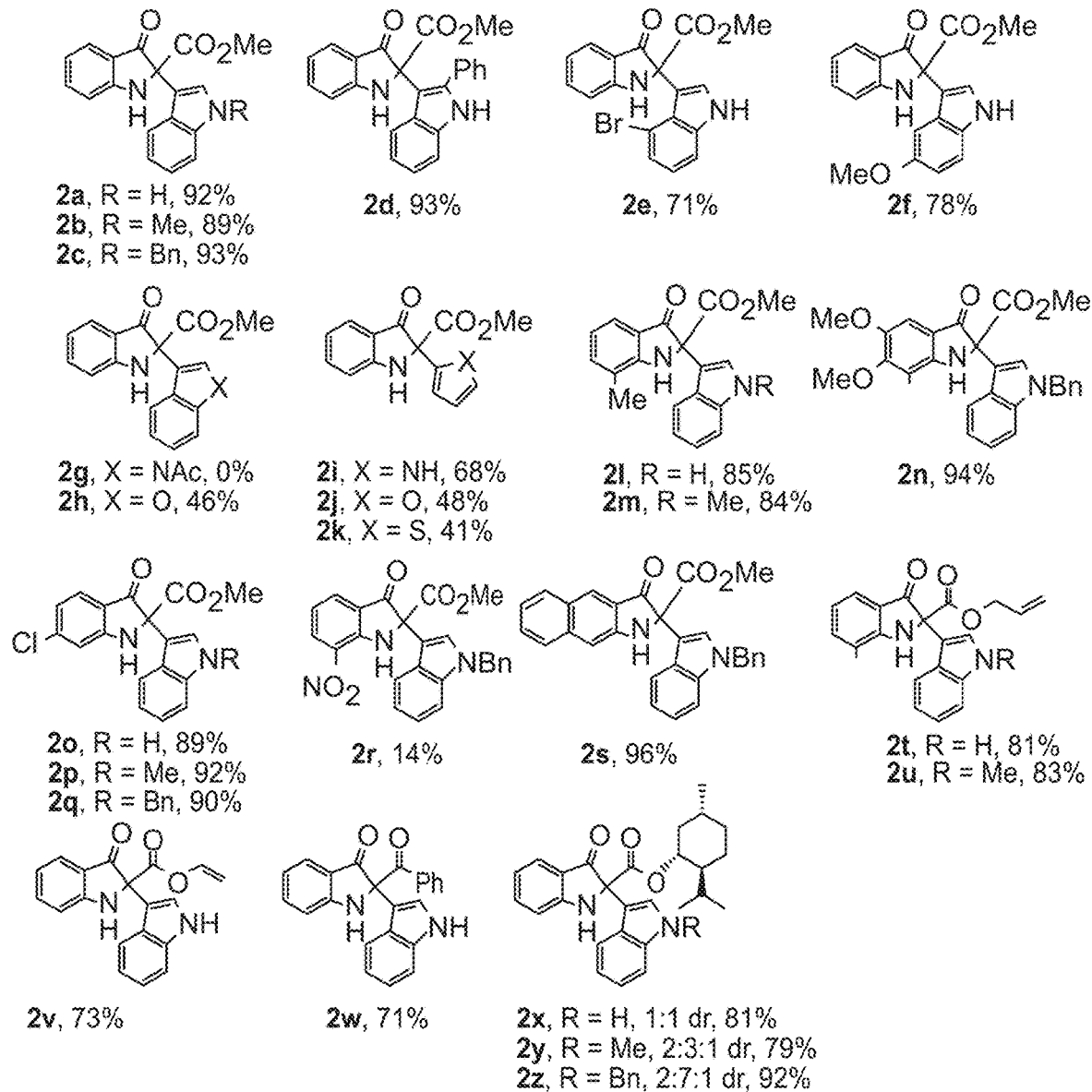
FIG. 4 depicts an extension of coupling conditions to other 2-Indolylindolin-3-ones.
Figure 4:
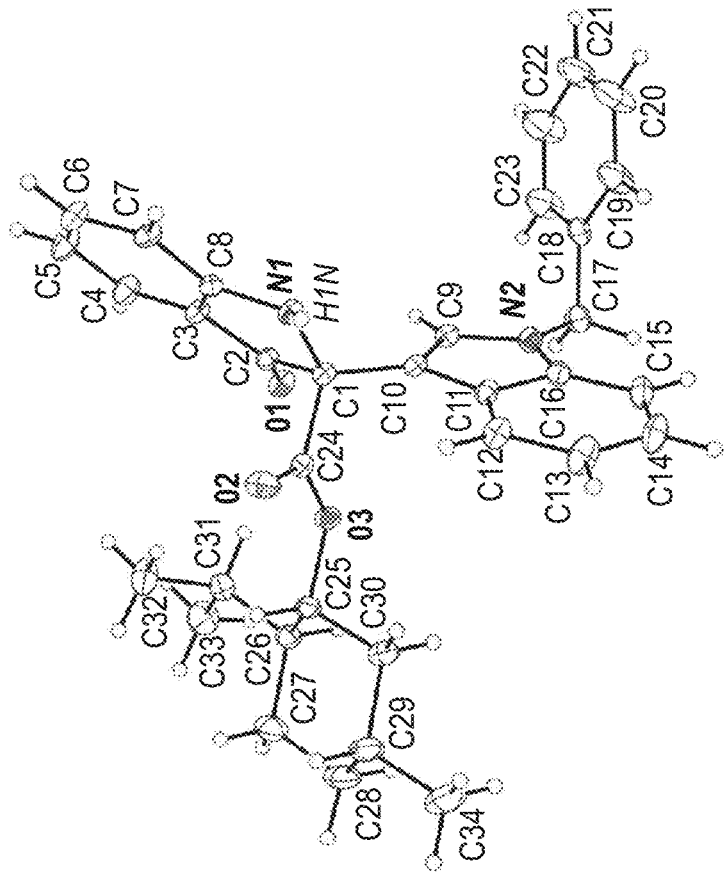
Figure 4:
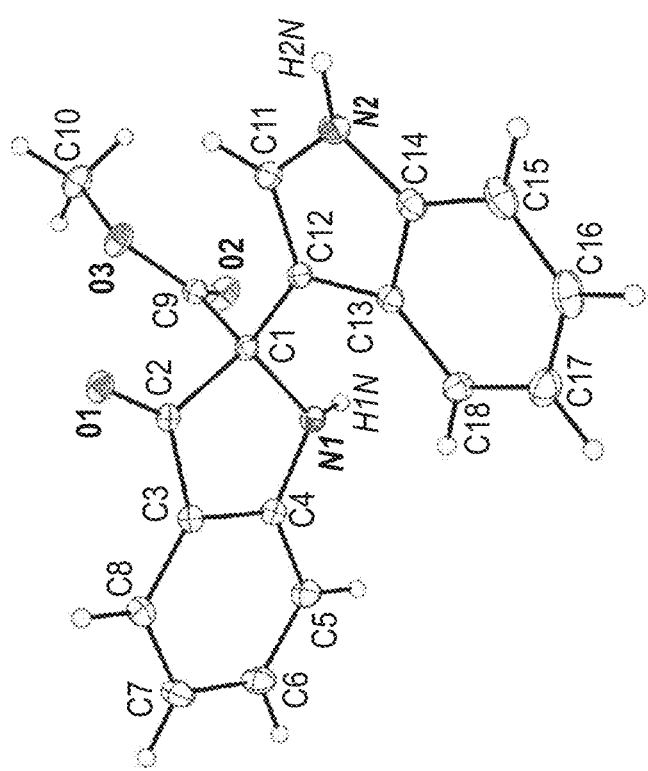

To test the scope of the dual catalytic process, other indole derivatives with varying steric and electronic properties were subjected to the optimal reaction conditions (see FIG. 4). Use of a simple N-methyl or an N-benzyl protected indole as a trap did not appear to significantly affect the reaction rate, and adducts 2b and 2c were produced in excellent yields. The presence of a bulky substituent at C-2 position of the indole did not appear to impede the C-acylimine trapping process, as exemplified by formation of 2d in high yield (93%) over the standard reaction time. Consistent with the proposed electrophilic metalation activation mechanism, 4-bromoindole was compatible with the reaction conditions and produced 2e in reasonable yield, albeit with a longer reaction time (>24 h) than when an unsubstituted indole was used. Electron-rich 5-methoxyindole produced 2f in good yield and in a relatively short reaction time. Other types of heteroaromatics such as pyrrole, thiophene, furan and benzofuran were amenable to the reaction conditions and afforded adducts 2h-k in moderate yields, although heating the reaction mixture to reflux was required to drive the reaction to completion. Deactivated N-acylindoles were found to be unreactive (e.g., no formation of 2g).

Effects of substitution on the diazoazide partner were also examined. Substitution with an electron donating methyl or methoxy group gave better yields of adducts 21-n (84-94%) than the electron-withdrawing nitro group (2o, 14% along with 68-76% recovered starting material). The presence of halogen substituent (chloro) meta to the azide or extending the aromatic system were tolerated, furnishing adducts 2p-s in good yields. Allyl, vinyl, or menthyl esters adjacent to the diazo group were tolerated, as was phenyl ketone, affording 2t-2z in good to excellent yields.

Figure 5:
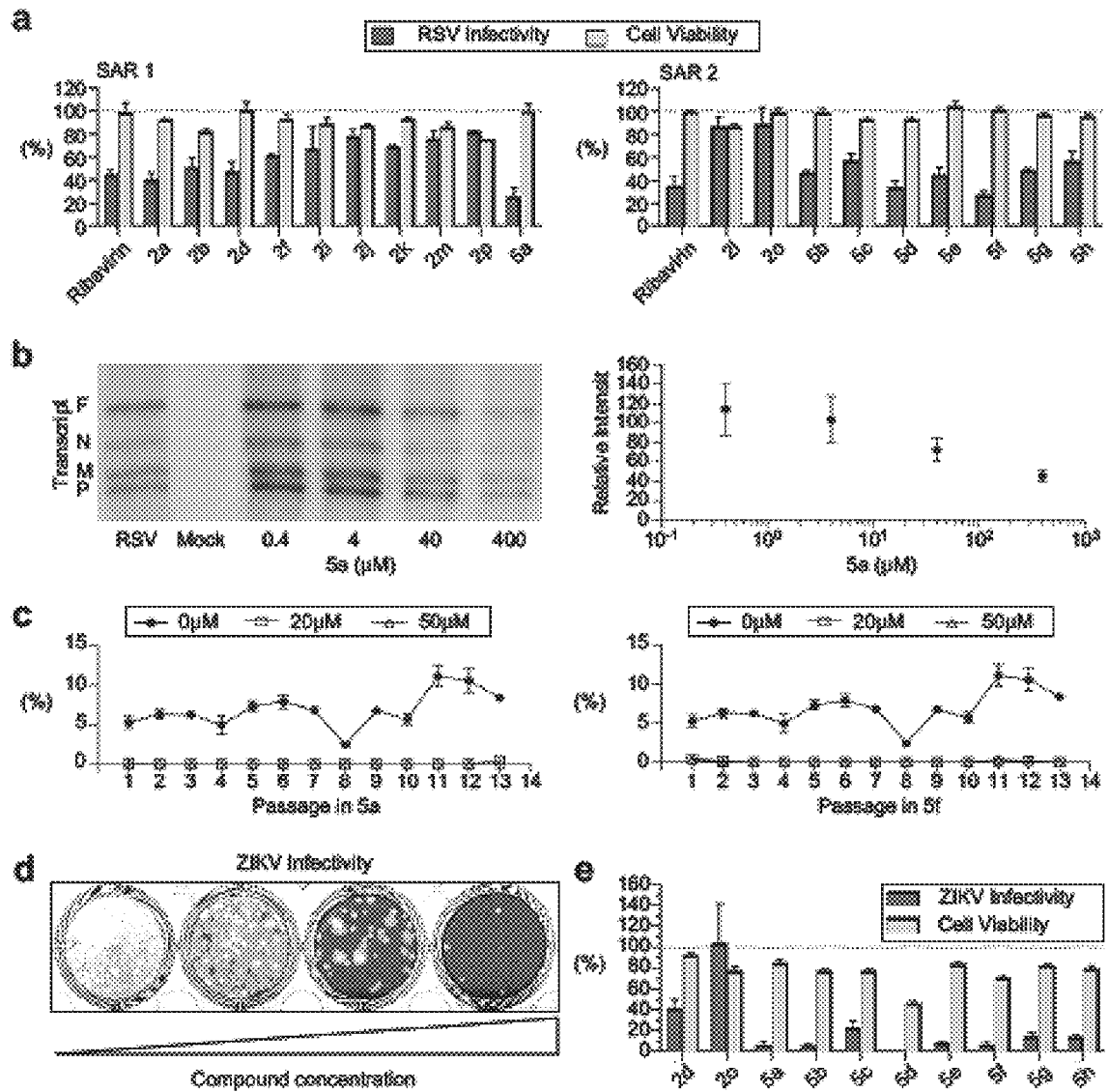
FIG. 5 depicts infectivity and cytotoxicity results.
Figure 6:
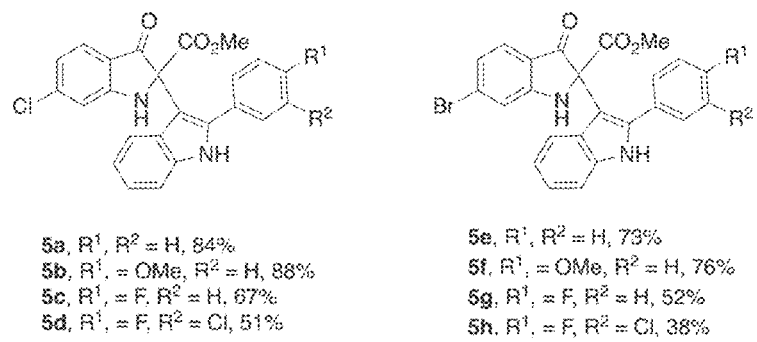
FIG. 6 depicts a series of second generation 2-Indolylindan-3-ones.

With rapid access to a library of truncated isatasine A analogues available, their potential antiviral activity against RSV was investigated. An initial library consisting of a select group of the compounds depicted in FIG. 4 and one new compound 5a (SAR 1) was screened at 10 μM concentration in cultured human airway epithelial cells (1HAEo-) cells for both antiviral activity and cytotoxicity (see FIG. 5*a*: screening for inhibition of RSV infection and cell viability as a measure of compound toxicity in the presence of indicated compounds at 10 μM concentration; 1HAEo-bronchial airway cells were infected with RSV; inoculum media was removed and media containing compounds at 10 μM was added 2 hours after infection; two days after infection progeny virus produced by the 1HAEo-cells was collected and Hela indicator cells were infected; percentage of virus infected HeLa cells was determined by indirect immunofluorescence the following day). From this initial group, compound 5a was identified as a promising candidate, displaying antiviral activity comparable to that of the known antiviral guanosine-analogue drug ribavirin, with no cytotoxicity. This result guided the selection of compounds for a second focused library (SAR 2), several examples of which included 2-aryl substitution at the 2-position of the indole nucleophile, and from which several compounds with improved antiviral activity and minimal toxicity were identified (see FIG. 6 for structures of 5a-h).

While numerous fusion inhibitors for RSV have been identified, including the prophylactic monoclonal antibody Palivizumab, they have yet to translate into therapy for the treatment of established RSV infections. This may be due to the nature of Palivizumab targeting only the entry step of the viral replication cycle. Therefore inhibiting the RSV replication complex after RSV has entered a cell was considered a desirable mechanism of action to block the spread of existing infection. To elucidate a mechanism of antiviral activity, root antiviral compound 5a was assayed for activity against the RSV viral replication complex that serves as a marker of RSV replication in the host cell. Decreasing viral transcription from the RSV replication complex was observed in a dose dependent manner in the presence of compound 5a in vitro (see FIG. 5b: (Left) in vitro RSV transcription was inhibited by compound 5a; one day after RSV infection 1HAEo-cells were lysed in transcription buffer containing $^{32}$P labelled uridine; viral transcripts for RSV Fusion (F), Nucleoprotein (N), Matrix (M) and Phospho (P) proteins were separated on a sequencing gel and the signal was measured after 3-5 days of exposure; (Right) results for 4 independent experiments).

To further assess the therapeutic potential of compounds identified in SAR 1 and SAR 2, a therapeutic index (TI) of each compound was identified (e.g., ratio of effective concentration at which viral replication is reduced by half (EC50) to cytotoxic concentration at which cell viability is reduced by half (CC50)). Compound 2p was included as a cytotoxicity control, having demonstrated cytotoxicity in SAR 1. Cell viability decreased rapidly with increasing concentration of compound 2p, with a CC50 value of 22.8 µM, while viral replication was not diminished at compound concentrations tolerated by the host cell. In contrast, compound 5a and the 5 series of compounds derived from 5a consistently inhibited viral replication at concentrations tolerated by the host cell. In SAR 2, addition of OMe at $R^1$ decreased the toxicity of these compounds, with CC50 values increasing from 42.5 µM for compound 5a, to 59.2 µM and 93.5 µM for compounds 5b and 5f respectively. Overall, the TI was increased from 4.1 for compound 5a to 12.3 with compound 5f. These increases in TI suggested that the compounds were capable of interfering with viral replication at concentrations tolerated by the host cell.

An established challenge to development of antiviral pharmaceuticals is the evolution of antiviral resistance. This is pronounced for viruses with RNA genome due to an inherent error-prone process of RNA-dependent RNA polymerase replication of a viral genome. Error prone replication results in a high mutation rate of RNA viruses that leads to development of antiviral resistance. As such, development of resistant mutants to compounds 5a and 5f was undertaken, as the site of mutations could provide further insights into the nature of the viral target. However, despite development of resistance against other transcription inhibitors in 6-8 passages, 14 serial passages over five weeks did not result in the development of viruses resistant to either compound (see FIG. 5c: no resistance emerged during serial passage of RSV in compounds 5a and 5f; 1HAEo-cells infected with RSV; two hours after infection inoculum media were removed and replaced with media containing compound 5a or 5f; two to three days after infection, the progeny virus was collected from the cells and transferred onto a new 1HAEo-monolayer; an aliquot was stored in liquid nitrogen for quantification via indirect immunofluorescence). This may suggest that the burden of resistant mutations to evade these compounds is too great, reducing RSV virulence due to mutagenic catastrophe.

ZIKV constitutes a virus distinct from RSV with a markedly different intracellular replication strategy. Both viruses encode a viral RdRp essential to viral replication; however, the structure and function of RSV RdRp and ZIKV RdRp are quite different. RSV is a Pneumoviridae family virus with a negative sense RNA genome, and hence RSV RdRp must be packaged with an infecting virion for transcription to occur. RSV polymerase recognizes cis-acting 'gene start' and 'gene end' elements of the viral genome to produce subgenomic mRNAs enabling translation of viral proteins. In contrast, ZIKV is a Flaviviridae family virus having a positive sense RNA genome. Therefore, the ZIKV genome can be directly translated into one large viral polyprotein by host ribosomes without a need for production of viral subgenomic mRNAs. Thus the primary function of ZIKV RdRp is to facilitate genome replication through a negative sense antigenome intermediate. As RSV and ZIKV represent taxonomically distinct viruses, antiviral activity of the isatisine A-inspired bis(indole) compounds were examined against ZIKV to determine whether their antiviral activities may be broadly acting. ZIKV infection was screened in the presence of compounds 2d, 2o, 5a, and 5a derivatives (5b-5h) in VERO cells. Significant inhibition of ZIKV by compound 5a and all 5a derivatives was observed (see FIGS. 5d and e: screening for inhibition of ZIKV infection and cell viability as a measure of compound toxicity at 10 µM; A549 cells were infected with ZIKV; inoculum media were removed and media containing the compounds at a concentration of 10 µM were added four hours after infection; progeny virus was collected and quantified on Vero cells by titering plaque assay, n=3). These data suggested that compound 5a and derivatives may hold broad spectrum antiviral activity, providing a broader array of root compounds from which lead compounds can be developed.

As such, a dual catalytic cascade process was discovered that rapidly assembles drug-like bis(indole) scaffolds under mild, convenient conditions whose only by-products are 2 equiv of N2. Indole trapping agents served to activate a Cu(OTf)$_2$ precatalyst, while also producing a Bronsted acid catalyst required for Friedel-Crafts alkylation of indoles by the intermediate C-acylimines. Preliminary experiments demonstrated that added chiral acids afforded moderate enantioselectivity. Some of the bis(indole) products showed promising antiviral activity against important pathogens RSV and ZIKV. The modular nature of the synthetic transformation may allow for the development of improved analogues against these and other undesirable pathogens.

TABLE 1

Survey of Reaction Conditions

| Entry | Conditions | Yield (%) 2a |
|---|---|---|
| 1 | 10 mol % Cu(hfacac)$_2$; PhMe; reflux | 42[a] |
| 2 | 10 mol % Cu(hfacac)$_2$; PhMe; rt | trace |
| 3 | 10 mol % CuOTf·PhMe; DCM; rt | 12[b] |
| 4 | 10 mol % Cu(OTf)$_2$, DCM, rt, 24 h | 92 |
| 5 | as above, gram-scale | 83 (74)[c] |
| 6. | 10 mol % Cu(OTf)$_2$, DCM, rt, no indole, 72 h | 0 |
| 7 | 10 mol % Cu(0) powder, DCM, rt | NR |
| 8 | 10 mol % Cu(OTf)$_2$, PhMe, rt, 24 h | 26 |
| 9 | 10 mol % Cu(OTf)$_2$, Et$_2$O, rt, 24 h | trace |
| 10 | 10 mol % Cu(OTf)$_2$, CHCl$_3$, rt, 24 h | 68[d] |
| 11 | 10 mol % Cu(OTf)$_2$, DCM, 0° C., 24 h | trace |
| 12[e] | 10 mol % Cu(OTf)$_2$, L*, PhMe, rt, 24 h | trace |

[a]Product isolated as a mixture of regioisomers.
[b]1a was rapidly consumed with formation of multiple colored products.
[c]Gram-scale reaction with direct recrystallization of crude product.
[d]Multiple colored products were observed.
[e]L* = bis(oxazoline) ligands shown above.

Example 2

Figure 7:
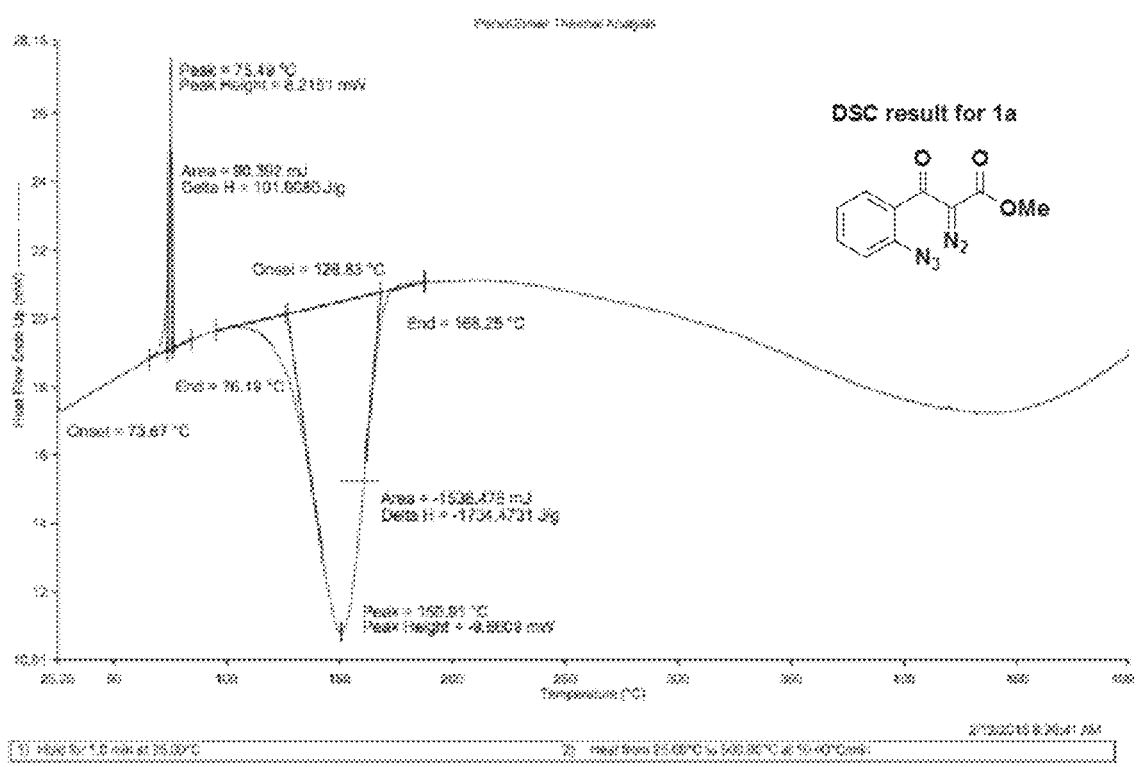

Further Experimental Details on Dual Catalytic Synthesis of Antiviral Compounds Based on Metallocarbene-Azide Cascade Chemistry Compound Stability Studies Differential Scanning calorimetry (DSC): An example of a DSC experiment for compound 1a is depicted in FIG. 7. These data show the temperature at which crystals of 1a began to melt (endotherm, positive peak, 75.5° C.) and began to decompose (exotherm, negative peak, 127° C. to 168° C.). Heat released after decomposition was about 1730 J/g material.

Figure 8:
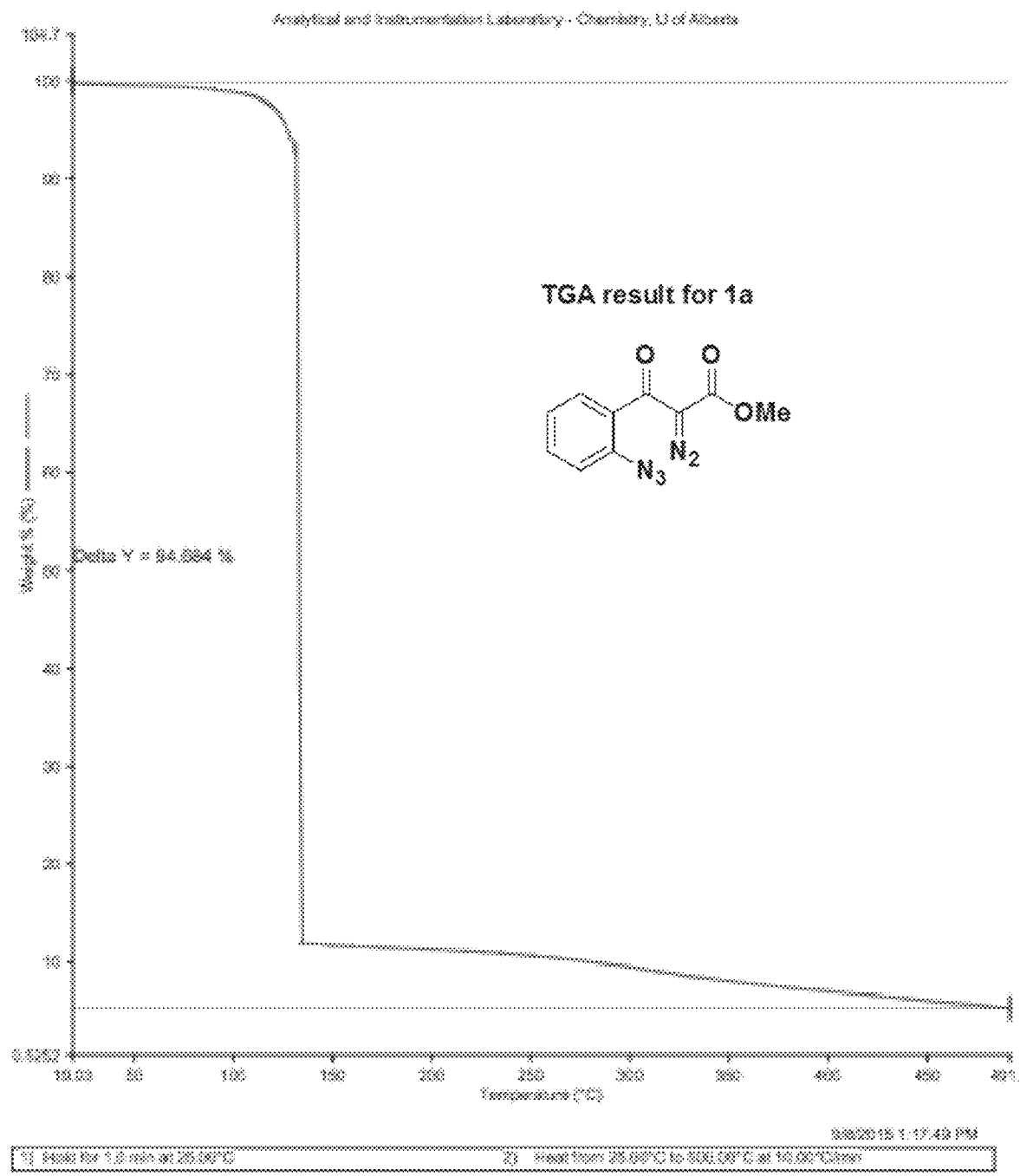

Thermogravimetric analysis (TGA): The decomposition pattern was further monitored using a TGA experiment. An example of a TGA experiment for compound 1a is shown in FIG. 8. It was found that dicarbonyl stabilized diazo crystals of 1a generally exhibited one sharp inflection point, starting at temperatures around 130° C., in agreement with the DSC experiment. No substantial mass change was noticed during the solid to liquid phase transition, indicative of no decomposition of material during melting phase transition.

Both of these experiments shed some light on the thermal stability of 1a. These experiments provided evidence that the metal catalyzed transformation, associated with the starting material 1a, at ambient temperature (22° C. to 40° C.), described in the next section (vide infra), was not merely heat driven as the starting material 1a was stable at this temperature range. Moreover, using the DSC data, it was anticipated that there would be less risk of detonation, due to thermal runaway, associated with compound 1a, or analogous diazoazides, provided the material was stored at freezer temperature (<0° C.) when not in use. Long-term storage (>1 week) is generally not advisable for compound 1a, especially for a large-scale preparation, but it was noticed that compound 1a and the other analogues survived with little or no decomposition during storage at freezer temperature (−20° C.) for >3 months (monitored weekly using $^1$H NMR).

These experiments (DSC and TGA) alone should not, however, be taken as an indication that the material is completely safe for handling. Other parameters, for example potential shock sensitivity, are equally important. Attempts to carry out a hammer test for compound 1a (ca. 0.5 mg) to evaluate its shock sensitivity were inconclusive. A small spark was observed, but in the absence of a reliable benchmark, it was not possible to draw any conclusions regarding the shock sensitivity of 1a. Similar to other common potentially explosive materials used in organic synthesis laboratories, such as peroxides, it is cautioned to potential users to treat the starting material 1a and analogues with due care and respect. Any unanticipated detonation of these diazo azide starting materials was not observed, and most large-scale reactions involving these substrates were performed in a well-ventilated fume hood equipped with a blast shield. It is recommended to wear a Kevlar® apron and safety gloves and using earplugs as added safety precautions, especially for large-scale reactions.

Mechanistic Considerations

Copper Oxidation State in the Catalytic Cycle

Conversion Studies (% Recovery):

Copper (II) oxidation state:

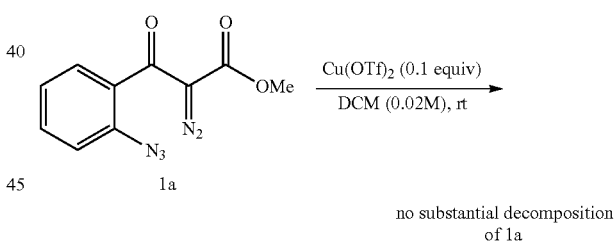

no substantial decomposition of 1a

A solution of diazo-azide 1a (50 mg, 0.20 mmol) in DCM (5 mL) was added to a solution of Cu(OTf)$_2$ (7.3 mg, 0.020 mmol) in DCM (5 mL) at room temperature via syringe pump over 1 h. Once addition was complete, the reaction was monitored by TLC for consumption of the diazo-azide starting material. After 24 h, the solution was extracted with water (10 mL, 3×) to remove the copper salt, and the DCM solution was dried with MgSO$_4$, filtered and concentrated under reduced pressure. The crude oil was purified using silica gel flash column chromatography eluting with 20% EtOAc/Hexanes. This procedure resulted in recovery of diazo-azide 1a, in 81-93% (three repeats). Using identical conditions but allowing the mixture to stir for 5 d instead of 24 h resulted in recovery of 73-84% (three repeats) starting material 1a. Analysis of TLC and NMR spectra of the crude mixture revealed the presence of starting material, and a faint spot on the baseline using 20% EtOAc/Hexanes as the eluent (TLC).

Copper (I) Oxidation State:

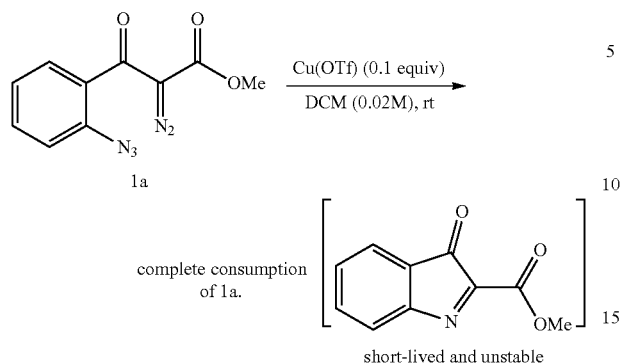

short-lived and unstable

A solution of diazo-azide 1a (50 mg, 0.20 mmol) in DCM (5 mL) was added to a solution of Cu(OTf)(PhMe) (10 mg, 0.020 mmol) in DCM (5 mL) at room temperature via syringe pump over 1 h. Once addition was complete, the reaction was monitored by TLC for consumption of the diazo-azide starting material. After 24 h, the solution was extracted with water (10 mL, 3×) to remove the copper salt, the DCM solution was dried with MgSO$_4$, filtered and concentrated under reduced pressure. The crude oil was purified using silica gel flash column chromatography eluting with 20% EtOAc/Hexanes. This procedure resulted in recovery of trace amount of 1a (<5%). Analysis of a TLC chromatogram of the crude mixture revealed the presence of multiple colored spots. A crude NMR spectra revealed an intractable mixture of multiple compounds.

Conversion Studies (in-Situ IR Analysis and $^1$H-NMR Spectroscopy)

Copper (II) Oxidation State:

Using IR Spectroscopy:

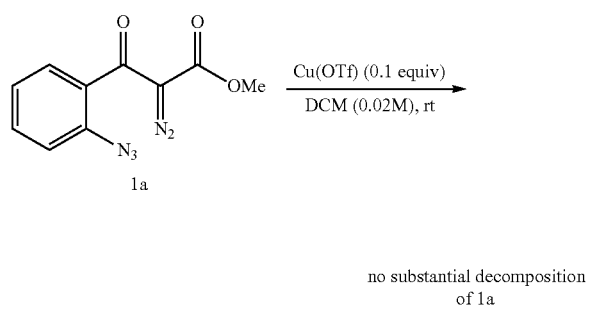

no substantial decomposition of 1a

Figure 9A:
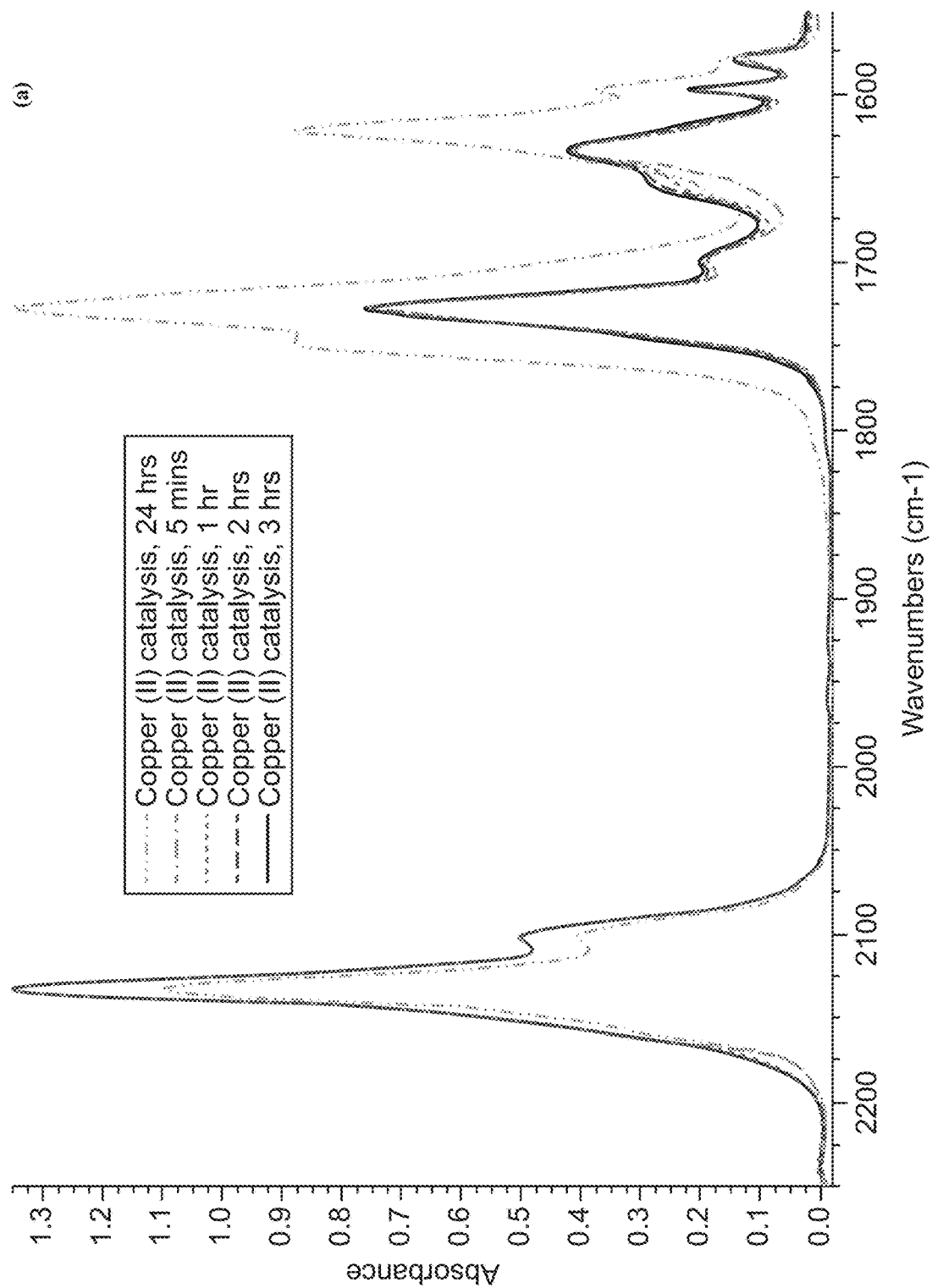
Figure 9:
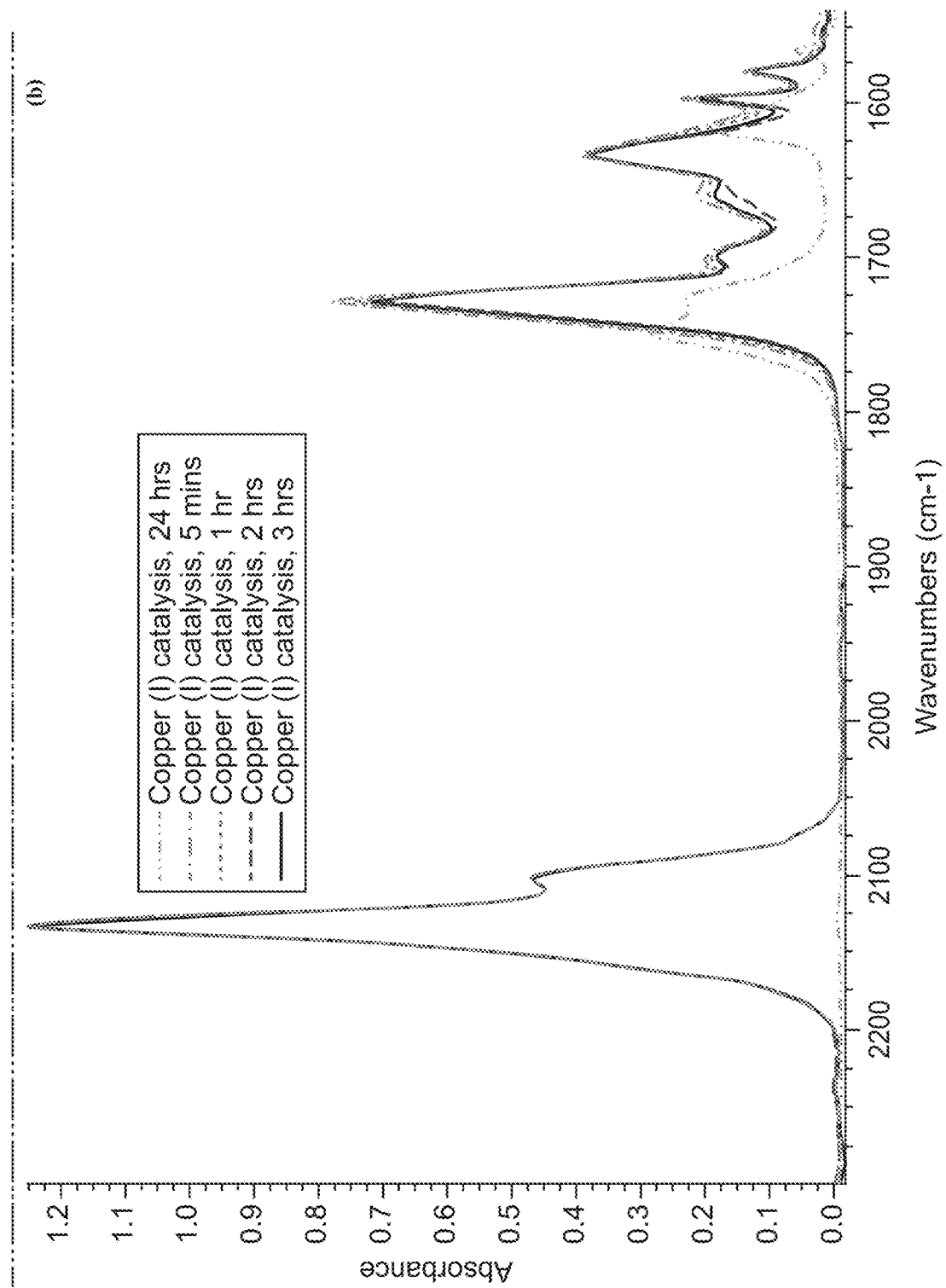

A solution of diazo-azide 1a (50 mg, 0.20 mmol) in DCM (5 mL) was added to a solution of Cu(OTf)$_2$ (7.6 mg, 0.02 mmol) in DCM (5 mL) at room temperature via syringe pump over 1 h. Once addition was complete, the reaction was monitored by TLC for consumption of the diazo-azide starting material. An aliquot of the stirred solution (0.5 mL), was taken after ca. 5 min, 1 h, 2 h, 3 h, and 24 h of stirring, each aliquot was diluted with DCM (1 mL). The diluted solution was analyzed using IR spectroscopy and plotted as overlaid spectra (FIG. 9a).

Copper (I) Oxidation State:

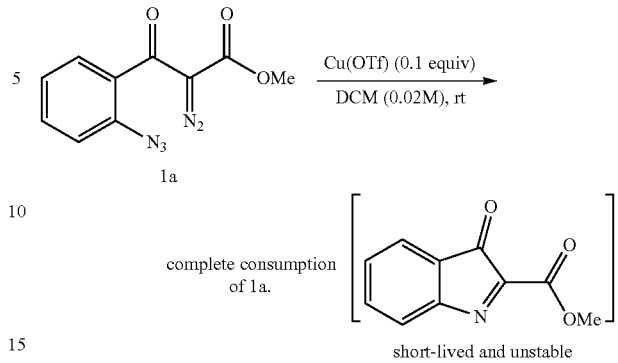

short-lived and unstable

A solution of diazo-azide 1a (50 mg, 0.20 mmol) in DCM (5 mL) was added to a solution of Cu(OTf)(PhMe) (10 mg, 0.020 mmol) in DCM (5 mL) at room temperature via syringe pump over 1 h. Once addition was complete, the reaction was monitored by TLC for consumption of the diazo-azide starting material. An aliquot of the stirred solution (0.5 mL), was taken after ca. 5 min, 1 h, 2 h, 3 h and 24 h of stirring, each aliquot was diluted with DCM (1 mL). The diluted solution was analyzed using IR spectroscopy and plotted as overlaid spectra (FIG. 9b).

A complete absence of a broad peak at 2137 cm$^{-1}$ indicated complete decomposition of the diazoketone and the azide functional groups. An increase in the absorbance and broadening of signal around 1730 cm$^{-1}$ was noticed on diazo-azide starting material upon exposure with copper (II) triflate over 24 h, indicative of carbonyl interaction (dative bond) with copper (II), which did not progress to substantial diazo-ketone decomposition (notice continued substantial absorbance at 2137 cm-1). However, a notable decrease in the absorbance of the signal around 2137 cm$^{-1}$ was noticed on diazo-azide starting material upon exposure with copper (I) triflate over 24 h, indicative of complete decomposition of diazoketone and azide over a 24 h period. This time period is within the observed optimized reaction time (16-36 h, depending on substitution of indole substrate) for azide-metallocarbene coupling, followed by Friedel-Crafts alkylation with indole. This pair of experiments, together with the recovery analysis, and $^1$H-NMR spectroscopy (vide infra) provided a distinction between the catalytic behaviors of the two copper oxidation states.

Using $^1$H-NMR Spectroscopy:

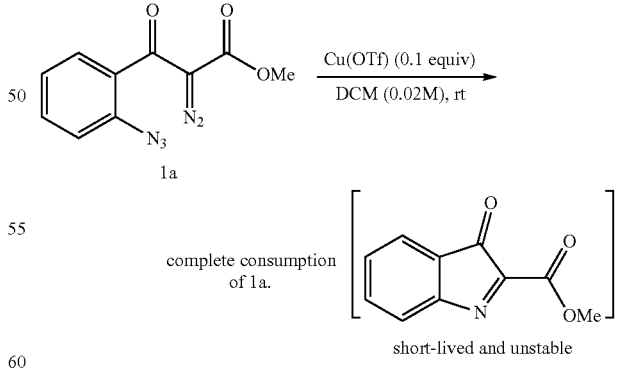

short-lived and unstable

Figure 10:
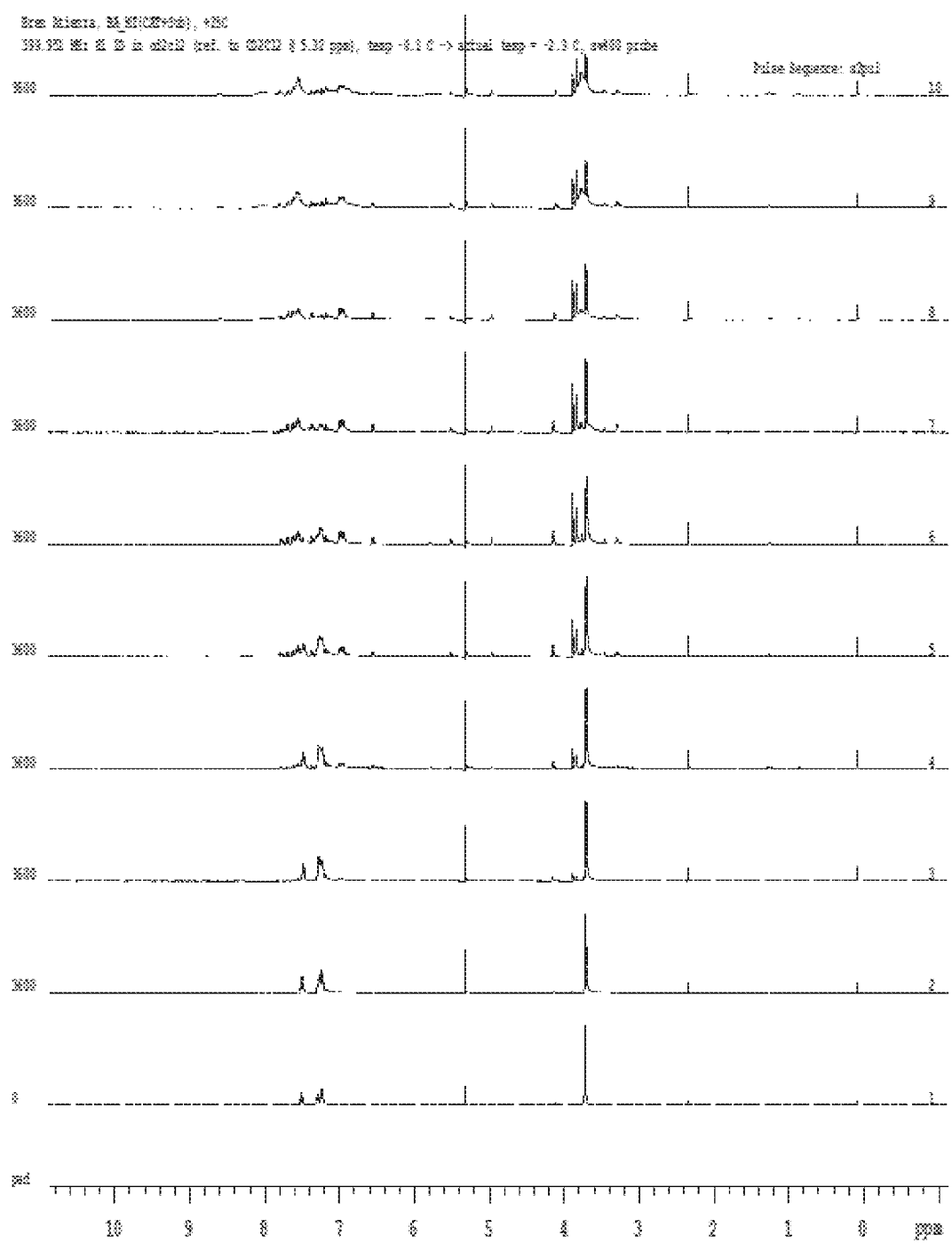
FIG. 10 depicts decomposition analysis of compound 1a, in the presence of Cu (I) catalyst, using NMR.

In a 2.0 mL vial, a solution of diazo-azide 1a (10 mg, 0.040 mmol) in deuterated DCM (0.5 mL) at room temperature was added to Cu(OTf)(PhMe) (ca. 2.0 mg, 0.0039 mmol) as a solid. The solution was quickly transferred in an NMR tube, capped with septum, and purged with argon. NMR spectra (400 MHz) were acquired once per hour over a 10 h period. The array of spectra was plotted. After 8-10 h, the starting material 1a was completely consumed. These data, corroborated with the IR results, provided evidence that copper (I) was the kinetically competent oxidation state during conversion of diazoazide into C-acylimine (see FIG. 10).

After extensive analysis of the copper oxidation state necessary for decomposition of starting material 1a, it was posited that copper (I) was the kinetically competent oxidation state. This, however, was not expected since the initially loaded catalyst was copper (II) triflate.

Formation of Active Copper (I) Catalyst from Copper (II) Precatalyst

Using UV Spectroscopy, Formation of a New σ-Copper Indole Complex:

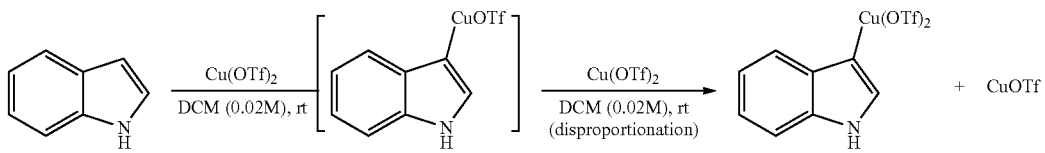

Figure 11:
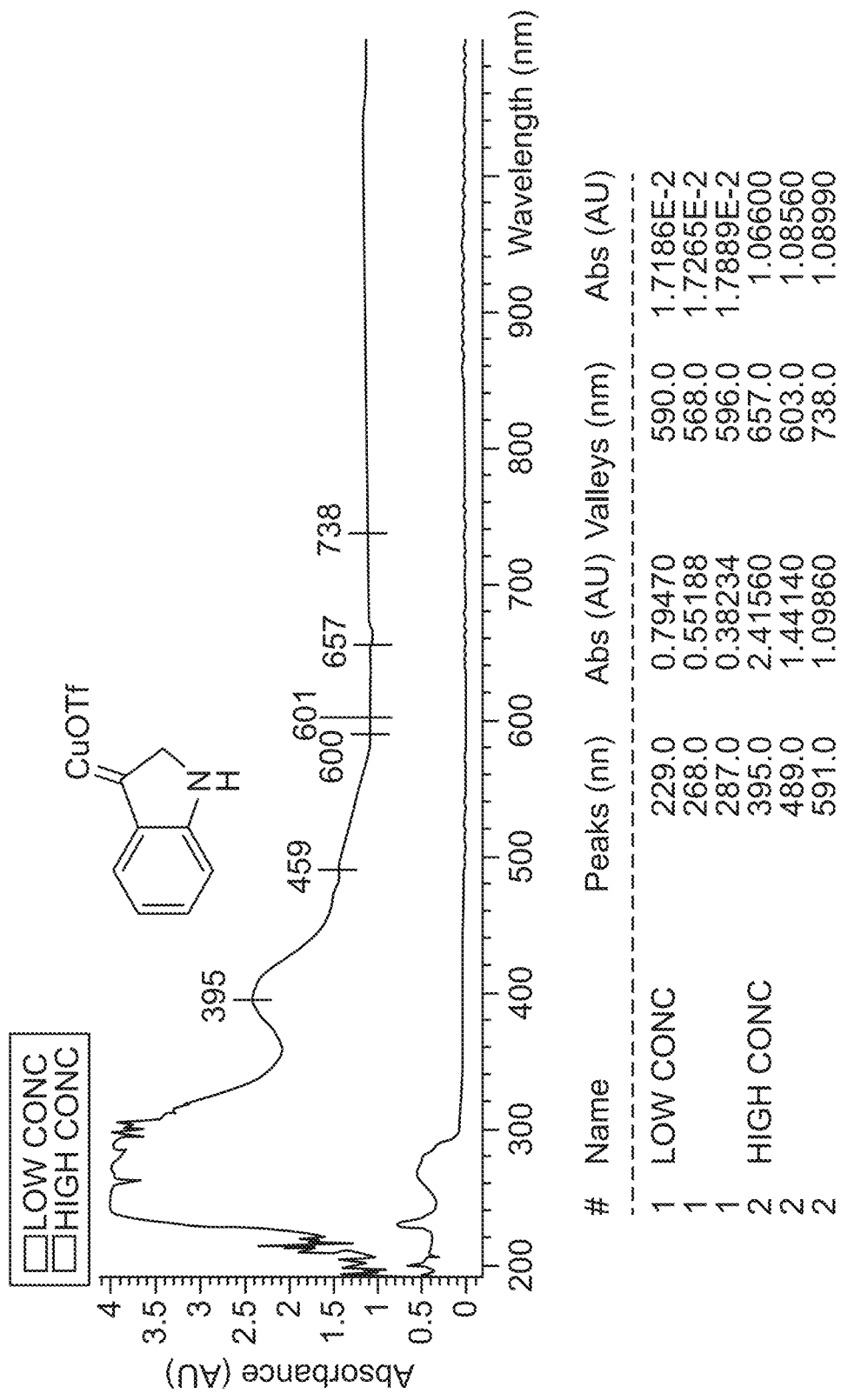
FIG. 11 depicts UV-VIS spectra of solution A (Example 2)

Solution A: A solution of indole (55 mg, 0.20 mmol) was added to Cu(OTf)$_2$ (7.3 mg, 0.020 mmol) in DCM (5 mL) at room temperature. Once addition was complete, formation of light green solution occurred after 1 h. An aliquot of this solution (1 mL) was diluted with 5 mL of DCM and was subjected to UV spectroscopy. Solution B: An aliquot (1 mL) of a solution of indole dissolved in DCM (0.02 M, 10 mL) at room temperature was also subjected to UV spectroscopy. Solution C: An aliquot (1 mL) of a solution of Cu(OTf)$_2$ dissolved in DCM (0.02 M, 10 mL) at room temperature was also subjected to UV spectroscopy. Further dilution was necessary until peaks (>300 nm) could be seen. After analysis of the three spectra, formation a broad new peak at 395 nm was seen from Solution A, indicating formation of a new colored complex (FIG. 11). This new peak at 395 nm did not persist and generally had low relative concentration. Hence, a concentrated reaction mixture was needed to observe the absorption at 395 nm. Notably, similar copper-indole species was detected by Toste et. al. upon mixing of Cu(II) chiral phosphate and indole [Rauniyar, V.; Wang, Z. J.; Burks, H. E.; Toste, F. D. *J. Am. Chem. Soc.* 2011, 133, 8486-8489].

Using ESI-MS, Detection of the Mass Fragments Corresponding to the Ddimer and the Copper-Indole Complex:

Primary reaction:

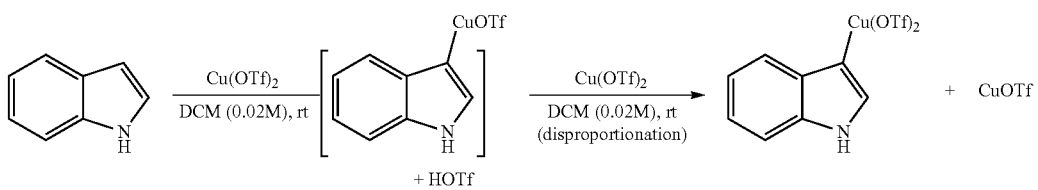

Possible pathway to dimer:

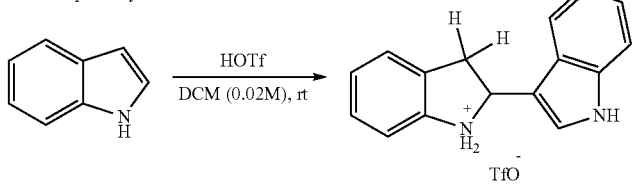

(mass detected in crude reaction)

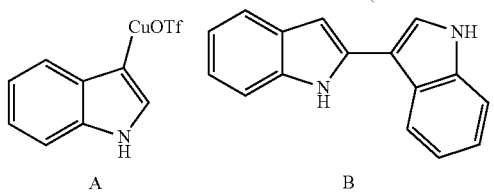

A        B

Figure 12:
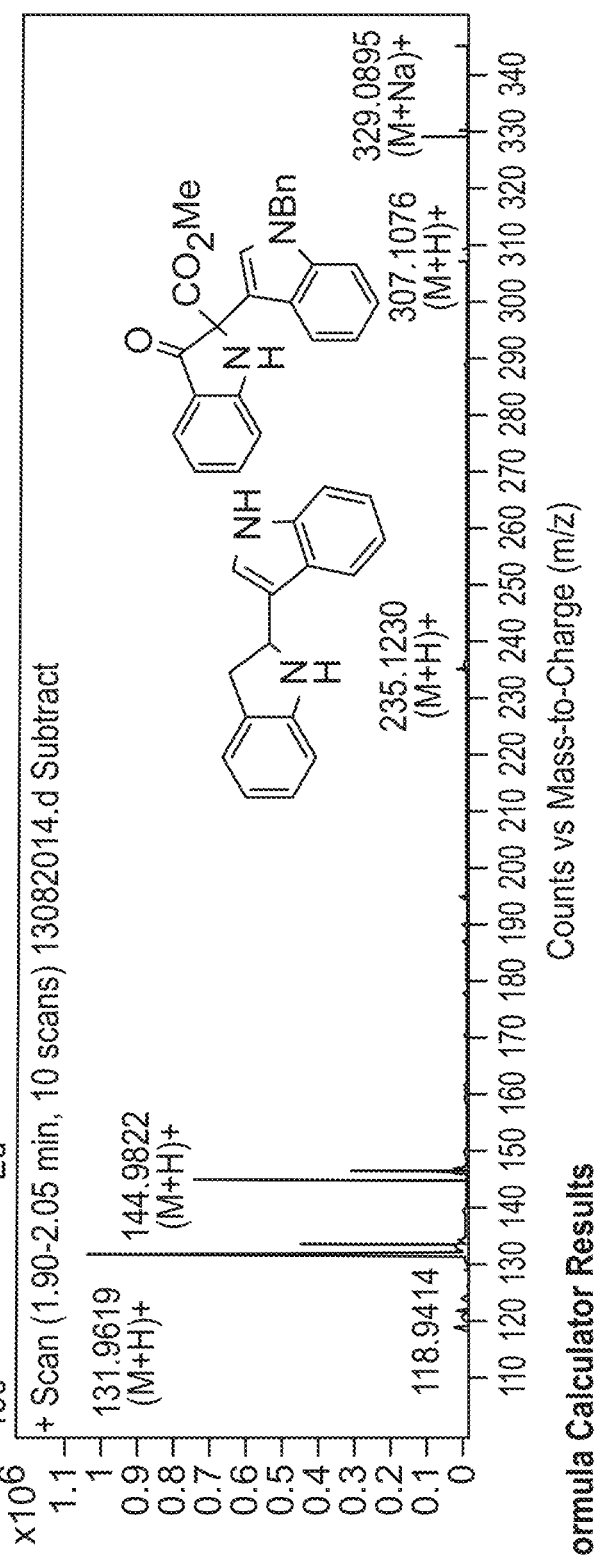
Figure 13:
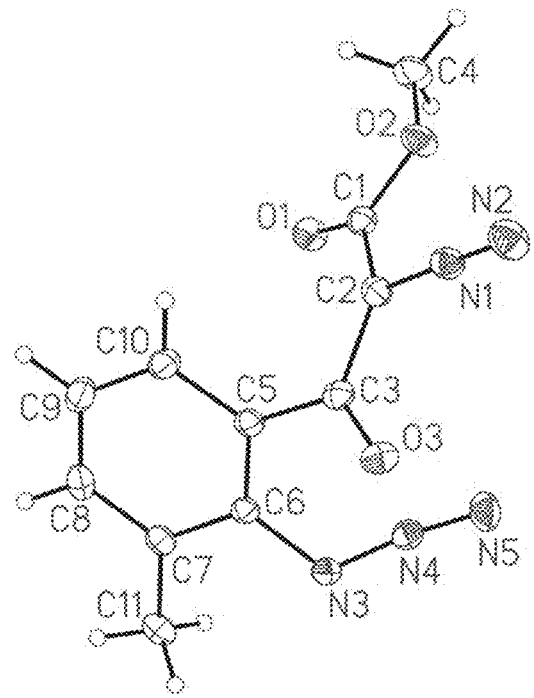
Figure 14:
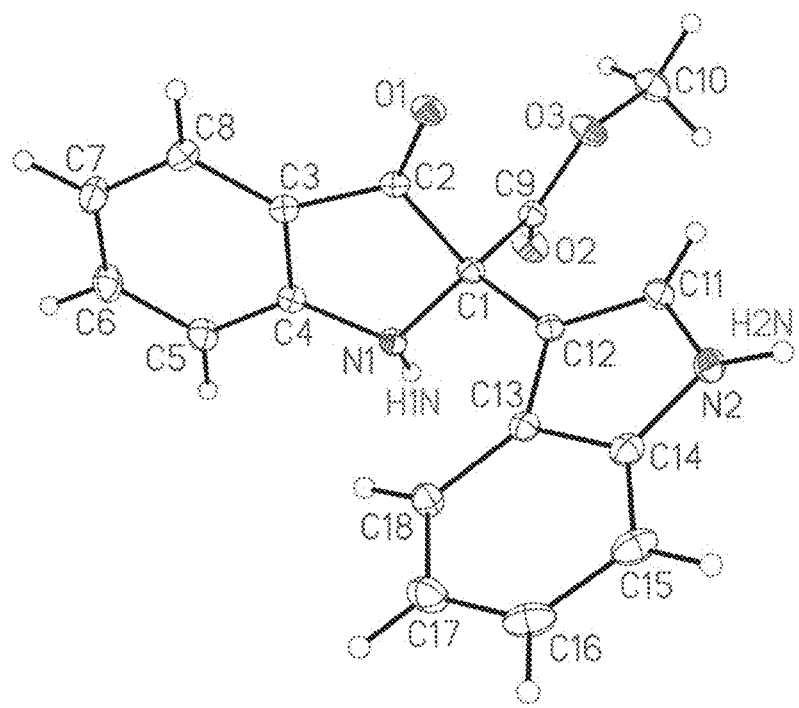
Figure 15:
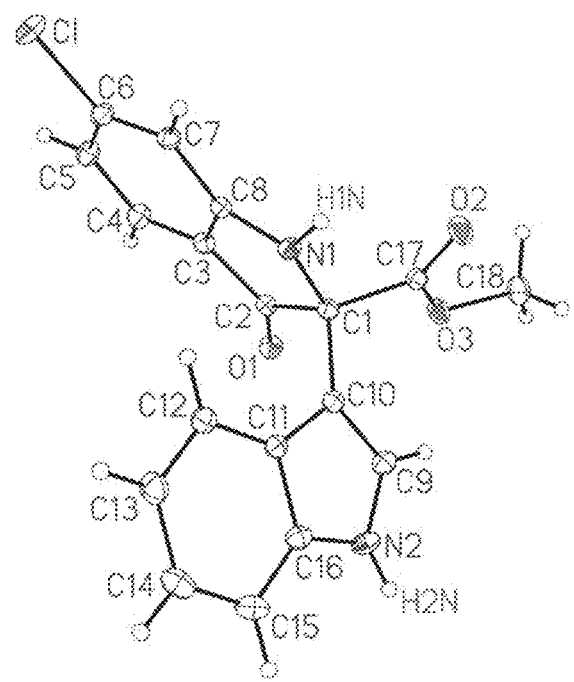
FIG. 15 depicts an ORTEP structure for compound 2o.
Figure 16:
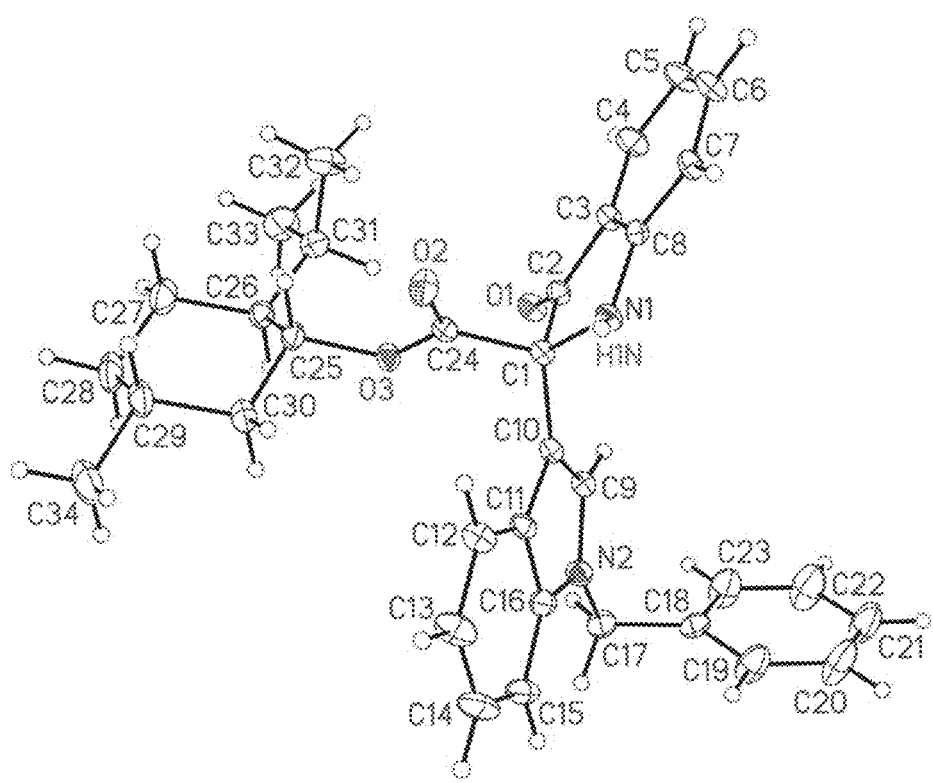
FIG. 16 depicts an ORTEP structure for compound 2za.
Figure 17:
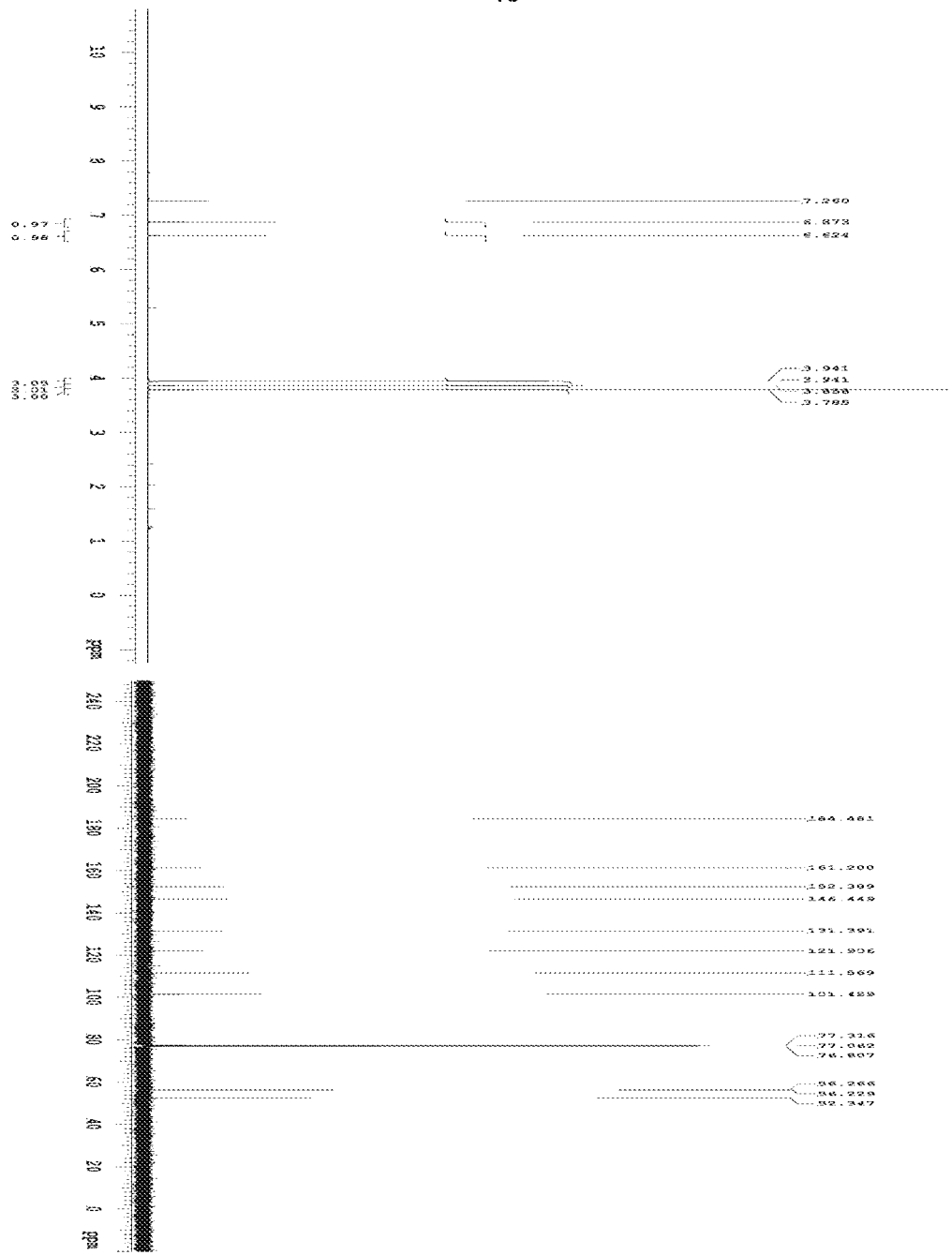
FIG. 17 depicts an NMR spectrum of compound 1c.
Figure 18:
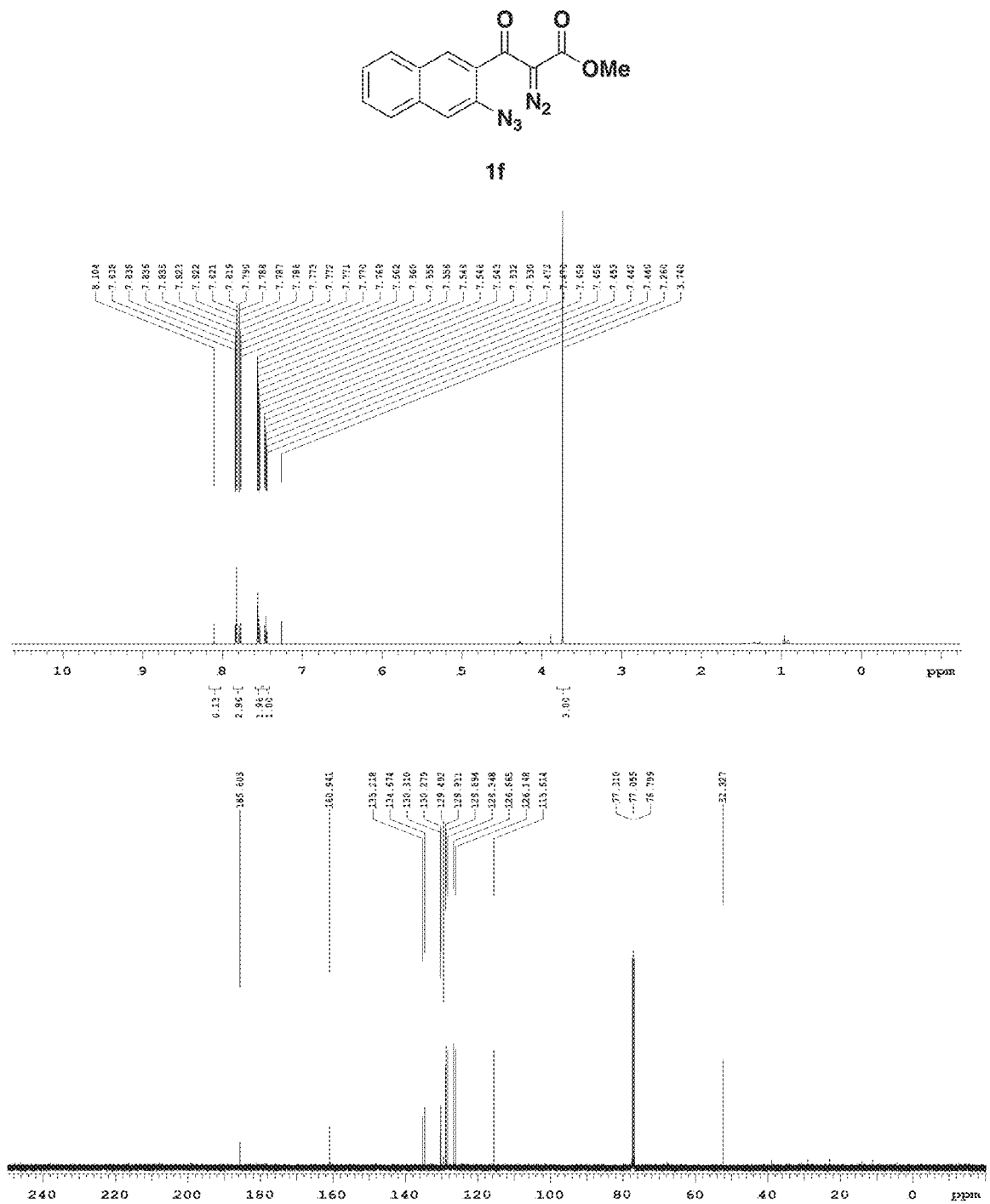
FIG. 18 depicts an NMR spectrum of compound 1f.
Figure 19:
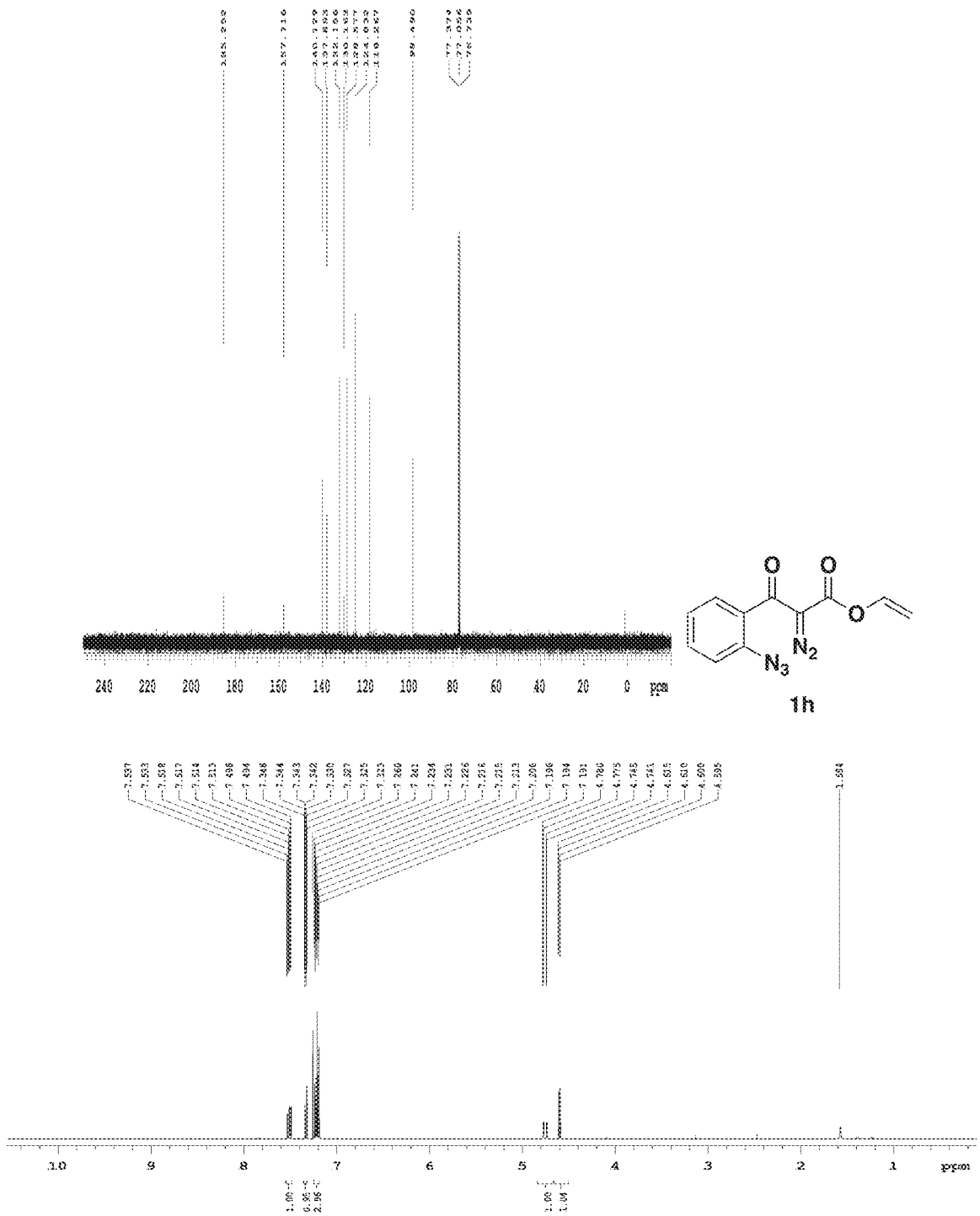
FIG. 19 depicts an NMR spectrum of compound 1h.
Figure 20:
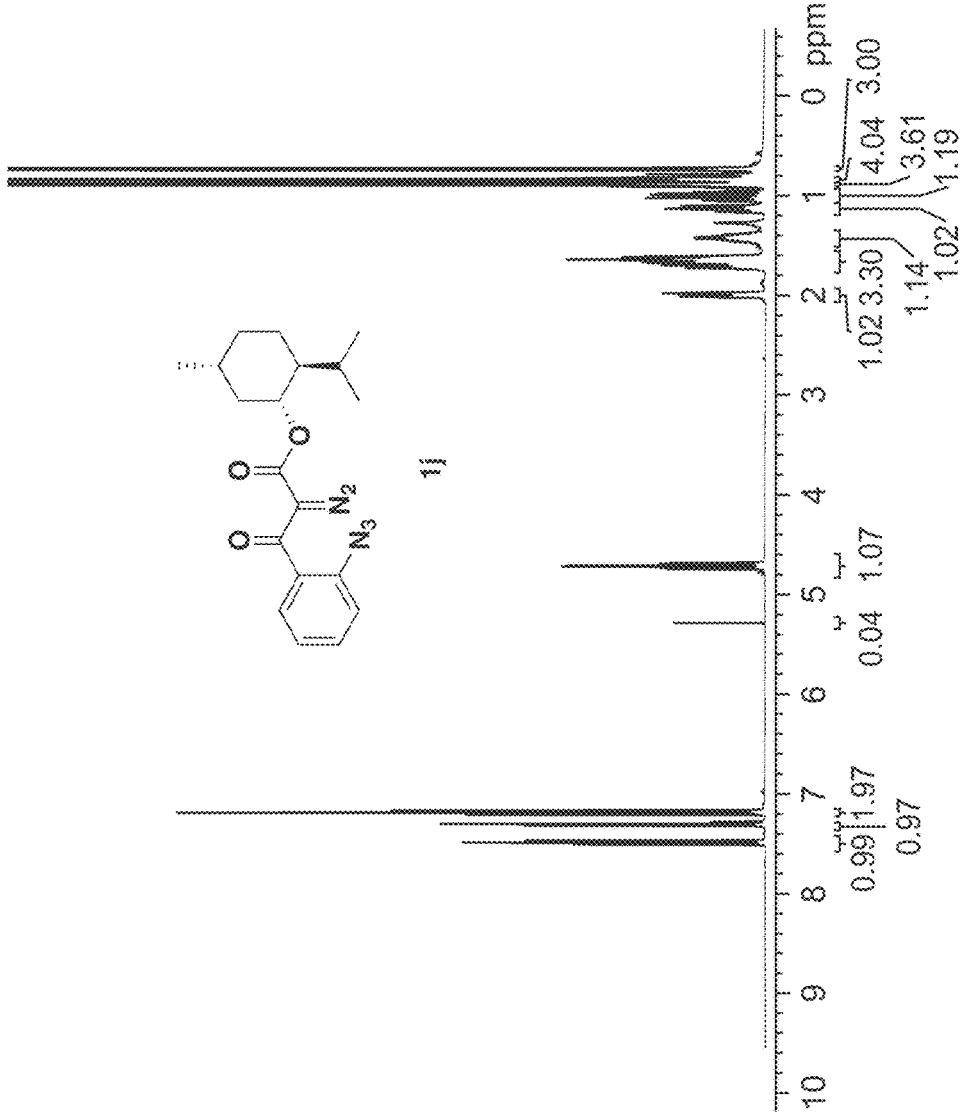
FIG. 20 depicts an NMR spectrum of compound 1j.
Figure 20:
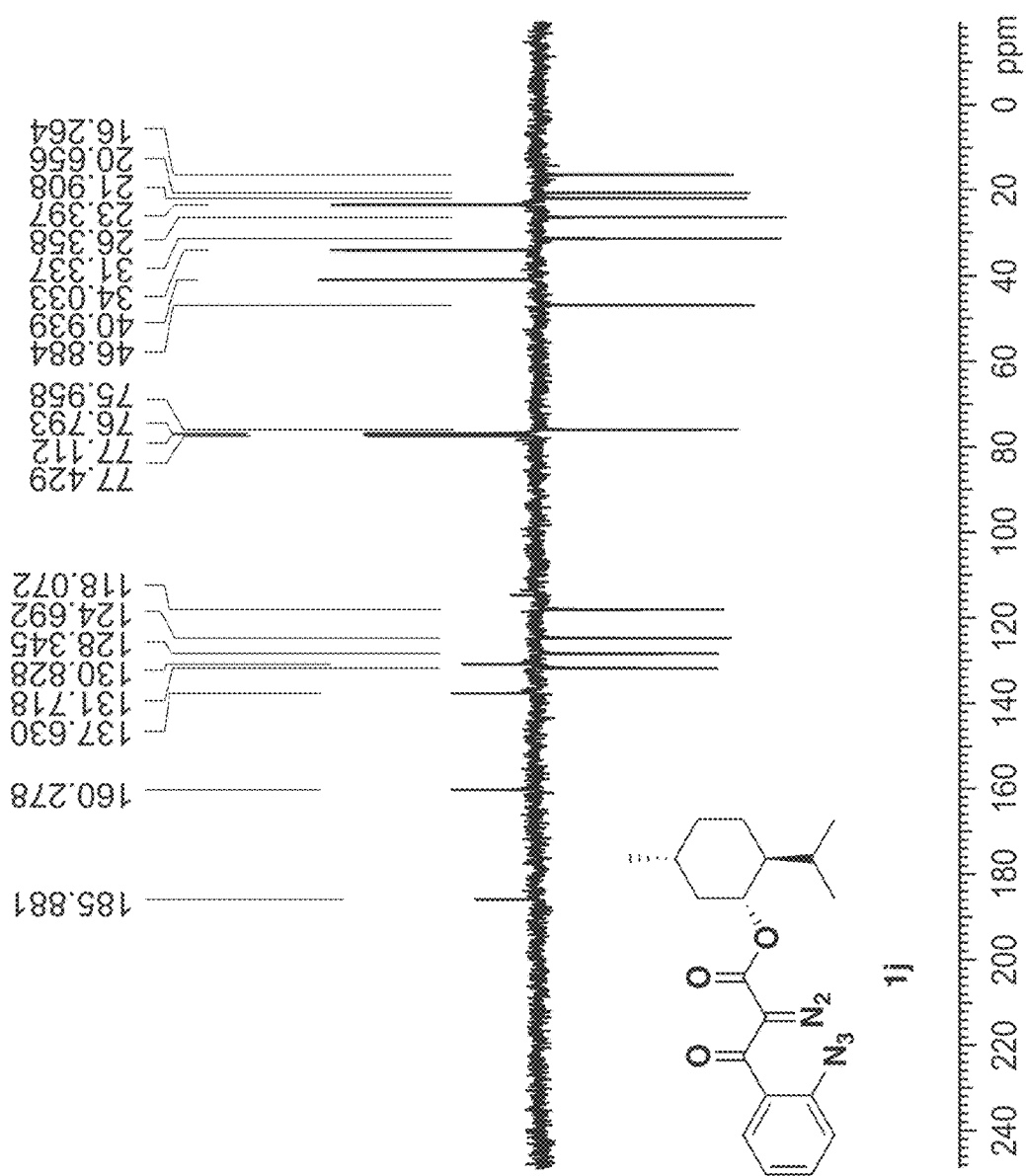
Figure 21:
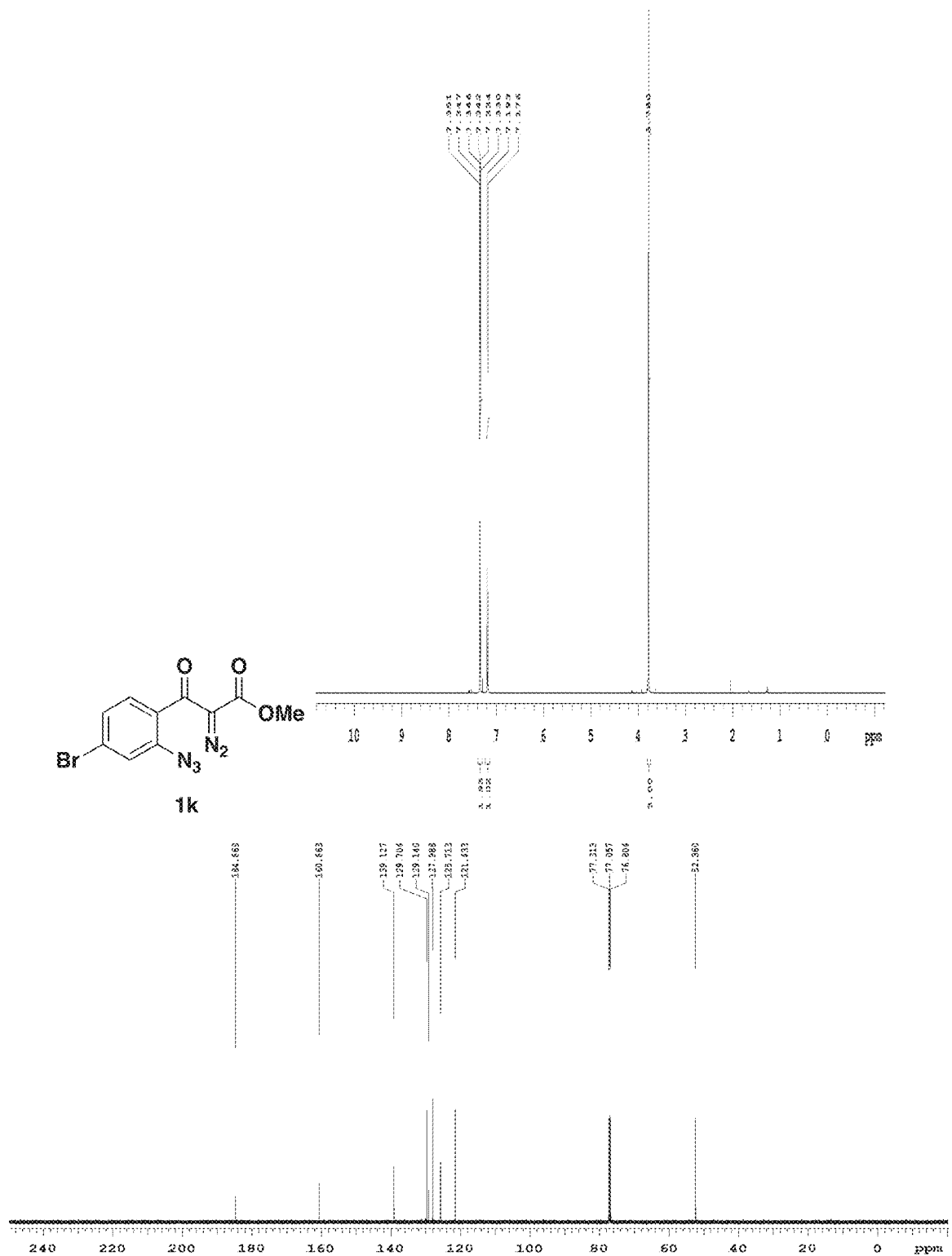
FIG. 21 depicts an NMR spectrum of compound 1k.
Figure 22:
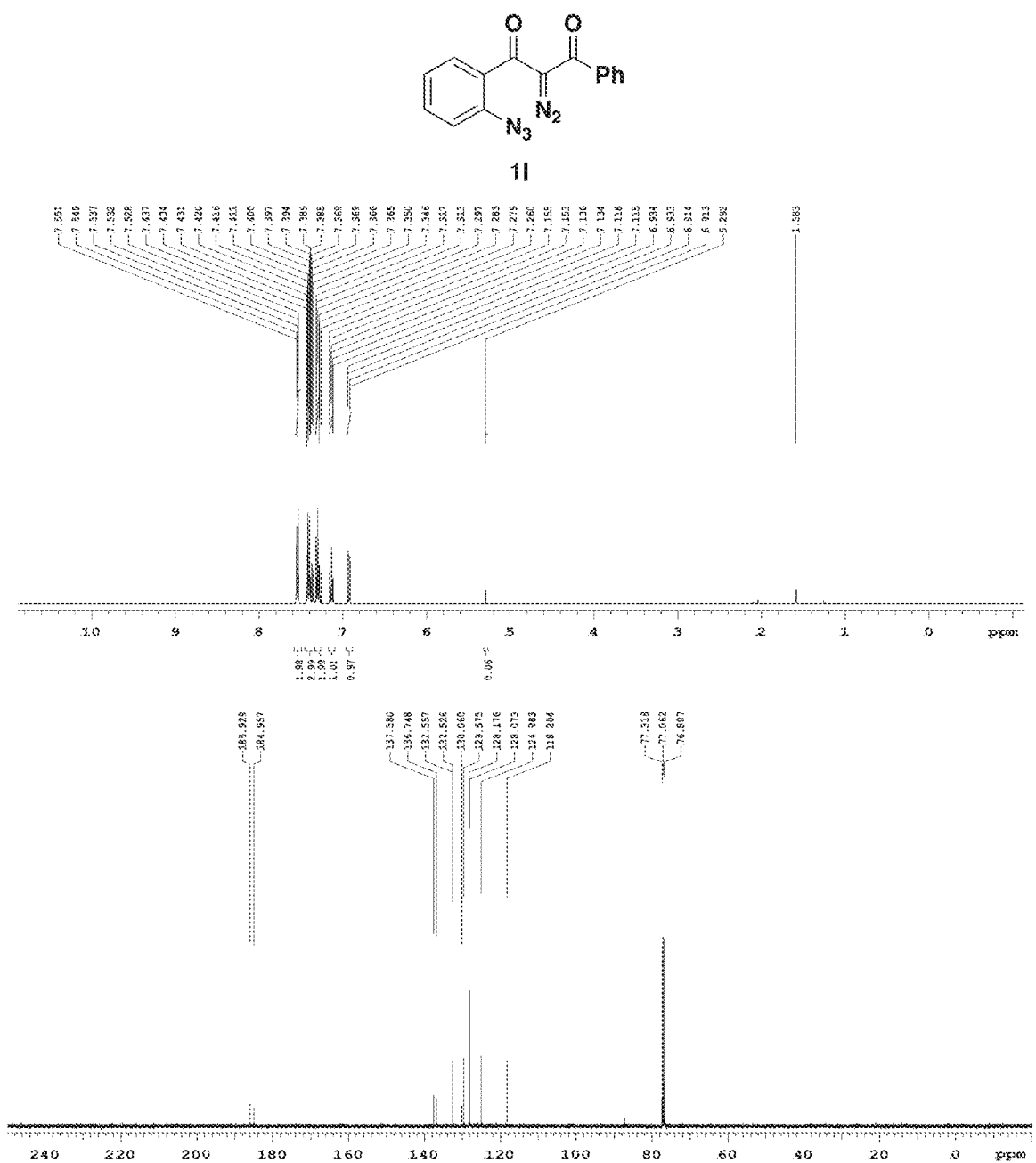
FIG. 22 depicts an NMR spectrum of compound 1l.
Figure 23:
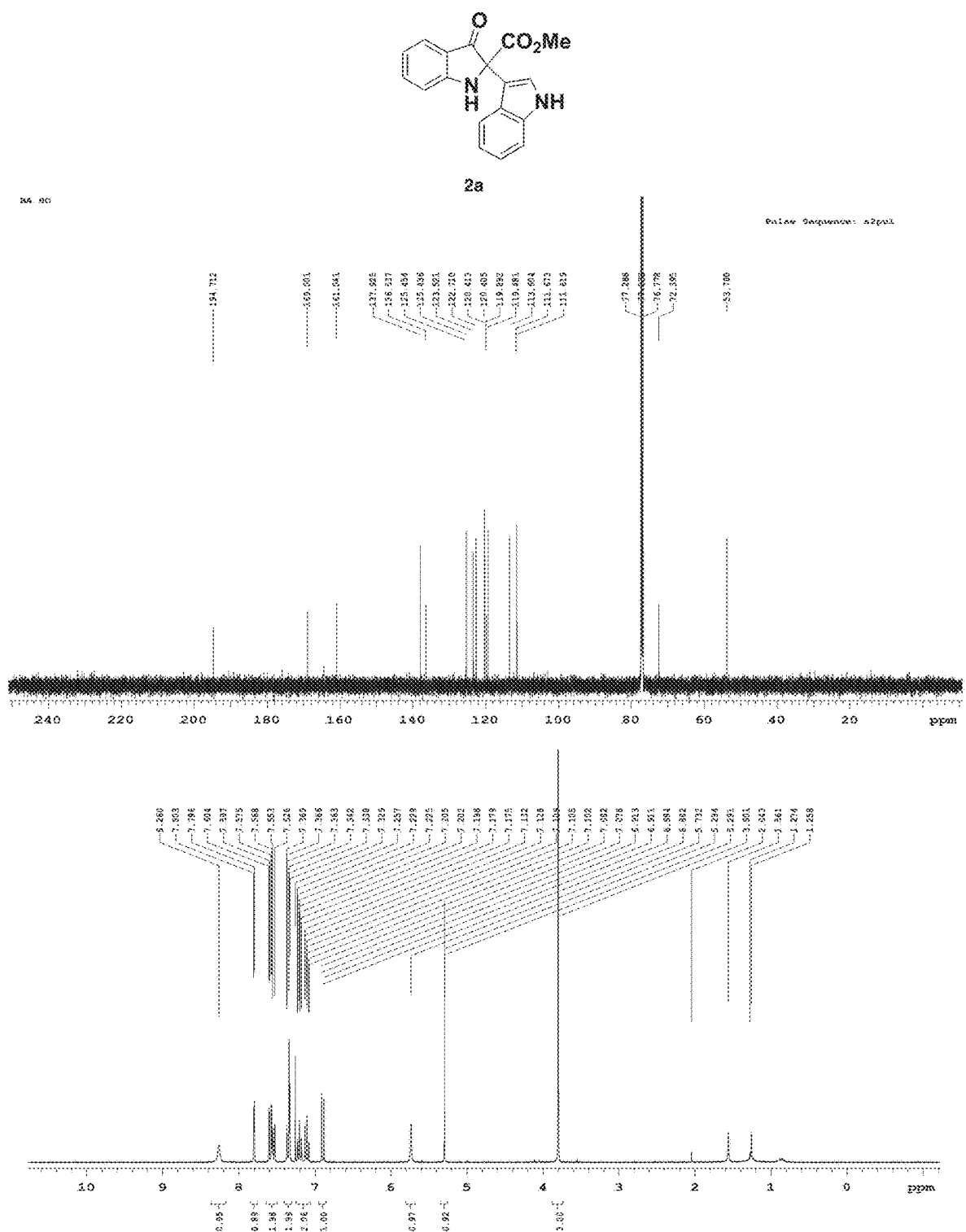
Figure 24:
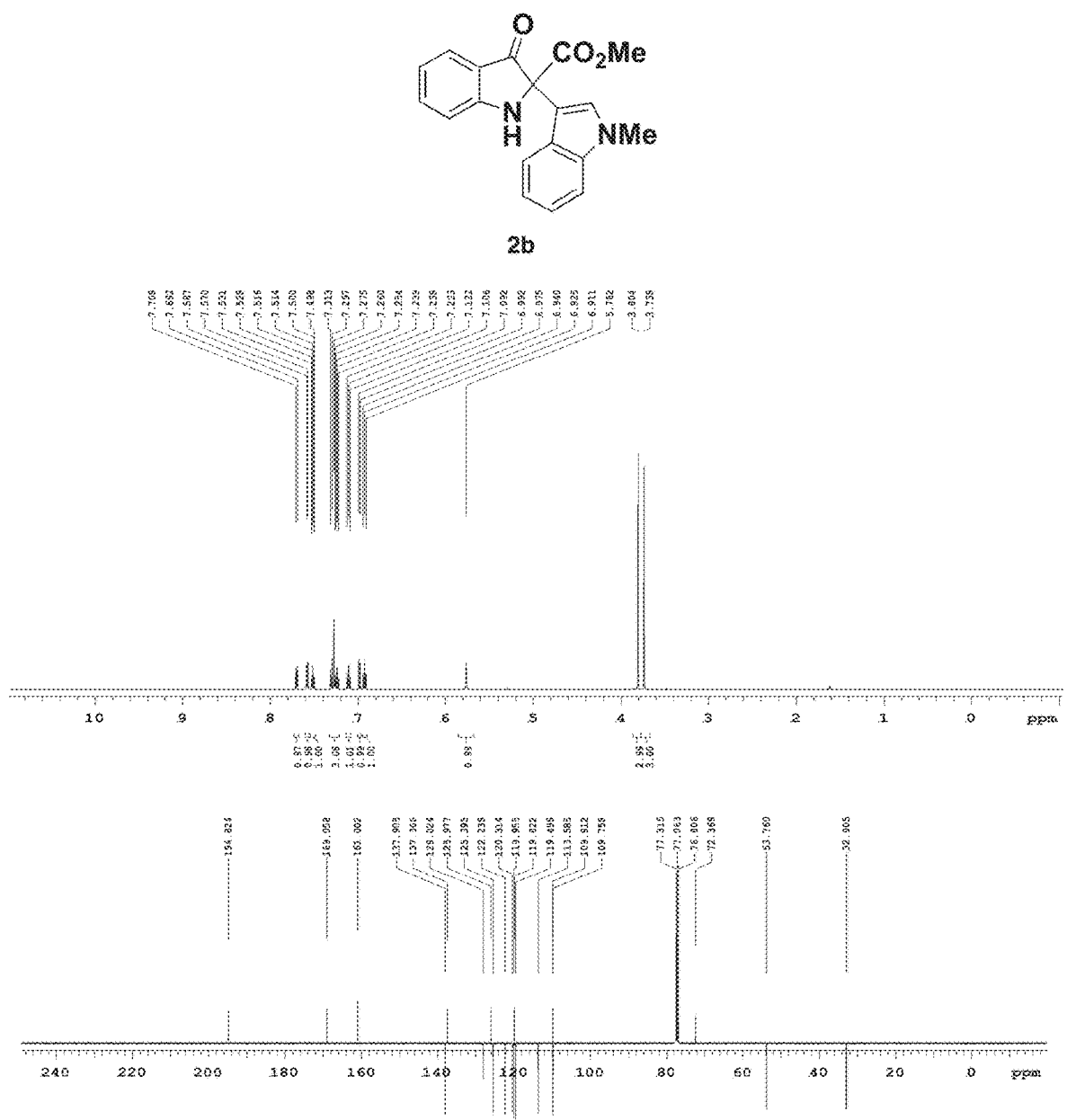
FIG. 24 depicts an NMR spectrum of compound 2b.
Figure 25:
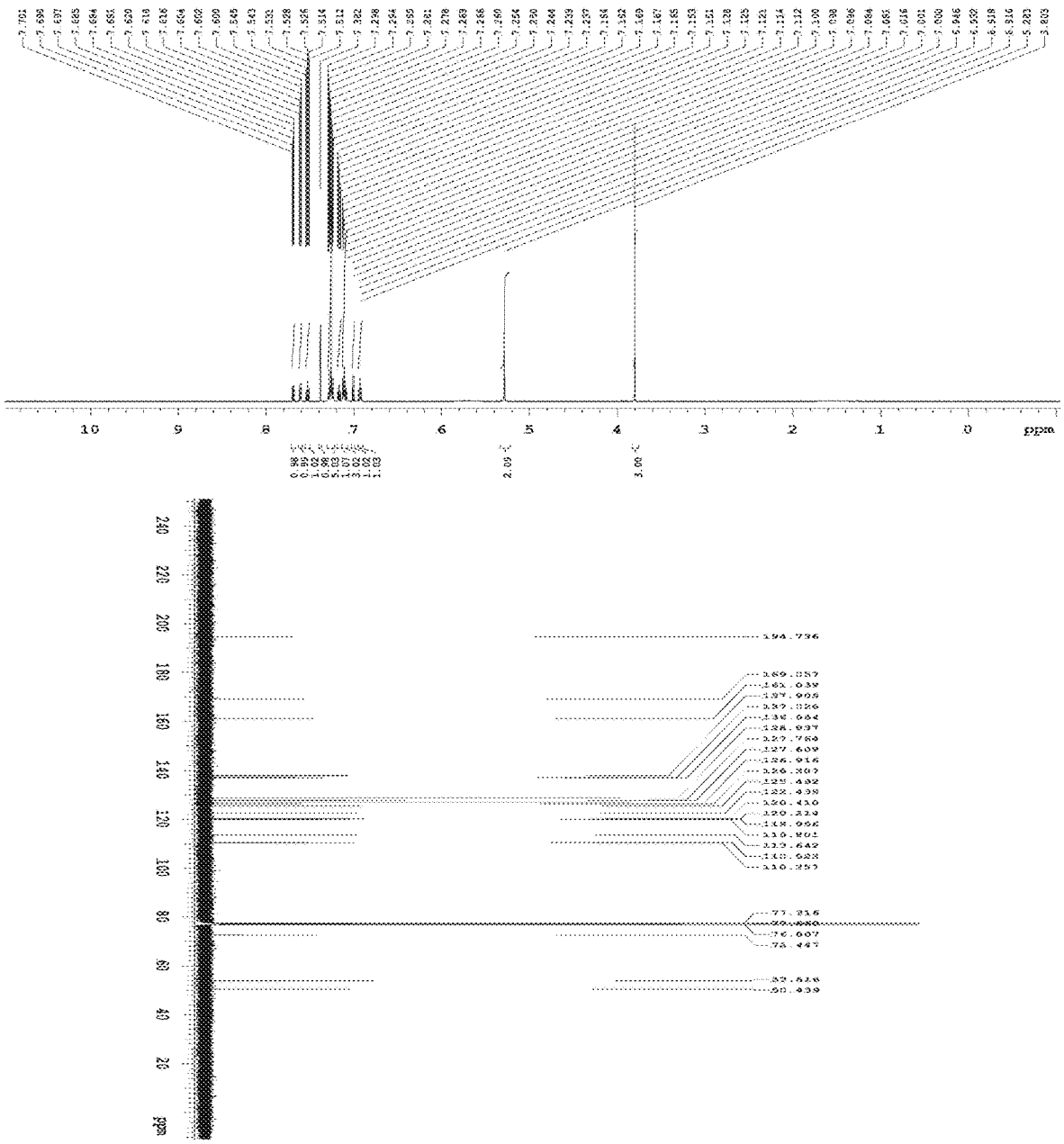
FIG. 25 depicts an NMR spectrum of compound 2c.
Figure 26:
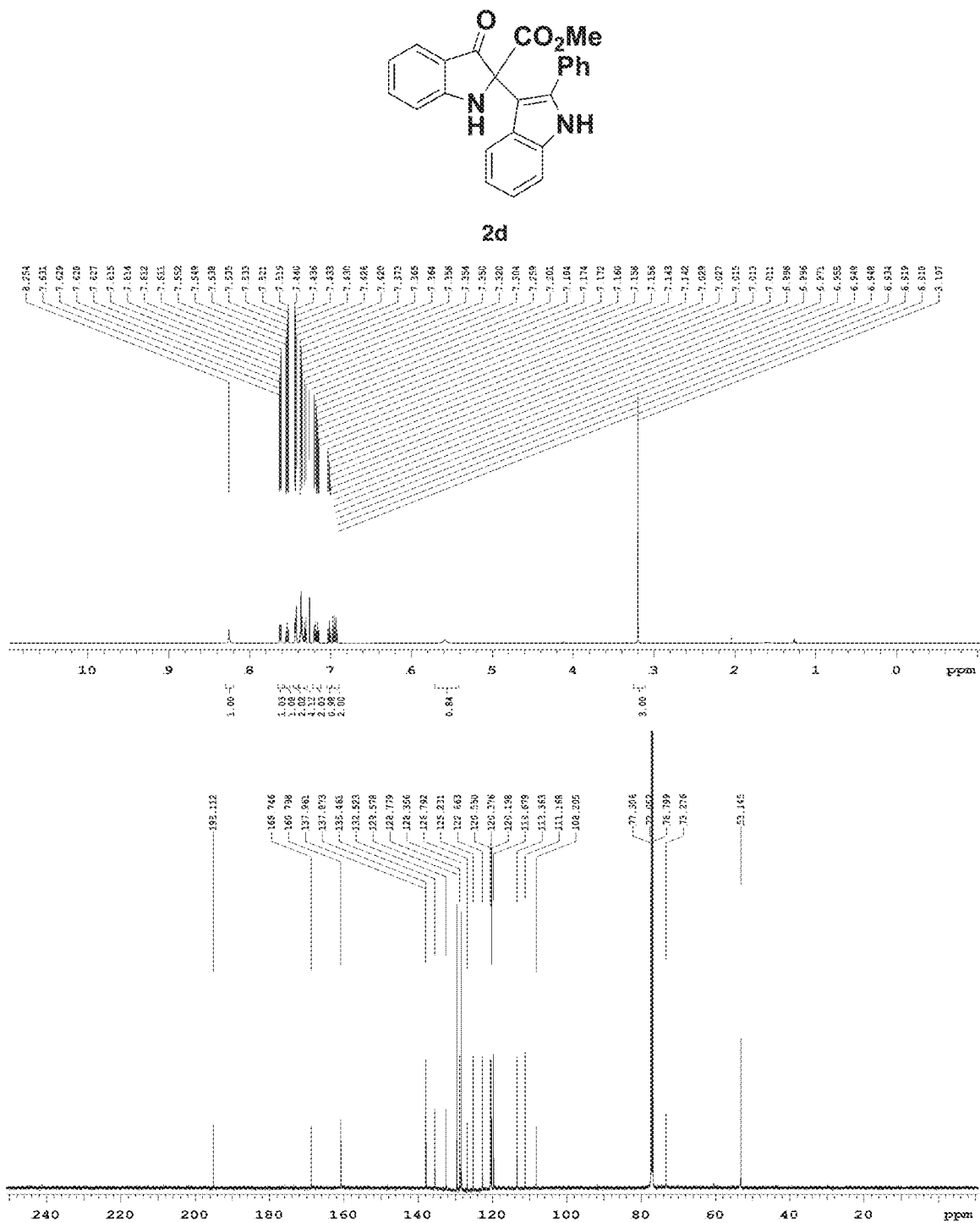
FIG. 26 depicts an NMR spectrum of compound 2d.
Figure 27:
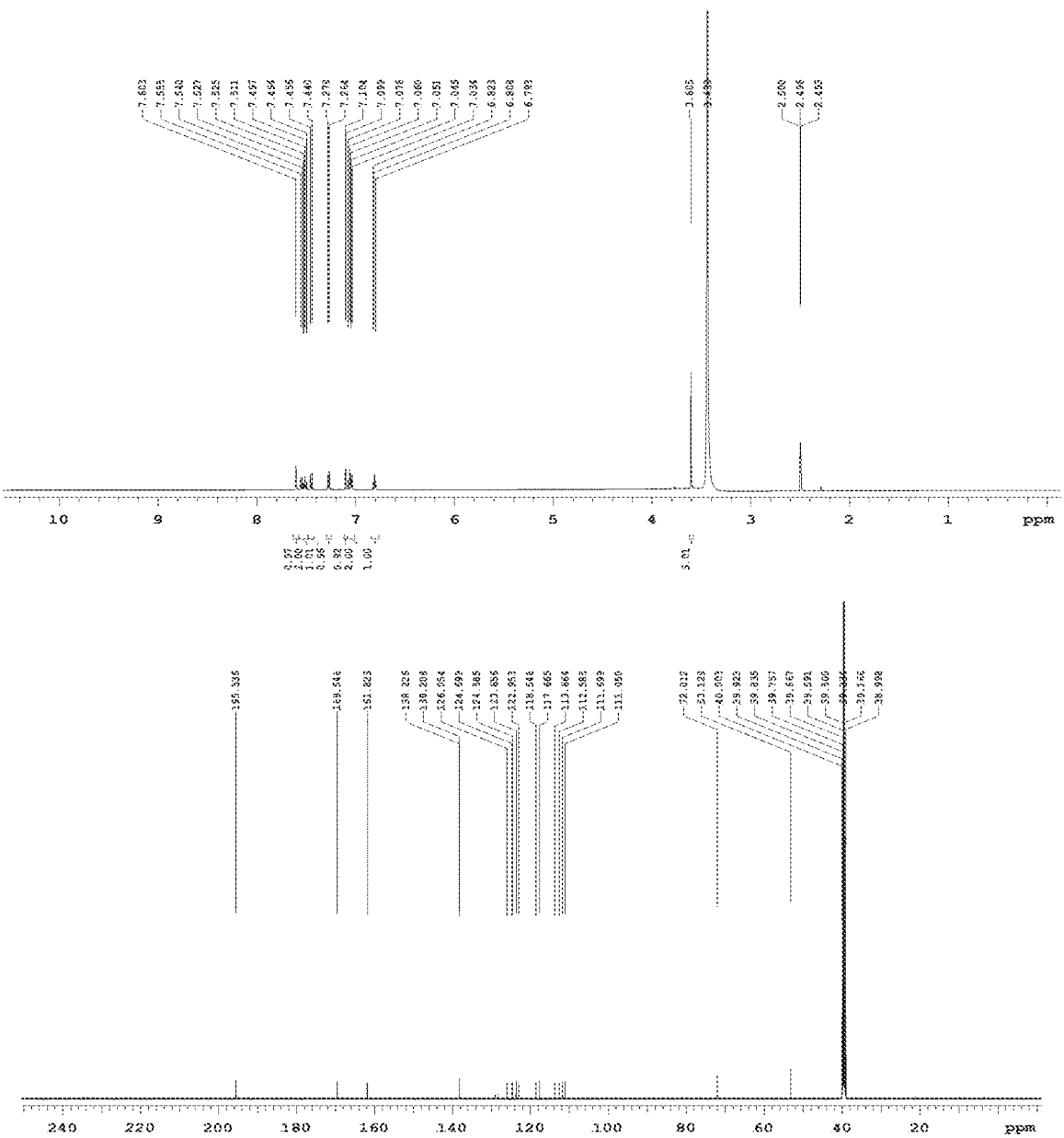
FIG. 27 depicts an NMR spectrum of compound 2e.
Figure 28:
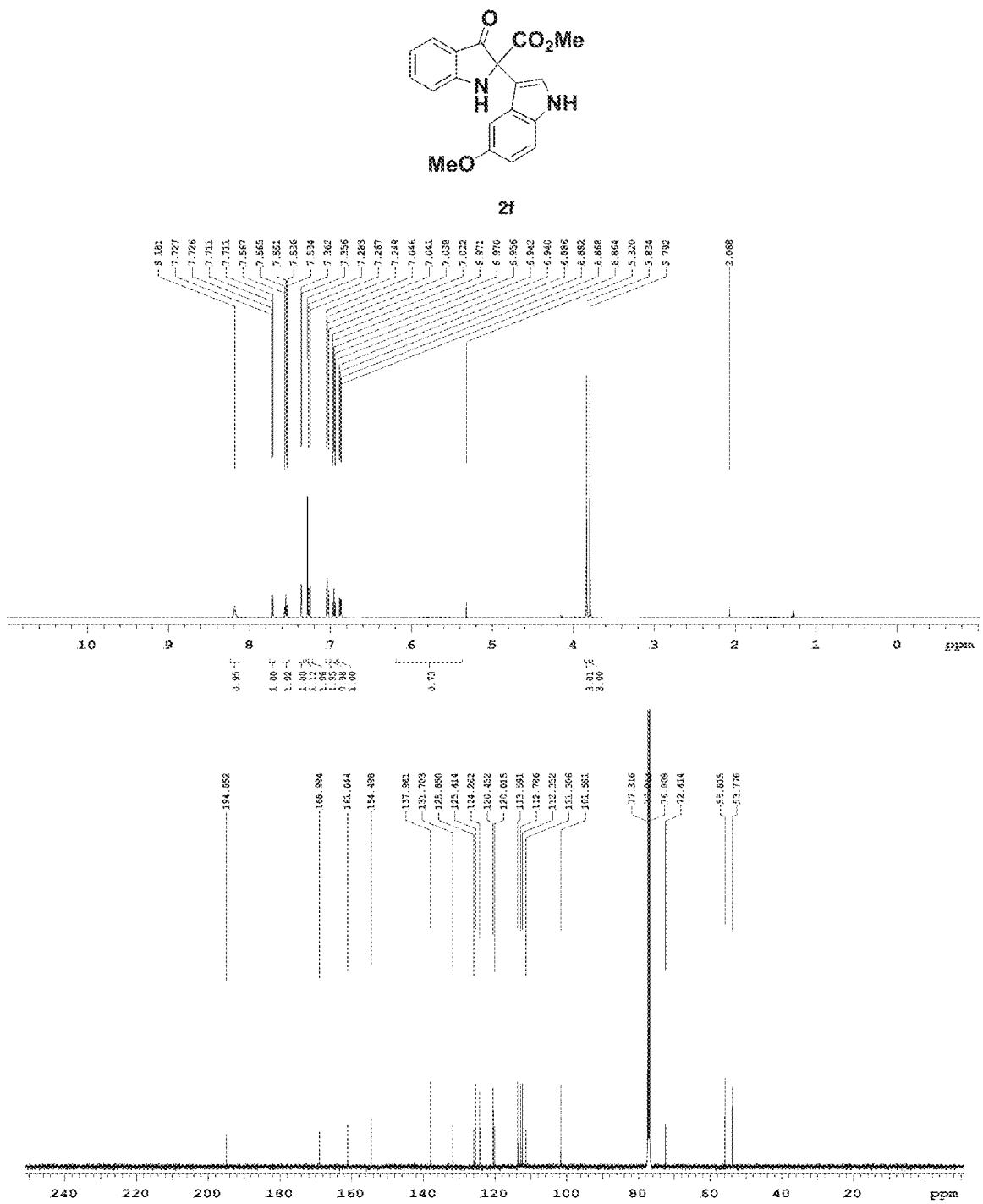
FIG. 28 depicts an NMR spectrum of compound 2f.
Figure 29:
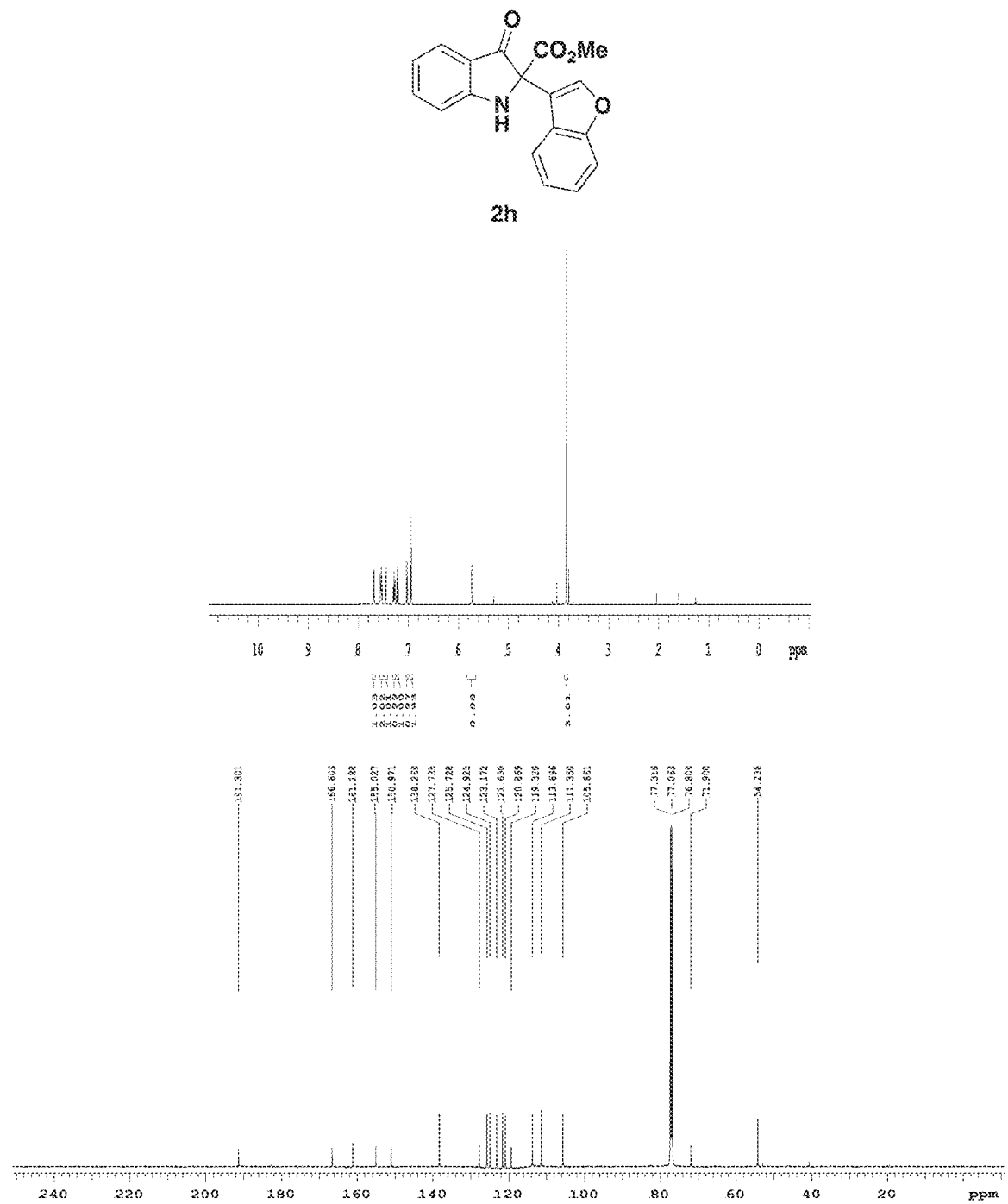
FIG. 29 depicts an NMR spectrum of compound 2h.
Figure 30:
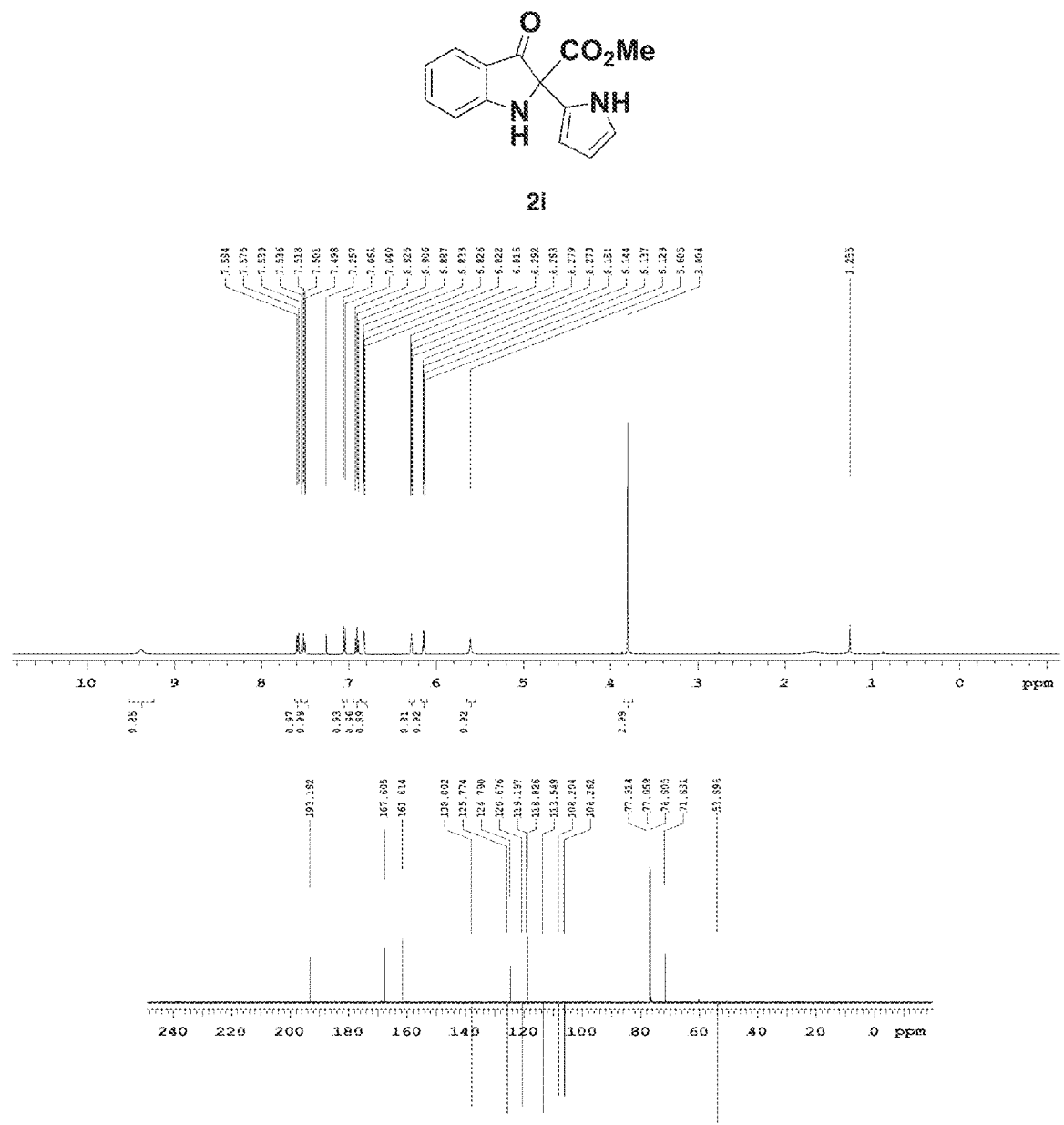
FIG. 30 depicts an NMR spectrum of compound 2i.
Figure 31:
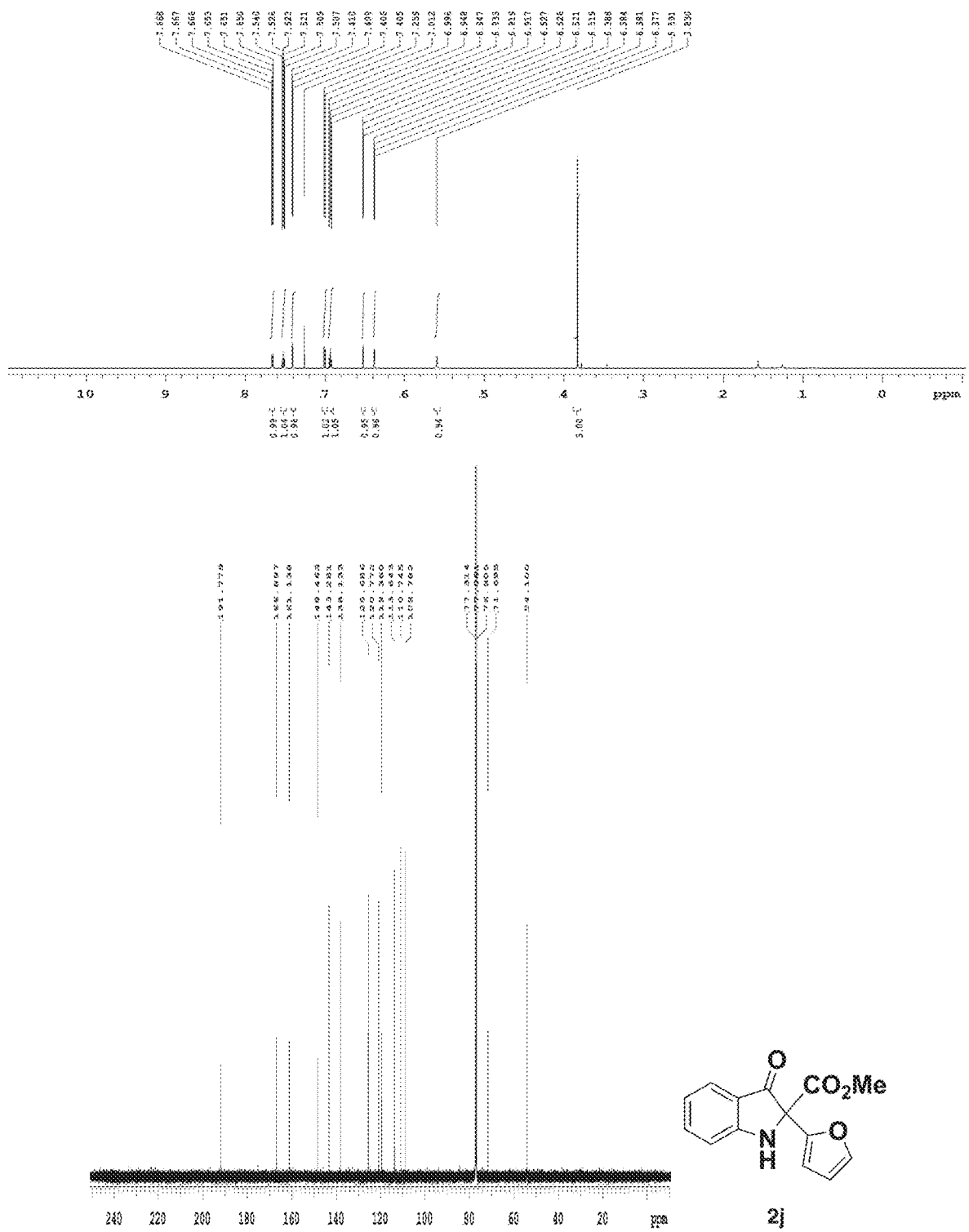
FIG. 31 depicts an NMR spectrum of compound 2j.
Figure 32:
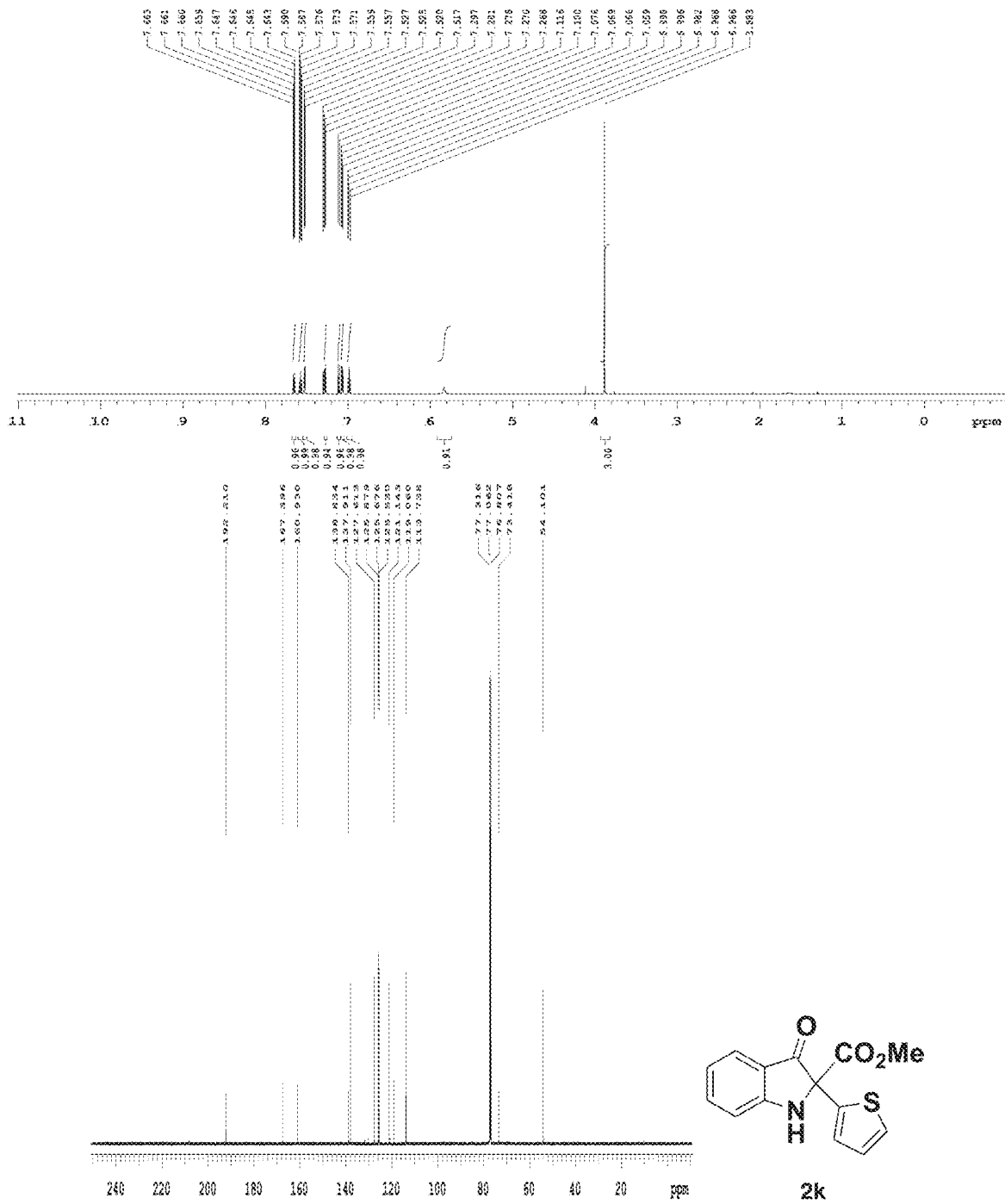
FIG. 32 depicts an NMR spectrum of compound 2k.
Figure 33:
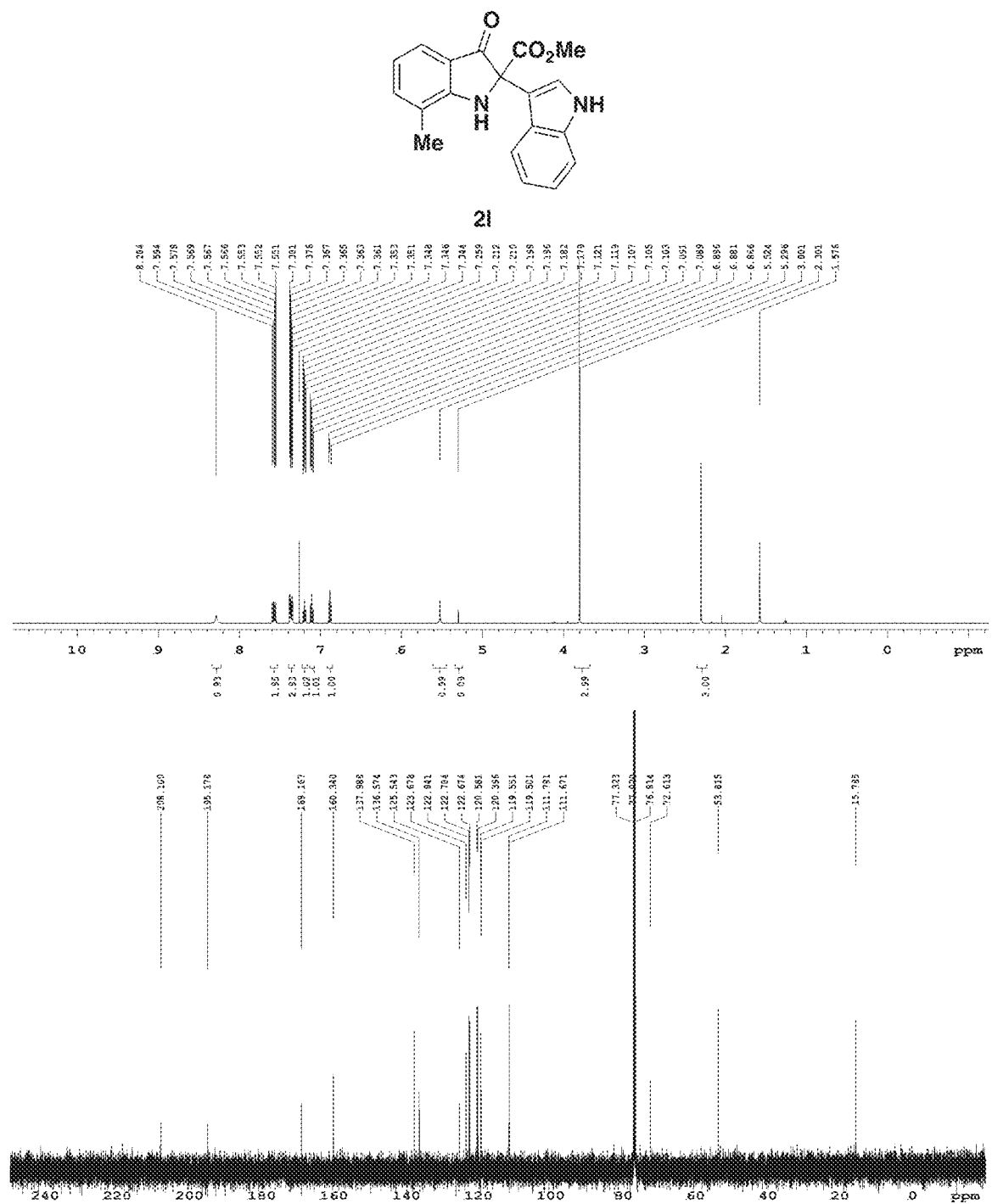
FIG. 33 depicts an NMR spectrum of compound 2l.
Figure 34:
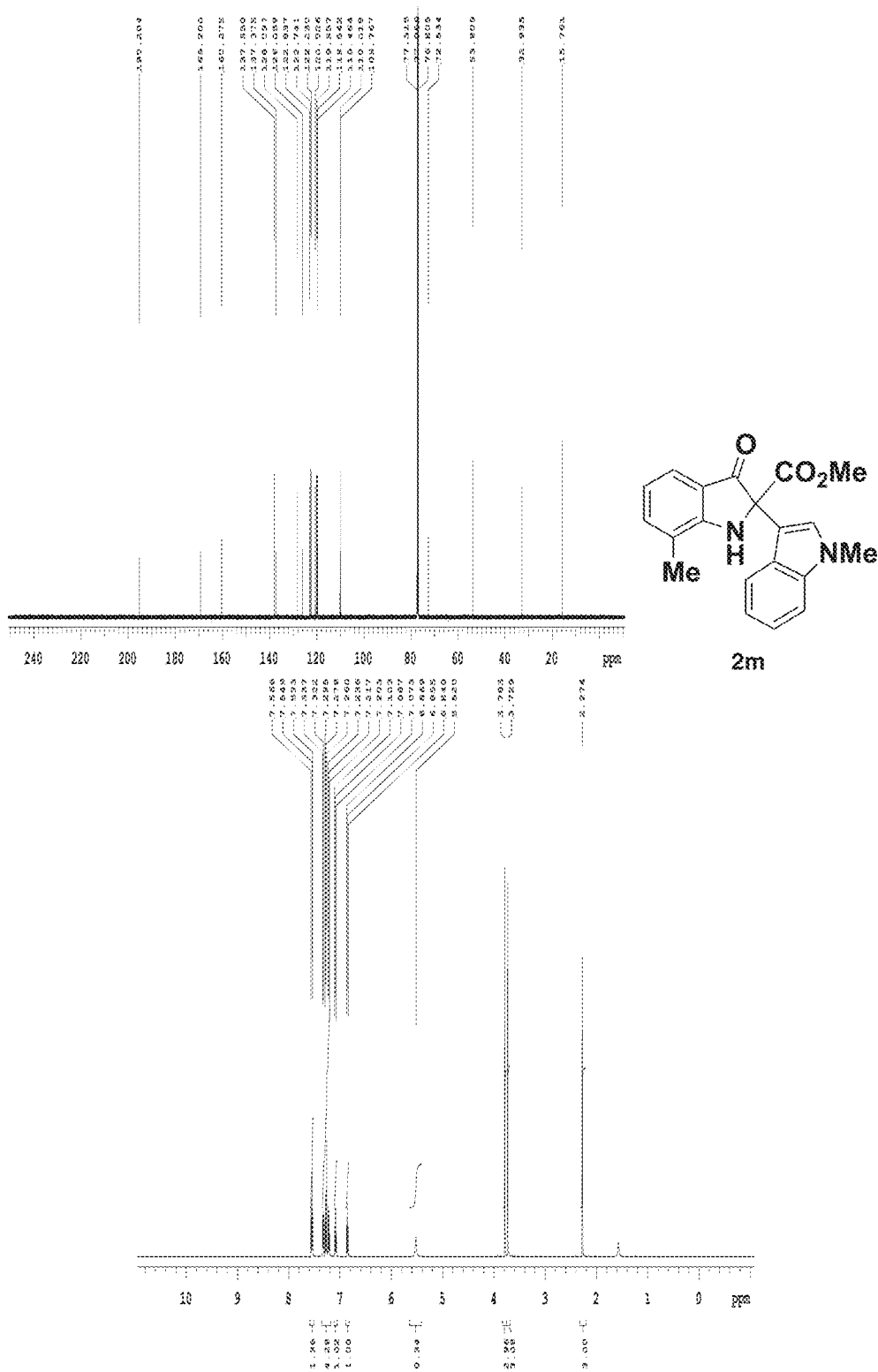
FIG. 34 depicts an NMR spectrum of compound 2m.
Figure 35:
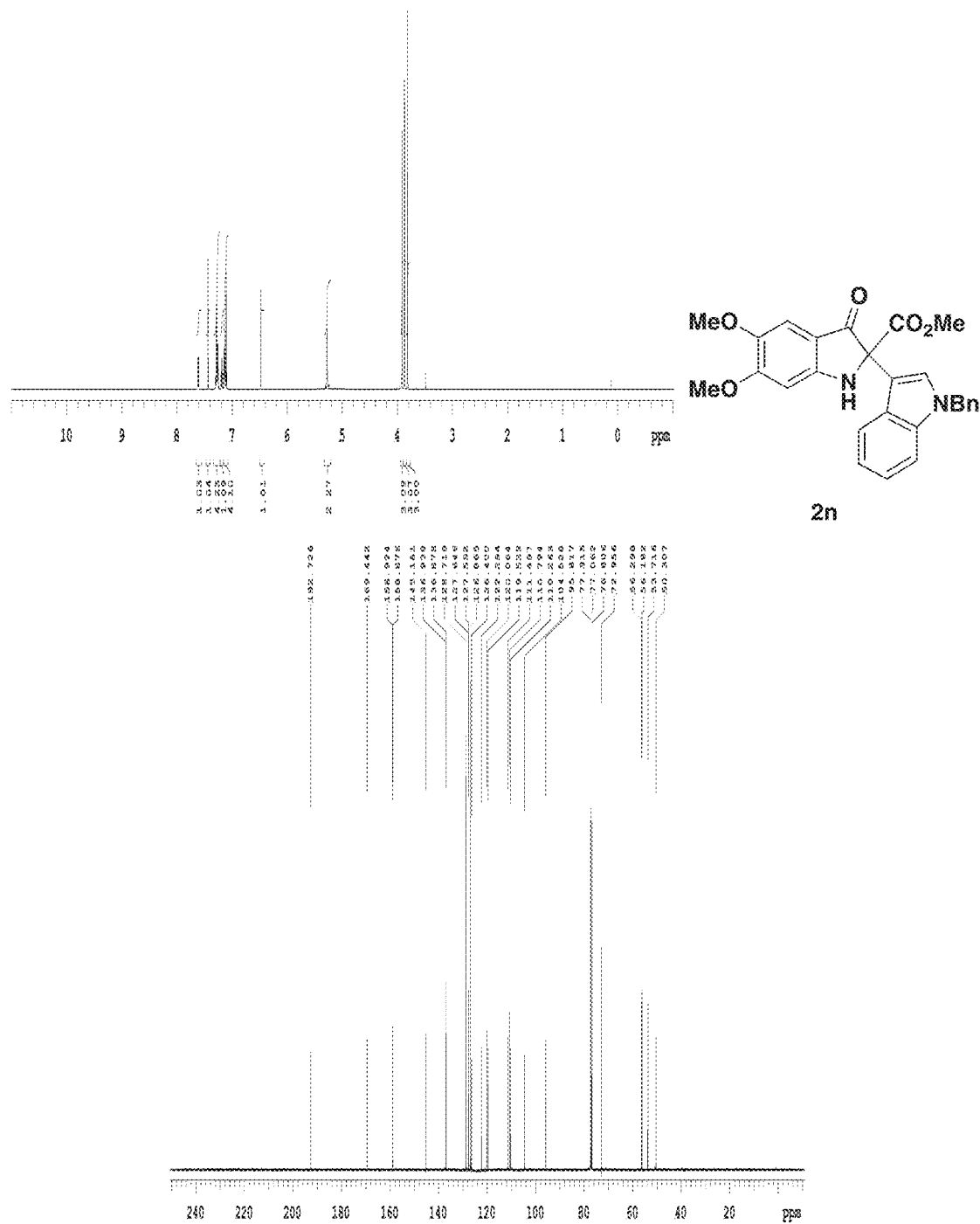
FIG. 35 depicts an NMR spectrum of compound 2n.
Figure 36:
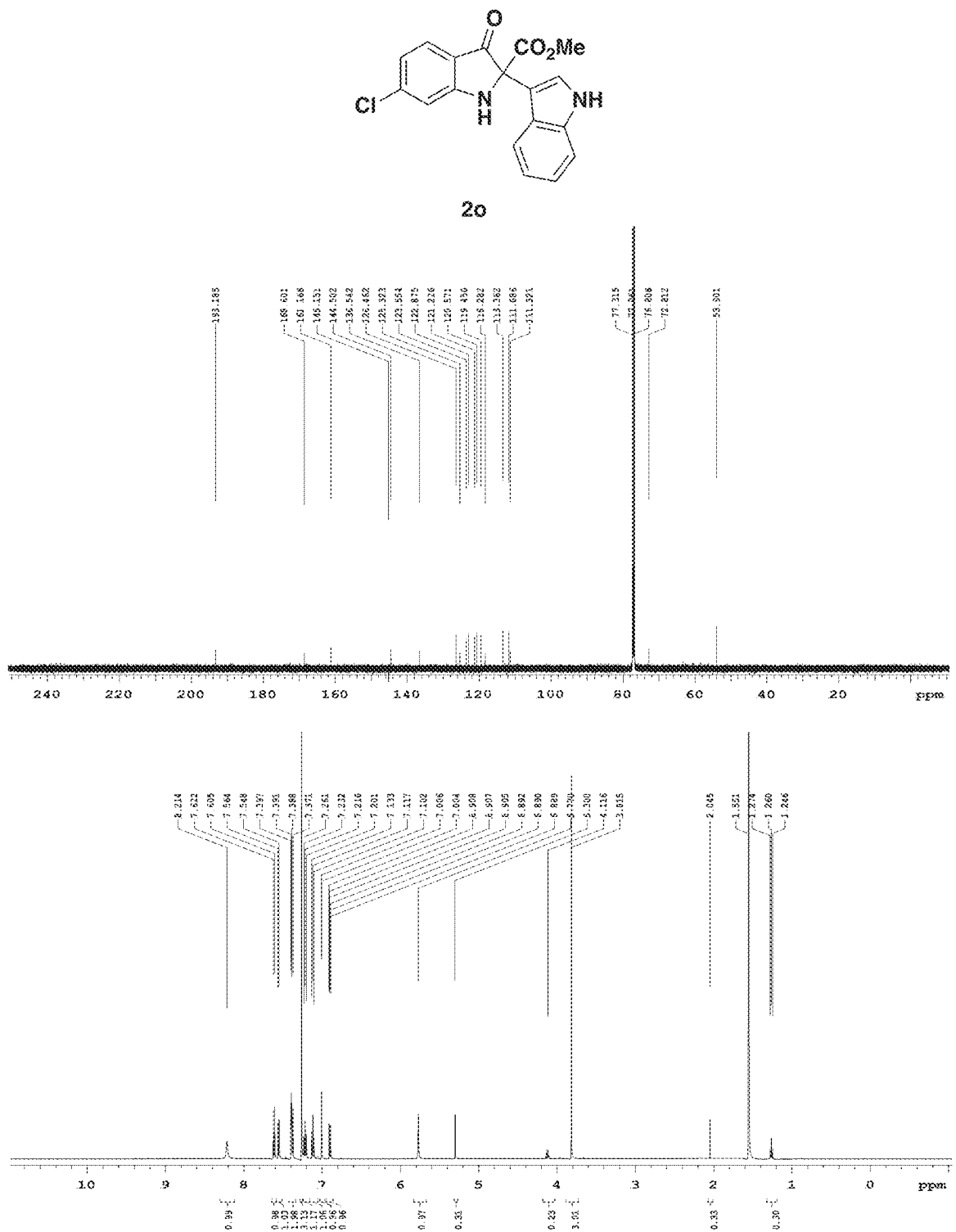
FIG. 36 depicts an NMR spectrum of compound 2o.
Figure 37:
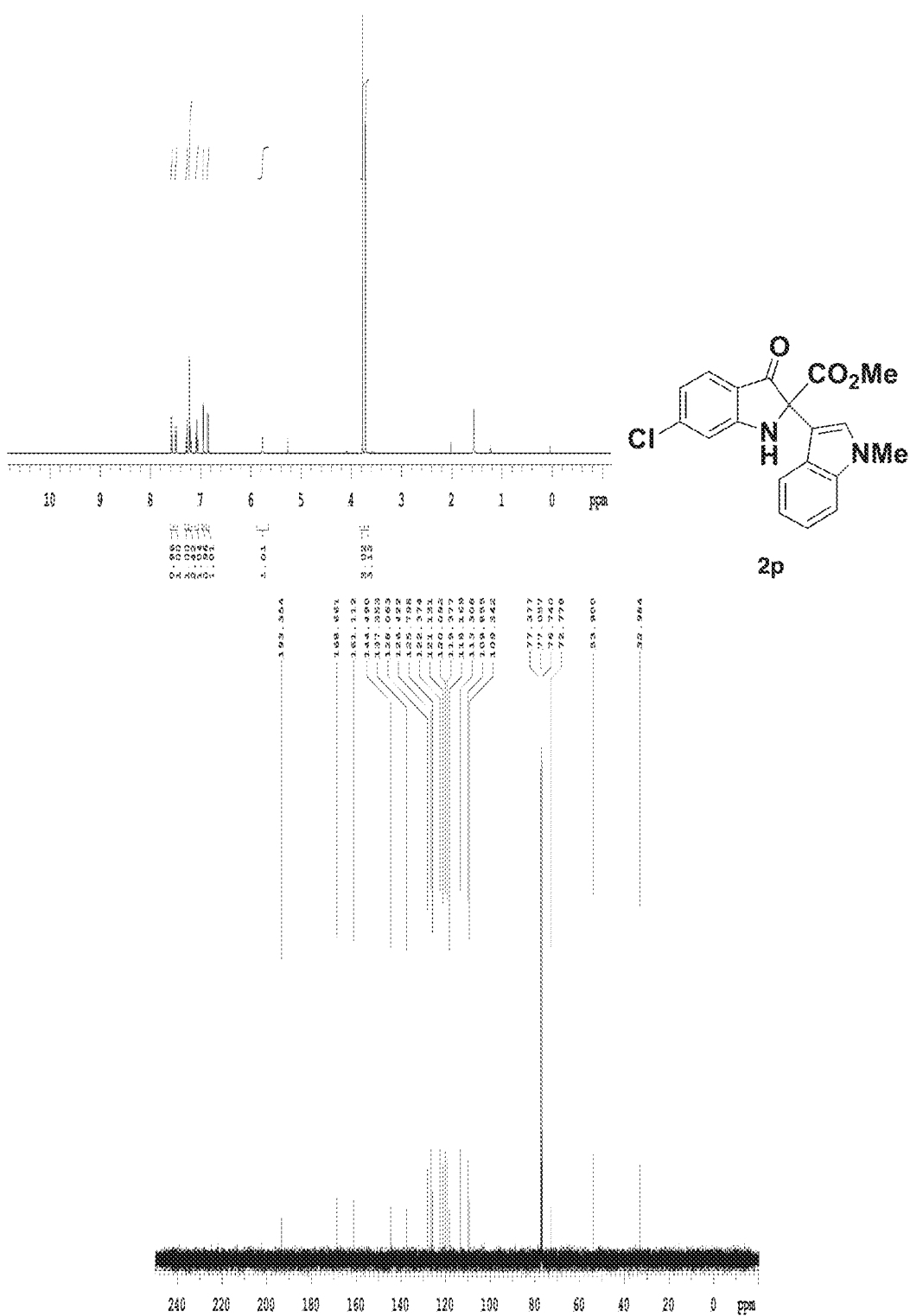
FIG. 37 depicts an NMR spectrum of compound 2p.
Figure 38:
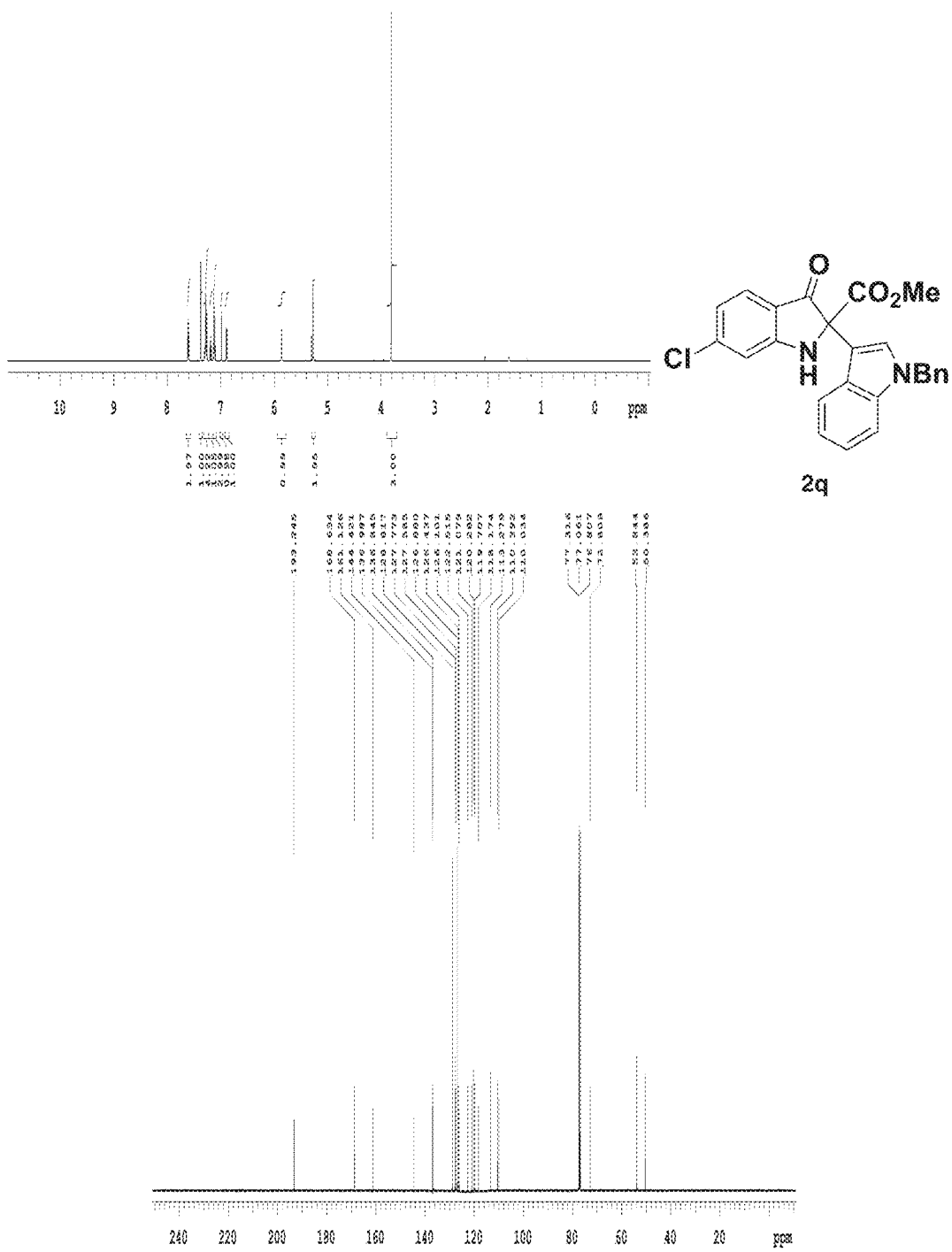
FIG. 38 depicts an NMR spectrum of compound 2q.
Figure 39:
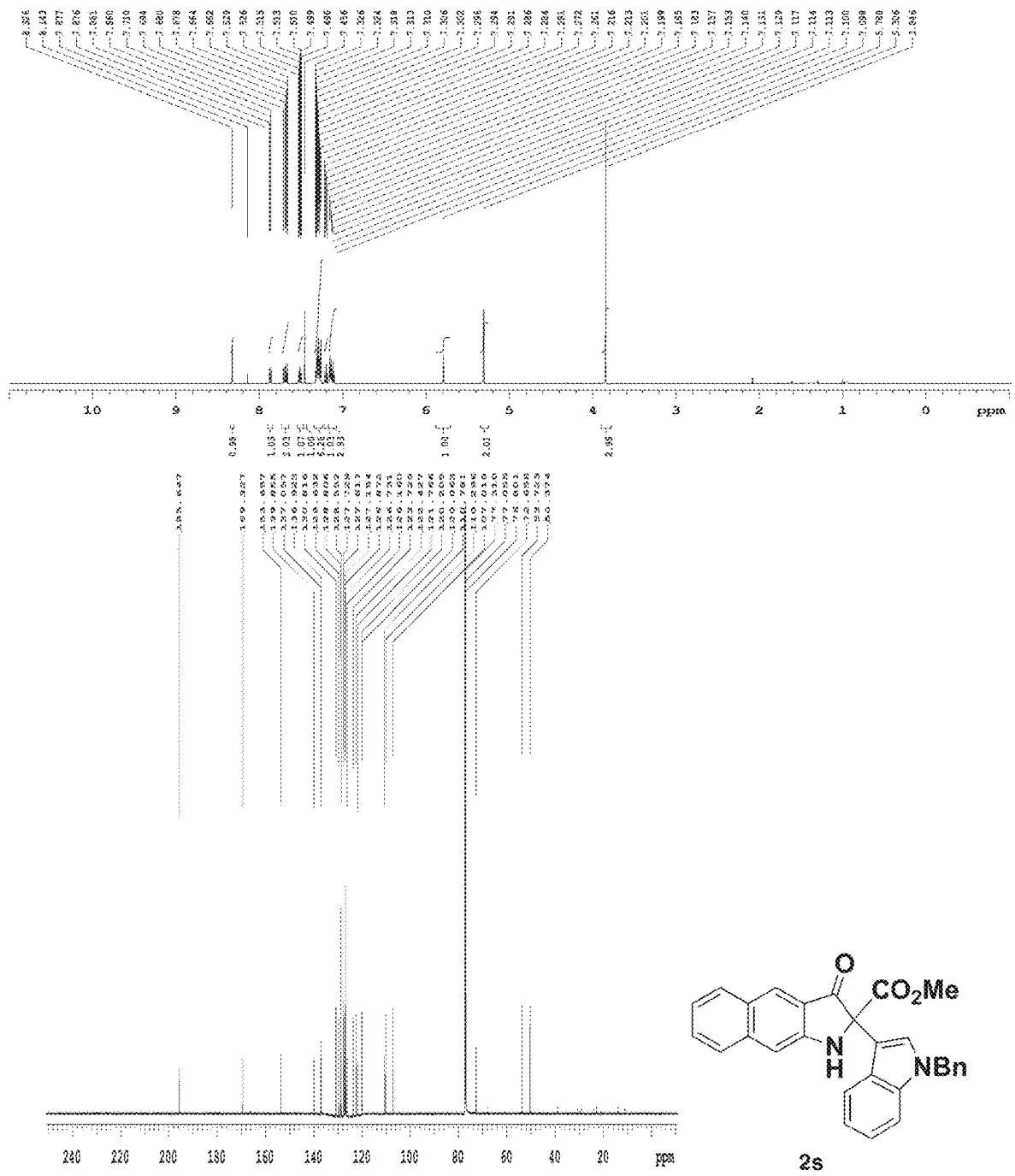
FIG. 39 depicts an NMR spectrum of compound 2s.
Figure 40:
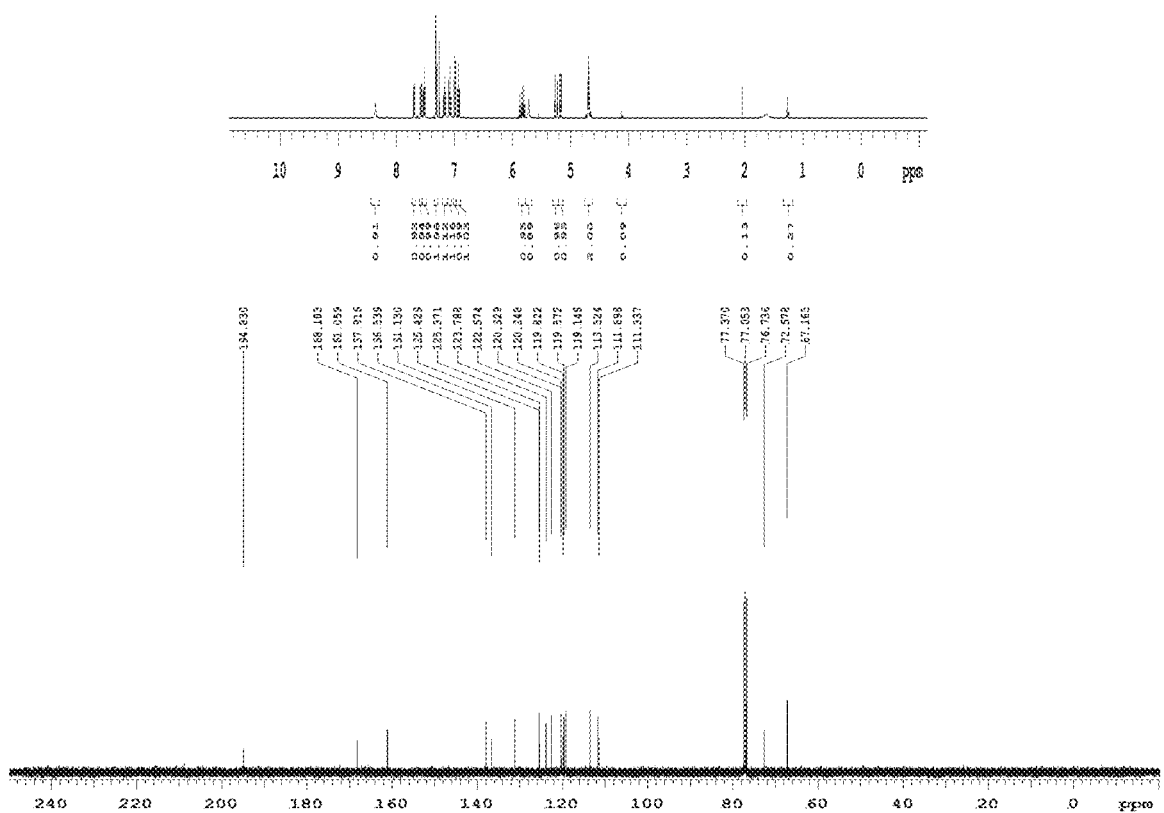
FIG. 40 depicts an NMR spectrum of compound 2t.
Figure 41:
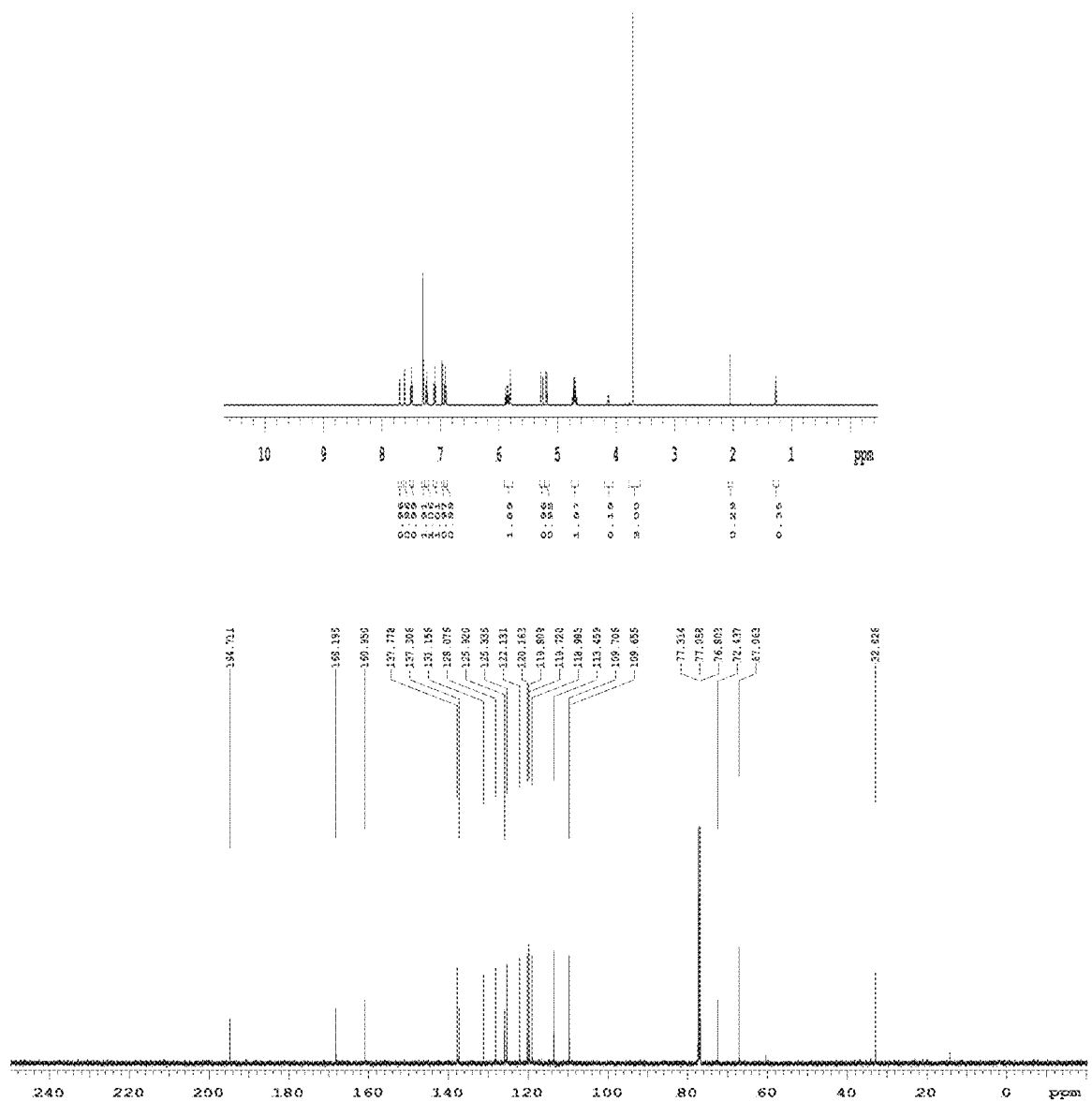
FIG. 41 depicts an NMR spectrum of compound 2u.
Figure 42:
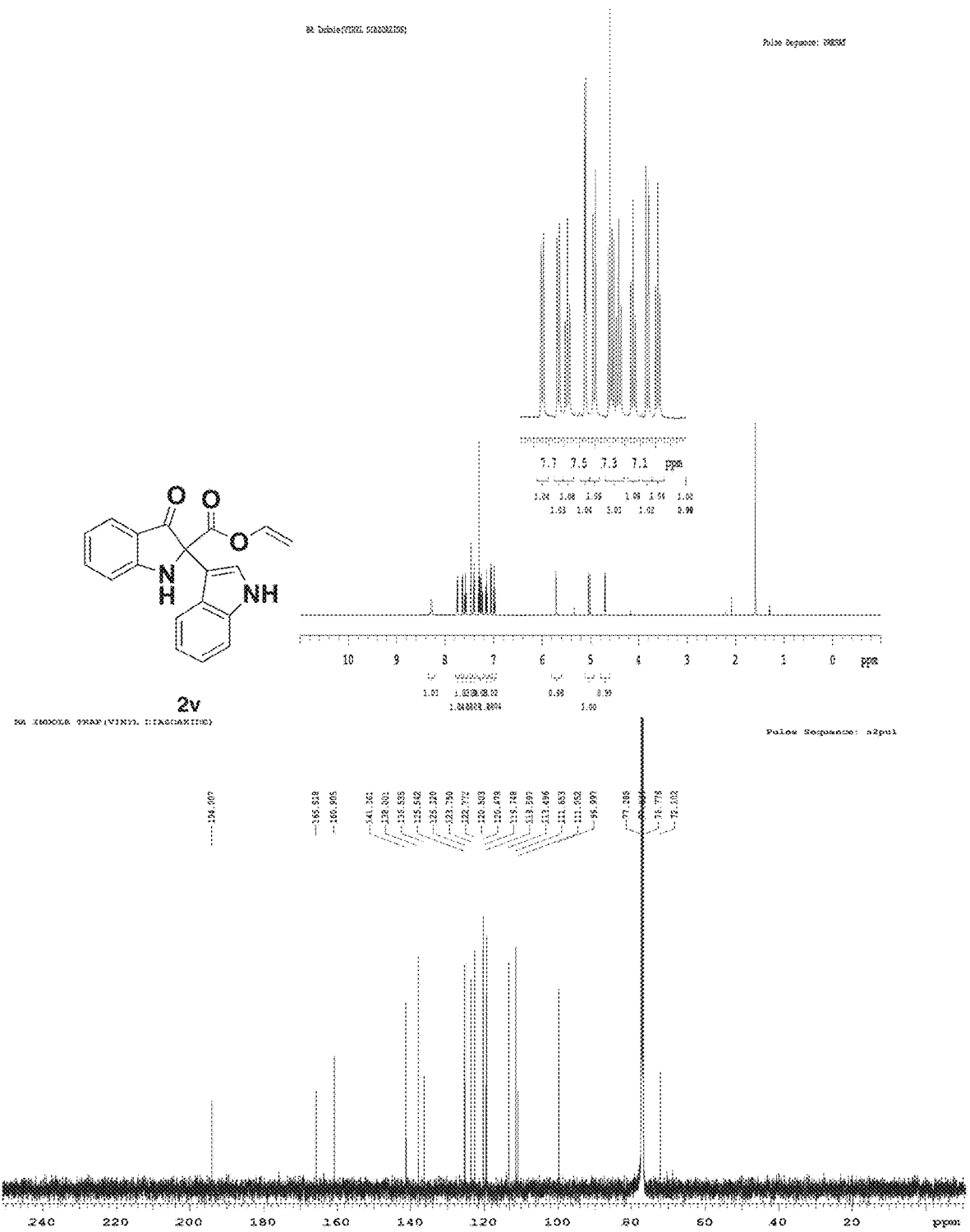
FIG. 42 depicts an NMR spectrum of compound 2v.
Figure 43:
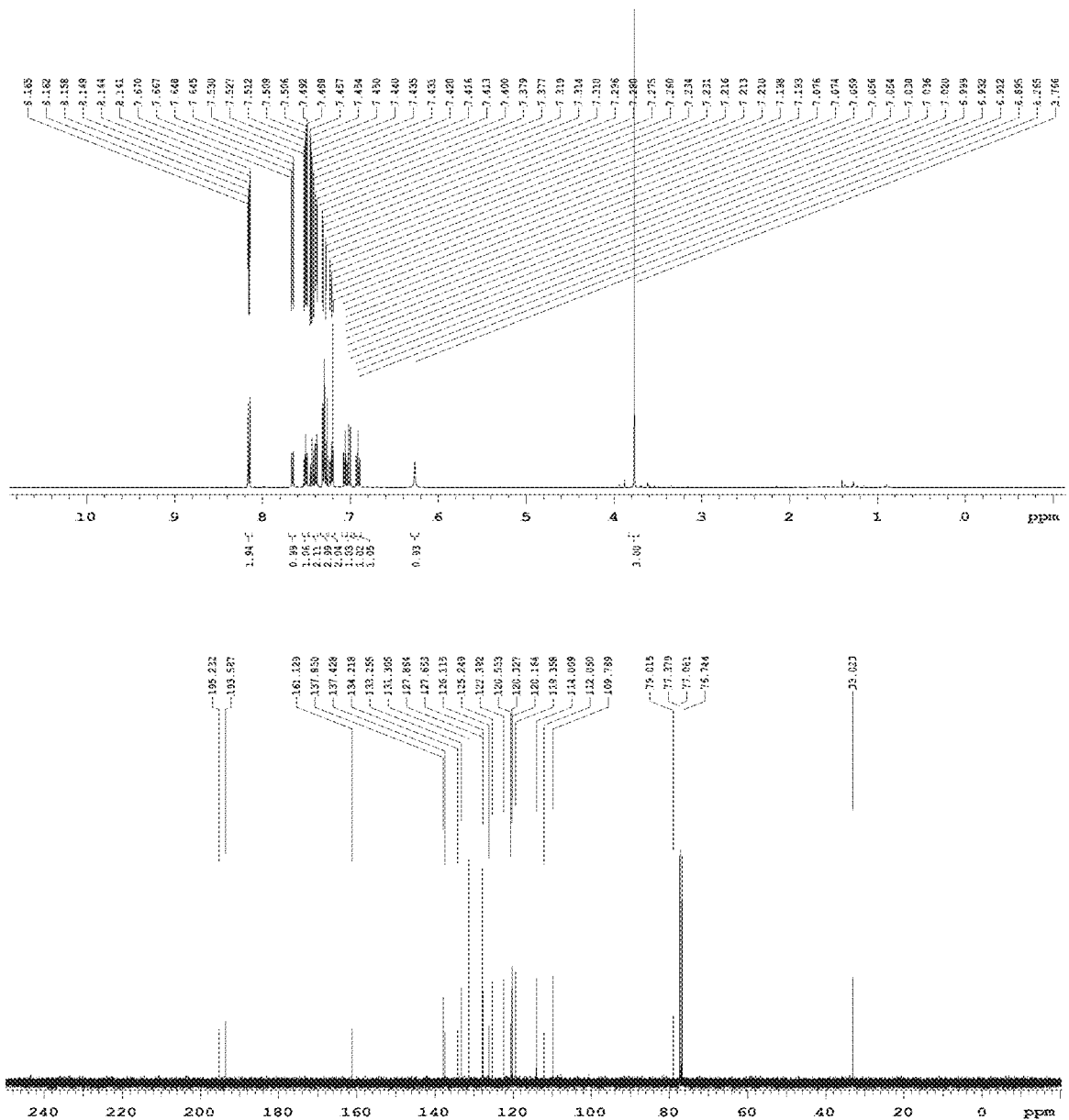
FIG. 43 depicts an NMR spectrum of compound 2w.
Figure 44:
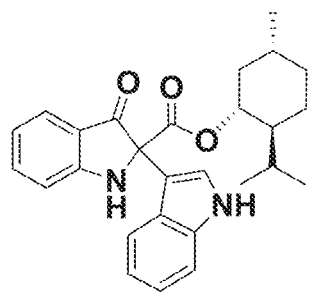
FIG. 44 depicts an NMR spectrum of compound 2xa:2xb.
Figure 44:
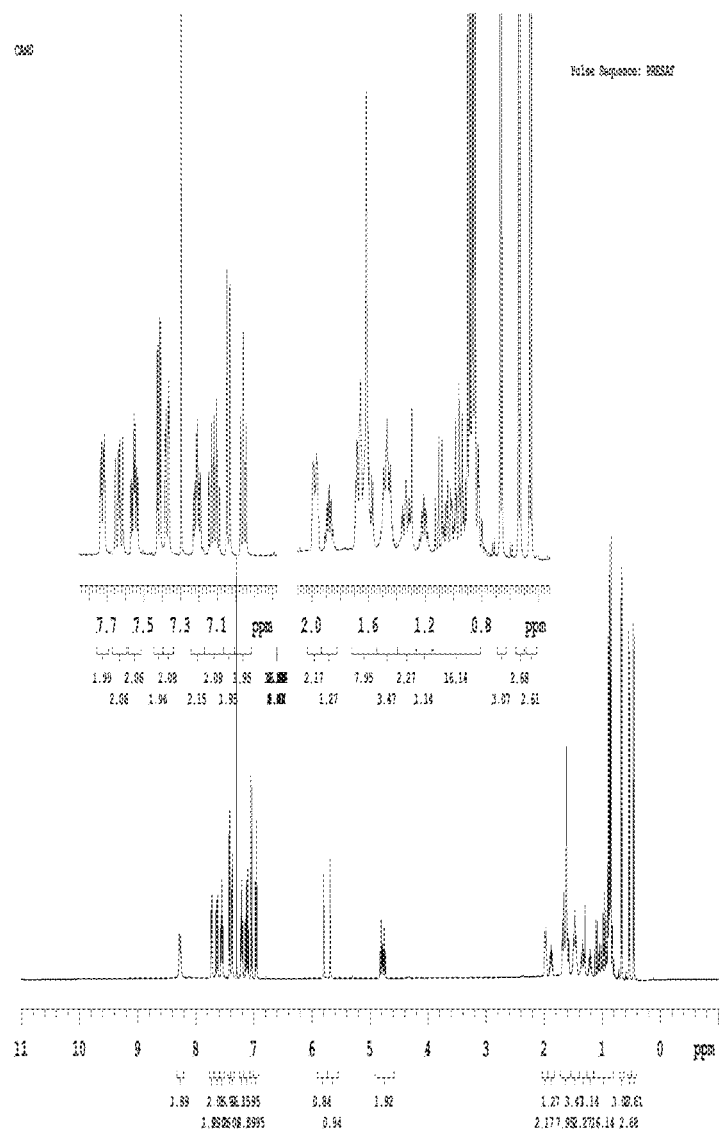
Figure 44:
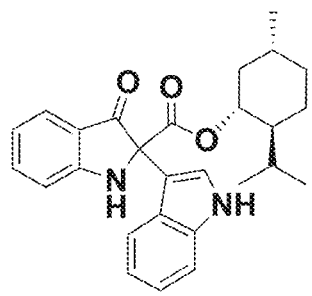
Figure 44:
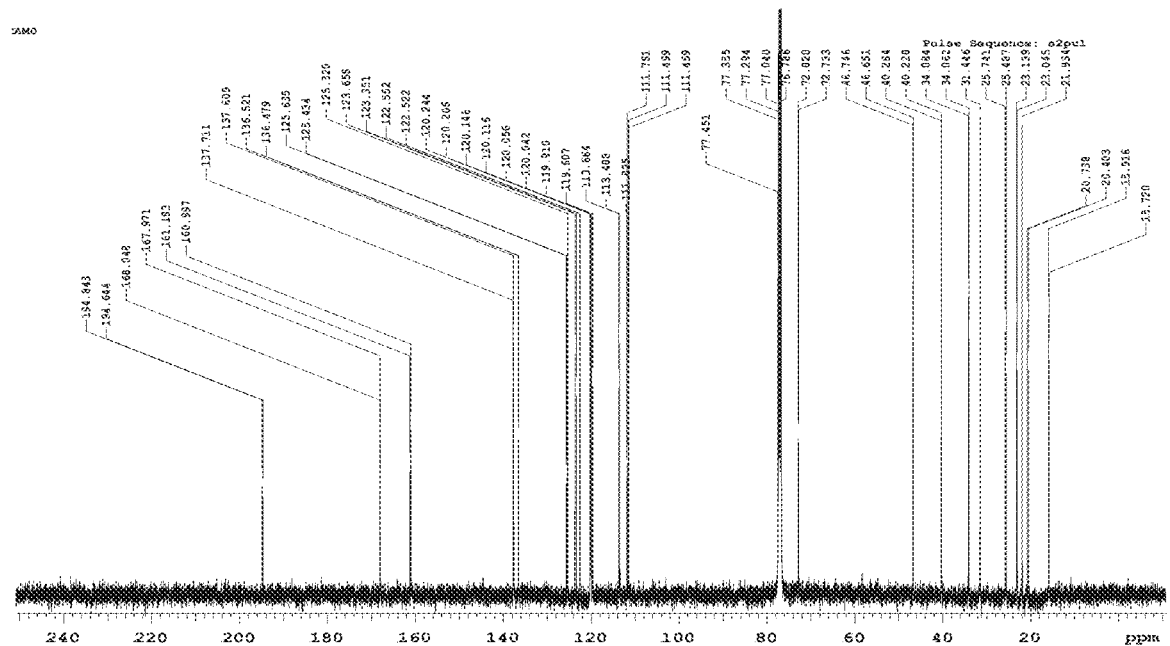
Figure 45:
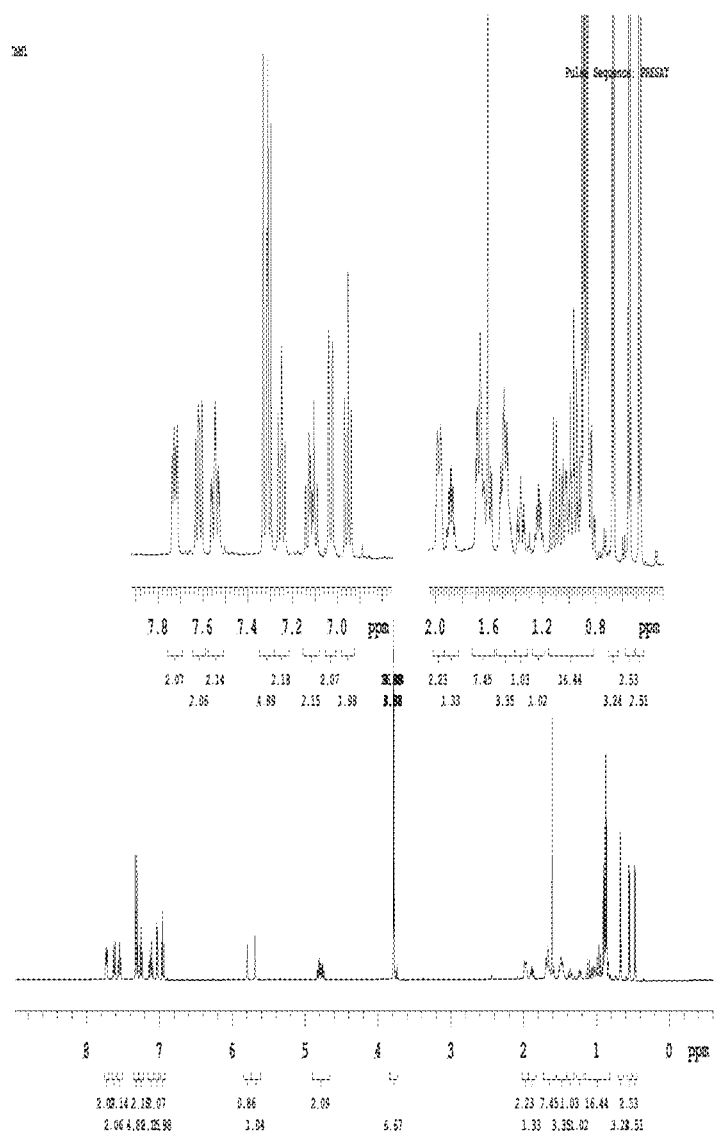
FIG. 45 depicts an NMR spectrum of compound 2ya:2yb.
Figure 45:
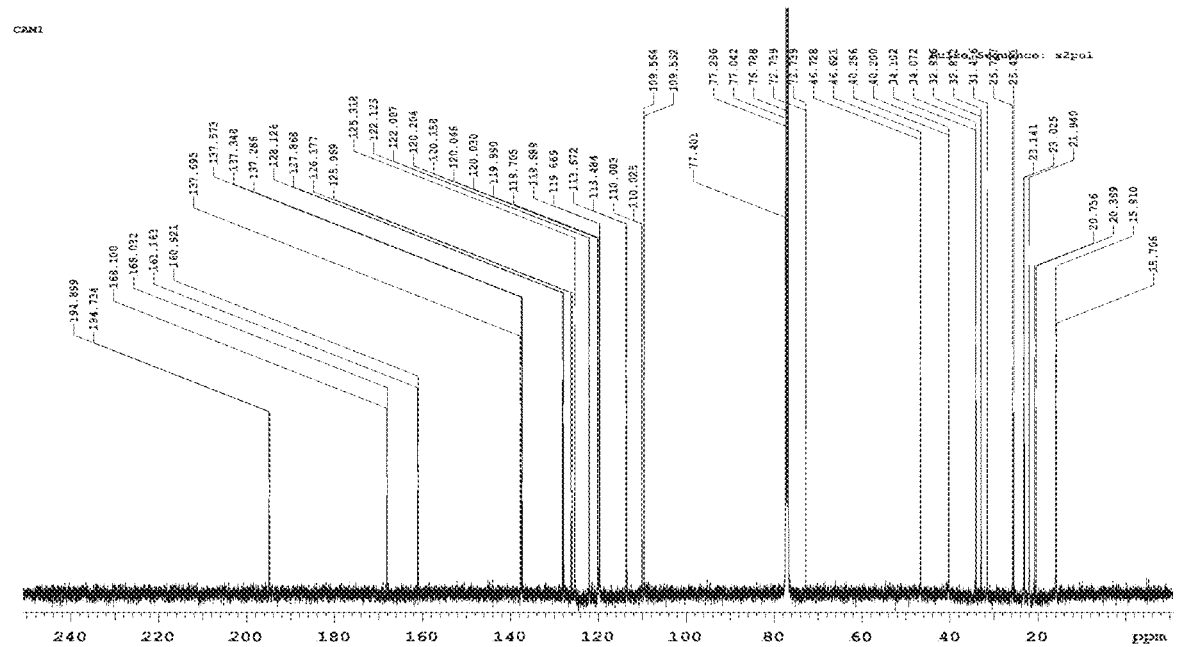
Figure 46:
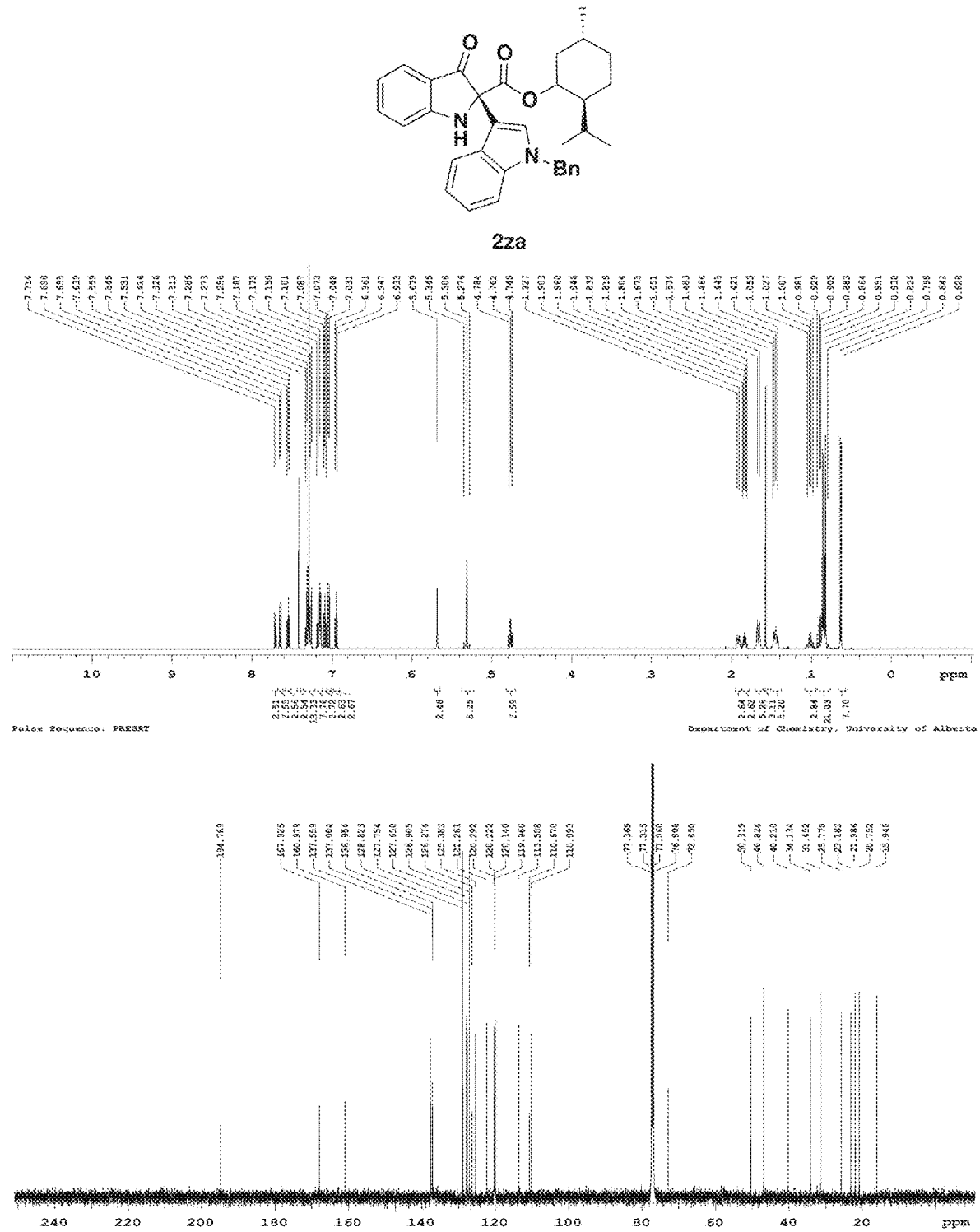
FIG. 46 depicts an NMR spectrum of compound 2za.
Figure 47:
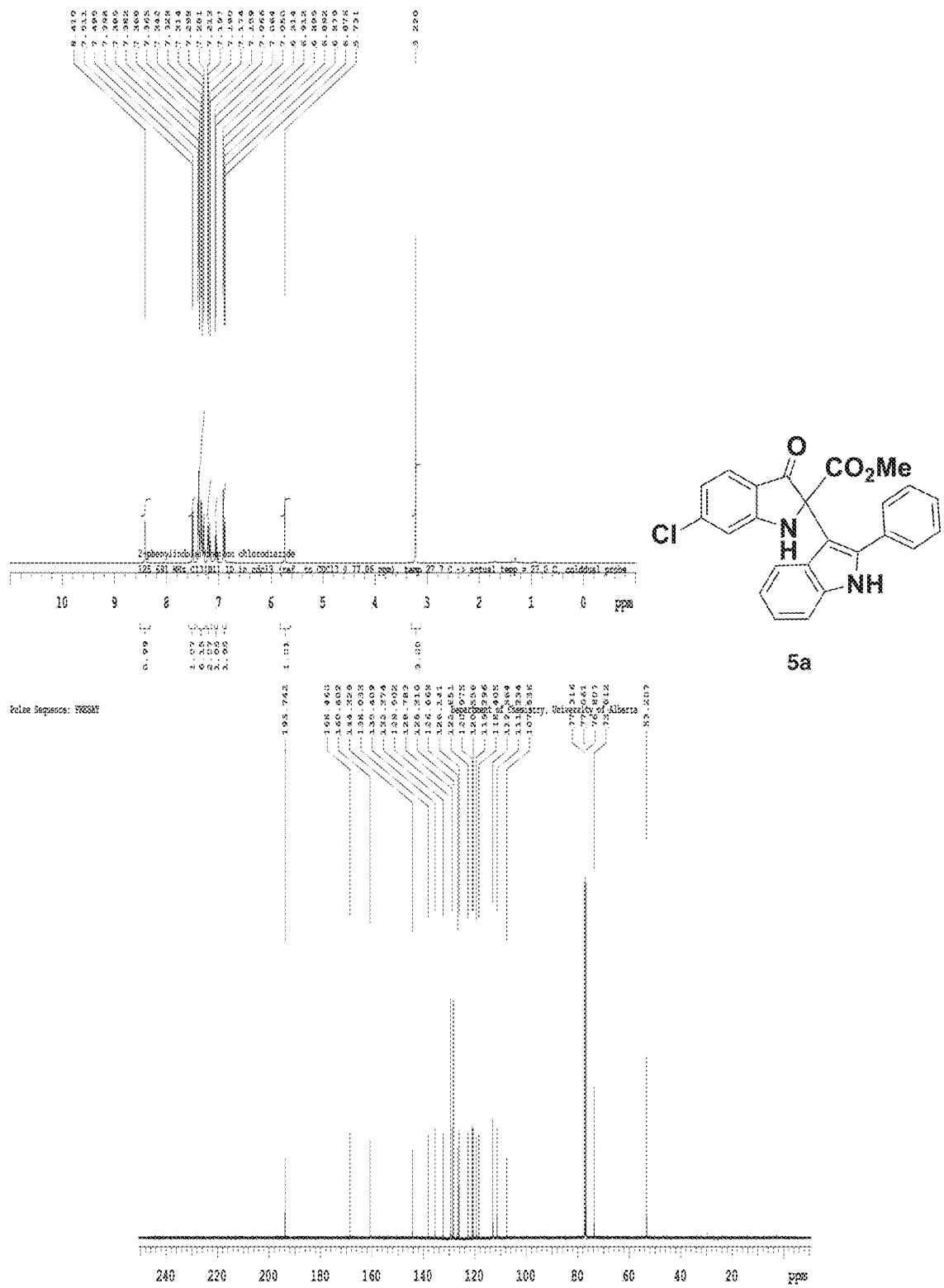
Figure 48:
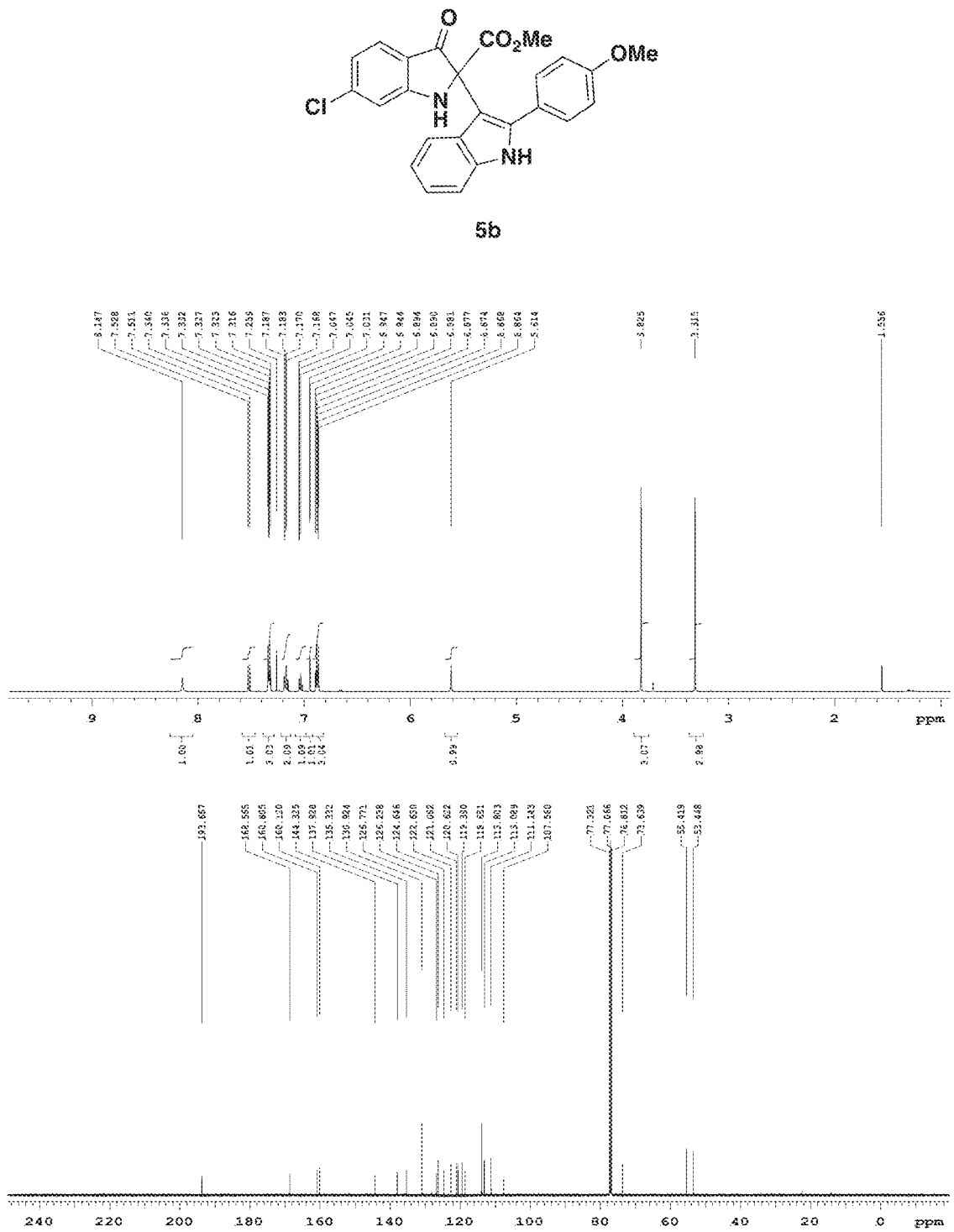
FIG. 48 depicts an NMR spectrum of compound 5b.
Figure 49:
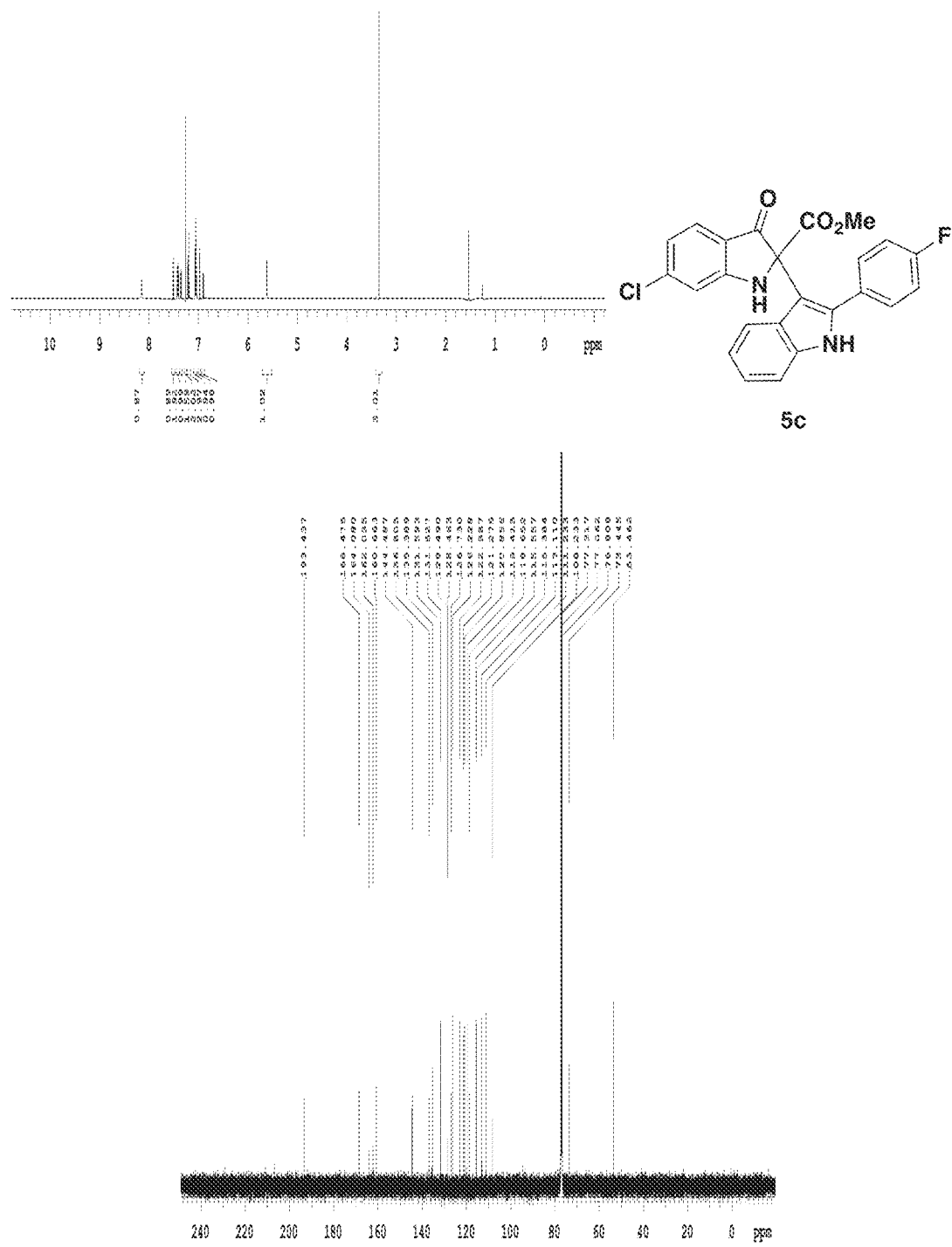
FIG. 49 depicts an NMR spectrum of compound 5c.
Figure 50:
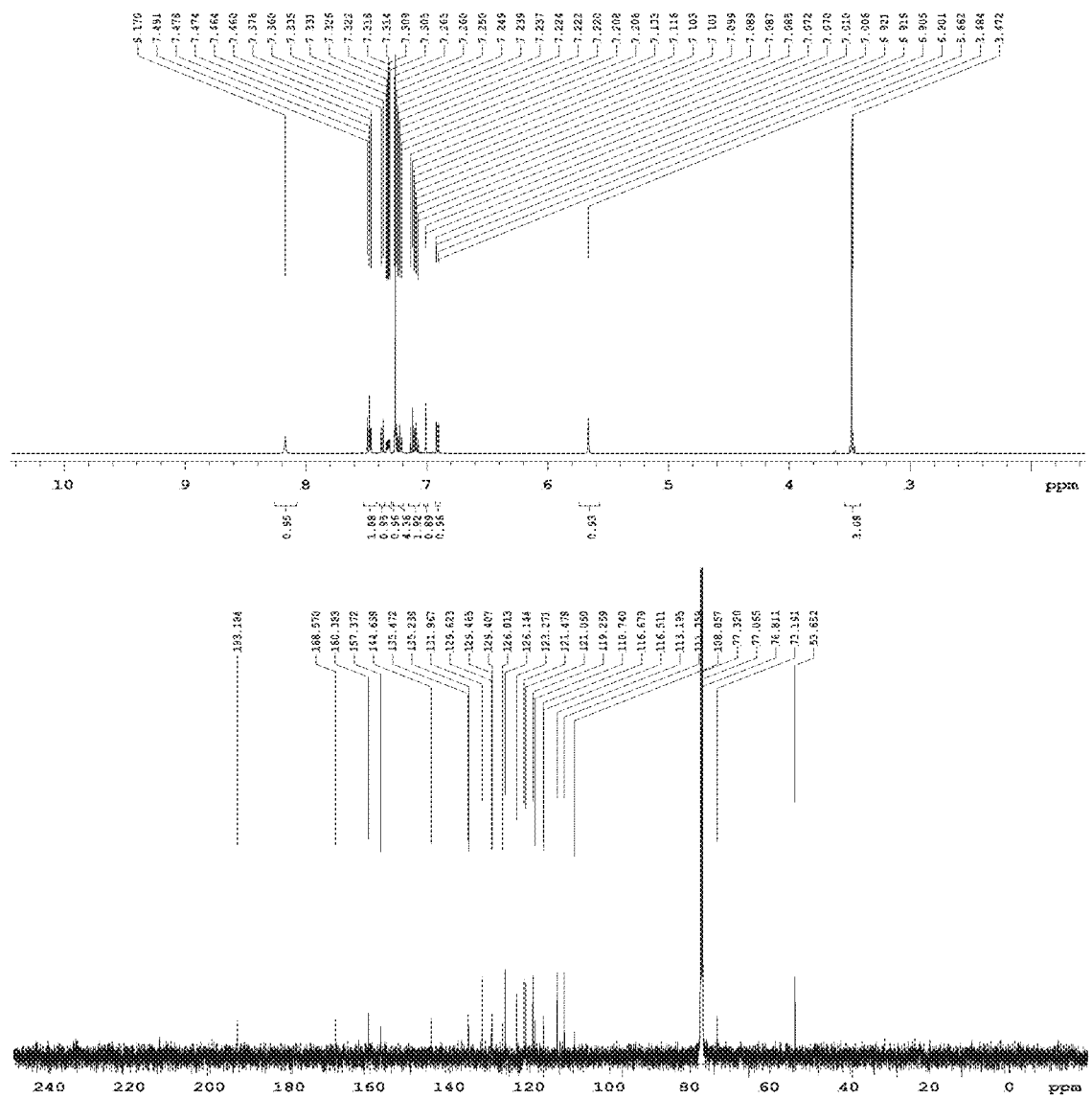
FIG. 50 depicts an NMR spectrum of compound 5d.
Figure 51:
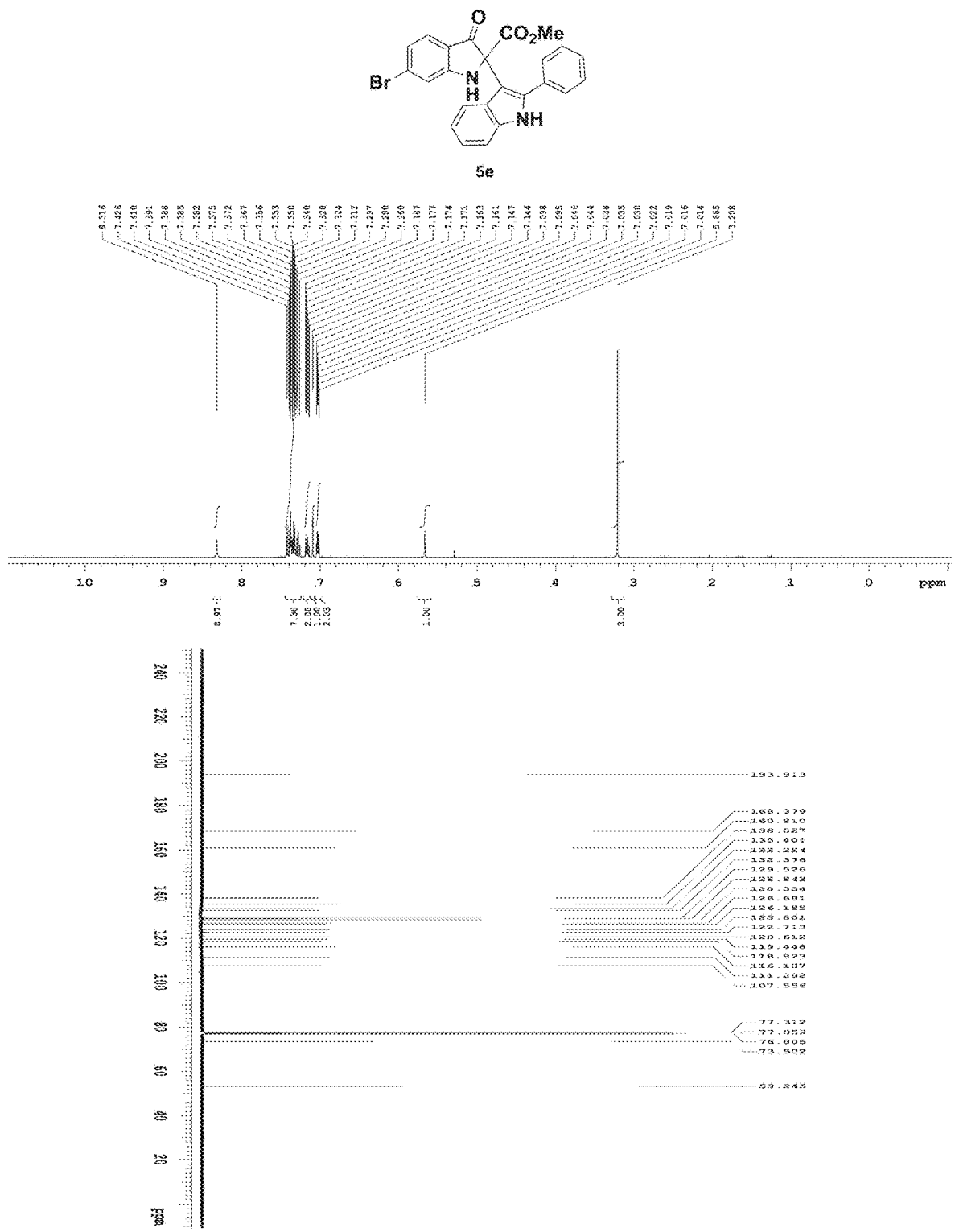
FIG. 51 depicts an NMR spectrum of compound 5e.
Figure 52:
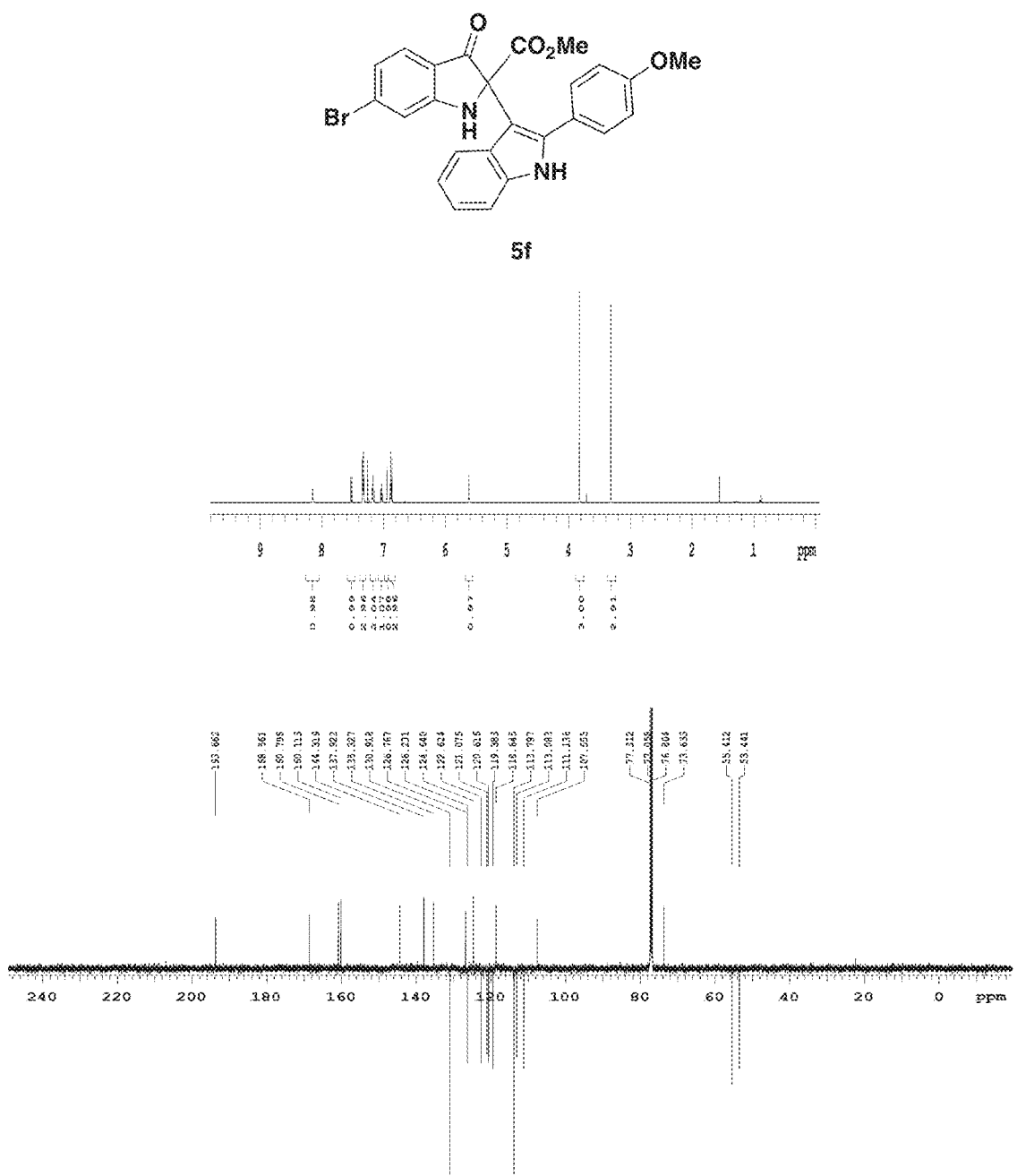
FIG. 52 depicts an NMR spectrum of compound 5f.
Figure 53:
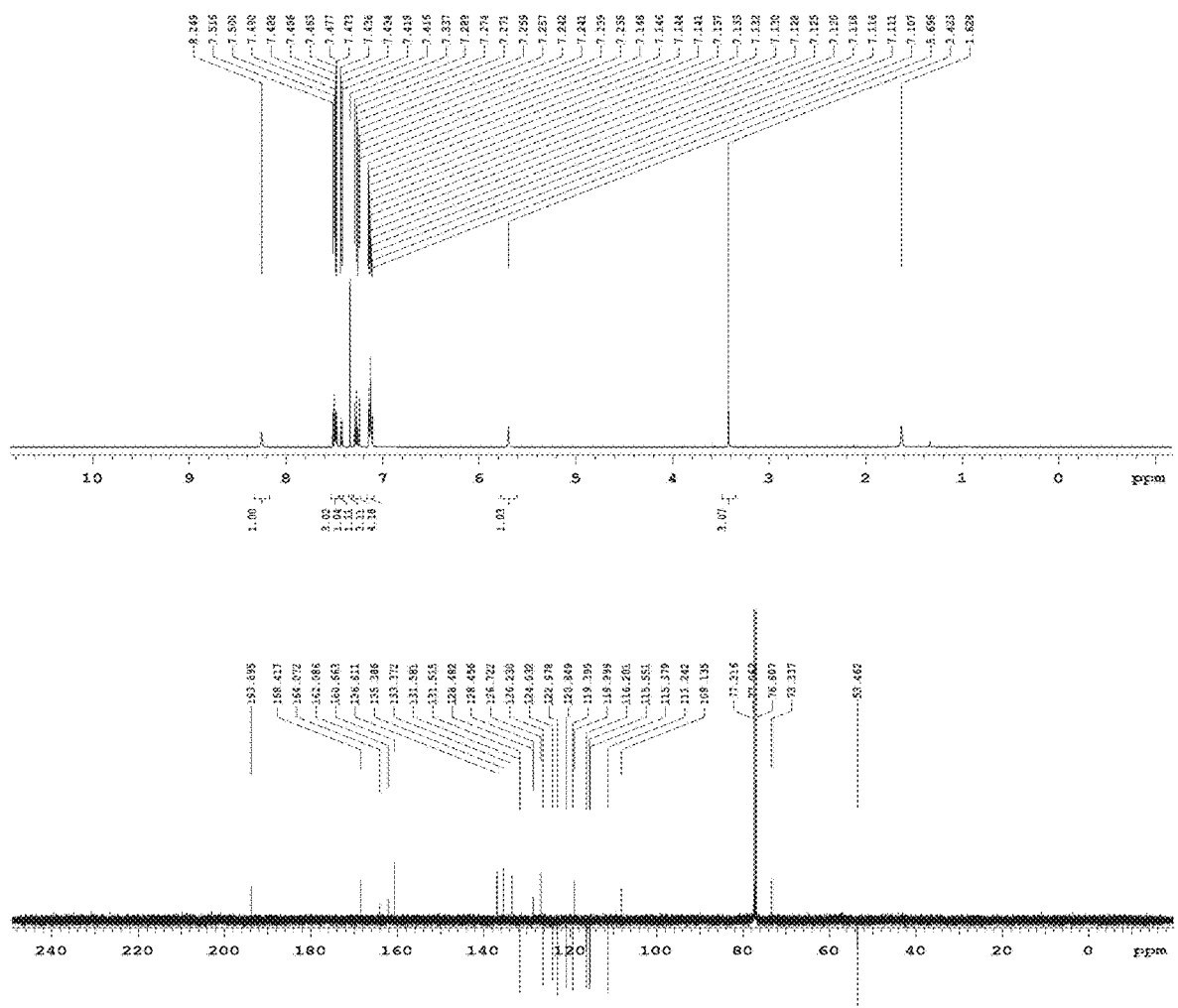
FIG. 53 depicts an NMR spectrum of compound 5g.
Figure 54:
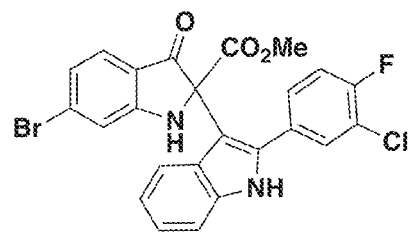
FIG. 54 depicts an NMR spectrum of compound 5h.
Figure 54:
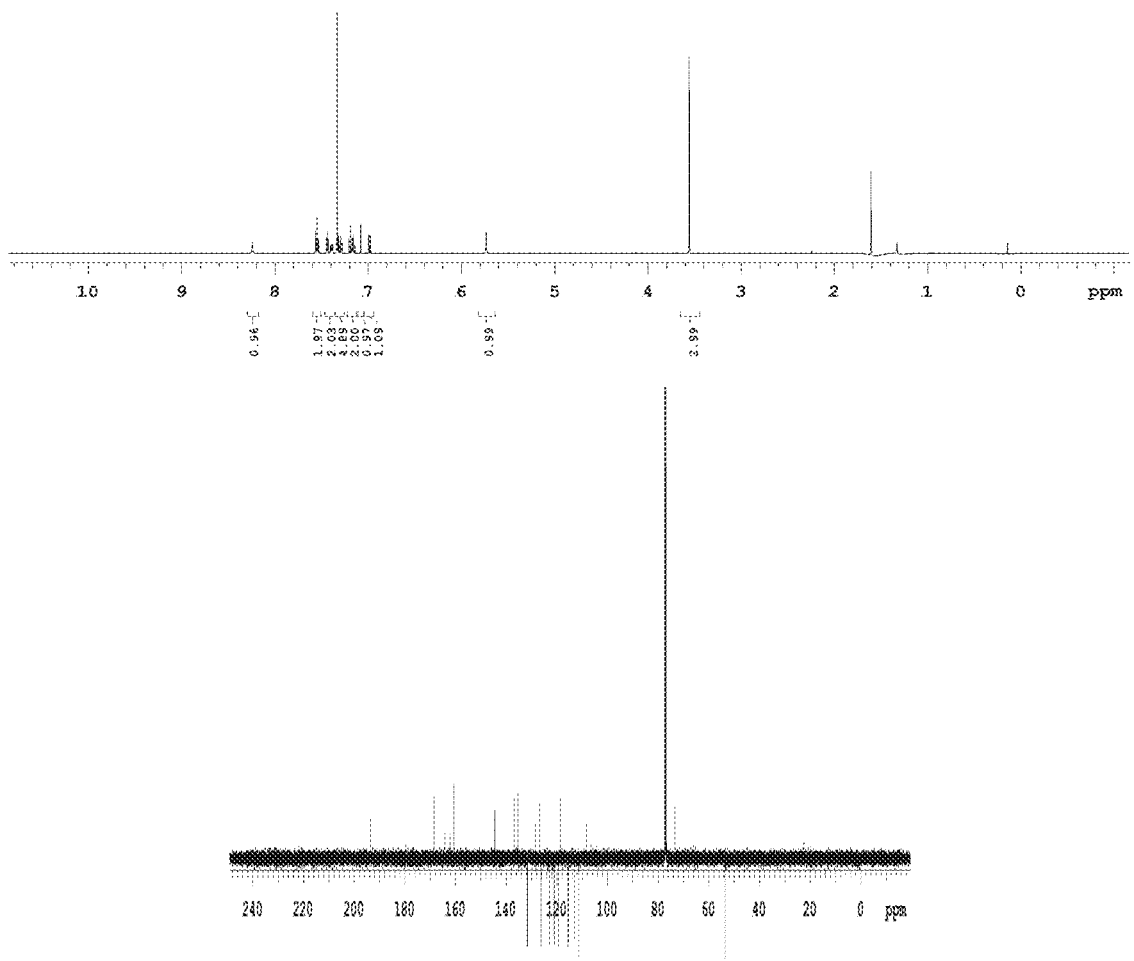

A solution of indole (55 mg, 0.20 mmol) was added to Cu(OTf)$_2$ (7.3 mg, 0.020 mmol) in DCM (5 mL) at room temperature. Once addition was done, formation of light green solution occurred after one hour. An aliquot of this solution (1 mL) was diluted with acetonitrile and directly subjected to ESI-MS analysis. After analysis of the ESI-MS (FIG. 12), the following fragments were detected and partially ascribed to the formation: A HRMS calc'd for C$_9$H$_6$CuF$_3$NO$_3$S [M]+327.9316, found 327.9645 (fleeting), for B HRMS calc'd for C$_{16}$H$_{14}$N$_2$O [M+H]+235.1230, found 235.1230, and protonated and sodiated 2a. NB.: Compound B was likewise detected in crude reaction mixture to make 2a.

Given an apparent reaction between the indole and copper (II) triflate to afford an initially colored complex, the absorption detected through UV-VIS spectroscopy, and literature precedent [Rauniyar, V.; Wang, Z. J.; Burks, H. E.; Toste, F. D. J. Am. Chem. Soc. 2011, 133, 8486-8489], it was posited reduction of copper (II) triflate through the initially formed metallated indole, followed by disproportionation reaction. This disproportionation reaction could theoretically generate copper (I) triflate, and copper (III) triflate indole complex. The latter could reductively eliminate to copper (I) triflate and indole triflate. Based on these experiments, the kinetically competent copper (I) triflate was proposed to result from a redox process involving copper (II) precatalyst and indole. However, this proposal on its own could not explain the substantial difference in isolated yield of 2a between Cu(OTf)$_2$ and CuOTf. An additional component in the reaction, presumably derived from the activation reaction of Cu(OTf)$_2$ and indole, was necessary for efficient Friedel Crafts alkylation with indole. It was proposed that a Bronsted acid catalyst, either TfOH or its salt with indole dimer B, acted to catalyze Friedel-Crafts addition of indole to the intermediate C-acylimine formed from metallocarbene-azide coupling.

Evidence for Bronsted Acid Catalysis of Friedel-Crafts Alkylation

NOTE: Since the putative C-acylimine occuring in the Cu(I)-catalyzed coupling step was transient and could not be isolated, isolable C-acylimine 6 was used as a model to help understand the second catalytic cycle.

Stirring C-acylimine 6 with Indole in the Presence of Cu(OTf)(PhMe):

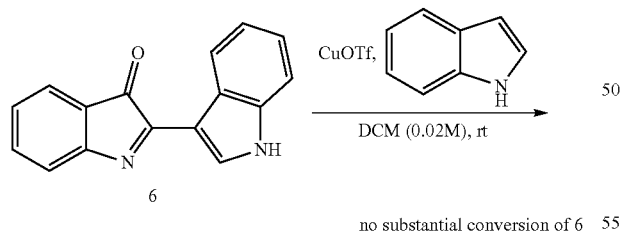

no substantial conversion of 6

A solution of C-acylimine 6 (50 mg, 0.19 mmol) and indole (50 mg, 0.20 mmol) was added to Cu(OTf)(PhMe) (9.7 mg, ca 0.020 mmol) in DCM (5 mL) at room temperature. Once addition was complete, the solution was allowed to stir overnight. After stirring for 16 h, the solution was extracted with water (5 mL, 2×), and the organic layer was dried with MgSO$_4$, filtered and concentrated under reduced pressure. Analysis of crude reaction mixture indicated that substantial quantities of 6 were present. Upon purification via a short pad of silica (20% EtOAc/Hexanes), ca. 91% of 6 was recovered. This model reaction showed that, although copper (I) triflate could convert 1a to the C-acylimine (see previous experiments), copper (I) could not efficiently catalyze the Friedel-Crafts alkylation reaction with indole.

Stirring C-Acylimine 6 with Indole in the Presence of TfOH:

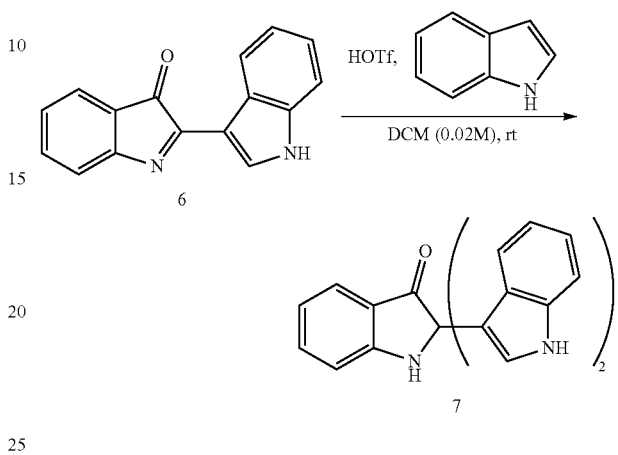

A solution of C-acylimine 6 (50 mg, 0.19 mmol) and indole (50 mg, 0.20 mmol) was mixed with excess TfOH (ca. 50 µL, ca. 0.57 mmol) in DCM (5 mL) at room temperature. Once mixing was complete, within 5 minutes a change in color was noticed, from deep purple to light orange. The solution was diluted with water (5 mL) and extracted with DCM (5 mL, 3×). The organic layer was dried using MgSO$_4$ concentrated under reduced pressure. Analysis of the crude mixture indicated that 6 was completely consumed, and adduct 7 can be detected using crude NMR. Purification of 7, however, was hampered by the presence of several side products.

Stirring C-Acylimine 6 with Indole in the Presence of CSA:

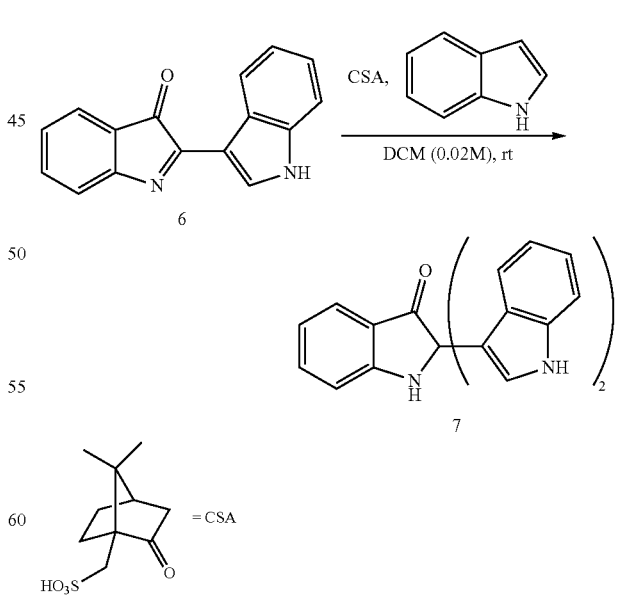

A solution of C-acylimine 6 (50 mg, 0.19 mmol) and indole (50 mg, 0.20 mmol) was mixed with camphorsulfonic acid CSA (4.0 mg, ca. 0.020 mmol) in DCM (5 mL) at room temperature. Once addition was complete, the solution gradually (overnight) changed color from deep purple to a yellow suspension. Analysis of the TLC indicated that 6 was completely consumed. The suspension was filtered. The filtered solid was dissolved in deuterated DMSO and was analyzed using NMR spectroscopy. Analysis of the spectra revealed that the 2:1 adduct, 7, (indole:indol-3-one), along with water and DMSO, were the only detectable components present in solution.

These results indicates that Bronsted acid, produced during the reduction of copper (II) triflate by indole, could activate the C-acylimine towards Friedel-Crafts alkylation reaction.

Using a (+)-Camphorsulfonic Acid as a Chiral Co-Catalyst:

A solution of diazo-azide 1a (50 mg, 0.20 mmol) in DCM (5 mL) was added to a solution of indole (46 mg, 0.39 mmol), Cu(OTf)$_2$ (7.3 mg, 0.020 mmol), and the (+)-CSA (4.0 mg, ca. 0.02 mmol) in DCM (5 mL) at room temperature via syringe pump over 1 h. The reaction mixture turned light green over 2 h, then slowly turned dark brown over 24 h. Once addition was complete, the reaction was monitored by TLC for consumption of 1a. Upon consumption of 1a, the reaction mixture was poured in an Erlenmeyer flask, thoroughly dissolved in ethyl acetate (ca 10 mL), dried over MgSO$_4$, filtered, concentrated under reduced pressure and purified by flash chromatography. (NB.: crude mixture after concentration was insoluble in DCM. In this case, necessarily, ethyl acetate was used as a solvent to load the sample onto silica gel (silica gel, 7:3 hexanes:EtOAc). All pure fractions of 2a were concentrated together to afford yellow oil. Upon standing for at least 24 hours, this oil slowly formed a yellow solid. Analysis of the yellow oil using chiral HPLC revealed that the product was formed in a 68:32 enantiomeric ratio. HPLC condition: Chiralpak AD-H, 80:20, Hexanes:i-PrOH, rt, retention time=33.77 min (major), 37.71 min (minor).

X-Ray Crystallographic Data

The X-ray crystallographic data depicted in FIG. 13-16 entails ORTEP structures of select compounds:

ORTEP structure for compound 1a (FIG. 13): Compound-Methyl 2-diazo-3-(2-azido-3-methylphenyl)-3-oxopropanoate; Formula-C$_{11}$H$_9$N$_5$O$_3$.

ORTEP Structure for compound 2a (FIG. 14): Compound-Methyl 3-oxo-1,3-dihydro-1'H,2H-2,3'-biindole-2-carboxylate; Formula-C$_{18}$H$_{14}$N$_2$O$_3$.

ORTEP Structure for compound 2o (FIG. 15): Compound-Methyl 6-chloro-3-oxo-1,3-dihydro-1'H,2H-2,3'-biindole-2 carboxylate; Formula-C$_{18}$H$_{13}$ClN$_2$O$_3$.

ORTEP Structure for compound 2za (FIG. 16): Compound-(−)-Menthyl (2R)-1'-benzyl-3-oxo-1,3-dihydro-1'H, 2H-2,3'-biindole-2-carboxylate; Formula-C$_{34}$H$_{36}$N$_2$O$_3$.

NMR Spectra of the Starting Materials and Products

Please see FIG. 17-54.

The presence of significant signals for residual water in the $^1$H NMR spectra of 2a, 2e, 2l, 2o, 2t and 2v may raise questions about proof of purity. It should be noted that the presence of one or more heavy halogen atoms and/or an unprotected indole nitrogen atom rendered these compounds only sparingly soluble in common deuterated NMR solvents (CDCl$_3$, CD$_2$Cl$_2$, C$_6$D$_6$, C$_3$D$_6$O, CD$_3$OD, and C$_2$D$_6$SO). Consequently, minor amounts of water contaminant in these solvents may appear to have anomalously enhanced signals relative to those of the compounds of interest. $^1$H NMR spectra of these compounds were not representative of the bulk material, and cannot be used as the sole judge or proof of purity.

However, the following observations from data presented above were reasonable proof of purity, apart from the $^1$H-NMR spectra presented in the next section: (i) reasonable accuracy of experimental elemental analysis (C, H, and N) compared to theoretical value (0.05-0.34%) in those cases where combustion analysis was performed; (ii) sharp (1-3° C.) and high (>100° C.) melting points; (iii) substantially higher melting points compared to reported literature value (2a and 2b) [Jessing, M.; Barran, P. S. Heterocycles 2011, 82, 1739-1745]; and, high degree of crystallinity, and with X-ray crystal structures and measurements for 2a, 2o, and 2za.

Example 3

A model of a Respiratory Syncytial Virus (RSV) L protein was built, using SWISS-MODEL (on the internet at swiss-model(dot)expasy(dot)org). Figures obtained using Chimera and Pymol.

RSV L protein is an RNA-directed RNA polymerase.

Molecular dynamic simulations were carried out to refine the model using NAMD on Graham clusters (Compute Canada). Molecular docking experiments were performed using the Schrödinger Small Molecule Discovery Suite and figures obtained using Pymol. The results are depicted in FIG. 55 and FIG. 56.

Figure 55:
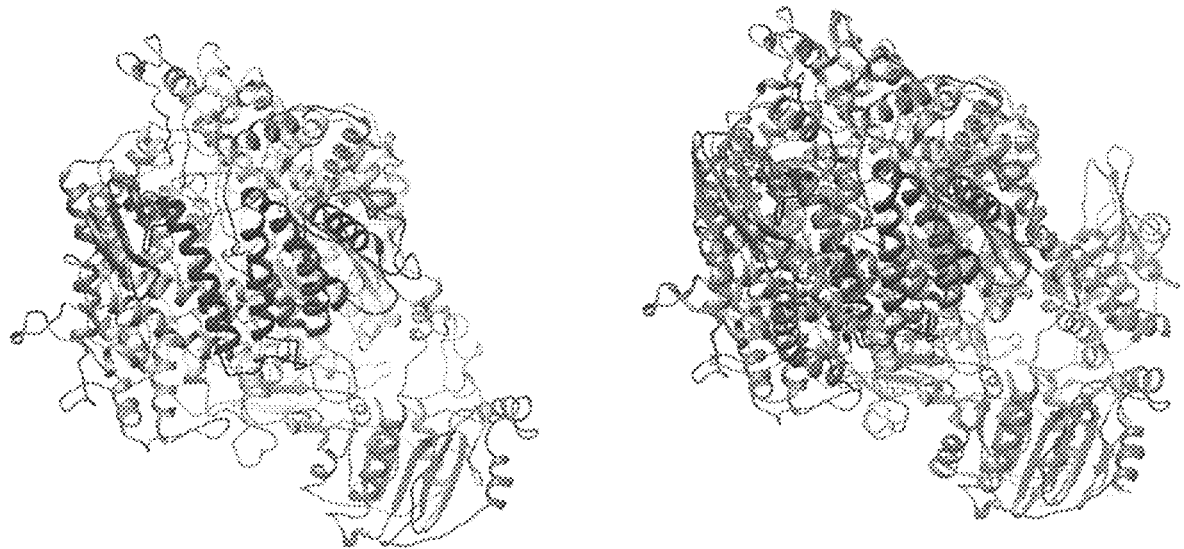
FIG. 55 depicts homology modelling of a Respiratory Syncytial Virus (RSV) L protein based on the VSV L structure. Model of RSV L protein (left), Alignment of the RSV model with L protein of VSV. (VSV: Vesicular Stomatitis Virus).

FIG. 55 depicts homology modelling of the RSV L protein based off the VSV L structure. Model of RSV L protein (left), Alignment of the RSV model with L protein of VSV. (VSV: Vesicular Stomatitis Virus).

Figure 56:
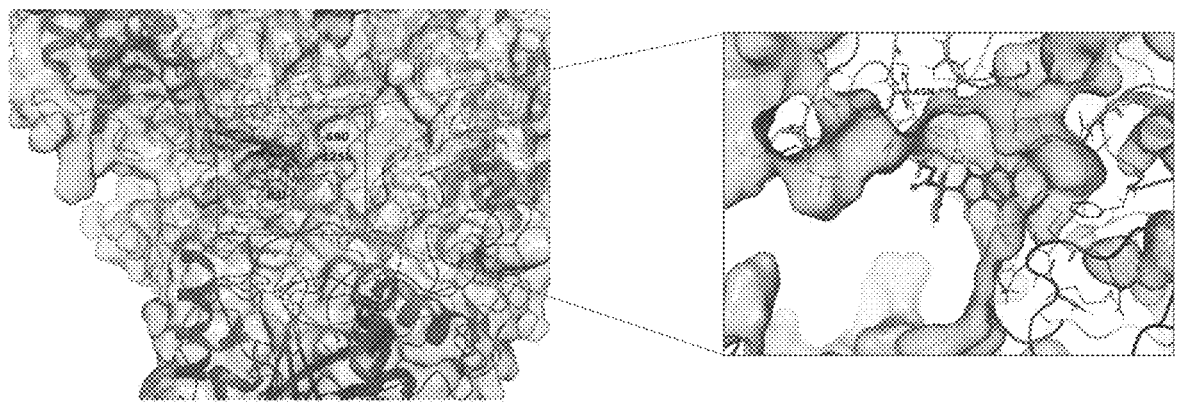
FIG. 56 depicts molecular docking of an active compound (compound 5a) of the present disclosure into the active site of RSV L protein showing two hydrogen bonds to the catalytic ASP 686. Active site was defined using binding site map implanted in Schrödinger Small Molecule Discovery Suite.

FIG. 56 depicts molecular docking of the active compound (compound 5a) into the active site of RSV L protein showing two hydrogen bonds to the catalytic ASP 686. The active site was defined using binding site map implanted in Schrödinger Small Molecule Discovery Suite.

REFERENCES (1) (a) Padwa, A.; Weingarten, M. D. *Chem. Rev.* 1996 96,223-270. (b) Doyle, M. P.; McKervey, M. A.; Ye, T. *Modern Catalytic Methods for Organic Synthesis with Diazo Compounds: From Cyclopropanes to Ylides*; Wiley: New York, 1998.

(2) (a) Padwa, A.; Hornbuckle, S. F. *Chem. Rev.* 1991, 91, 263-309. (b) Vanecko, J. A.; Wan, H.; West, F. G.; *Tetrahedron* 2006, 62, 1043-1062. (c) Murphy, G. K.; Stewart, C.; West, F. G. *Tetrahedron* 2013, 69, 2667-2686.

(3) Bott, T. M.; Atienza, B. J.; West, F. G. *RSC Adv.* 2014, 4, 31955-31959.

(4) Liu, J. F.; Jiang, Z. Y.; Wang, R. R.; Zheng, Y. T.; Chen, J. J.; Zhang, X. M.; Ma, Y. B. *Org. Lett.* 2007, 9, 4127-4129.

(5) (a) Karadeolian, A.; Kerr, M. A. *J. Org. Chem.* 2010, 75, 6830-6841. (b) Karadeolian, A.; Kerr, M. A. *Angew. Chem. Int. Ed.* 2010, 49, 1133-1135. (c) Lee, J.; Panek, J. S. *Org. Lett.* 2011, 13, 502-505. (d) Lee, J.; Panek, J. S. *J.Org. Chem.* 2015, 80, 2959-2971. (e) Zhang, X.; Mu, T.; Zhan, F.; Ma, L.; Liang, G. *Angew. Chem. Int. Ed.* 2011, 50, 6164-6166. (f) Wu, W.; Xiao, M.; Wang, J.; Li, Y.; Xie, Z. 9*Org. Lett.* 2012, 14, 1624-1627. (g) Patel, P.; Ramana, C. V. I *Org. Chem.* 2012, 77, 10509-10515. (h) Xiao, M.; Wu, W.; Wei, L.; Jin, X.; Yao, X.; Xie, Z. *Tetrahedron* 2015, 3705-3714.

(6) Nair, H.; Nokes, D. J.; Gessner, B. D.; Dherani, M.; Madhi, S. A.; Singleton, R. J.; O'Brien, K. L.; Roca, A.; Wright, P. F.; Bruce, N.; Chandran, A.; Theodoratou, E.; Sutanto, A.; Sedyaningsih, E. R.; Ngama, M.; Munywoki, P. K.; Kartasasmita, C.; Simoes, E. A.; Rudan, I.; Weber, M. W.; Campbell, H. *Lancet* 2010, 375, 1545-1555.

(7) Faria, N. R.; Azevedo Rdo, S.; Kraemer, M. U.; Souza, R.; Cunha, M. S.; Hill, S. C.; Theze, J.; Bonsall, M. B.; Bowden, T. A.; Rissanen, I.; Rocco, I. M.; Nogueira, J. S.; Maeda, A. Y.; Vasami, F. G.; Macedo, F. L.; Suzuki, A.; Rodrigues, S. G.; Cruz, A. C.; Nunes, B. T.; Medeiros, D. B.; Rodrigues, D. S.; Nunes Queiroz, A. L.; da Silva, E. V.; Henriques, D. F.; Travassos da Rosa, E. S.; de Oliveira, C. S.; Martins, L. C.; Vasconcelos, H. B.; Casseb, L. M.; Simith Dde, B.; Messina, J. P.; Abade, L.; Lourenco, J.; Carlos Junior Alcantara, L.; de Lima, M. M.; Giovanetti, M.; Hay, S. I.; de Oliveira, R. S.; Lemos Pda, S.; de Oliveira, L. F.; de Lima, C. P.; da Silva, S. P.; de Vasconcelos, J. M.; Franco, L.; Cardoso, J. F.; Vianez-Junior, J. L.; Mir, D.; Bello, G.; Delatorre, E.; Khan, K.; Creatore, M.; Coelho, G. E.; de Oliveira, W. K.; Tesh, R.; Pybus, O. G.; Nunes, M. R.; Vasconcelos, P. F., *Science* 2016, 352, 345-349.

(8) Mlakar, J.; Korva, M.; Tul, N.; Popovic, M.; Poljsak-Prijatelj, M.; Mraz, J.; Kolenc, M.; Resman Rus, K.; Vesnaver Vipotnik, T.; Fabjan Vodusek, V.; Vizjak, A.; Pizem, J.; Petrovec, M.; Avsic Zupanc, T. *N Engl. J. Med.* 2016, 374, 951-958.

(9) Salomon, R. G.; Kochi, J. K. *J. Am. Chem. Soc.* 1973, 95, 3300-3310.

(10) Despite the high nitrogen content of substrate 1a, we have not observed explosive decomposition under standard conditions. Analysis by DSC and TGA indicate thermal instability above 127° C. (See Supporting Information). Nonetheless, use of a blast shield and appropriate protective wear (earplugs, Kevlar lab coat and gloves) is recommended for gram-scale reactions.

(11) Phipps, R. J.; Grimster, N. P.; Gaunt, M. J. *J. Am. Chem. Soc.* 2008, 130, 8172-8174.

(12) Ribas, X.; Jackson, D. A.; Donnadieu, B.; Mahia, J.; Parella, T.; Xifra, X.; Hedman, B.; Hodgson, K. O.; Llobet, A.; Stack, T. D. P. *Angew. Chem. Int. Ed.* 2002, 41, 2991-2994.

(13) When the conditions of Table 1, entry 4 were carried out in the presence of various bases (pyridine, triethylamine, various inorganic bases), no conversion was observed. While these results are consistent with the Bronsted acid requirement, they may also be attributable to inhibition of the initial redox activation step by base coordination to Cu(II).

(14) (a) Aburatani, S.; Uenishi, J. *Heterocycles* 2008, 75, 1407-1416. (b) Quartarone, G.; Charmet, A. P.; Ronchin, L.; Tortato, C.; Vavasori, A. *J. Phys. Org. Chem.* 2014, 27, 680-689. (c) Guo, T.; Han, S.-L.; Liu, Y.-C.; Liu, H.-M. *Tetrahedron Lett.* 2016, 57, 1097-1099.

(15) (a) Suárez-Castillo, O. R.; Mélendez-Rodriguez, M.; Morales-Garcia, A. L.; Cano-Escudero, I. C.; Contreras-Martinez, Y. M. A.; Moreles-Rios, M. S.; Joseph-Nathan, P. *Heterocycles* 2009, 78, 1463-1476. (b) Xu, X.-H.; Liu, G.-K.; Azuma, A.; Tokunaga, E.; Shibata, N. *Org. Lett.* 2011, 13, 4854-4857.

(16) For related indole additions to an indolenones catalyzed by chrial Brønsted acid, see: (a) Rueping, M.; Raja, S.; Nunez, A. *Adv. Synth. Catal.* 2011, 353, 563-568. (b) Yin, Q.; You, S.-L. *Chem. Sci* 2011, 2, 1344-1348.

(17) Sun, Z.; Pan, Y.; Jiang, S.; Lu, L. *Viruses* 2013, 5, 211-225.

(18) Chapman, J.; Abbott, E.; Alber, D. G.; Baxter, R. C.; Bithell, S. K.; Henderson, E. A.; Carter, M. C.; Chambers, P.; Chubb, A.; Cockerill, G. S.; Collins, P. L.; Dowdell, V. C.; Keegan, S. J.; Kelsey, R. D.; Lockyer, M. J.; Luongo, C.; Najarro, P.; Pickles, R. J.; Simmonds, M.; Taylor, D.; Tyms, S.; Wilson, L. J.; Powell, K. L. *Antimicrob. Agents Chemother.* 2007, 51, 3346-3353.

(19) Noton, S. L.; Fearns, R. *Virology* 2015, 479-480C, 545-554.

(20) Selisko, B.; Wang, C.; Harris, E.; Canard, B. *Curr. Opin. Virol.* 2014, 9, 74-83.

(21) Jessing, M.; Barran, P. S. *Heterocycles* 2011, 82, 1739-1745.

(22) Hallak, L. K.; Spillmann, D.; Collins, P. L.; Peeples, M. E. *J. Virol.* 2000, 74, 10508-10513.

(23) Canter, D. M.; Jackson, R. L.; Perrault, J. *Virology* 1993, 194, 518-529.

(24) Noton, S. L.; Nagendra, K.; Dunn, E. F.; Mawhorter, M. E.; Yu, Q.; Fearns, R. *J. Virol.* 2015, 89, 7786-7798.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A compound having the formula (V)

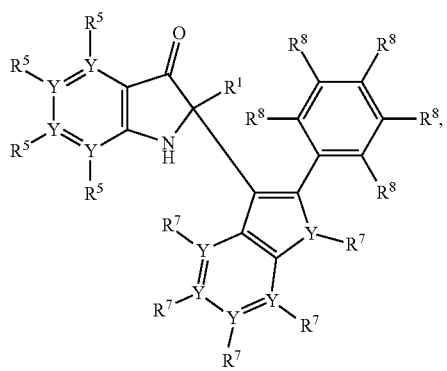

(V)

or a stereoisomer, a racemate, a tautomer, a pharmaceutically acceptable salt, or a solvate thereof, wherein:

Y is independently C or a heteroatom;

R1 is an ester, an amide, or a heterocycle;

R5 is independently absent, H, C1-C10 alkyl, C10-C20 alkyl, C2-C10 alkenyl, C10-C20 alkenyl, C2-C10 alkynyl, C10-C20 alkynyl, C3-C20 carbocycle, aryl, benzyl, heterocycle, C1-C10 alkoxy, C10-C20 alkoxy, alcohol, ether, ketone, carboxylic acid, ester, thiol, thioether, amine, amide, carbamate, nitro, cyano, or halo, each of which is optionally substituted; or two of R5, together with the atoms to which they are attached, are connected to form a cycle or heterocycle, each of which is optionally substituted;

R7 is independently absent, H, C1-C10 alkyl, C10-C20 alkyl, C2-C10 alkenyl, C10-C20 alkenyl, C2-C10 alkynyl, C10-C20 alkynyl, C3-C20 carbocycle, aryl, benzyl, heterocycle, C1-C10 alkoxy, C10-C20 alkoxy, alcohol, ether, ketone, carboxylic acid, ester, thiol, thioether, amine, amide, carbamate, nitro, cyano, or halo, each of which is optionally substituted; or two of R7, together with the atoms to which they are attached, are connected to form a cycle or heterocycle, each of which is optionally substituted; and, R8 is independently H, C1-C10 alkyl, C10-C20 alkyl, C2-C10 alkenyl, C10-C20 alkenyl, C2-C10 alkynyl, C10-C20 alkynyl, C3-C20 carbocycle, aryl, benzyl, heterocycle, C1-C10 alkoxy, C10-C20 alkoxy, alcohol, ether, ketone, carboxylic acid, ester, thiol, thioether, amine, amide, carbamate, nitro, cyano, or halo, each of which is optionally substituted; or two of R8, together with the atoms to which they are attached, are connected to form a cycle or heterocycle, each of which is optionally substituted.

2. A compound having the formula (VI)

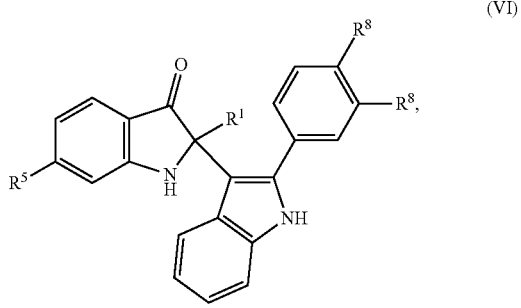

(VI)

or
a stereoisomer, a racemate, a tautomer, a pharmaceutically acceptable salt, or a solvate thereof,
wherein:
R1 is an ester;
R5 is a halo; and,
R8 is independently H, C1-C10 alkoxy, or halo, each of which is optionally substituted.

3. The compound of claim 2, having the structure

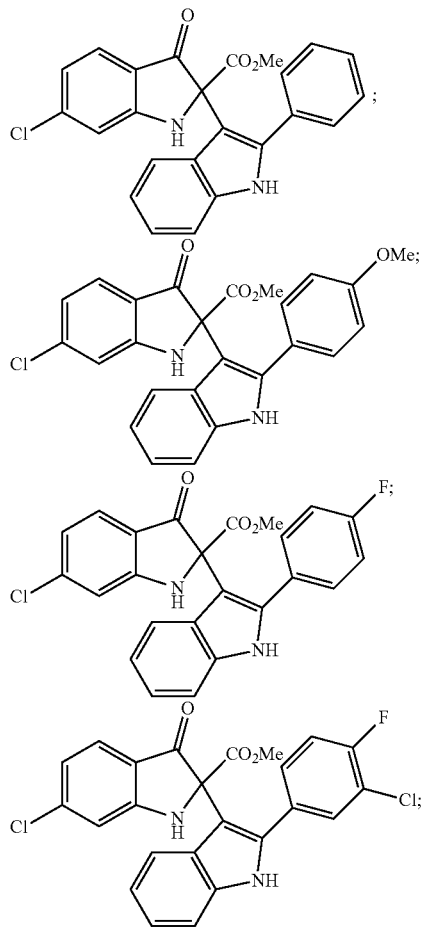

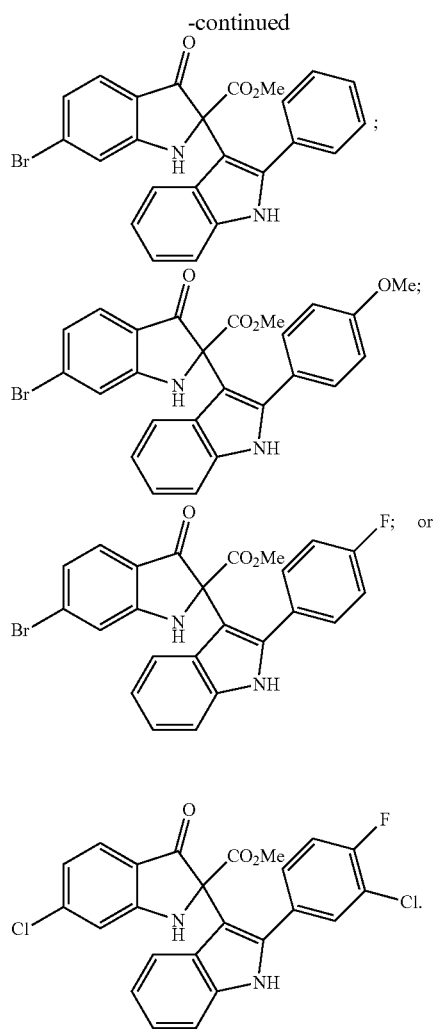

4. A pharmaceutical composition comprising:
a) a compound of claim 1; and
b) a pharmaceutically acceptable carrier, diluent, or vehicle.

* * * * *

UNITED STATES PATENT AND TRADEMARK OFFICE
CERTIFICATE OF CORRECTION

| | | |
|---|---|---|
| PATENT NO. | : 11,566,018 B2 | |
| APPLICATION NO. | : 16/971269 | |
| DATED | : January 31, 2023 | |
| INVENTOR(S) | : Frederick Glenn West et al. | |

It is certified that error appears in the above-identified patent and that said Letters Patent is hereby corrected as shown below:

In the Drawings

On sheet 4 of 58, in Figure 4 (Cont.), Line 2, delete "(1 R," and insert -- (1R, --.

In the Specification

In Column 1, Line 21, delete "agwe." and insert -- age. --.

In Column 10, Lines 44-45, delete "Cu catalyst. In another embodiment, the transition metal catalyst is Cu(hfacac)$_2$, Cu(OTf)$_2$, or CuOTf.Ph(CH$_3$)." and insert the same on Column 10, Line 43, as a continuation of the same paragraph.

In Column 10, Line 56, delete "syntheized" and insert -- synthesized --.

In Column 10, Line 63, delete "syntheized" and insert -- synthesized --.

In Column 11, Line 3, delete "syntheized" and insert -- synthesized --.

In Column 11, Lines 21-22, delete "mumpus" and insert -- mumps --.

In Column 11, Line 36, delete "syntheized" and insert -- synthesized --.

In Column 11, Line 42, delete "syntheized" and insert -- synthesized --.

In Column 11, Line 48, delete "syntheized" and insert -- synthesized --.

In Column 11, Line 54, delete "syntheized" and insert -- synthesized --.

In Column 12, Line 6, delete "mumpus" and insert -- mumps --.

Signed and Sealed this
Ninth Day of January, 2024

Katherine Kelly Vidal
*Director of the United States Patent and Trademark Office*

CERTIFICATE OF CORRECTION (continued)
U.S. Pat. No. 11,566,018 B2

In Column 12, Line 10, delete "usewherein" and insert -- use wherein --.

In Column 13, Line 28, delete "FIG." and insert -- FIGS. --.

In Column 16, Line 50, delete "FIG." and insert -- FIGS. --.

In Column 16, Line 53, delete "FIG." and insert -- FIGS. --.

In Column 17, Line 44, delete "Pestivirus" and insert -- Pestivirus. --.

In Column 17, Line 54, delete "Morbillivirus" and insert -- Morbillivirus. --.

In Column 17, Line 56, delete "mumpus" and insert -- mumps --.

In Column 19, Line 10, delete "C1" and insert -- $C_1$ --.

In Column 20, Line 23, delete "$C_2$-$C_{20}$" and insert -- $C_{10}$-$C_{20}$ --.

In Column 20, Line 23, delete "$C_2$-$C_{20}$" and insert -- $C_{10}$-$C_{20}$ --.

In Column 20, Line 25, delete "$C_2$-$C_{20}$" and insert -- $C_{10}$-$C_{20}$ --.

In Column 20, Line 29, delete "$C_2$-$C_{20}$" and insert -- $C_{10}$-$C_{20}$ --.

In Column 20, Line 30, delete "$C_2$-$C_{20}$" and insert -- $C_{10}$-$C_{20}$ --.

In Column 20, Line 30, delete "$C_2$-$C_{20}$" and insert -- $C_{10}$-$C_{20}$ --.

In Column 20, Line 32, delete "$C_2$-$C_{20}$" and insert -- $C_{10}$-$C_{20}$ --.

In Column 20, Line 38, delete "$C_2$-$C_{20}$" and insert -- $C_{10}$-$C_{20}$ --.

In Column 20, Line 39, delete "$C_2$-$C_{20}$" and insert -- $C_{10}$-$C_{20}$ --.

In Column 20, Line 39, delete "$C_2$-$C_{20}$" and insert -- $C_{10}$-$C_{20}$ --.

In Column 20, Line 41, delete "$C_2$-$C_{20}$" and insert -- $C_{10}$-$C_{20}$ --.

In Column 21, Line 7, delete "$C_2$-$C_{20}$" and insert -- $C_{10}$-$C_{20}$ --.

In Column 21, Line 9, delete "$C_2$-$C_{20}$" and insert -- $C_{10}$-$C_{20}$ --.

In Column 21, Line 22, delete "$C_2$-$C_{20}$" and insert -- $C_{10}$-$C_{20}$ --.

In Column 21, Line 23, delete "$C_2$-$C_{20}$" and insert -- $C_{10}$-$C_{20}$ --.

CERTIFICATE OF CORRECTION (continued)
U.S. Pat. No. 11,566,018 B2

In Column 21, Line 23, delete "$C_2$-$C_{20}$" and insert -- $C_{10}$-$C_{20}$ --.

In Column 21, Line 32, delete "$C_2$-$C_{20}$" and insert -- $C_{10}$-$C_{20}$ --.

In Column 21, Line 34, delete "$C_2$-$C_{20}$" and insert -- $C_{10}$-$C_{20}$ --.

In Column 30, Lines 51-62, delete " 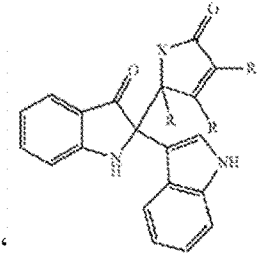 " and insert -- 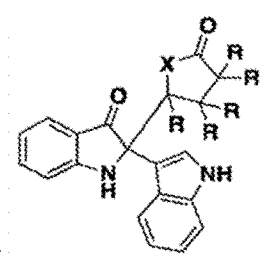 --.

In Column 35, Line 24, delete "$C_2$-$C_{20}$" and insert -- $C_{10}$-$C_{20}$ --.

In Column 35, Line 26, delete "$C_2$-$C_{20}$" and insert -- $C_{10}$-$C_{20}$ --.

In Column 35, Line 29, delete "$C_2$-$C_{20}$" and insert -- $C_{10}$-$C_{20}$ --.

In Column 35, Line 30, delete "$C_2$-$C_{20}$" and insert -- $C_{10}$-$C_{20}$ --.

In Column 35, Line 30, delete "$C_2$-$C_{20}$" and insert -- $C_{10}$-$C_{20}$ --.

In Column 35, Line 32, delete "$C_2$-$C_{20}$" and insert -- $C_{10}$-$C_{20}$ --.

In Column 35, Line 39, delete "$C_2$-$C_{20}$" and insert -- $C_{10}$-$C_{20}$ --.

In Column 35, Line 41, delete "$C_2$-$C_{20}$" and insert -- $C_{10}$-$C_{20}$ --.

In Column 35, Line 47, delete "C1" and insert -- $C_1$ --.

In Column 36, Line 7, delete "$C_2$-$C_{20}$" and insert -- $C_{10}$-$C_{20}$ --.

In Column 36, Line 9, delete "$C_2$-$C_{20}$" and insert -- $C_{10}$-$C_{20}$ --.

In Column 36, Line 12, delete "$C_2$-$C_{20}$" and insert -- $C_{10}$-$C_{20}$ --.

In Column 36, Line 13, delete "$C_2$-$C_{20}$" and insert -- $C_{10}$-$C_{20}$ --.

In Column 36, Line 13, delete "$C_2$-$C_{20}$" and insert -- $C_{10}$-$C_{20}$ --.

In Column 36, Line 15, delete "$C_2$-$C_{20}$" and insert -- $C_{10}$-$C_{20}$ --.

In Column 36, Line 21, delete "$C_2$-$C_{20}$" and insert -- $C_{10}$-$C_{20}$ --.

In Column 36, Line 22, delete "$C_2$-$C_{20}$" and insert -- $C_{10}$-$C_{20}$ --.

CERTIFICATE OF CORRECTION (continued)
U.S. Pat. No. 11,566,018 B2

In Column 36, Line 24, delete "$C_2$-$C_{20}$" and insert -- $C_{10}$-$C_{20}$ --.

In Column 36, Line 55, delete "$C_2$-$C_{20}$" and insert -- $C_{10}$-$C_{20}$ --.

In Column 36, Line 56, delete "$C_2$-$C_{20}$" and insert -- $C_{10}$-$C_{20}$ --.

In Column 36, Line 56, delete "$C_2$-$C_{20}$" and insert -- $C_{10}$-$C_{20}$ --.

In Column 36, Line 58, delete "$C_2$-$C_{20}$" and insert -- $C_{10}$-$C_{20}$ --.

In Column 36, Line 61, delete "$C_2$-$C_{20}$" and insert -- $C_{10}$-$C_{20}$ --.

In Column 36, Line 62, delete "$C_2$-$C_{20}$" and insert -- $C_{10}$-$C_{20}$ --.

In Column 36, Line 62, delete "$C_2$-$C_{20}$" and insert -- $C_{10}$-$C_{20}$ --.

In Column 36, Line 64, delete "$C_2$-$C_{20}$" and insert -- $C_{10}$-$C_{20}$ --.

In Column 37, Line 5, delete "$C_2$-$C_{20}$" and insert -- $C_{10}$-$C_{20}$ --.

In Column 37, Line 6, delete "$C_2$-$C_{20}$" and insert -- $C_{10}$-$C_{20}$ --.

In Column 37, Line 12, delete "$C_2$-$C_{20}$" and insert -- $C_{10}$-$C_{20}$ --.

In Column 37, Line 13, delete "$C_2$-$C_{20}$" and insert -- $C_{10}$-$C_{20}$ --.

In Column 37, Line 15, delete "$C_2$-$C_{20}$" and insert -- $C_{10}$-$C_{20}$ --.

In Column 42, Line 29, delete "catalyst" and insert -- catalyst; --.

In Column 42, Line 58, delete "syntheized" and insert -- synthesized --.

In Column 42, Line 64, delete "syntheized" and insert -- synthesized --.

In Column 43, Line 3, delete "syntheized" and insert -- synthesized --.

In Column 43, Line 22, delete "mumpus" and insert -- mumps --.

In Column 43, Line 33, delete "syntheized" and insert -- synthesized --.

In Column 43, Line 38, delete "syntheized" and insert -- synthesized --.

In Column 43, Line 43, delete "syntheized" and insert -- synthesized --.

In Column 43, Line 49, delete "syntheized" and insert -- synthesized --.

CERTIFICATE OF CORRECTION (continued)
U.S. Pat. No. 11,566,018 B2

In Column 44, Line 2, delete "mumpus" and insert -- mumps --.

In Column 44, Line 28, delete "Metal-Locarbene" and insert -- Metallocarbene --.

In Column 44, Line 31, delete "indolenones" and insert -- indolinones --.

In Column 44, Line 61, delete "umpollung" and insert -- umpolung --.

In Column 45, Line 29, delete "6" and insert -- $\delta$ --.

In Column 45, Line 51, delete "calorimetry" and insert -- Calorimetry --.

In Column 45, Line 64, delete "[a" and insert -- [$\alpha$ --.

In Column 46, Line 45, delete "Et0Ac" and insert -- EtOAc --.

In Column 47, Line 9, delete "$C_{1o}H_7N_6O_5$" and insert -- $C_{10}H_7N_6O_5$ --.

In Column 47, Line 12, delete "broadennin)." and insert -- broadening). --.

In Column 47, Line 27, delete "napthoic" and insert -- naphthoic --.

In Column 47, Line 59, delete "6" and insert -- $\delta$ --.

In Column 48, Line 19, delete "$^1$HNMR" and insert -- $^1$H NMR --.

In Column 48, Line 50, delete "$[M+Na]^+$" and insert -- $[M+Na]^+$ --.

In Column 49, Line 17, delete "$C_{11}H_{11}N_3O_2$" and insert -- $C_{15}H_{11}N_3O_2$ --.

In Column 50, Line 29, delete "cm$^1$;" and insert -- cm$^{-1}$; --.

In Column 50, Line 38, delete "$[M+H]^+$" and insert -- $[M+H]^+$ --.

In Column 52, Line 5, delete "$[M+H]^+$" and insert -- $[M+H]^+$ --.

In Column 53, Line 50, delete "8" and insert -- $\delta$ --.

In Column 54, Line 12, delete "6" and insert -- $\delta$ --.

In Column 54, Line 67, delete "$[M+H]^+$" and insert -- $[M+H]^+$ --.

In Column 56, Line 6, delete "$C_{18}H_{13}ClN_2O_3Na$" and insert -- $C_{18}H_{13}^{35}ClN_2O_3Na$ --.

In Column 56, Line 64, delete "136.8 128.8," and insert -- 136.8, 128.8, --.

In Column 56, Line 66, delete "C25H19³⁵ClN₂NaO₃" and insert -- $C_{25}H_{19}{}^{35}ClN_2NaO_3$ --.

In Column 59, Line 67, delete "8" and insert -- δ --.

In Column 60, Line 7, delete "8" and insert -- δ --.

In Column 60, Line 59, delete "8" and insert -- δ --.

In Column 60, Line 63, delete "8" and insert -- δ --.

In Column 62, Line 34, delete "cm-¹" and insert -- cm-¹; --.

In Column 62, Line 59, delete "cm-¹¹H" and insert -- cm-¹; ¹H --.

In Column 63, Line 16, delete "cm-¹" and insert -- cm-¹; --.

In Column 63, Line 48, delete "6" and insert -- δ --.

In Column 64, Line 9, delete "123.8 122.7," and insert -- 123.8, 122.7, --.

In Column 64, Line 38, delete "FIRMS" and insert -- HRMS --.

In Column 67, Line 8, delete "tthe" and insert -- the --.

In Column 68, Line 55, delete "isatasine" and insert -- isatisine --.

In Column 71, Line 28, delete "Cu(0)" and insert -- Cu(O) --.

In Column 76, Line 40, delete "Ddimer" and insert -- dimer --.

In Columns 75-76, Lines 64-67, delete " 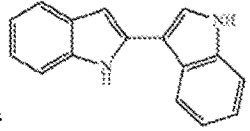 " and insert -- 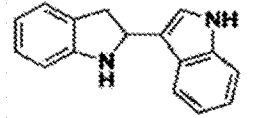 --.

In Column 77, Line 21, delete "disproportation" and insert -- disproportionation --.

In Column 77, Line 39, delete "occuring" and insert -- occurring --.

In Column 79, Line 60, delete "FIG." and insert -- FIGS. --.

In Column 80, Line 8, delete "FIG." and insert -- FIGS. --.

In Column 81, Line 14, delete "J.Org." and insert -- J. Org. --.

In Column 81, Line 17, delete "9Org." and insert -- Org. --.

CERTIFICATE OF CORRECTION (continued)
U.S. Pat. No. 11,566,018 B2

In Column 81, Line 18, delete "I" and insert -- J. --.

In Column 82, Line 17, delete "indolenones" and insert -- indolinones --.

In Column 82, Line 18, delete "chrial" and insert -- chiral --.

SEQUENCE LISTING

<160> NUMBER OF SEQ ID NOS: 1

<210> SEQ ID NO 1
<211> LENGTH: 2165
<212> TYPE: PRT
<213> ORGANISM: Homo sapiens

<400> SEQUENCE: 1

```
Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Ile Ser Leu Lys Lys Leu
50                  55                  60

Ser Ile Thr Gln Ser Leu Ile Ser Lys Tyr His Lys Gly Glu Ile Lys
65                  70                  75                  80

Ile Glu Glu Pro Thr Tyr Phe Gln Ser Leu Leu Met Thr Tyr Lys Ser
            85                  90                  95

Met Thr Ser Ser Glu Gln Ile Thr Thr Thr Asn Leu Leu Lys Lys Ile
            100                 105                 110

Ile Arg Arg Ala Ile Glu Ile Ser Asp Val Lys Val Tyr Ala Ile Leu
            115                 120                 125

Asn Lys Leu Gly Leu Lys Glu Lys Asp Lys Ile Lys Ser Asn Asn Gly
        130                 135                 140

Gln Asp Glu Asp Asn Ser Val Ile Thr Thr Ile Ile Lys Asp Ile
145                 150                 155                 160

Leu Leu Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Ser Ile Leu Thr Gln Tyr Arg Ser Ser
    210                 215                 220

Glu Val Lys Asn His Gly Phe Ile Leu Ile Asp Asn His Thr Leu Asn
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365
```

```
Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
                420                 425                 430

Met Val Asp Glu Arg Gln Ala Met Asp Ala Val Lys Val Asn Cys Asn
            435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
                500                 505                 510

Leu Ile Val Leu Ser Gly Leu Arg Phe Tyr Arg Glu Phe Arg Leu Pro
            515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
                580                 585                 590

Asn Glu Cys Asp Leu Tyr Asn Cys Val Val Asn Gln Ser Tyr Leu Asn
            595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
                660                 665                 670

Leu Lys Ala Gly Ile Ser Asn Lys Ser Asn Arg Tyr Asn Asp Asn Tyr
            675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
                740                 745                 750

Ile Arg Asp His Ile Val Asp Leu Asn Asn Val Asp Glu Gln Ser Gly
            755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
```

```
             785                 790                 795                 800
Lys Phe Ser Ile Thr Ala Leu Ile Asn Gly Asp Asn Gln Ser Ile Asp
                    805                 810                 815
Ile Ser Lys Pro Val Arg Leu Met Glu Gly Gln Thr His Ala Gln Ala
                    820                 825                 830
Asp Tyr Leu Ala Leu Asn Ser Leu Lys Leu Leu Tyr Lys Glu Tyr
                    835                 840                 845
Ala Gly Ile Gly His Lys Leu Lys Gly Thr Glu Thr Tyr Ile Ser Arg
    850                 855                 860
Asp Met Gln Phe Met Ser Lys Thr Ile Gln His Asn Gly Val Tyr Tyr
865                 870                 875                 880
Pro Ala Ser Ile Lys Lys Val Leu Arg Val Gly Pro Trp Ile Asn Thr
                    885                 890                 895
Ile Leu Asp Asp Phe Lys Val Ser Leu Glu Ser Ile Gly Ser Leu Thr
                    900                 905                 910
Gln Glu Leu Glu Tyr Arg Gly Glu Ser Leu Leu Cys Ser Leu Ile Phe
                    915                 920                 925
Arg Asn Val Trp Leu Tyr Asn Gln Ile Ala Leu Gln Leu Lys Asn His
    930                 935                 940
Ala Leu Cys Asn Asn Lys Leu Tyr Leu Asp Ile Leu Lys Val Leu Lys
945                 950                 955                 960
His Leu Lys Thr Phe Phe Asn Leu Asp Asn Ile Asp Thr Ala Leu Thr
                    965                 970                 975
Leu Tyr Met Asn Leu Pro Met Leu Phe Gly Gly Gly Asp Pro Asn Leu
                    980                 985                 990
Leu Tyr Arg Ser Phe Tyr Arg Arg Thr Pro Asp Phe Leu Thr Glu Ala
                    995                 1000                1005
Ile Val His Ser Val Phe Ile Leu Ser Tyr Tyr Thr Asn His Asp
    1010                1015                1020
Leu Lys Asp Lys Leu Gln Asp Leu Ser Asp Asp Arg Leu Asn Lys
    1025                1030                1035
Phe Leu Thr Cys Ile Ile Thr Phe Asp Lys Asn Pro Asn Ala Glu
    1040                1045                1050
Phe Val Thr Leu Met Arg Asp Pro Gln Ala Leu Gly Ser Glu Arg
    1055                1060                1065
Gln Ala Lys Ile Thr Ser Glu Ile Asn Arg Leu Ala Val Thr Glu
    1070                1075                1080
Val Leu Ser Thr Ala Pro Asn Lys Ile Phe Ser Lys Ser Ala Gln
    1085                1090                1095
His Tyr Thr Thr Thr Glu Ile Asp Leu Asn Asp Ile Met Gln Asn
    1100                1105                1110
Ile Glu Pro Thr Tyr Pro His Gly Leu Arg Val Val Tyr Glu Ser
    1115                1120                1125
Leu Pro Phe Tyr Lys Ala Glu Lys Ile Val Asn Leu Ile Ser Gly
    1130                1135                1140
Thr Lys Ser Ile Thr Asn Ile Leu Glu Lys Thr Ser Ala Ile Asp
    1145                1150                1155
Leu Thr Asp Ile Asp Arg Ala Thr Glu Met Met Arg Lys Asn Ile
    1160                1165                1170
Thr Leu Leu Ile Arg Ile Leu Pro Leu Asp Cys Asn Arg Asp Lys
    1175                1180                1185
Arg Glu Ile Leu Ser Met Glu Asn Leu Ser Ile Thr Glu Leu Ser
    1190                1195                1200
```

```
Lys Tyr Val Arg Glu Arg Ser Trp Ser Leu Ser Asn Ile Val Gly
    1205                1210                1215

Val Thr Ser Pro Ser Ile Met Tyr Thr Met Asp Ile Lys Tyr Thr
    1220                1225                1230

Thr Ser Thr Ile Ala Ser Gly Ile Ile Ile Glu Lys Tyr Asn Val
    1235                1240                1245

Asn Ser Leu Thr Arg Gly Glu Arg Gly Pro Thr Lys Pro Trp Val
    1250                1255                1260

Gly Ser Ser Thr Gln Glu Lys Lys Thr Met Pro Val Tyr Asn Arg
    1265                1270                1275

Gln Val Leu Thr Lys Lys Gln Arg Asp Gln Ile Asp Leu Leu Ala
    1280                1285                1290

Lys Leu Asp Trp Val Tyr Ala Ser Ile Asp Asn Lys Asp Glu Phe
    1295                1300                1305

Met Glu Glu Leu Ser Ile Gly Thr Leu Gly Leu Thr Tyr Glu Lys
    1310                1315                1320

Ala Lys Lys Leu Phe Pro Gln Tyr Leu Ser Val Asn Tyr Leu His
    1325                1330                1335

Arg Leu Thr Val Ser Ser Arg Pro Cys Glu Phe Pro Ala Ser Ile
    1340                1345                1350

Pro Ala Tyr Arg Thr Thr Asn Tyr His Phe Asp Thr Ser Pro Ile
    1355                1360                1365

Asn Arg Ile Leu Thr Glu Lys Tyr Gly Asp Glu Asp Ile Asp Ile
    1370                1375                1380

Val Phe Gln Asn Cys Ile Ser Phe Gly Leu Ser Leu Met Ser Val
    1385                1390                1395

Val Glu Gln Phe Thr Asn Val Cys Pro Asn Arg Ile Ile Leu Ile
    1400                1405                1410

Pro Lys Leu Asn Glu Ile His Leu Met Lys Pro Pro Ile Phe Thr
    1415                1420                1425

Gly Asp Val Asp Ile His Lys Leu Lys Gln Val Ile Gln Lys Gln
    1430                1435                1440

His Met Phe Leu Pro Asp Lys Ile Ser Leu Thr Gln Tyr Val Glu
    1445                1450                1455

Leu Phe Leu Ser Asn Lys Thr Leu Lys Ser Gly Ser Asn Val Asn
    1460                1465                1470

Ser Asn Leu Ile Leu Ala His Lys Ile Ser Asp Tyr Phe His Asn
    1475                1480                1485

Thr Tyr Ile Leu Ser Thr Asn Leu Ala Gly His Trp Ile Leu Ile
    1490                1495                1500

Ile Gln Leu Met Lys Asp Ser Lys Gly Ile Phe Glu Lys Asp Trp
    1505                1510                1515

Gly Glu Gly Tyr Ile Thr Asp His Met Phe Ile Asn Leu Lys Val
    1520                1525                1530

Phe Phe Asn Ala Tyr Lys Thr Tyr Leu Leu Cys Phe His Lys Gly
    1535                1540                1545

Tyr Gly Arg Ala Lys Leu Glu Cys Asp Met Asn Thr Ser Asp Leu
    1550                1555                1560

Leu Cys Val Leu Glu Leu Ile Asp Ser Ser Tyr Trp Lys Ser Met
    1565                1570                1575

Ser Lys Val Phe Leu Glu Gln Lys Val Ile Lys Tyr Ile Leu Ser
    1580                1585                1590
```

```
Gln Asp Ala Ser Leu His Arg Val Lys Gly Cys His Ser Phe Lys
1595                1600                1605

Leu Trp Phe Leu Lys Arg Leu Asn Val Ala Glu Phe Thr Val Cys
1610                1615                1620

Pro Trp Val Val Asn Ile Asp Tyr His Pro Thr His Met Lys Ala
1625                1630                1635

Ile Leu Thr Tyr Ile Asp Leu Val Arg Met Gly Leu Ile Asn Ile
1640                1645                1650

Asp Arg Ile Tyr Ile Lys Asn Lys His Lys Phe Asn Asp Glu Phe
1655                1660                1665

Tyr Thr Ser Asn Leu Phe Tyr Ile Asn Tyr Asn Phe Ser Asp Asn
1670                1675                1680

Thr His Leu Leu Thr Lys His Ile Arg Ile Ala Asn Ser Glu Leu
1685                1690                1695

Glu Ser Asn Tyr Asn Lys Leu Tyr His Pro Thr Pro Glu Thr Leu
1700                1705                1710

Glu Asn Ile Leu Thr Asn Pro Val Lys Ser Asn Asp Lys Lys Thr
1715                1720                1725

Leu Ser Asp Ser Cys Ile Gly Lys Asn Val Asp Ser Ile Met Leu
1730                1735                1740

Pro Leu Leu Ser Asn Lys Lys Leu Ile Lys Ser Ser Thr Met Ile
1745                1750                1755

Arg Thr Asn Tyr Ser Arg Gln Asp Leu Tyr Asn Leu Phe Pro Thr
1760                1765                1770

Val Val Ile Asp Lys Ile Ile Asp His Ser Gly Asn Thr Ala Lys
1775                1780                1785

Ser Asn Gln Leu Tyr Thr Thr Thr Ser His Gln Ile Ser Leu Val
1790                1795                1800

His Asn Ser Thr Ser Leu Tyr Cys Met Leu Pro Trp His His Ile
1805                1810                1815

Asn Arg Phe Asn Phe Val Phe Ser Ser Thr Gly Cys Lys Ile Ser
1820                1825                1830

Ile Glu Tyr Ile Leu Lys Asp Leu Lys Ile Lys Asp Pro Asn Cys
1835                1840                1845

Ile Ala Phe Ile Gly Glu Gly Ala Gly Asn Leu Leu Leu Arg Thr
1850                1855                1860

Val Val Glu Leu His Pro Asp Ile Arg Tyr Ile Tyr Arg Ser Leu
1865                1870                1875

Lys Asp Cys Asn Asp His Ser Leu Pro Ile Glu Phe Leu Arg Leu
1880                1885                1890

Tyr Asn Gly His Ile Asn Ile Asp Tyr Gly Glu Asn Leu Thr Ile
1895                1900                1905

Pro Ala Thr Asp Ala Thr Asn Asn Ile His Trp Ser Tyr Leu His
1910                1915                1920

Ile Lys Phe Ala Glu Pro Ile Ser Leu Phe Val Cys Asp Ala Glu
1925                1930                1935

Leu Pro Val Thr Val Asn Trp Ser Lys Ile Ile Ile Glu Trp Ser
1940                1945                1950

Lys His Val Arg Lys Cys Lys Tyr Cys Ser Ser Val Asn Lys Cys
1955                1960                1965

Thr Leu Ile Val Lys Tyr His Ala Gln Asp Asp Ile Asp Phe Lys
1970                1975                1980

Leu Asp Asn Ile Thr Ile Leu Lys Thr Tyr Val Cys Leu Gly Ser
```

-continued

|  | 1985 |  |  |  | 1990 |  |  |  | 1995 |  |  |  |
|---|---|---|---|---|---|---|---|---|---|---|---|---|
| Lys | Leu | Lys | Gly | Ser | Glu | Val | Tyr | Leu | Val | Leu | Thr | Ile | Gly | Pro |
|  | 2000 |  |  |  | 2005 |  |  |  | 2010 |  |  |  |
| Ala | Asn | Val | Phe | Pro | Val | Phe | Asn | Val | Val | Gln | Asn | Ala | Lys | Leu |
|  | 2015 |  |  |  | 2020 |  |  |  | 2025 |  |  |  |
| Ile | Leu | Ser | Arg | Thr | Lys | Asn | Phe | Ile | Met | Pro | Lys | Lys | Ala | Asp |
|  | 2030 |  |  |  | 2035 |  |  |  | 2040 |  |  |  |
| Lys | Glu | Ser | Ile | Asp | Ala | Asn | Ile | Lys | Ser | Leu | Ile | Pro | Phe | Leu |
|  | 2045 |  |  |  | 2050 |  |  |  | 2055 |  |  |  |
| Cys | Tyr | Pro | Ile | Thr | Lys | Lys | Gly | Ile | Asn | Thr | Ala | Leu | Ser | Lys |
|  | 2060 |  |  |  | 2065 |  |  |  | 2070 |  |  |  |
| Leu | Lys | Ser | Val | Val | Ser | Gly | Asp | Ile | Leu | Ser | Tyr | Ser | Ile | Ala |
|  | 2075 |  |  |  | 2080 |  |  |  | 2085 |  |  |  |
| Gly | Arg | Asn | Glu | Val | Phe | Ser | Asn | Lys | Leu | Ile | Asn | His | Lys | His |
|  | 2090 |  |  |  | 2095 |  |  |  | 2100 |  |  |  |
| Met | Asn | Ile | Leu | Lys | Trp | Phe | Asn | His | Val | Leu | Asn | Phe | Arg | Ser |
|  | 2105 |  |  |  | 2110 |  |  |  | 2115 |  |  |  |
| Thr | Glu | Leu | Asn | Tyr | Asn | His | Leu | Tyr | Met | Val | Glu | Ser | Thr | Tyr |
|  | 2120 |  |  |  | 2125 |  |  |  | 2130 |  |  |  |
| Pro | His | Leu | Ser | Glu | Leu | Leu | Asn | Ser | Leu | Thr | Thr | Asn | Glu | Leu |
|  | 2135 |  |  |  | 2140 |  |  |  | 2145 |  |  |  |
| Lys | Lys | Leu | Ile | Lys | Ile | Thr | Gly | Ser | Leu | Leu | Tyr | Asn | Phe | Arg |
|  | 2150 |  |  |  | 2155 |  |  |  | 2160 |  |  |  |
| Asn | Glu |  |  |  |  |  |  |  |  |  |  |  |
|  | 2165 |  |  |  |  |  |  |  |  |  |  |  |